United States Patent
Kipnis et al.

(10) Patent No.: US 11,944,665 B2
(45) Date of Patent: Apr. 2, 2024

(54) METHODS AND COMPOSITIONS FOR MODULATING LYMPHATIC VESSELS IN THE CENTRAL NERVOUS SYSTEM

(71) Applicant: University of Virginia Patent Foundation, Charlottesville, VA (US)

(72) Inventors: Jonathan Kipnis, Charlottesville, VA (US); Antoine Louveau, Charlottesville, VA (US); Sandro Da Mesquita, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 327 days.

(21) Appl. No.: 16/306,483

(22) PCT Filed: May 31, 2017

(86) PCT No.: PCT/US2017/035285
§ 371 (c)(1),
(2) Date: Nov. 30, 2018

(87) PCT Pub. No.: WO2017/210343
PCT Pub. Date: Dec. 7, 2017

(65) Prior Publication Data
US 2019/0269758 A1   Sep. 5, 2019

Related U.S. Application Data

(60) Provisional application No. 62/344,164, filed on Jun. 1, 2016.

(51) Int. Cl.
| | |
|---|---|
| *A61K 38/18* | (2006.01) |
| *A61K 38/17* | (2006.01) |
| *A61K 41/00* | (2020.01) |
| *A61N 5/06* | (2006.01) |
| *A61P 25/00* | (2006.01) |
| *A61P 25/28* | (2006.01) |
| *C07K 16/22* | (2006.01) |
| *C07K 16/28* | (2006.01) |
| *A61N 5/067* | (2006.01) |

(52) U.S. Cl.
CPC ...... *A61K 38/1866* (2013.01); *A61K 38/1709* (2013.01); *A61K 38/1825* (2013.01); *A61K 41/0057* (2013.01); *A61K 41/0071* (2013.01); *A61N 5/062* (2013.01); *A61P 25/00* (2018.01); *A61P 25/28* (2018.01); *C07K 16/22* (2013.01); *C07K 16/2863* (2013.01); *A61N 5/067* (2021.08)

(58) Field of Classification Search
CPC . A61K 38/1866; A61K 41/0057; A61P 25/00; A61N 5/062; C07K 16/22; C07K 16/2863
See application file for complete search history.

(56) References Cited

U.S. PATENT DOCUMENTS

| | | | | |
|---|---|---|---|---|
| 8,852,936 B2 * | 10/2014 | Saaristo | ................. | A61K 35/26 435/372 |
| 2004/0214766 A1 * | 10/2004 | Alitalo | ................... | A61K 31/00 514/44 R |
| 2014/0093520 A1 * | 4/2014 | Bading | ................. | C07K 14/52 424/172.1 |

FOREIGN PATENT DOCUMENTS

| | | |
|---|---|---|
| EP | 1132098 A1 | 9/2001 |
| JP | 2007-506754 A | 3/2007 |
| WO | 2001/021214 A1 | 3/2001 |
| WO | 2005/030240 A2 | 4/2005 |
| WO | 2017/190074 A1 | 11/2017 |
| WO | 2017/210343 A1 | 12/2017 |
| WO | 2020/102627 A1 | 5/2020 |

OTHER PUBLICATIONS

Stopa et al., Altered ependyma and leptomeninges in transgenic mice that over express FGF2 and amyloid precursor protein: evidence for early hydrocephalus. 52nd Annual Meeting of the Society for Research into Hydrocephalus and Spina Bifida. Feb. 3, 2009;6(Suppl. 1):S4, 2 pages.

Gogineni et al., "Inhibition of VEGF-C Modulates Distal Lymphatic Remodeling and Secondary Metastasis", PLOS ONE, vol. 8, No. 7, pp. 1-15, Jul. 2013.

Iliff et al., "A Paravascular Pathway Facilitates CSF Flow Through the Brain Parenchyma and the Clearance of Interstitial Solutes, Including Amyloid B", Sci Transl Med., vol. 4, No. 147, pp. 1-22, Aug. 15, 2012.

International Search Report and Written Opinion dated Aug. 29, 2017 in Application No. PCT/US17/35285.

Louveau et al., "Structural and functional features of central nervous system lymphatics", Nature, vol. 523, No. 7560, pp. 337-341, Jul. 16, 2015.

(Continued)

*Primary Examiner* — Olga N Chernyshev

(74) *Attorney, Agent, or Firm* — McCarter & English, LLP; Marcie B. Clarke

(57) ABSTRACT

In some embodiments herein, methods, compositions, and uses for modulating lymphatic vessels of the central nervous system are described. In some embodiments, methods, compositions, or uses for treating, preventing, or ameliorating symptoms of a neurodegenerative disease comprise by increasing flow via meningeal lymphatic vessels are described. In some embodiments, methods, compositions, or uses for treating, preventing, or ameliorating symptoms of inflammatory neurological disease be inhibiting or preventing immune cell migration through meningeal lymphatic vessels are described.

3 Claims, 101 Drawing Sheets

Specification includes a Sequence Listing.

(56) References Cited

OTHER PUBLICATIONS

Tammela et al., "Photodynamic Ablation of Lymphatic Vessels and Intralymphatic Cancer Cells Prevents Metastasis", Sci Transl Med, vol. 3, No. 69, pp. 1-8, Feb. 9, 2011.
Tarasoff-Conway et al., "Clearance systems in the brain—implications for Alzheimer disease", Nat Rev Neurol., vol. 11, No. 8, pp. 457-470, Aug. 2015.
Filiano et al., "Unexpected role of interferon-γ in regulating neuronal connectivity and social behavior", Nature, vol. 535, No. 7612, pp. 425-429, Jul. 21, 2016.
Zhang et al., Intranasal nanoparticles of basic fibroblast growth factor for brain delivery to treat Alzheimer's disease. Int J Pharm. Jan. 3, 20140;461(1-2):192-202.
Mathios et al., Anti-PD-1 antitumor immunity is enhanced by local and abrogated by systemic chemotherapy in GBM. Sci Transl Med. Dec. 2, 20161;8(370):370ra180, 22 pages.
Mizoguchi et al., Molecular characteristics of glioblastoma with 1p/19q co-deletion. Brain Tumor Pathol. Jul. 2012;29(3):148-53.
Strik et al., A case of spinal glioblastoma multiforme: immunohistochemical study and review of the literature. J Neurooncol. Dec. 2000;50(3):239-43.
Partanen et al., VEGF-C and VEGF-D expression in neuroendocrine cells and their receptor, VEGFR-3, in fenestrated blood vessels in human tissues. FASEB J. Oct. 2000;14(13):2087-96.

* cited by examiner

Lyve-1 DAPI

Lyve-1 CD31

Lyve-1  Prox1-tdTOMATO DAPI

Lyve-1 Podoplanin

Fig. 3A
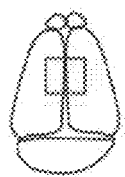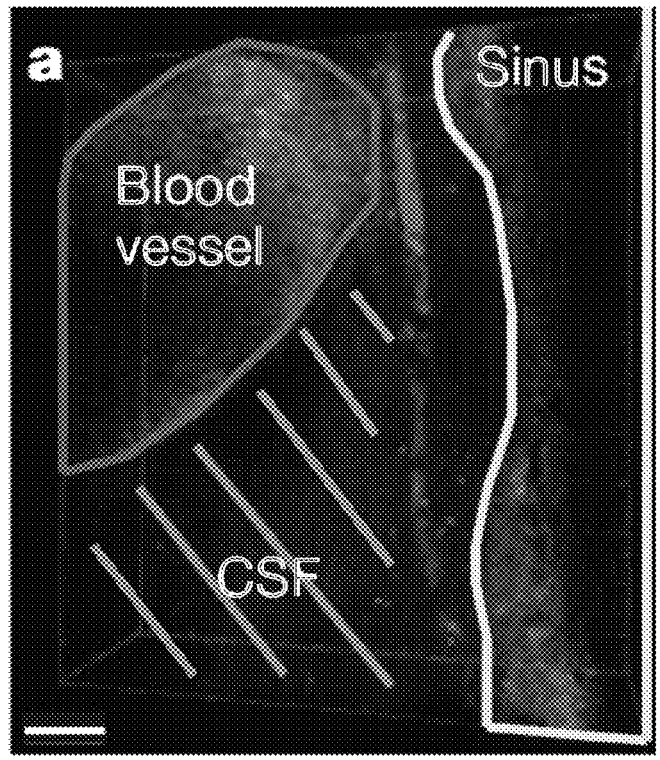
Fig. 3B
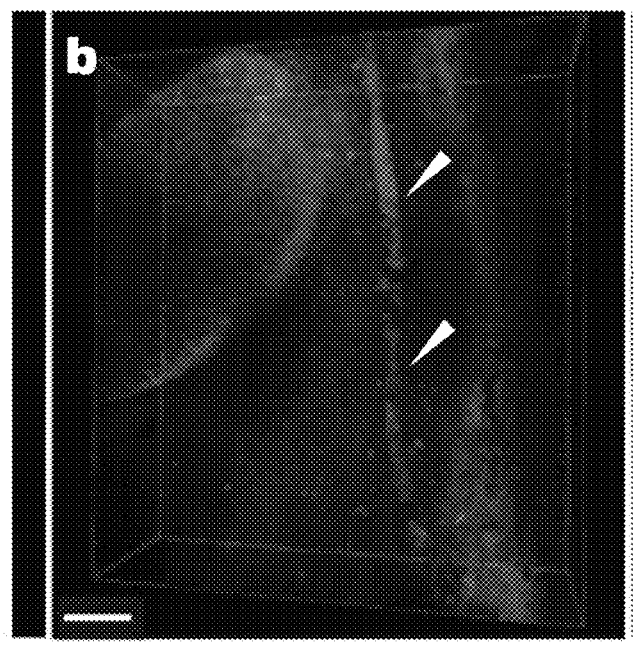
QDot 655 (ICV) Fluorescein (IV)

CD3e MHCII Lyve-1

Superficial cervical LN

Deep cervical lymph nodes

Lyve-1

| | Diameter | Branching |
|---|---|---|
| Diaphragm | 32.75±1.052 | 3.24±0.2922 |
| Superior Sagittal Sinus | 16.70±0.58*** | 0.41±0.097** |
| Transverse Sinus | 23.76±1.771* | 1.08±0.241* |

Lyve-1 CD11c-YFP

Lyve-1 CD11c-YFP

Fig. 12G
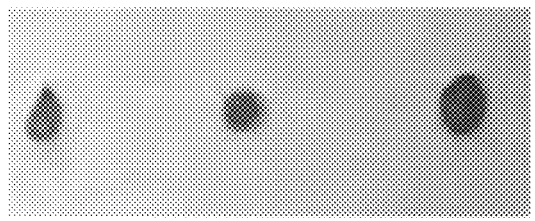
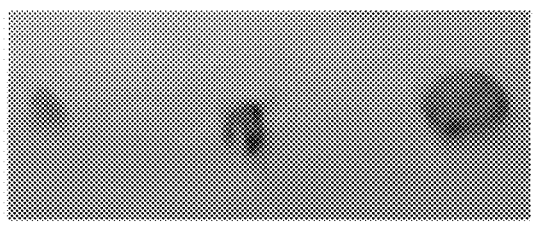
Fig. 12H
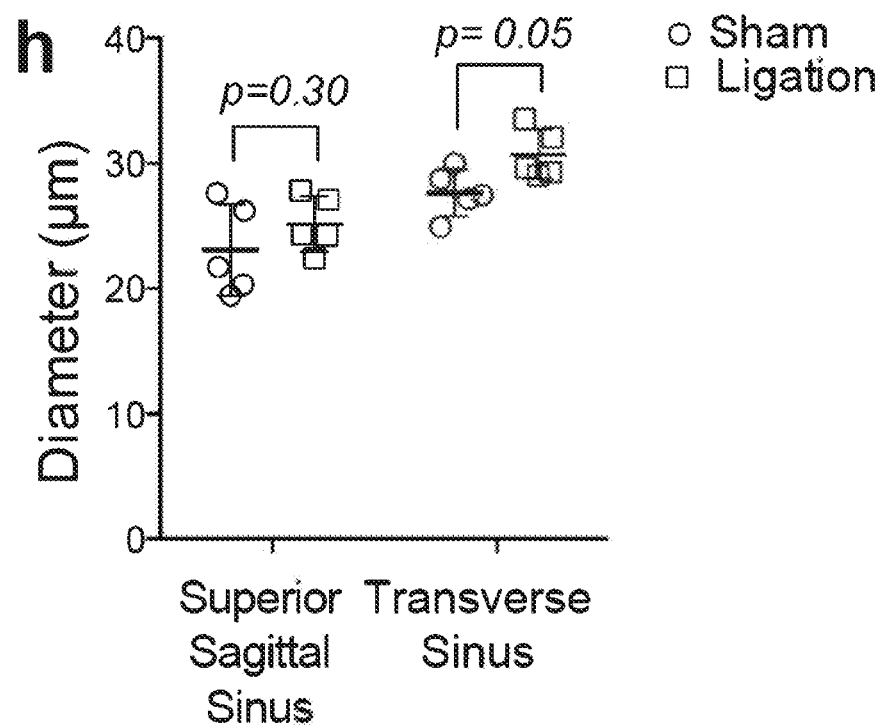

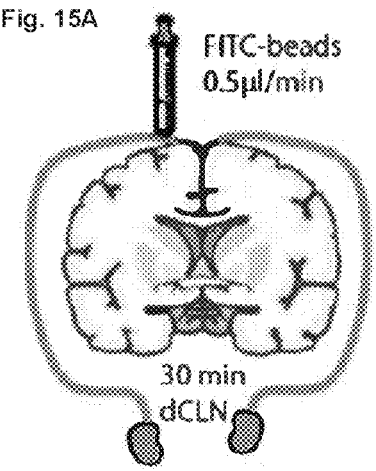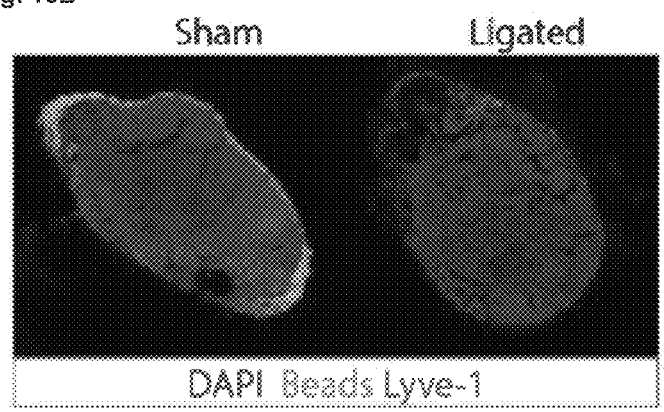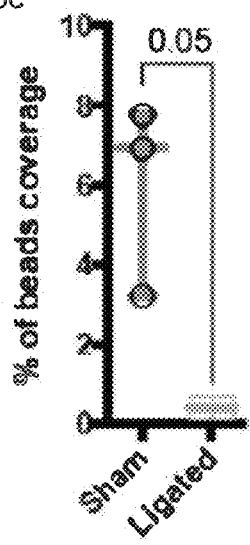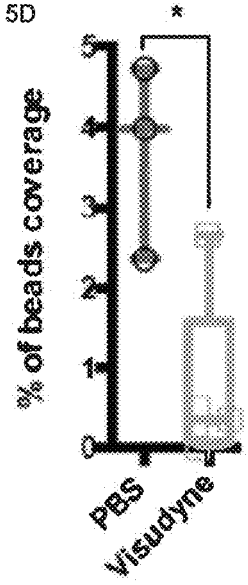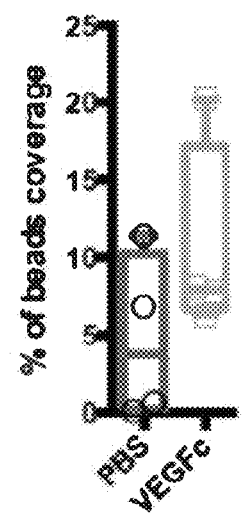

DAPI LYVE-1 Aβ$_{42}$-HiLyte647

DAPI LYVE-1 OVA-A647

DAPI LYVE-1 OVA-A647

LYVE-1⁺ vessels in SSS

CD31⁺ vessels in SSS

Non-AD cortical meninges

AD cortical meninges

DAPI GFAP Aβ

LYVE-1⁺ vessels

Acquisition

Probe trial

Probe trial

Reversal

Transverse Sinus

Transverse Sinus

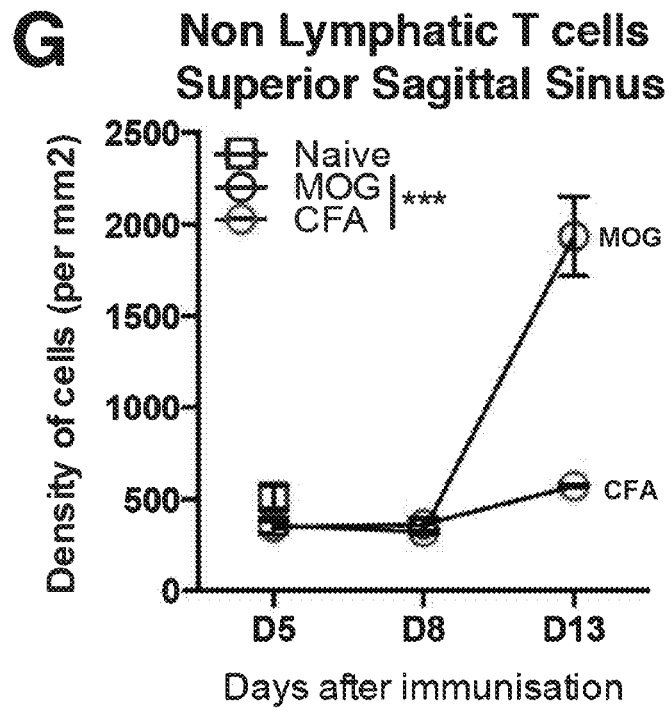
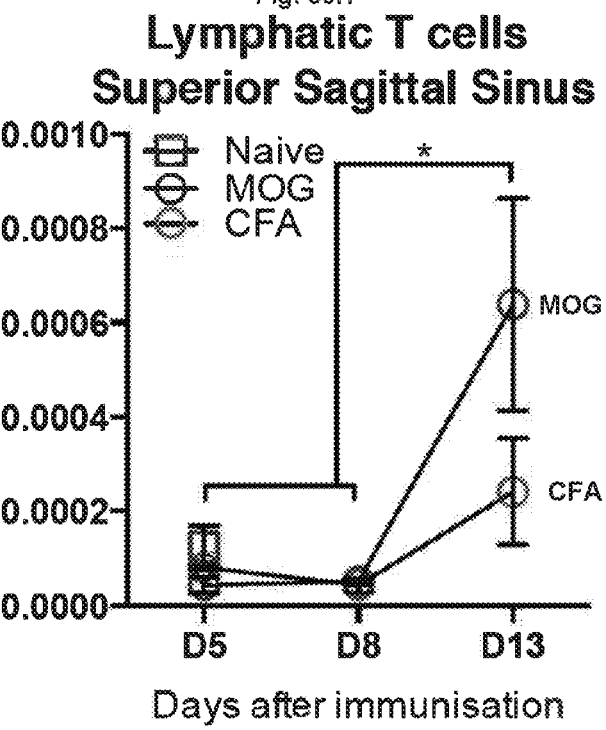

Fig. 50I
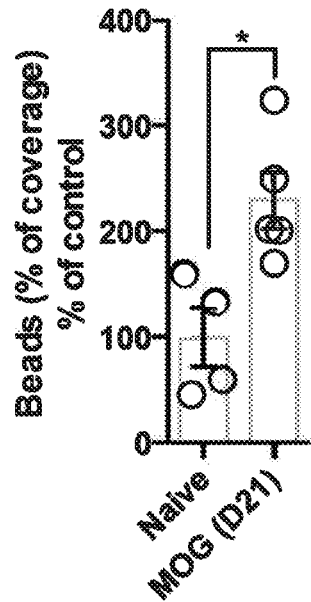
Fig. 51A
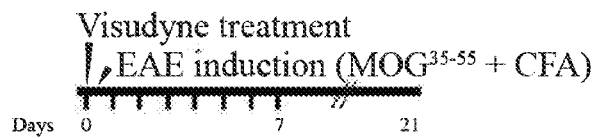
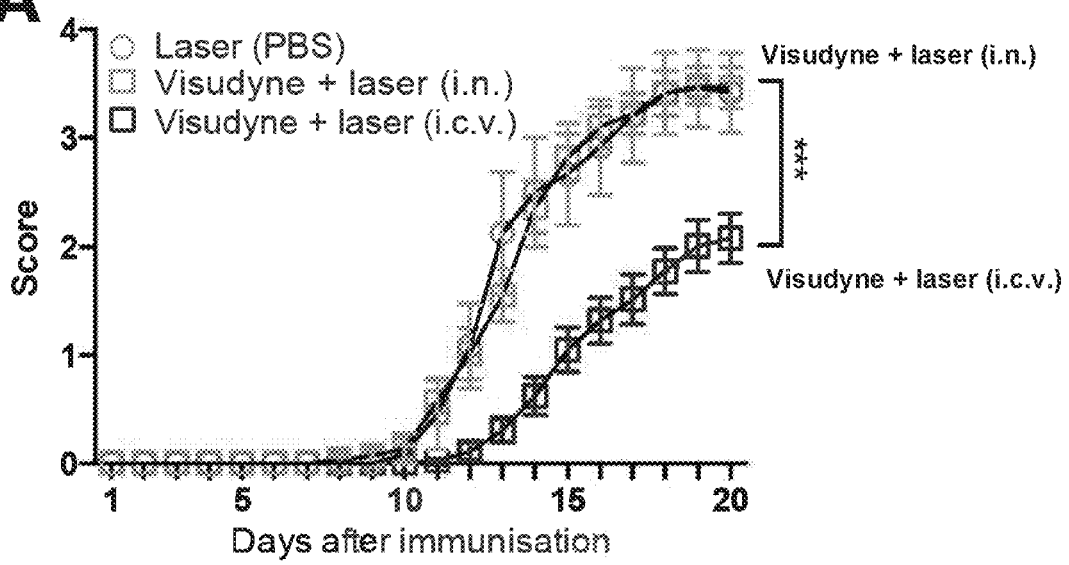

METHODS AND COMPOSITIONS FOR MODULATING LYMPHATIC VESSELS IN THE CENTRAL NERVOUS SYSTEM

INCORPORATION BY REFERENCE TO ANY PRIORITY APPLICATIONS

The present application is the national phase of International Application No. PCT/US2017/035285, filed May 31, 2017, which claims the benefit of U.S. Provisional App. No. 62/344,164 filed Jun. 1, 2016, which is hereby incorporated by reference in its entirety.

STATEMENT REGARDING FEDERALLY SPONSORED R&D

This invention was made with government support under Grant Nos. AG034113 and NS061973, each awarded by the National Institutes of Health. The government has certain rights in the invention.

REFERENCE TO SEQUENCE LISTING

The present application is being filed along with a Sequence Listing in electronic format. The Sequence Listing is provided as a file entitled SEQUENCEUVA005WO.TXT, created and last modified May 26, 2017, which is 27.922 bytes in size. The information in the electronic format of the Sequence Listing is incorporated herein by reference in its entirety.

BACKGROUND

Neurological diseases impact millions of people worldwide, and include degenerative and inflammatory neurological diseases. Among degenerative neurological diseases. Alzheimer's Disease (AD) is the most prevalent form of dementia worldwide (Andrieu et al., 2015) and is distinctively characterized by early and marked cognitive impairment (Andrieu et al., 2015; Ballard et al., 2011). The vast majority (>98%) of AD cases are sporadic (Blennow et al., 2006), and in such cases the etiology of the amyloid pathology is poorly understood (Benilova et al., 2012; Blennow et al., 2006). This is in contrast to familial AD, where rare hereditary dominant mutations in amyloid precursor protein (APP) or in presenilins 1 and 2 drive the uncontrolled formation of amyloid-beta (Hardy and Selkoe, 2002). The brain's pathological hallmarks of AD are intracellular neurofibrillary tangles and extracellular amyloid plaques, the latter being a product of the amyloidogenic processing of APP and the resulting deposition of amyloid-beta in the brain parenchyma (Benilova et al., 2012; Hardy and Selkoe, 2002; Ittner and Götz, 2011). Increasing aggregation of diffusible amyloid-beta peptides from the ISF and the CSF into toxic oligomeric intermediates and their accumulation in the brain parenchyma (Hong et al., 2011; Iliff et al., 2012) are believed to be precipitating factors for different neuroinflammatory abnormalities (Guillot-Sestier et al., 2015; Hong et al., 2016; Matarin et al., 2015), such as the formation of neurofibrillary tangles (Ittner and Götz, 2011) and the pronounced neuronal dysfunction (Palop et al., 2007; Sun et al., 2009; Walsh et al., 2002) in the AD brain.

Multiple Sclerosis (MS) is an inflammatory neurological disease in which the immune system targets and damages myelin sheaths, leading to neuronal dysfunction and associated devastating motor and cognitive impairments (Compston and Coles, 2002, 2008; Liblau et al., 2013; Weiner, 2004). MS affects about 2.5 million people worldwide. Its etiology remains unknown, but both genetic predisposition and environmental factors have been implicated in its development. Indeed, geographic locations toward the equator and certain infections appear to have some influence (Farez et al., 2015; Goodin, 2014).

Organs generally function less effectively with age. For example, skin becomes less elastic, muscle tone is lost, and heart function declines. Aging is a substantial risk factor for numerous neurological diseases, including neurodegenerative diseases and inflammatory neurological diseases.

FIELD

Several embodiments herein relate generally to compositions, methods, and uses for modulating lymphatic vessels in the central nervous system. Modulating lymphatic vessels, in accordance with some embodiments, are used to treat, prevent, or ameliorate symptoms of neurodegenerative diseases such as Alzheimer's disease (AD) and inflammatory neurological diseases such as multiple sclerosis (MS).

SUMMARY

Some embodiments include a method of increasing flow of fluid in the central nervous system of a subject. In one embodiment, the method comprises determining (e.g., identifying) the subject to be in need of increased fluid flow in the central nervous system, and administering an effective amount of a composition comprising, consisting essentially of, or consisting of a flow modulator such as a VEGFR3 agonist and/or Fibroblast Growth Factor 2 (FGF2) to a meningeal space of the subject in need, so that the amount of VEGFR3 agonist and/or FGF2 increases the diameter of a meningeal lymphatic vessel of the subject. In one embodiment, the method increases fluid flow in the central nervous system of the subject. In some embodiments, determining the subject to be in need of increased fluid flow comprises determining the subject to have a neurodegenerative disease, determining the subject to have a risk factor for the neurodegenerative disease, or both. In some embodiments, the neurodegenerative disease is selected from the group consisting of one or more of the following: Alzheimer's disease (AD), dementia, Parkinson's disease, cerebral edema, amyotrophic lateral sclerosis (ALS). Pediatric Autoimmune Neuropsychiatric Disorders Associated with Streptococcal Infections (PANDAS), meningitis, hemorrhagic stroke, autism spectrum disorder (ASD), brain tumor, and epilepsy. In some embodiments, determining the subject to be in need of increased fluid flow comprises determining the subject to have Alzheimer's disease. In some embodiments, determining the subject to be in need of increased fluid flow comprises determining the subject to have a risk factor for AD selected from the group consisting of at least one of the following: diploidy for apolipoprotein-E-epsilon-4 (apo-E-epsilon-4), a variant in apo-J, a variant in phosphatidylinositol-binding clathrin assembly protein (PICALM), a variant in complement receptor 1 (CR3), a variant in CD33 (Siglee-3), or a variant in triggering receptor expressed on myeloid cells 2 (TREM2), age, familial AD, or a symptom of dementia. In some embodiments, the VEGFR3 agonist and/or FGF2 is administered selectively or otherwise localized to the meningeal space of the subject. In some embodiments, the VEGFR3 agonist and/or FGF2 is administered to the subject by a route selected from the group consisting of at least one of the following: nasal administration, transcranial administration, contact with cerebral spinal fluid (CSF) of the subject, pumping into CSF of the subject, implantation into the skull or brain, contacting a thinned skull or skull portion of the subject with the VEGFR3 agonist and/or FGF2, or expression in the subject of a nucleic acid encoding the VEGFR3 agonist and/or FGF2, or a combination of any of the listed routes. In some embodiments, the VEGFR3 agonist is administered. In some embodiments, the VEGFR3 agonist is selected from the group consisting of one or more of the following: VEGF-c, VEGF-d, or an analog, variant, or fragment thereof. In some embodiments, the effective amount of VEGFR3 agonist and/or FGF2 is administered to the subject after determining the subject to have the risk factor for the neurodegenerative disease. In some embodiments, the effective amount of VEGFR3 agonist and/or FGF2 is administered to the subject after determining the subject to have the neurodegenerative disease. In some embodiments, the diameter of the meningeal lymphatic vessel is increased by at least 5%, 10%, 15%, 20%, 30%, 50% or more (e.g., when post-administration is compared to pre-administration). In some embodiments, the diameter of the meningeal lymphatic vessel is increased in a manner that increases flow of fluid in the CNS (e.g., brain), for example by at least 10%, 20%, 30%, 50%, or more (e.g., when post-administration is compared to pre-administration). In some embodiments, increasing fluid flow in the central nervous system of the subject comprises increasing a rate of perfusion of fluid throughout an area of the subject's brain. In some embodiments, the central nervous system of the subject comprises amyloid-beta plaques, and wherein increasing the fluid flow reduces the quantity of amyloid-beta plaques. In some embodiments, increasing the flow reduces the quantity of accumulated amyloid-beta plaques by at least 5%. In some embodiments, at least some of the accumulated amyloid-beta plaques are in the meninges of the subject's brain. In some embodiments, increasing the fluid flow in the CNS increases clearance of soluble molecules in the brain of the subject (e.g., by at least 10%, 20%, 30%, 50%, or more). As an example, administration of the composition comprising the flow modulator in some embodiments increases the fluid flow in the CNS and increases clearance of soluble molecules in the CNS (e.g., brain, CSF) by more than about 10%, 20%, 30%, 50%, or more as compared to pre-administration. In some embodiments, increasing the fluid comprises cerebral spinal fluid (CSF), interstitial fluid (ISF), or both. Some embodiments include the composition for use in increasing flow of fluid in the central nervous system of the subject.

Several embodiments include a method of reducing a quantity of accumulated amyloid-beta plaques in a subject having a neurodegenerative disease or a risk factor therefor. In one embodiment, the method comprises determining the subject to have the neurodegenerative disease or the risk factor, and administering a composition comprising, consisting of, or consisting essentially of a VEGFR3 agonist and/or FGF2 to a meningeal space of the subject, so that fluid flow in the central nervous system of the subject is increased. Thus, the method can reduce the quantity of accumulated amyloid-beta plaques in the subject. In some embodiments, at least some of the accumulated amyloid-beta plaques are in the meninges of the subject's brain. In some embodiments, the quantity of accumulated amyloid-beta plaques is reduced by at least 5%, 10%, 20% or more. In some embodiments, cognitive function of the subject, for example in short- or long-term memory task, is improved. In some embodiments, the increased fluid flow in the central nervous system of the subject comprises an increased rate of perfusion of fluid throughout an area of the subject's brain.

In some embodiments, administering the composition comprising, consisting of, or consisting essentially of the VEGFR3 agonist and/or FGF2 increases the diameter of a meningeal lymphatic vessel of the subject's brain by at least 5%, 10%, 15%, 20%, 30%, 50% or more, thus increasing fluid flow. In some embodiments, flow of fluids in the CNS (e.g., brain) of the subject is increased by at least 10%, 20%, 30%, 40%, 50%, or more. In some embodiments, the subject has the neurodegenerative disease. In some embodiments, the method further comprises determining the subject to have the neurodegenerative disease. In some embodiments, the neurodegenerative disease is selected from the group consisting of one or more of the following: Alzheimer's disease (AD), dementia, Parkinson's disease, cerebral edema, amyotrophic lateral sclerosis (ALS), Pediatric Autoimmune Neuropsychaitric Disorders Associated with Streptococcal Infections (PANDAS), meningitis, hemorrhagic stroke, autism spectrum disorder (ASD), brain tumor, and epilepsy. In some embodiments, the subject has the risk factor for the neurodegenerative disease. In some embodiments, the method further comprises determining the subject to have the risk factor for the neurodegenerative disease. In some embodiments, the risk factor comprises a risk factor for Alzheimer's disease selected from the group consisting of one or more of the following: diploidy for apolipoprotein-E-epsilon-4 (apo-E-epsilon-4), a variant in apo-J, a variant in phosphatidylinositol-binding clathrin assembly protein (PICALM), a variant in complement receptor 1 (CR3), a variant in CD33 (Siglee-3), or a variant in triggering receptor expressed on myeloid cells 2 (TREM2), age, familial AD, or a symptom of dementia. Some embodiments include the composition is for use in reducing a quantity of accumulated amyloid-beta plaques in a subject having a neurodegenerative disease or a risk factor therefor.

Some embodiments include a method of increasing clearance of molecules from a central nervous system (CNS) of a subject, comprising administering a composition comprising, consisting of, or consisting essentially of VEGFR3 agonist and/or FGF2 to a meningeal space of the subject, so that fluid flow in the CNS of the subject is increased. The method can thus increase clearance of molecules from the CNS of the subject. In some embodiments, the increased clearance of molecules from the CNS of the subject comprises an increased rate of movement of molecules from the CNS to deep cervical lymph nodes. In some embodiments, the increased clearance of molecules from the CNS of the subject reduces accumulation of the molecules in the brain. In some embodiments, amyloid-beta plaques are cleared from the CNS of the subject. In some embodiments, at least some amyloid-beta plaques are cleared from meningeal portions of the central nervous system of the subject. In some embodiments, a quantity of accumulated amyloid-beta plaques in the CNS is reduced by at least 5%, 10%, 15%, 20%, or more. In some embodiments, the increased fluid flow in the central nervous system of the subject comprises an increased rate of perfusion of fluid throughout an area of the subject's brain. In some embodiments, cognitive function of the subject, for example in short- or long-term memory task, is improved. In some embodiments, the method further comprises determining the subject to have a neurodegenerative disease, or a risk factor for a neurodegenerative disease. In some embodiments, the neurodegenerative disease is selected from the group consisting of at least one of the following: Alzheimer's disease (AD), dementia, Parkinson's disease, cerebral edema, amyotrophic lateral sclerosis (ALS), Pediatric Autoimmune Neuropsychiatric Disorders Associated with Streptococcal Infections (PANDAS), meningitis, hemorrhagic stroke, autism spectrum disorder (ASD), brain tumor, and epilepsy. In some embodiments, the method comprises determining the subject to have Alzheimer's disease. In some embodiments, the method comprises determining the subject to have a risk factor for Alzheimer's disease selected from the group consisting of one or more of the following: diploidy for apolipoprotein-E-epsilon-4 (apo-E-epsilon-4), a variant in apo-J, a variant in phosphatidylinositol-binding clathrin assembly protein (PICALM), a variant in complement receptor 1 (CR3), a variant in CD33 (Siglee-3), or a variant in triggering receptor expressed on myeloid cells 2 (TREM2), age, familial AD, or a symptom of dementia. In some embodiments, the VEGFR3 agonist is administered. In some embodiments, the VEGFR3 agonist is selected from the group consisting of one or more of the following: VEGF-c, VEGF-d, or an analog, variant, or fragment thereof. In some embodiments, the VEGFR3 agonist and/or FGF2 is administered selectively to the meningeal space of the subject. In some embodiments, the VEGFR3 agonist and/or FGF2 is administered to the subject by a route selected from the group consisting of one or more of the following: nasal administration, transcranial administration, contact cerebral spinal fluid (CSF) of the subject, pumping into CSF of the subject, implantation into the skull or brain, contacting a thinned skull or skull portion of the subject with the VEGFR3 agonist and/or FGF2, or expression in the subject of a nucleic acid encoding the VEGFR3 agonist and/or FGF2, or a combination of any of the listed routes. In some embodiments, the effective amount of VEGFR3 agonist and/or FGF2 is administered to the subject after determining the subject to have the risk factor for the neurodegenerative disease. In some embodiments, the effective amount of VEGFR3 agonist and/or FGF2 is administered to the subject after determining the subject to have the neurodegenerative disease. In some embodiments, the fluid comprises cerebral spinal fluid (CSF), interstitial fluid (ISF), or both. Some embodiments include the composition for use in increasing clearance of molecules from a central nervous system (CNS) of the subject.

Some embodiments include a method of decreasing immune cell migration through a meningeal lymphatic vessel in a subject. In one embodiment, the method comprises (a) administering a composition comprising, consisting of, or consisting essentially of a VEGFR3 antagonist to a meningeal space of the subject, or (b) ablating a meningeal lymphatic vessel of the subject, or a combination of (a) and (b). The method can thus decrease immune cell migration through the meningeal lymphatic vessel in the subject. In some embodiments, the lymphatic vessels are selectively ablated by ligation, optical activation of visudyne in the lymphatic vessel, or both. In some embodiments, the VEGFR3 antagonist is administered selectively to a meningeal space of the subject. In some embodiments, the VEGFR3 antagonist is administered to the subject by a route selected from the group consisting of at least one of the following: nasal administration, transcranial administration, contact with cerebral spinal fluid (CSF) of the subject, pumping into CSF of the subject, implantation into the skull or brain, contacting a thinned skull or skull portion of the subject with the VEGFR3 antagonist, or expression in the subject of a nucleic acid encoding the VEGFR3 antagonist, or a combination of any of the listed routes. In some embodiments, the VEGFR3 antagonist is administered to a subject who does not have a disease characterized by increase angiogenesis, for example cancer or a tumor. In some embodiments, the VEGFR3 antagonist comprises an antibody specific for VEGFR3 or VEGF-c or VEGF-d. In some embodiments, the method further comprises determining the subject to have an inflammatory neurological disease or a risk factor therefor. In some embodiments, the risk factor is selected from the group consisting of at least one of the following: familial multiple sclerosis, infection, advanced age, suspicion that the subject has multiple sclerosis, or at least one symptom of inhibited neuromotor function. In some embodiments, the inflammatory neurological disease comprises or consists essentially of a demyelinating disease of the central nervous system. In some embodiments, the inflammatory neurological disease comprises or consists essentially of multiple sclerosis. In some embodiments, decreasing immune cell migration through the meningeal lymphatic vessel comprises a decrease in movement of immune cells from the parenchyma of the subject's brain to deep cervical lymph nodes of the subject. In some embodiments, the movement is decreased by at least 5%, for example at least 5%, 10%, 15%, 20%, 25%, 30%, 40%, 50%, or more (e.g., the amount of cells that migrate pre- and post-administration). As such, in some embodiments, inflammation in the CNS (e.g., brain) of the subject is decreased. In some embodiments, the immune cell migration comprises migration of lymphocytes. In some embodiments, decreasing immune cell migration through the meningeal lymphatic vessel comprises decreasing a density of lymphocytes in the meningeal lymphatic vessel. In some embodiments, the lymphocytes comprise or consist essentially of T cells. In some embodiments, the density is decreased by at least 5%, 10%, 15%, 20%, 25%, 30%, 40%, 50%, or more (e.g., as a comparison of pre- and post-administration). As such, in some embodiments, inflammation in the CNS (e.g., brain) of the subject is decreased. In some embodiments, decreasing immune cell migration through the meningeal lymphatic vessels decreases a quantity of activated T cells in the deep cervical lymph nodes that have a migratory phenotype. In some embodiments, the migratory phenotype comprises a CD11a+ phenotype, a CD49d+ phenotype, or both. In some embodiments, decreasing immune cell migration through the meningeal lymphatic vessel decreases a quantity of in T cells in the central nervous system that produce inflammatory cytokines. In some embodiments, the inflammatory cytokines comprise IL-17, IFN-gamma, or both. In some embodiments, neuromotor function of the subject is improved. Some embodiments include the composition for use in decreasing immune cell migration through a meningeal lymphatic vessel in the subject.

Some embodiments include a method of reducing inflammation in the nervous system of a subject having an inflammatory neurological disease of the central nervous system, or a risk factor therefor. The method can comprise (a) administering a composition comprising, consisting of, or consisting essentially of a VEGFR3 antagonist to a meningeal space of the subject; or (b) ablating a meningeal lymphatic vessel of the subject; or a combination of (a) and (b), in which the VEGFR3 antagonist, ablation, or both, decrease immune cell migration through the meningeal lymphatic vessel in the subject. The method can thus reduce inflammation in the central nervous system. In some embodiments, the inflammatory neurological disease comprises or consists essentially of a demyelinating disease of the central nervous system. In some embodiments, the inflammatory neurological disease comprises or consists essentially of multiple sclerosis. In some embodiments, the subject has the inflammatory neurological disease. In some embodiments, the subject has the risk factor for the inflammatory neurological disease. In some embodiments, the method further comprises determining that the subject has the risk factor for the inflammatory neurological disease. In some embodiments, the risk factor is selected from the group consisting of at least one of the following: familial multiple sclerosis, suspicion that the subject has multiple sclerosis, infection, advanced age, or at least one symptom of inhibited neuromotor function. In some embodiments, the lymphatic vessels are selectively ablated by ligation, optical activation of visudyne in lymphatic vessels, or both. In some embodiments, the VEGFR3 antagonist is administered selectively to a meningeal space of the subject. In some embodiments, the VEGFR3 antagonist is administered to the subject by a route selected from the group consisting of at least one of the following: nasal administration, transcranial administration, contact with cerebral spinal fluid (CSF) of the subject, pumping into CSF of the subject, implantation into the skull or brain, contacting a thinned skull or skull portion of the subject with the VEGFR3 antagonist, or expression in the subject of a nucleic acid encoding the VEGFR3 antagonist, or a combination of any of the listed routes. In some embodiments, the VEGFR3 antagonist comprises or consists essentially of an antibody specific for VEGFR3 or VEGF-c or VEGF-d. In some embodiments, decreasing immune cell migration through the meningeal lymphatic vessel comprises a decrease in movement of immune cells from the parenchyma of the subject to deep cervical lymph nodes of the subject. In some embodiments, decreasing immune cell migration through the meningeal lymphatic vessel comprises a decrease in movement of lymphocytes from cerebral spinal fluid in the subject to deep cervical lymph nodes of the subject. In some embodiments, decreasing immune cell migration through the meningeal lymphatic vessel comprises decreasing a density of the immune cells in the meningeal lymphatic vessel. In some embodiments, the density is decreased by at least 10% (e.g., when comparing pre- and post-administration). In some embodiments, the immune cells comprise lymphocytes. In some embodiments, the lymphocytes comprise or consist essentially of T cells. In some embodiments, reducing inflammation in the central nervous system comprises decreasing a quantity of activated T cells in the deep cervical lymph nodes that have a migratory phenotype. In some embodiments, the migratory phenotype comprises a CD11a+ phenotype, a CD49d+ phenotype, or both. In some embodiments, decreasing immune cell migration through the meningeal lymphatic vessels decreases a quantity of in T cells in the central nervous system that produce inflammatory cytokines. In some embodiments, the inflammatory cytokines comprise IL-17. IFN-gamma, or both. In some embodiments, the method further comprises ameliorating a neuromotor symptom in the subject. In some embodiments, neuromotor function of the subject is improved. Some embodiments include the composition for use in reducing inflammation in the nervous system of the subject.

BRIEF DESCRIPTION OF THE DRAWINGS

FIG. 1A is a schematic representation of the whole-mount dissection of the dura mater. SSS, superior sagittal sinus; TS, transverse sinus. FIG. 1B is a representative images of CD3e labelling in whole-mount meninges (scale bar, 2,000 µm). Insets, higher magnification of the boxes highlighted in b (scale bar, 90 µm (top inset) or 150 µm (bottom inset)). DAPI, 4',6-diamidino-2-phenylindole. FIG. 1C is a schematic representation of a coronal section of whole-mount meninges. FIG. 1D is a representative image of a coronal section of whole-mount meninges (scale bar, 200 µm). FIG. 1E is a representative images of CD3e and CD31 immunolabelling in a coronal section of whole-mount meninges. Scale bar, 100 µm. Inset, higher magnification of the box highlighted in the left panel (scale bar, 30 µm, inset, 4 µm) shows CD31 labeling in the lumen and CD3e labeling outside the lumen. FIG. 1F shows quantification of the percentage of sinusal T cells localized abluminally vs luminally to the superior sagittal sinus (mean±s.e.m.; n=18 fields analysed from 3 independent animals; ***p=0.0008, Mann-Whitney test). FIG. 1G is a series of panels that show CD3e and MHCII express. The left panel shows representative images of CD3e and MHCII-expressing cells around the superior sagittal sinus (meningeal cartoons here and elsewhere depict the location of the presented images; scale bar, 50 µm). The middle panel shows higher magnification of the box highlighted on the left (scale bar, 10 µm). The right panel shows high magnification of CD3- and MHCII-expressing cells (scale bar, 10 µm). FIG. 1H is a representative image of CD31 and CD3e labelling around the superior sagittal signal (scale bar, 30 µm). Arrowheads indicate CD3e labeling. FIG. 1I is a graph showing quantification of the number of T cells per mm of vessels in the perisinusal CD31+ vessels and in similar diameter meningeal blood vessels (mean±s.e.m.; n=3 animals; *P=0.05, one-tailed Mann-Whitney test). FIG. 1J is a representative image of Lyve-1 labelling on whole-mount meninges (scale bar, 1,000 µm). FIG. 1K shows higher magnification of Lyve-1-expressing vessels (scale bar, 70 µm); arrowheads indicate Lyve-1+ macrophages. FIG. 1L is a representative image of CD31 and Lyve-1 labelling of a coronal section of the superior sagittal sinus (scale bar, 70 µm). CD31 and Lyve-1 labeling are each observed to the left of the dashed line, but generally do not overlap, and the sinusal lumen is shown with an arrowhead. FIG. 1M is an image and a corresponding inset showing higher magnification of a Lyve-1 positive vessel presenting a conduit-like structure (scale bar, 50 µm). Inset, ×1.7 magnification of the Lyve-1+ vessel presented in the panel to the left; arrowhead points to the lumen of the vessel.

FIG. 2A is a series of representative images of Prox1 expression in the nuclei of Lyve-1$^+$ vessels in the dural sinuses of Prox1$^{tdT}$ mice (scale bars, 10p m)(in order of left-to-right, the four panels show Lyve-1, Prox1-tdTOMATO, DAPI, and overlay). FIG. 2B is a series of representative images of podoplanin and Lyve-1 labelling on dural sinuses (scale bar, 40 µm) (in order of left-to-right, the three panels show Lyve-1. Podoplanin, and overlay). FIG. 2C is a series of representative images of VEGFR3 and Lyve-1 staining on dural sinuses (scale bar, 20 µm)(in order of left-to-right, the three panels show VEGFR3. Lyve-1, and overlay). For FIGS. 2D and 2E Adult mice were injected i.c.v. (cisterna *magna*) with 4 µg of rhVEGF-c (Cys156Ser) or with PBS. Meninges were harvested 7 and 14 days after the injection. FIG. 2D is a set of representative images of Lyve-1 and Prox1 labelling of meninges at day 7 after injection (scale bars, 30 µm) (the panel on the left shows injection with PBS, and the panel on the right shows injection with rhVEGF-c). FIG. 2E is a graph showing quantification of the meningeal lymphatic vessel diameter (mean±s.e.m.; n=4 mice each group, *P<0.05, two-way ANOVA with Bonferroni post hoc test). FIGS. 2F and 2G are a series of representative images of smooth muscle cells (alpha-smooth muscle actin, α-SMA) and Lyve-1 labelling on dural sinuses (scale bars, 50 μm (g) or 20 μm(g)). In FIG. 2G, the top panel shows Lyve-1 and the bottom panel shows α-SMA. FIG. 2H is a representative low power micrograph (transmission electron microscopy) of a meningeal lymphatic vessel (scale bar, 5 μm). Inset, higher magnification of the box highlighted in FIG. 2H. Yellow arrowheads 1 show basement membrane; red arrowheads 2 show anchoring filaments (collagen fibres); and green arrowheads 3 show cellular junction.

FIGS. 3A-J are a series of microscope images and graphs showing functional characterization of meningeal lymphatic vessels. Representative z-stacks of the superior sagittal sinus of adult mice injected intravenously (i.v.) with fluorescein and intracerebroventricularly (i.c.v.) with QDot655 (n-3 mice). FIGS. 3A and 3B are low-magnification images showing fluorescein labelling in a meningeal blood vessel and in the superior sagittal sinus (scale bars, 20 μm in FIGS. 3A and 3B). In contrast, QDot655 labelling (arrowheads) is prominent in the perisinusal vessel. FIGS. 3C and 3D are coronal section of the z-sack presented in FIGS. 3A and 3B (scale bars, 20 μm in FIGS. 3C and 3D). CSF, cerebrospinal fluid. The arrowhead in FIG. 3E shows a CSF-filled vessel. FIG. 3E is a set of panels of a representative z-stack of cerebrospinal fluid-filled vessel from a mouse injected i.c.v. with both QDot655 and Alexa488-conjugated anti-Lyve-1 antibody (n=3 mice; scale bars, 30 μm)(the left-most panel shows QDot655, the middle panel shows Anti-Lyve-1 Alexa 488, and the left panel shows overlay). FIG. 3F is a set of panels showing image of immunolabelling for CD3e and MHCII along with Lyve-1 in the meninges. The top panel is a representative image of immunolabelling for CD3e and MHCII along with Lyve-1 in the meninges (scale bar, 15 μm). The bottom panel is a representative image of 3D reconstruction of the meningeal lymphatic vessels showing the luminal localization of the CD3e and MHCHII-expressing cells (scale bar, 20 μm). For FIGS. 3G and 3H, adult mice were injected i.c.v. with 5 μl of 10% Evans blue. Superficial cervical lymph nodes (FIG. 3G, arrowheads) and deep cervical lymph nodes (FIG. 3H) were analysed 30 min after injection (n=5 mice); white arrowheads indicate the lymph nodes; yellow arrowheads indicate the Evans blue-filled vessels arising near the internal jugular vein into the deep cervical lymph nodes (FIG. 3H). For FIGS. 3I and 3J, the collecting vessels draining into the deep cervical lymph nodes (yellow arrowheads in h) were ligated or sham-operated. Eight hours after the ligation, the meninges were collected and immunolabelled for Lyve-1. Representative images of immunolabelling for Lyve-1 in the transverse sinus of ligated and sham-operated mice (FIG. 3I; scale bars, 30 μm). Dot plots represent measurement of the meningeal lymphatic vessel diameters (FIG. 3J; mean±s.e.m.; n=5 mice each group from 2 independent experiments; *P=0.031, Mann-Whitney test).

FIG. 4A is a representative image of CD31 staining in whole-mount meninges (scale bar, 2,000 μm). FIG. 4B is a representative images of T cells (CD3e, arrowheads) in the dura-arachnoid, pia, dural sinuses, and choroid plexus (scale bars, 70 μm). FIG. 4C shows quantification of T-cell density in different meningeal compartments (mean±s.e.m.; N=6 animals each group from 2 independent experiments; *P<0.001; Kruskal-Wallis test with Dunn's post hoc test). FIG. 4D shows quantification of MHCII-expressing cells in different meningeal compartments (mean±s.e.m.; n=6 animals each group from 2 independent experiments; *P<0.001; Kruskal-Wallis test with Dunn's post hoc test). For FIG. 4E, adult mice injected i.v. with 100 μl of DyLight 488 lectin 5 min before euthanasia to enable labelling of the cardiovascular system. Meninges were harvested and stained with anti-CD3e. FIG. 4E is a representative orthogonal image of T-cell localization in the lumen (white arrowhead 11) and outside of the sinus (yellow arrowheads 12; n=2 mice; scale bar, 70 μm). For FIG. 4F, adult mice were injected i.v. with 10 μg of FITC-conjugated anti-CD45 antibody or FITC-conjugated isotype antibody. Meninges were harvested one hour after the injection and labelled with anti-CD3e. FIG. 4F is a series of representative images of CD3e immunolabelling around dural sinuses are shown. CD45-positive cells do not co-localize with CD3e+ cells (a), suggesting an abluminal localization of the latter (n=2 mice each group; scale bars, 20 μm). FIG. 4G shows a representative 3D reconstruction of the lymphatic vessels localization around the superior sagittal sinus. Adult mice were injected i.v. with 100 μl of DyLight 488 lectin 5 min before euthanasia in order to stain the cardiovascular system. Meninges were harvested and labeled with anti-Lyve 1. The lack of lectin staining in the Lyve-1-positive meningeal lymphatic vessels suggests that they are independent of the cardiovascular system (n=3 mice; scale bars, left, 50 μm and right, 120 μm). The mounting of the whole meninges results in the flattening of the sinus, thus it does not appear tubular.

FIG. 5 is a series of microscope images and graphs showing identification, characterization and validation of the expression of classical lymphatic endothelial cell markers by the meningeal lymphatic vessels.

FIG. 6A, shows gating strategy employed to identify lymphatic endothelial cells (CD31+ podoplanin+). Lymphatic endothelial cells are identified as singlet, live cells, CD45− and CD31+ podoplanin+. FIG. 6B depicts representative dot plots for lymphatic endothelial cells (CD31+ podoplanin+) in the diaphragm, skin, and dura mater of adult mice.

FIG. 7A is a representative image of a formalin-fixed coronal section of human superior sagittal sinus. FIGS. 7B and 7C are each representative images of Lyve-1 staining on coronal section of human superior sagittal sinus (scale bar, 100 μm).

The box in c highlights the presence of Lyve-1-expressing macrophages in human meninges, as seen in mice. FIG. 7D is a set of representative images of Lyve-1 (left panel) and CD68 (right panel) staining of coronal sections of human superior sagittal sinus. Note the absence of CD68 positivity on Lyve-1 positive structures (scale bars, 50 µm). FIG. 7E is a representative images of podoplanin (right panel) and Lyve-1 (left panel) staining of coronal sections of human superior sagittal sinus (scale bars, 50 µm).

FIG. 8A is a representative images of CCL21 (middle panel) and Lyve-1 (left panel) labelling of the meningeal lymphatic vessels (scale bars, 10 µm). Overlay is shown in the right panel FIGS. 8B and 8C are each representative images of VE-Cadherin and Lyve-1 staining on meningeal blood vessels (FIG. 8B) and meningeal lymphatic vessels (FIG. 8C), arrowheads point to the VE-Cadherin aggregates; scale bars, 10 µm). FIGS. 8D-F are each representative images of Claudin-5 and Lyve-1 staining on meningeal blood (FIG. 8D) and lymphatic (FIG. 8E, for which left panel shows Claudin-5 and right panel shows Lyve-1) vessels, and diaphragm lymphatic vessels (FIG. 8F, for which left panel shows Claudin-5 and right panel shows Lyve-1); arrowheads point to Claudin-5 aggregates (scale bars, 10 µm). FIGS. 8G and 8H are each representative images of integrin-α9 and Lyve-1 labelling on skin (FIG. 8G; ear) and meninges whole mount (FIG. 8H). In FIG. 8G, lower right panel shows Lyve-1, the upper right panel shows integrin-α9, and the left panel shows overlay. Scale bars, 40 µm. No integrin-α9 expressing valves were detected in the meningeal lymphatic vessels. FIG. 8I is a representative low power micrographs (transmission electron microscopy) of the meningeal lymphatic vessels (scale bar, 2 µm); 1, lumen; SC, supporting cell; BEC, lymphatic endothelial cell; BEC, sinusal endothelial cell. Red arrowheads point to anchoring filaments. FIG. 8J is a diagram table summarizing morphological features of the lymphatic network in different regions of the meninges and the diaphragm. Diameters are expressed in µm and branching as number of branches per mm of vessel; (mean±s.e.m.; n=4 animals each group from 2 independent experiments. *P<0.05, P<0.01, *P<0.001; two-way ANOVA with Bonferroni post hoc tests). For statistics, the presented comparisons were between the diaphragm and the superior sagittal sinus and between the superior sagittal sinus and the transverse sinuses.

FIG. 9A is a representative z-stack of QDot655 filled cerebrospinal fluid drainage both in the blood vasculature (sinus) and in the meningeal lymphatic vessels after i.c.v. injection (scale bar, 20 µm). FIG. 9B is a representative image of CD31 and Lyve-1 immunostaining on whole-mount meninges. Adult mice were injected i.c.v. with 2.5 µg of Alexa 488 conjugated anti-Lyve-1 antibody. Thirty minutes after the injection, the meninges were harvested and stained with anti-CD31. Injected in vivo, the Lyve-1 antibody illuminates the lymphatic vessels (scale bar, 20 µm). FIG. 9C is a representative z-stack of the superior sagittal sinus of adult mice injected i.v. with QDot655 and i.c.v. with Alexa488 conjugated anti-Lyve-1 antibody. FIG. 9C, panel "i" is a coronal section of the z-stack presented in panel c. The signal from the remaining skull and/or collagen-rich structure above the meninges was recorded (blue). FIG. 9C, panel ii is a reconstruction of the z-stack presented in panel c showing the localization of the meningeal lymphatic vessels under the skull (scale bars, 50 µm).

FIG. 10A is a representative images of T cells (CD3e) and lymphatic endothelial cells (Lyve-1) on dural sinuses (scale bar, 20 µm). Panels ii and iii of FIG. 10A are, Orthogonal sections representing T-cell localization around Panel ii and within Panel iii the Lyve-1 structures (scale bars, 51 m). FIG. 10B shows quantification of the sinusal T cells and MHCII-expressing cells within the lymphatic vessels (mean±s.e.m., n=7-8 mice from 3 independent experiments). FIGS. 10C-D show representative images of Lyve-1 staining on dural meninges from CD11cYFP mice (scale bars, 20 µm). CD11c positive cells (most probably dendritic cells) can be found inside the meningeal lymphatic vessels. FIG. 10E is a representative image of B220+ cells and lymphatic endothelial cells (Lyve-1) immunolabelling in the meninges (arrowheads indicate B220+CD11c− cells; scale bar 20 µm). FIG. 10F is a representative dotplot of B220+ cells (gated on singles, live, CD45+) within the dural sinuse expressing CD19; ~40% of the B220+ cells express CD19.

In FIGS. 11A-C, Adult mice were injected i.c.v. with 5 µl of 10% Evans blue. The meninges were harvested 30 min after injection and Evans blue localization was assessed by confocal microscopy. FIG. 11A is a representative image of Evans blue localization in both the sinus and the meningeal lymphatic vessels (n=9 mice; scale bars, 40 µm). The right panel shows Lyve-1, the middle panel shows Evans blue, and the left panel shows overlay. FIG. 11B is a representative profile of Evans blue (31) and Lyve-1 (32) relative fluorescence intensity on a cross-section of the image presented in FIG. 11A, FIG. 11C shows Quantification of the average intensity of Evans blue in the sinus, the lymphatic vessels and the meninges of adult mice (mean±s.e.m., n=16 analysed fields form 4 independent animals; **P<0.01, Kruskall-Wallis with Dunn's multiple comparisons test). For FIGS. 11D-E adult mice were injected intranasally with 5 µl of 10% Evans blue. The successful targeting of the nasal mucosa (FIG. 11D) and the lack of accumulation of Evans blue in the deep cervical lymph nodes (FIG. 11E) 30 min after the injection are demonstrated.

FIGS. 12A-H are a series of microscope images and graphs showing effects of deep cervical lymph node resection and of the lymphatic vessels ligation on the meningeal immune compartment. FIGS. 12A-E show the deep cervical lymph nodes were resected (xDCLN) or sham-operated. Three weeks after resection, the meninges were harvested, single cells isolated, and analysed for T-cell content by flow cytometry. FIG. 12A shows gating strategy to analyse meningeal T cells. Meningeal T cells are selected for singlets. CD45+, live cells and TCRβ+. FIG. 12B is a representative dot plot for CD8+ and CD4+ cells in meninges of sham and xDCLN mice. FIG. 12C shows quantification of total T cells (TCRβ+), CD4+ and CD8+ in the meninges of xDCLN and sham mice (mean±s.e.m.; n=3 animals each group; *P<0.018. P<0.006 (CD8), *P<0.003 (TCRb); Student's t-test; a representative, out of two independently perform, is presented). FIG. 12D shows representative expression of CD62L and CD44 by CD4+ T cells phenotype in sham and xDCLN mice (n=3 mice per group). FIG. 12E shows representative histogram for CD71 expression by meningeal CD4+ T cells in sham and xDCLN mice (n=3 mice per group). FIG. 12F shows representative images of the ligation surgery. To highlight the lymph vessels, Evans blue was injected i.c.v. before the surgery. Black arrowhead points to the node, yellow arrowhead points to the ligated Evans blue-filled vessels. FIG. 12G shows sham-operated or ligated animals were injected i.c.v. with 5 µl of 10% Evans blue. The deep cervical lymph nodes were harvested 30 min after the injection and analysed for Evans blue content. Representative images of the Evans blue accumulation in the deep cervical lymph nodes of the sham-operated and ligated animals are presented. FIG. 12H shows quantification of the meningeal lymphatic vessel diameter in the superior sagittal sinus and the transverse sinuses in sham mice and after ligation of the collecting lymphatic vessels (mean±s.e.m., n=5 mice per group from 2 independent experiments; two-way ANOVA with Bonferroni post hoc test).

FIG. 14A shows schematic of the experiment. FIG. 14B shows Adult mice injected i.c.v. (cisterna *magna*) with 5 or 20 µg of Visudyne (or PBS as control), which was activated using 690 nm laser (FIG. 14A). Meninges were stained for Lyve-1, Prox1 and CD31 24 hrs post-ablation. Disruption of lymphatics in superior sagittal (FIG. 14B) and transverse sinuses (cFIG. 14C). In FIG. 14C, the top panel refers to a control, the middle mane refers to 20,000 ng of Visudyne, and the bottom panel refers to 5,000 ng of Visudyne. No effect on the blood vessels (n=2 mice/group).

FIGS. 15A-E are a series of diagrams, microscope images, and graphs showing modulation of the meningeal lymphatic affects drainage into the cervical lymph nodes. FIG. 15A shows a scheme of the measurement of lymphatic drainage. Fluorescent microbeads (0.5 µm in diameter-5 µl) were injected in the lateral ventricle of mice at a rate of 0.5 µl/min. 30 min later, the deep cervical lymph nodes were harvested, sliced and immunostained for the presence of fluorescent beads. FIG. 15B is a pair of representative sections of deep cervical lymph nodes from sham operated (left) and ligated (right) mice immunostained for lymphatic vasculature (Lyve-1), fluorescent microbeads and Lyve-1. Note the accumulation of microbeads in the subcapsular space of the lymph nodes in the sham operated mice (left). FIG. 15C shows quantification of the coverage of dCLN section by fluorescent beads in the sham and ligated mice. N=3-4 mice per group, Student-t-test. d. Quantification of the coverage of dCLN section by fluorescent beads in PBS and Visudyne injected mice (24 h after ablation). N=3-5 mice per group, *$p<0.05$, Student-t-test. e. Quantification of the coverage of dCLN section by fluorescent beads in PBS and VEGF-c injected mice (5 days after VEGF-c injection). N=4 mice per group.

FIG. 16A shows measurement of lymphatic drainage in young versus old mice. Quantification of the coverage of dCLN section by fluorescent beads in young (10 weeks old) and old (24 months) male mice. N=4-6 mice per group, *$p<0.05$, Student-t-test. FIG. 16B shows quantification of the coverage of dCLN section by fluorescent beads in WT and J20 mice. N=4-6 mice per group.

FIG. 17A: C57B16/J mice were immunized with CFA/Mog35-55 and their meninges were dissected and analyzed at different time points after immunization. While on days 3 and 5, no change in diameter of meningeal lymphatic vessels was observed, on day 7 a significant increase was evident. FIG. 17B: meninges excised from CFA/Mog35-55 immunized mice were also labeled for T cell (CD3) contents and cell numbers were enumerated. Significant decrease in cell counts was observed on day 7 with dramatic increase on day 13, at the onset of the disease. FIG. 17C: mice underwent survival surgery for deep cervical lymph nodes removal. Sham-operated animals and naive mice were used as controls. Three weeks after excision, animals were immunized with CFA/Mog35-55 and EAE was followed. Excision of deep cervical lymph nodes ameliorated EAE development and its severity, in line with previously published works 39. FIG. 17D: adult mice were subjected to deep cervical lymph node afferent lymphatic ligation or sham operated. On the same day, EAE was induced by subcutaneous injection of 200 µg emulsified MOG35-55 peptide in complete Freund adjuvant. Mice were scored daily to assess disease progression. Repeated measure 2-way ANOVA was used for statistical analysis. Panel ii of FIG. 17D shows an image of deep cervical lymph nodes from the indicated surgical procedure.

FIG. 18A shows mice injected i.c.v. (cisterna *magna*) with 2 µl of Visudyne, which was activated using 690 nm laser of multiphoton microscope through thin skull. Two hours after the ablation, the meninges were collected and stained for lymphatic endothelial cell (Lyve-1) and blood vessels (laminin). Disruption of lymphatic vessels is evident at the area of ablation (super sagittal sinus (FIG. 18B), but a trend to disruption was also seen in transverse sinuses (FIG. 18C). No effect on the blood vessels was observed (FIG. 18D; n=2 mice/group).

In FIG. 19A, SCID mice were reconstituted with CD4+ T cells expressing the fluorophore KikGR. Two weeks later the skull above the sagittal sinus was thinned and meningeal T cells were imaged by two-photon imaging in the anesthetized animal. After taking the pre-conversion image, the thinned mouse skull was exposed to an ultraviolet light source for 2-3 minutes before reimaging the same region post-conversion. The laser was tuned to 1000 nm (KikGR-GFP) or 1075 nm (KikGR-RFP) for imaging. FIG. 19B-C show photoconversion via unthinned skull. FIG. 19B shows CD4+ KikGR reconstituted SCID mouse was exposed to focused UV light for 5 minutes with some areas protected from light by aluminum foil. The black box roughly denotes the imaging area. FIG. 19C shows the dura mater was isolated and immediately imaged by confocal microscopy. Photoconversion was observed in regions that received UV light (above the dotted line was shielded, below the dotted line was unshielded). Scale bar represents 50 µm.

FIG. 20A is a representative dot-plot of the meningeal CD4 T cells. FIG. 20B shows meningeal CD4 T cell quantification. As shown in FIG. 20C, in order to assess that the anti-CD3e is depleting and not just internalizing the TCR complex, OTI-GFP mice were transcranially injected with 15 µg of anti-mCD3e f(ab')2 of control f(ab')2 once, and the meninges were harvested 24 h after the injection. Representative dot plot of the GFP+ populations in the meninges of control or injected mice are shown.

FIG. 21A is a set of representative consecutive slices of deep cervical lymph node in sham (left series) and ligated (right series) animals. Notably, beads are not observed in the deep cervical lymph nodes of the ligated series. FIG. 21B shows quantification of the beads coverage in the sham and ligated animals. Each color represents one animal, each dot being one lymph node.

FIGS. 50A-50I are a series of graphs showing a lack of inflammation-induced lymphangiogenesis of the meningeal lymphatic endothelial cells.

FIGS. 51A-D are a series of graphs showing that ablation of lymphatic drainage ameliorate MOG-specific T cells activation in the deep cervical lymph nodes resulting in ameliorated disease development.

DETAILED DESCRIPTION

Figure 1A:
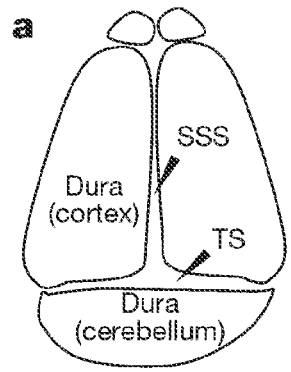
FIGS. 1A-M are a series of microscope images and graphs showing albuminal distribution of meningeal T cells and identification of Lyve-1 expressing vessels adjacent to the dural sinuses.
Figure 1B:
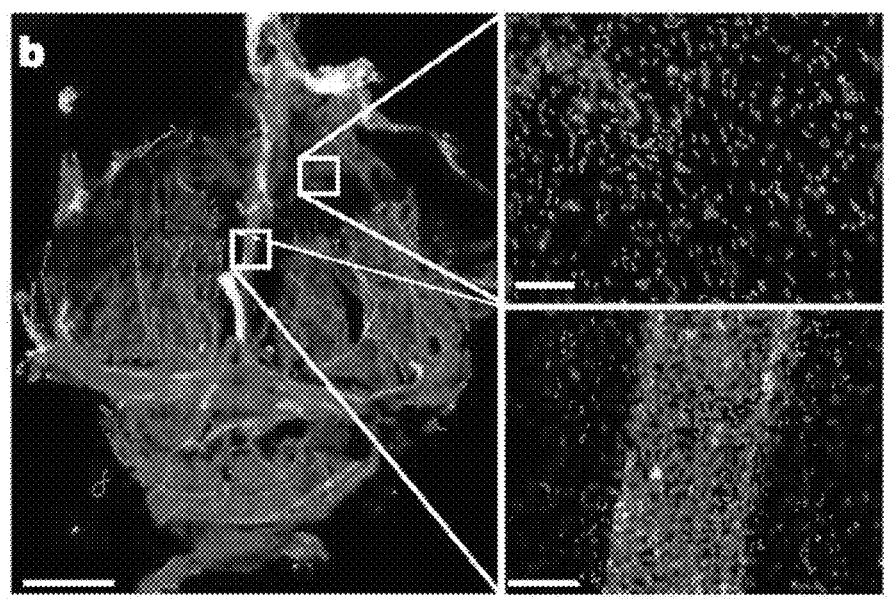
Figure 1C:
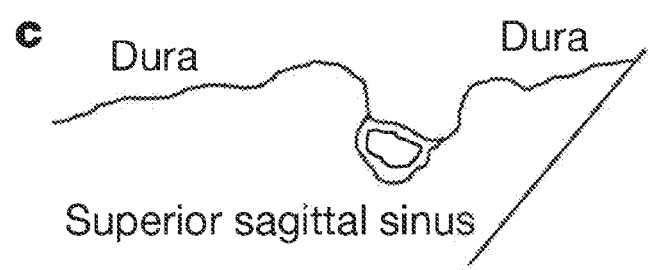
Figure 1D:
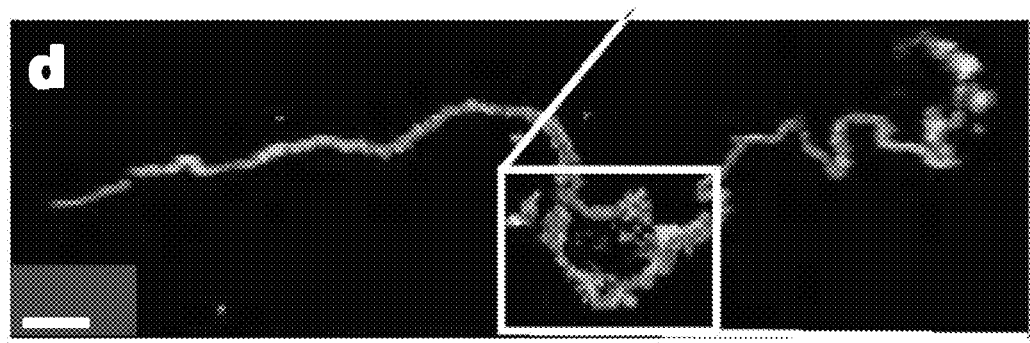
Figure 1E:
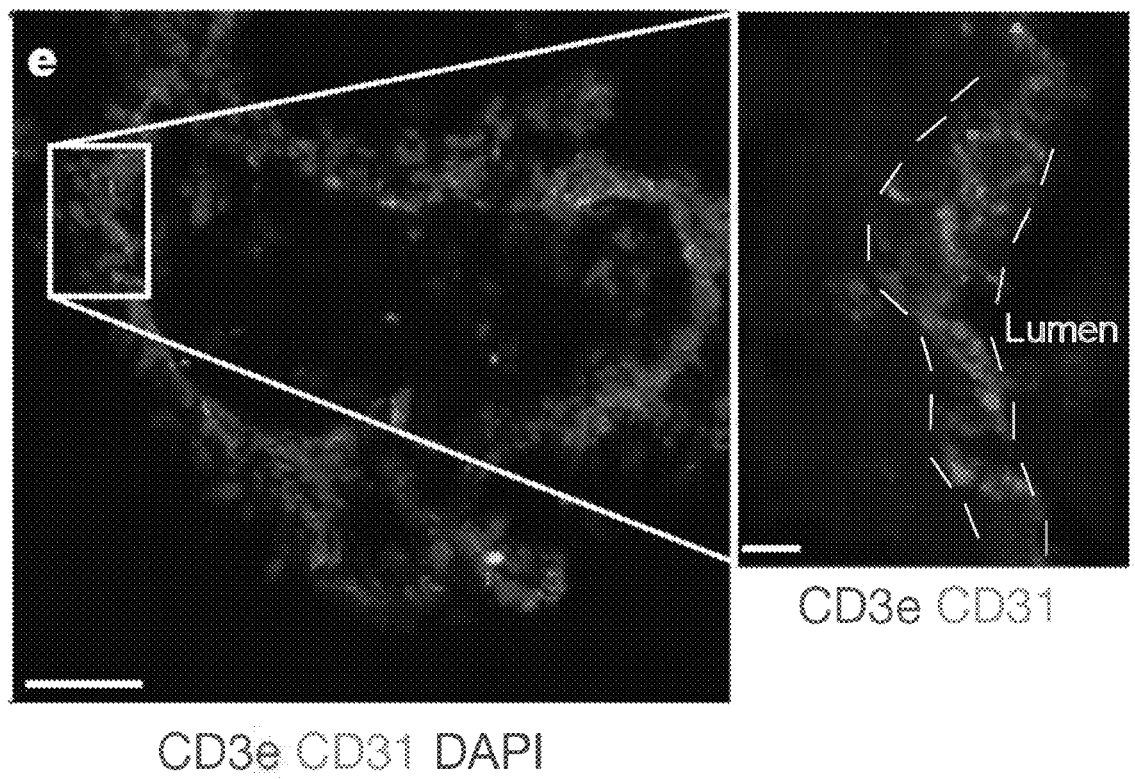
Figure 1F:
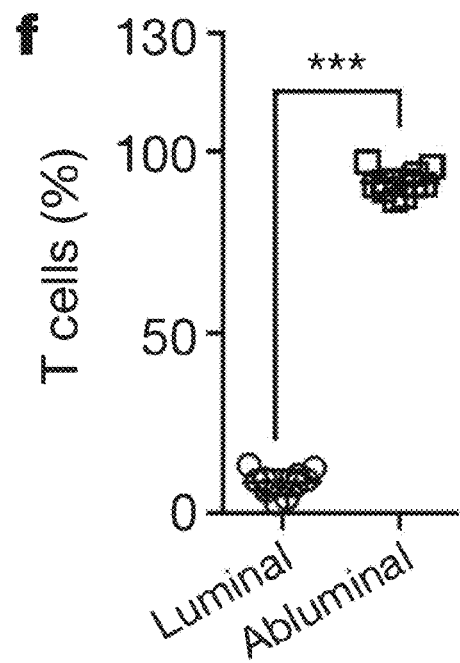
Figure 1G:
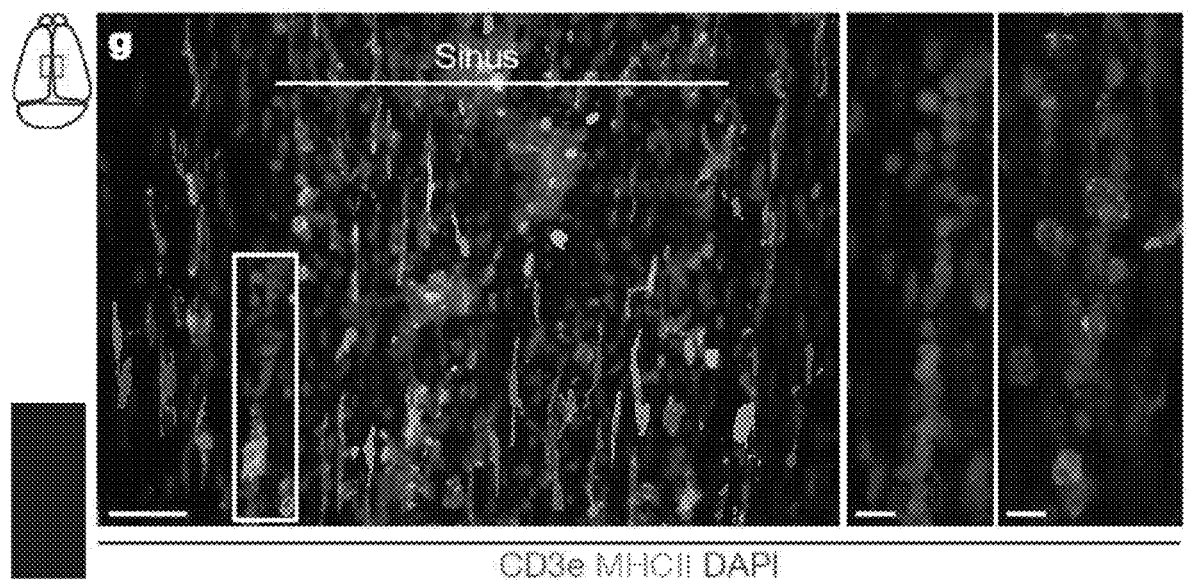
Figure 1H:
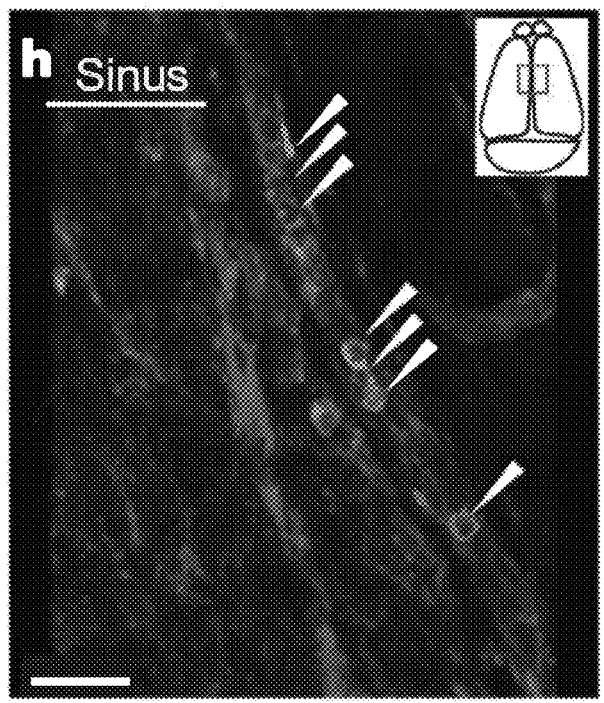
Figure 1I:
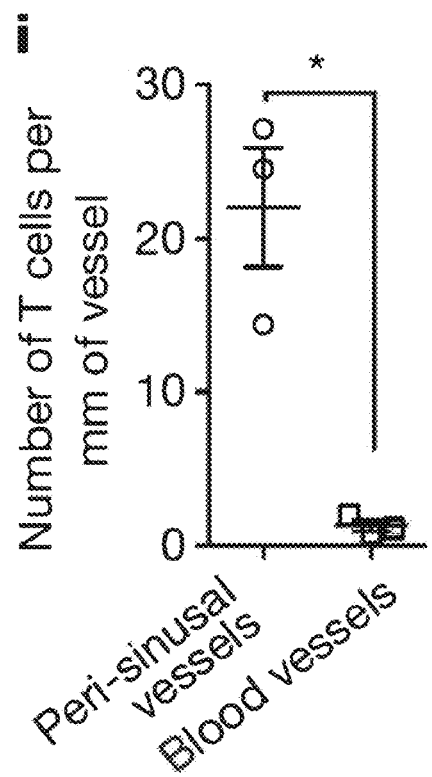
Figure 1J:
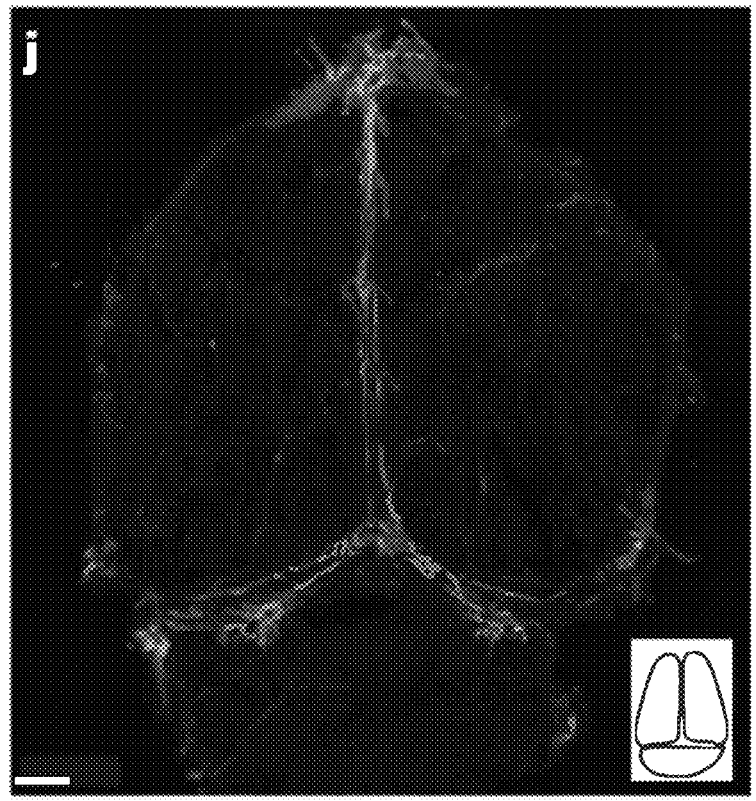
Figure 1K:
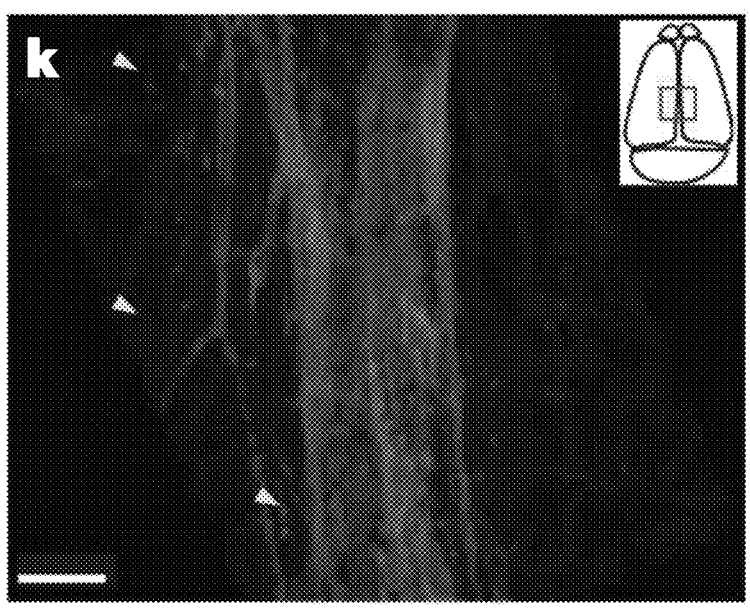
Figure 1L:
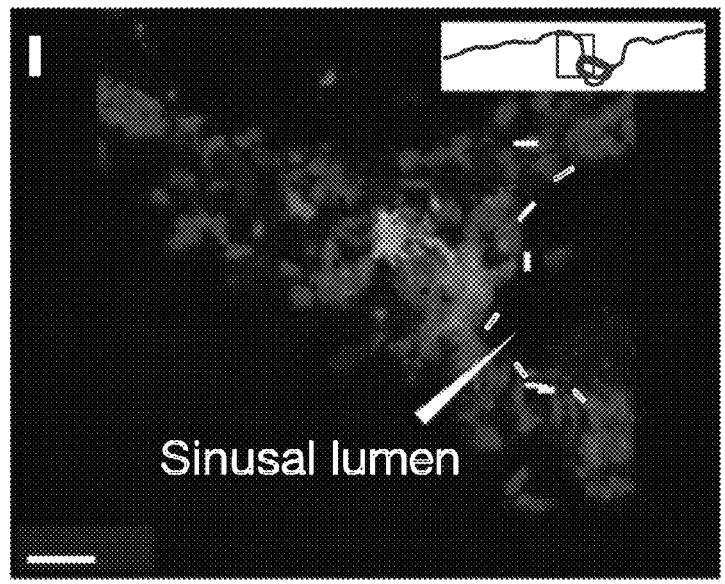
Figure 1M:
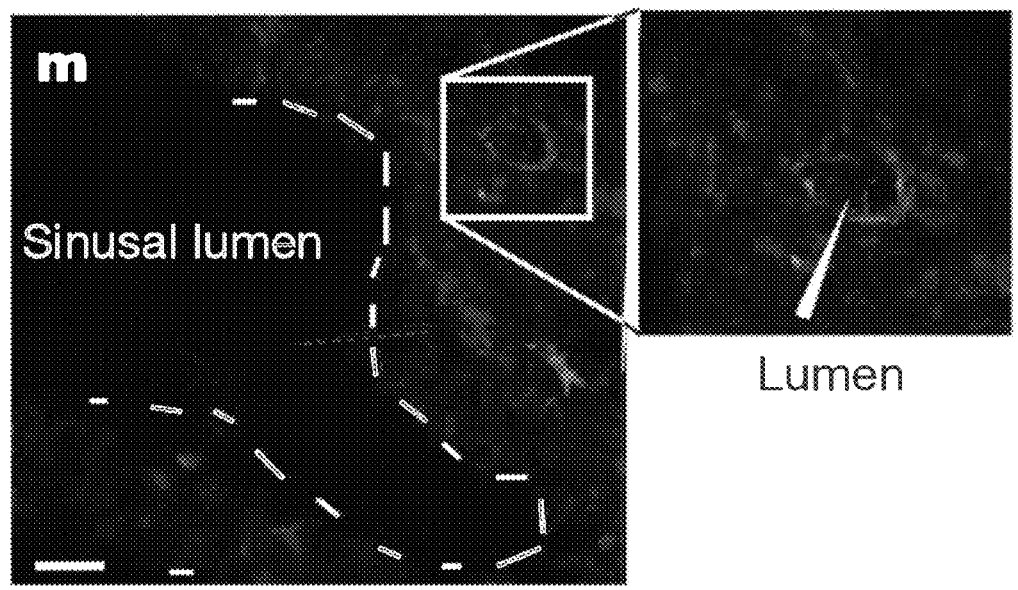

Traditionally, the central nervous system was viewed as being immune privileged, and was believed to lack a classical lymphatic drainage system. As described herein, a lymphatic system is present in meningeal spaces, and functions in draining macromolecules, immune cells, and debris from the central nervous system (CNS). Moreover, it has been discovered herein that modulating drainage by the meningeal lymphatic drainage can affect certain diseases of the brain and central nervous system, but the effect of a given modulation is dependent on the particular disease (e.g., experiments described herein show that reducing meningeal lymphatic drainage can ameliorate some neurological diseases, while exacerbating others). In particular, as described in several embodiments herein, reducing drainage by meningeal lymphatic vessels can reduce the flow in fluids of the CNS such as, cerebral spinal fluid (CSF) and interstitial fluid (ISF), and can exacerbate symptoms of neurodegenerative diseases characterized by increases in concentration and/or accumulations of molecules in the central nervous system, for example, Alzheimer's disease (AD). Modulating lymphatic vessels to increase flow in accordance with some embodiments herein can alleviate symptoms of AD, including cognitive symptoms, and accumulation of amyloid-beta plaques. On the other hand, inhibiting immune cell migration through meningeal lymphatic vessels can ameliorate physiological and motor symptoms of inflammatory neurological diseases such as multiple sclerosis (MS). Accordingly, in some embodiments, methods, compositions, and uses for treating, preventing, inhibiting, or ameliorating symptoms of neurodegenerative diseases associated with increased concentration and/or the accumulation of macromolecules, cells, and debris in the CNS (for example, AD, which is associated with the accumulation of amyloid-beta plaques) are described. The methods, compositions, and uses can increase drainage by lymphatic vessel, and thus increase flow in CSF and ISF. In some embodiments, methods, compositions, and uses for treating, preventing, inhibiting, or ameliorating symptoms of inflammatory neurological diseases such as MS are described. The methods, compositions, and uses can reduce and/or inhibit immune cell migration through lymphatic vessels. Several embodiments herein are particularly advantageous because they include one, several or all of the following benefits: (i) increased flow in the CNS; (ii) decreased accumulation of macromolecules, cells, or debris in the CNS (for example, decreased accumulation of amyloid-beta); (iii) maintenance of or improvement in cognitive function (for example memory function) in a subject suffering from, suspected of having, and/or at risk for dementia (such as in a neurodegenerative disease such as AD); (iv) decreased migration of activated immune cells (for example T cells) in the CNS; (v) decreased inflammation in the CNS; (iv) decreased immune-modulated destruction of myelinating cells such as oligodendrocytes; and/or (vii) maintenance of or improvement in motorneuron function in a subject suffering from, suspected of having, and/or at risk for an inflammatory neurological disease such as MS.

Flow and Flow Modulators

As used herein "flow" shall be given its ordinary meaning and shall also refer to a rate of perfusion through an area of the central nervous system of a subject. Flow in some embodiments, can be measured as a rate at which a label or tracer in CSF perfuses through a particular area of the central nervous system (see, e.g., Example 1). As such, flow can be compared between two subjects or two sets of conditions by ascertaining how quickly an injected label or tracer perfuses throughout a particular area or volume of the brain and/or other portion of the CNS.

As used herein. "flow modulators" shall be given its ordinary meaning and shall also broadly refer to classes of compositions that can increase or decrease the passage of substances into and out of meningeal lymphatic vessels, and thus can modulate flow in CSF and ISF, and/or, can modulate immune cell migration within, into, and out of the meningeal lymphatic vessels.

As shown herein, increasing the passage and substances into and out of meningeal lymphatic vessels can increase flow in CSF and ISF (see Examples 4-6 and FIGS. 26-29). Without being limited by theory, it is contemplated, according to several embodiments herein, that removal of macromolecules through meningeal lymphatic vessels can keep their concentrations low in the CSF, allowing a gradient to clear macromolecules from the parenchyma. As such, the higher the rate of drainage of molecules by meningeal lymphatic vessels, the higher the rate of flow of molecules in the CNS (e.g., in CSF and ISF). Furthermore, the higher the rate of fluid flow and drainage in the CNS, the higher the rate of clearance and/or the lower the concentration of cells, macromolecules, waste, and debris form the CNS. In some embodiments, flow modulators increase the diameter of meningeal lymphatic vessels, which increases drainage, resulting in increased flow in the CSF and ISF. In some embodiments, flow modulators increase the number of meningeal lymphatic vessels, thus increasing net drainage, resulting in increased flow in the CSF and ISF. Examples of suitable flow modulators for increasing flow (for example by increasing meningeal lymphatic vessel diameter) in accordance with various embodiments herein include, but are not limited to, VEGFR3 agonists, for example VEGF-c and VEGF-d, and Fibroblast Growth Factor 2 (FGF2), and functional fragments, variants, analogs, and mimetics of these molecules.

On the other hand, reducing the size, diameter, accessibility, or quantity of meningeal lymphatic vessels can reduce migration of immune cells through the meningeal lymphatic vessels (see Example 2 and FIG. 24). Without being limited by theory, it is contemplated that, according to several embodiments herein, limiting access to meningeal lymphatic vessels by immune cells (for example by ligating, blocking, reducing the diameter of, ablating, or reducing the quantity of meningeal lymphatic vessels) limits migration of immune cells into and out of the meningeal lymphatic vessels, and thus limits their migration from one area to another. For example, migration of immune cells from the brain to or from the deep cervical lymph nodes via the meningeal lymphatic vessels can be restricted. As such, entry and/or exit of immune cells to or from the meningeal lymphatic vessels can be blocked by flow modulators that decrease the diameter, size, quantity or function of meningeal lymphatic vessels, or by surgical procedures that minimize, limit access to, or ablate meningeal lymphatic vessels. Examples of suitable flow modulators for limiting access, size (e.g. decreasing diameter), quantity, function, or diameter of meningeal lymphatic vessels (and thus decreasing flow and drainage) in accordance with various embodiments herein include, but are not limited to, VEGFR3 antagonists, as well as compositions for ablating and inhibiting meningeal lymphatic vessels, for example visudyne. Furthermore, in accordance with some embodiments herein, mechanically ablating or neutralizing meningeal lymphatic vessels, for example via ligation surgery, can reduce flow and/or migration by immune cells into and/or out of the meningeal lymphatic vessels.

In methods, uses, or compositions of some embodiments, a flow modulator (e.g., VEGFR3 agonists, VEGFR3 antagonists, or FGF) comprises or consists essentially of a polypeptide or protein that comprises a modification, for example a glycosylation. PEGylation, or the like.

In some embodiments, a composition or composition for use in accordance with methods and uses described herein comprises or consists essentially of one or more flow modulators (e.g., VEGFR3 agonists, VEGFR3 antagonists, FGF, or visudyne), and a pharmaceutically acceptable diluent or carrier. Examples of suitable pharmaceutically acceptable carriers and formulations are described in "Remington: The Science and Practice of Pharmacy" 22nd Revised Edition. Pharmaceutical Press, Philadelphia, 2012, which is hereby incorporated by reference in its entirety. In some embodiments, the composition comprises or consists essentially of a unit dose of a flow modulator effective for increasing flow of CNS fluids, increasing clearance of molecules in the CNS, reducing a quantity of accumulated amyloid-beta plaques, reducing immune cell migration, or reducing inflammation in accordance with methods or uses as described herein. In some embodiments, the composition comprises, or consists essentially of a single unit dose of flow modulator effective for increasing flow, increasing clearance reducing accumulate amyloid-beta plaques, reducing immune cell migration, or reducing inflammation. In some embodiments, the effective amount of flow modulator is about 0.00015 mg/kg to about 1.5 mg/kg (including any other amount or range contemplated as a therapeutically effective amount of a compound as disclosed herein), is less than about 1.5 mg/kg (including any other range contemplated as a therapeutically effective amount of a compound as disclosed herein), or is greater than 0.00015 mg/kg (including any other range contemplated as a therapeutically effective amount of a compound as disclosed herein).

VEGFR3 Agonists

VEGFR3, also known as FLT4, is a receptor tyrosine kinase, and its signaling pathway has been implicated in embryonic vascular development, and adult lymphangiogenesis. Upon binding of ligand, VEGFR3 dimerizes, and is activated through autophosphorylation. It is shown herein that VEGFR3 agonists are a class of flow modulators that increase the diameter of meningeal lymphatic vessels, and which increase drainage and the flow of CSF and ISF in accordance with some embodiments herein (see Examples 4-6, FIGS. 26, 27A-D, 28A, 28C). As such, VEGFR3 agonists are suitable for methods, compositions, and uses for treating, ameliorating, reducing the symptoms of, or preventing neurodegenerative diseases associated with accumulation of molecules in the brain, for example AD, in accordance with some embodiments herein. Accordingly, in some embodiments, such as methods or compositions for which increased drainage and flow are desired, a flow modulator comprises, consists of, or consists essentially of a VEGFR3 agonist.

An effective amount of VEGFR3 agonist in accordance with methods, compositions, and uses herein can be understood in terms of its ability to increase meningeal vessel diameter, by its ability to increase flow of CSF or ISF, or by its ability to treat, ameliorate, or prevent, by its ability to increase clearance of substances from the CNS, symptoms of a neurodegenerative disease such as AD, for example quantities of beta-amyloid plaques or measurements of cognitive function. Accordingly, in compositions, methods, and uses of some embodiments, an effective amount of VEGFR3 agonist increases meningeal vessel diameter by at least about 2%, for example, at least about 2%, 3%, 4%, 5%, 6%, 7%, 8%, 9%, 10%, 15%, 20%, 25%, 30%, 35%, 40%, 45%, 50%, 55%, 60%, 65%, 70%, or 75%, including ranges between any two of the listed values. In compositions, methods, and uses of some embodiments, an effective amount of VEGFR3 agonist increases flow of the CSF or ISF by at least about 2%, for example, at least about 2%, 3%, 4%, 5%, 6%, 7%, 8%, 9%, 10%, 15%, 20%, 25%, 30%, 35%, 40%, 45%, 50%, 55%, 60%, 65%, 70%, or 75%, including ranges between any two of the listed values.

Example VEGFR3 agonists suitable for methods, uses, and compositions in accordance with some embodiments herein include the polypeptides VEGF-c and VEGF-d, the amino acid sequences of which are shown in Table 1, below, as well as variants and analogs of VEGF-c and/or VEGF-d. By way of example, VEGF-c, in accordance with some embodiments herein has been demonstrated to increase the diameters of meningeal lymphatic vessels, and to increase drainage, CSF and ISF flow, and clearance in the CNS. See Example 4. In some embodiments, a VEGFR3 agonist comprises, consists of, or consists essentially of VEGF-c. In some embodiments, a VEGFR3 agonist comprises, consists of, or consists essentially of VEGF-d. In some embodiments, VEGF-c and VEGF-d together agonize VEGFR3, and can be provided in a single composition, or in separate compositions. In some embodiments, a VEGFR3 agonist comprises, consists or, or consists essentially of an analog, variant, or functional fragment, such as a mutant, ortholog, fragment, or truncation of VEGF-c or VEGF-d, for example a polypeptide comprising, or consisting essentially of an amino acid sequence having at least about 80% identity to SEQ ID NO: 1 or 2, for example at least about 80%, 85%, 90%, 95%, 97%, 98%, or 99% identity, including ranges between any two of the listed values.

As shown in Examples 5, 6, and 11, exogenous nucleotides encoding a VEGFR3 agonist, such as VEGF-c, can also be suitable for methods, uses, and compositions in accordance with some embodiments herein. Accordingly, in some embodiments, a nucleotide encoding VEGF-c or VEGF-d as describe herein is expressed in a subject in order to administer the VEGFR3 agonist to a subject. For example, an exogenous vector such as a retroviral, lentiviral, adenoviral, or adeno-associated viral vector comprising or consisting essentially of a nucleic acid encoding a VEGFR agonist as described here can be inserted into a host nucleic acid of the subject (for example in the genome of a somatic cell of the subject). In some embodiments, the vector further comprises transcriptional machinery to facilitate the transcription of the nucleic acid encoding the VEGFR agonist, for example, a core promoter, transcriptional enhancer elements, insulator elements (to insulate from repressive chromatin environments), and the like.

TABLE 1

Example VEGFR3 agonists

| Agonist | UniProt Accession | SEQ ID NO: |
| --- | --- | --- |
| VEGF-c | P49769 | 1 |
| VEGF-d | O43915 | 2 |

In methods or compositions of some embodiments, the VEGFR3 agonist comprises a modification, for example a glycosylation, PEGylation, or the like. In some embodiments, a composition for use in accordance with the methods described herein comprises the VEGFR3 agonist (e.g. VEGF-c and/or VEGF-d), and a pharmaceutically acceptable diluent or carrier.

VEGFR Antagonists

While VEGFR3 agonists have been shown to increase flow and drainage by meningeal lymphatic vessels, VEGFR3 antagonists in accordance with some embodiments herein are contemplated to have the opposite effect, altering meningeal lymphatic vessel structure and/or quantity to reduce the passage of substances in and out of meningeal lymphatic vessels of the subject. Accordingly, in some embodiments, for example when a decrease in migration of immune cells through meningeal lymphatic vessels is desired, a flow modulator comprises, consists of, or consists essentially of a VEGFR3 antagonist. For example, in methods or compositions for treating, ameliorating, preventing, or reducing symptoms of a neuroimmunological disease. e.g. MS, in some embodiments, the flow modulator can comprise or consist of, or consist essentially of a VEGFR antagonist.

In some embodiments, a VEGFR3 antagonist includes an antibody specific for VEGFR3 or VEGF-c or VEGF-d. For example, the antibody can comprise or consist essentially of a monoclonal antibody that binds specifically to VEGFR3 or VEGF-c or VEGF-d. By way of example, antibodies can be generated against VEGFR3 or VEGF-c or VEGF-d in a host organism, such as a rodent, clones can be produced using hybridoma technology, and screens can be performed to identify hybridomas that produce monoclonal antibodies with suitable binding to VEGFR3 or VEGF-c or VEGF-d. Optionally, a particular monoclonal antibody against VEGFR3 or VEGF-c or VEGF-d be further screened for variants which desired properties, for example higher affinity to VEGFR3 or VEGF-c or VEGF-d. Such a screen can be performed using techniques known to the skilled artisan, for example randomly mutating nucleic acid sequences encoding hypervariable regions of the antibody, and using phage display technology to screen for high affinity variants. In some embodiments, the VEGFR3 or VEGF-c or VEGF-d antibody comprises or consists essentially of a chimeric, humanized, or fully human antibody. In some embodiments, the VEGFR3 or VEGF-c or VEGF-d antibody binds specifically to an extracellular domain of VEGFR3 or VEGF-c or VEGF-d. An example polypeptide sequence of human VEGFR3 is available as Uniprot Accession No. P35916, and is provided herein as SEQ ID NO: 3. An example polypeptide sequence of human VEGF-c is available as Uniprot Accession No. P49769, and is provided herein as SEQ ID NO: 1. An example polypeptide sequence of human VEGF-d is available as Uniprot Accession No. 043915, and is provided herein as SEQ ID NO: 2.

In some embodiments, molecules that functionally have the same or similar effects as a VEGFR3 antagonist can be used instead of a VEGFR3 antagonist, even if these molecules do not directly interact with VEGFR3. For example, molecules that neutralize VEGFR ligands such as VEGF-c and/or VEGF-d can reduce VEGFR3 signaling. Accordingly, in methods, compositions, and uses of some embodiments, an antibody specific for VEGF-c or VEGF-d can be used in the place of a VEGFR3 antagonist.

In some embodiments, a decoy molecule functions to inhibit VEGFR3 signaling, and can be a VEGFR3 antagonist in accordance with methods, compositions, and uses herein. In some embodiments, an inactive VEGFR3 fragment or mutant can be used to reduce or inhibit VEGFR3 signaling. For example, a shorter secreted isoform of VEGFR3, "isoform 3" (SEQ ID NO: 4) has been shown to inhibit VEGFR3 signaling by binding to VEGFR3 agonists like VEGF-c and VEGF-d, thus reducing the amount of ligand available to activate functional VEGFR3.

FGF2

In some embodiments, the flow modulator comprises or consists essentially of Fibroblast Growth Factor 2 (FGF2). Without being limited by theory, it is contemplated that FGF2 can increase drainage (and flow) of CSF or ISF in meningeal lymphatic vessel, for example by increasing the diameter of meningeal lymphatic vessel. An example of a suitable FGF2 amino acid sequence in accordance with some embodiments is provided as Unitprot Accession No. P09038 (human FGF2) (SEQ ID NO: 5).

Visudyne

Visudyne is a substance which can accumulate in meningeal lymphatic vessels, and, upon activation with 689 nm non-thermal red light, can release oxygen species, ablating or destroying meningeal lymphatic vessels. Accordingly, Visudyne can be suitable as a flow modulator in accordance with some embodiments herein as an inhibitor of meningeal lymphatic vessels, which in turn reduces or inhibits passage of substances such as immune cells through meningeal lymphatic vessels, and/or flow. In some embodiments, the flow modulator comprises or consists essentially of visudyne.

Routes of Administration

Flow modulators in accordance with methods, compositions for use, or uses of embodiments herein can be administered to a subject using any of a number of suitable routes of administration, provided that the route of administration administers the flow modulator to the meningeal space of a subject. It is noted that many compounds do not readily cross the blood-brain barrier, and as such, some routes of administration such as intravenous will not necessarily deliver the flow modulator to the meningeal space (unless the flow modulator can readily cross the blood-brain barrier). By "administering to the meningeal space of a subject," as used herein (including variations of this root term), it is not necessarily required that a flow modulator be administered directly to the meningeal space, but rather, this term encompasses administering a flow modulator directly and/or indirectly to the meningeal space. It is contemplated that administering the flow modulator so that it is in fluid communication with the meningeal space of the subject in accordance with some embodiments herein (typically by administering the flow modulator on the "brain" side of the blood-brain barrier), the flow modulator will be administered to the meningeal space. Accordingly, in some embodiments, the flow modulator is not administered systemically. In some embodiments, the flow modulator is not administered systemically, but rather is administered to a fluid, tissue, or organ in fluid communication with the meningeal space, and on the brain side of the blood-brain barrier. In some embodiments, the flow modulator is not administered systemically, but rather is administered to the CNS. In some embodiments, the flow modulator is administered to the CNS, but is not administered to any organ or tissue outside of the CNS. In some embodiments, the flow modulator is not administered to the blood. In some embodiments, the flow modulator is not administered to a tumor, or to the vasculature of a tumor.

In some embodiments, the flow modulator is administered nasally. For example, the flow modulator can be provided in a nasal spray, or can be contacted directly with a nasal mucous membrane.

In some embodiments, the flow modulator is administered through contacting with CSF of the subject. For example, the flow modulator can be directly injected into CSF of a patient (for example into a ventricle of the brain). Suitable apparatuses for injection can include a syringe, or a pump that is inserted or implanted in the subject and in fluid communication with CSF. In some embodiments, a composition comprising or consisting essentially of the flow modulator, for example a slow-release gel, is implanted in a subject so that it is in fluid communication with CSF of the subject, and thus contacts the CSF.

In some embodiments, the flow modulator is administered transcranially. For example, a composition comprising or consisting essentially of the flow modulator such as a gel can be placed on an outer portion of the subject's skull, and can pass through the subject's skull. In some embodiments, the flow modulator is contacted with a thinned portion of the subject's skull to facilitate transcranial delivery.

In some embodiments, the flow modulator is administered by expressing a nucleic acid encoding the flow modulator in the subject. A vector comprising or consisting essentially of the nucleic acid, for example a viral vector such as a retroviral vector, lentiviral vector, or adenoviral vector, or adeno-associated viral vector (AAV) can be administered to a subject as described herein, for example via injection or inhalation. In some embodiments, expression of the nucleic acid is induced in the subject, for example via a drug or optical regulator of transcription.

In some embodiments, the flow modulator (e.g. the VEGFR3 agonist, FGF2, or VEGFR3 antagonist) is administered selectively to the meningeal space of the subject, or is for use in administration selectively to the meningeal space of the subject. As used herein administered "selectively" and variations of the root term indicate that the flow modulator is administered preferentially to the indicated target (e.g. meningeal space) compared to other tissues or organs on the same side of the blood brain barrier. As such, direct injection to meningeal spaces of the brain would represent "selective" administration, whereas administration to CSF in general via a spinal injection would not. In some embodiments, the flow modulator is administered selectively to the meningeal space, and not to portions of the CNS outside of the meningeal space, nor to any tissues or organs outside of the CNS. In some embodiments, the flow modulator is administered selectively to the CNS, and not to tissue or organs outside of the CNS such as the peripheral nervous system, muscles, the gastrointestinal system, musculature, or vasculature.

For any of the routes of administration listed herein in accordance with methods, uses, and compositions herein, it is contemplated that a flow modulator can be administered in a single administration, or in two or more administrations, which can be separated by a period of time. For example, in some embodiments, the flow modulator as described herein can be administered via a route of administration as described herein hourly, daily, every other day, every three days, every four days, every five days, every six days, weekly, biweekly, monthly, bimonthly, and the like. In some embodiments, the flow administration is administered in a single administration, but not in any additional administrations.

Some embodiments include methods of making a composition or medicament comprising or consisting essentially of a flow modulator as described herein suitable for administration according to a route of administration as described herein. For example, in some embodiments, a composition comprising or consisting essentially of a VEGFR3 agonist is prepared for nasal administration, administration to the CSF, or transcranial administration. For example, in some embodiments, a composition comprising or consisting essentially of a VEGFR3 antagonist is prepared for nasal administration, administration by contacting with CSF, or transcranial administration.

Neurodegenerative Diseases

Methods, uses, and compositions in accordance with some embodiments herein can be useful for treating, preventing, inhibiting, ameliorating, or reducing the symptoms of one or more neurodegenerative diseases, or compositions for use in these methods. These diseases can occur in subjects, for example humans, as well as non-human animals, such as non-human mammals, and non-human primates in particular.

In some embodiments, neurodegenerative, neurodevelopmental, neuroinflammatory, or neuropsychiatric diseases associated with accumulation of macromolecules, cells, and debris in the CNS are treated, prevented, inhibited, or reduced by methods, uses, or compositions that increase flow, drainage, and/or clearance in meningeal lymphatic vessels. In some embodiments, neurodegenerative diseases associated with accumulation of macromolecules, cells, and debris in the CNS are treated, prevented, inhibited, or reduced. Examples of neurodegenerative diseases include Alzheimer's disease (AD), dementia, Parkinson's disease, cerebral edema, amyotrophic lateral sclerosis (ALS), Pediatric Autoimmune Neuropsychiatric Disorders Associated with Streptococcal Infections (PANDAS), meningitis, hemorrhagic stroke, autism spectrum disorder (ASD), brain tumor, and epilepsy.

In some embodiments, the neurodegenerative disease can be prevented, treated, or ameliorated prophylactically. Accordingly, a subject having one or more risk factors for the neurodegenerative disease can be determined to be in need of receiving a method, use, or composition described herein. For example, a subject may have accumulated amyloid-beta plaques in their CNS, and may benefit from increased flow, increased drainage, increased clearance and/or reduction of amyloid-beta plaques, even if they do not yet have an AD diagnosis based on cognitive symptoms.

A number of risk factors for AD are suitable as risk factors in accordance with methods, compositions, and uses of some embodiments herein, for example familial AD, a genetic marker for AD, or a symptom of AD such as early dementia. The foremost risk factor for sporadic AD is age. However, increased risk of this form of AD has also been attributed to diverse genetic abnormalities. One of them is diploidy for apolipoprotein-Eε4 (Apo-Eε4), widely viewed as a major genetic risk factor promoting both early onset of amyloid-beta aggregation and defective amyloid-beta clearance from the brain (Deane et al., 2008; Zlokovic, 2013). Other genetic variants that significantly increase the risk for sporadic AD are Apo-J (or clusterin), phosphatidylinositol-binding clathrin assembly protein (PICALM), complement receptor 1 (CR1), CD33 or Siglec-3, and triggering receptor expressed on myeloid cells 2 (TREM2). All of these proteins, interestingly, have been implicated in different mechanisms of amyloid-beta removal from the brain (Bertram et al., 2008; Guerreiro et al., 2013; Harold et al., 2009; Lambert et al., 2009, 2013; Naj et al., 2011). In some embodiments, the risk factor for AD is selected from the group consisting of at least one of the following: diploidy for apolipoprotein-E-epsilon-4 (apo-E-epsilon-4), a variant in apo-J, a variant in phosphatidylinositol-binding clathrin assembly protein (PICALM), a variant in complement receptor 1 (CR3), a variant in CD33 (Siglee-3), or a variant in triggering receptor expressed on myeloid cells 2 (TREM2), age, or a symptom of dementia.

Inflammatory Neurological Diseases

Methods, uses, and compositions in accordance with some embodiments herein can be useful for treating, preventing, inhibiting, ameliorating, or reducing the symptoms of one or more inflammatory neurological diseases including but not limited to, demyelinating diseases of the central nervous system and multiple sclerosis (MS). These diseases can occur in subjects, for example humans, as well as non-human animals, such as non-human mammals, and non-human primates in particular. Without being limited by theory, it is contemplated, according to several embodiments herein, that meningeal lymphatic vessels function in regulation of tissue immune surveillance in addition to removing macromolecules, and debris. As shown herein, immune cells are found in, and pass through the meningeal lymphatic vessels. Examples 14-22. Moreover, it is shown herein that inflammatory symptoms and clinical (neuromotor) symptoms in EAE (experimental autoimmune encephalomyelitis), and inflammation-mediated model of MS, are ameliorated by inhibiting immune cell migration through meningeal lymphatic vessels. In some embodiments, methods, uses, or compositions are for treating a subject suffering from, suspected of having, or at risk for an inflammatory neurological disease. In some embodiments, methods, uses, or compositions are for treating a subject suffering from, suspected of having, or at risk for an inflammatory neurological disease who does not have cancer. In some embodiments, methods, uses, or compositions are for treating a subject suffering from, suspected of having, or at risk for an inflammatory neurological disease who does not have a tumor. In some embodiments, methods, uses, or compositions are for treating a subject suffering from, suspected of having, or at risk for an inflammatory neurological disease who does not have a disease characterized by increased angiogenesis such as, for example, a cancer or tumor.

In some embodiments, inflammatory neurological diseases are treated, prevented, inhibited, or reduced by methods, uses, or compositions that reduce, inhibit, or prevent migration of immune cells through meningeal lymphatic vessels. Examples of such diseases include inflammatory diseases, in which the activation and proliferation of immune cells such as T cells into to the CNS is facilitated by migration of these cells meningeal lymphatic vessels. Such diseases include inflammatory diseases in the central nervous system, for example demyelinating diseases such as MS. As noted above, in some embodiments, the inflammatory disease (such as MS) can be prevented, treated, or ameliorated prophylactically, and as such, a subject having risk factors for MS can be determined to be in need of receiving a method, use, or composition described herein. For example, a subject may have T cell infiltration in their CNS, and may benefit from decreasing the migration of immune cells through meningeal lymphatic vessels, for example by decreasing access to, diameter of, and/or quantity of meningeal lymphatic vessels, even if they do not yet have any large-scale demyelination, substantial motor impairment symptoms, or a classical MS diagnosis. A number of risk factors for MS are suitable as risk factors in accordance with some embodiments herein, for example familial MS, a genetic marker for MS, demyelination, a reduction in oligodendrocytes, infection, advanced age, or a symptom of MS such as loss of motor neuron function.

Methods, Compositions, or Uses for Increasing Flow

Some aspects include methods of, compositions for use, or uses for increasing flow in fluid in the central nervous system of a subject, or compositions for use in these methods. The methods or uses can include determining whether the subject is in need of increased fluid flow in the central nervous system. If the subject is in need of increased fluid flow, the method or use can include administering an effective amount of VEGFR3 agonist to a meningeal space of the subject. Without being limited by theory, the amount of VEGFR3 agonist can increase flow for example, by increasing the diameter of a meningeal lymphatic vessel of the subject, by increasing the quantity of meningeal lymphatic vessels of the subject, and/or by increasing drainage through meningeal lymphatic vessels of the subject. Thus, fluid flow in the central nervous system of the subject can be increased. In some embodiments, the fluid comprises cerebral spinal fluid (CSF), interstitial fluid (ISF), or both. In some embodiments, the VEGFR3 agonist comprises VEGF-c or VEGF-d or an analog, variant, or fragment thereof. It is also contemplated that for methods and uses in some embodiments herein, FGF2 can be substituted for the indicated VEGFR3 agonist in order to increase flow, or can be used in addition to a VEGFR3 agonist in order to increase flow.

Such methods of, compositions for, or use for increasing fluid flow in the CNS can be useful for treating, preventing, or ameliorating the symptoms of neurodegenerative diseases associated with the increased concentration and/or accumulation of molecules or cells or debris in the CNS. Accordingly, in some embodiments, a subject can be determined to be in need of increased fluid flow by determining whether the subject has a neurodegenerative disease, or is at risk of developing a neurodegenerative disease. The disease can be associated with the increased concentrations and/or accumulation of molecules or cells or debris in the CNS, for example Alzheimer's Disease (AD). In some embodiments, the subject can be determined to be at risk for the disease, for example through having familial occurrence of the disease, by having one or more genetic markers associated with the disease, through advanced age, or by exhibiting symptoms of the disease, for example early dementia in the case of AD. As used herein, "advanced age" refers to an age characterized by a decrease in memory function, decrease in CSF production, substantial increases in neuronal senescence, and in the context of some embodiments, can include at least 65 years of age in a human, for example, at least 60, 65, 70, 75, 80, or 85, including ranges between any of these values. In some embodiments, determining whether the subject is in need of increased fluid flow comprises determining the subject to have a neurodegenerative disease such as AD. In some embodiments, determining whether the subject is in need of increased fluid flow comprises determining the subject to have a risk factor for the neurodegenerative disease associated with the increased concentration and/or accumulation of molecules or macromolecules or cells or debris in the CNS as described herein. In some embodiments, determining whether the subject is in need of increased fluid flow comprises determining the subject to have a risk factor, and also determining the subject to have the disease itself. In some embodiments, the neurodegenerative disease is selected from the group consisting of at least one of the following: Alzheimer's disease (AD), dementia. Parkinson's disease, cerebral edema, amyotrophic lateral sclerosis (ALS), Pediatric Autoimmune Neuropsychiatric Disorders Associated with Streptococcal Infections (PANDAS), meningitis, hemorrhagic stroke, autism spectrum disorder (ASD), brain tumor, and epilepsy. In some embodiments, the neurodegenerative disease is Alzheimer's disease. In some embodiments, the risk factor is a risk factor for Alzheimer's disease as described herein. In some embodiments, the VEGFR3 agonist and/or FGF2 is administered to the subject after determining that the subject has a risk factor for the neurodegenerative disease (even if the subject does not necessarily have the disease itself), for example for prophylactic treatment or prevention. In some embodiments, the VEGFR3 agonist and/or FGF2 is administered to the subject after determining that the subject has the neurodegenerative disease.

Without being limited by theory, it is contemplated, according to several embodiments herein, that systemic administration is not required for the VEGFR3 agonist and/or FGF2 to effectively modulate meningeal lymphatic vessel size and drainage, or flow. Accordingly, in some embodiments, the VEGFR3 agonist and/or FGF2 is administered selectively to the meningeal space of the subject. In some embodiments, the VEGFR3 agonist and/or FGF2 is administered to the meningeal space, but is not administered outside the CNS. In some the VEGFR3 agonist and/or FGF2 is administered to the meningeal space, but is not administered to the blood. In some embodiments, the VEGFR3 agonist and/or FGF2 is administered to the subject by a route selected from the group consisting of at least one of the following: nasal administration, transcranial administration, contact with cerebral spinal fluid (CSF) of the subject, pumping into CSF of the subject, implantation into the skull or brain, contacting a thinned skull or skull portion of the subject with the VEGFR3 agonist and/or FGF2, or expression in the subject of a nucleic acid encoding the VEGFR3 agonist and/or FGF2, or a combination of any of the listed routes. In some embodiments, it is the VEGFR3 agonist that is administered. In some embodiments, the VEGFR3 agonist is selected from the group consisting of at least one of the following: VEGF-c, VEGF-d, or an analog, variant, or functional fragment thereof.

Figure 30A:
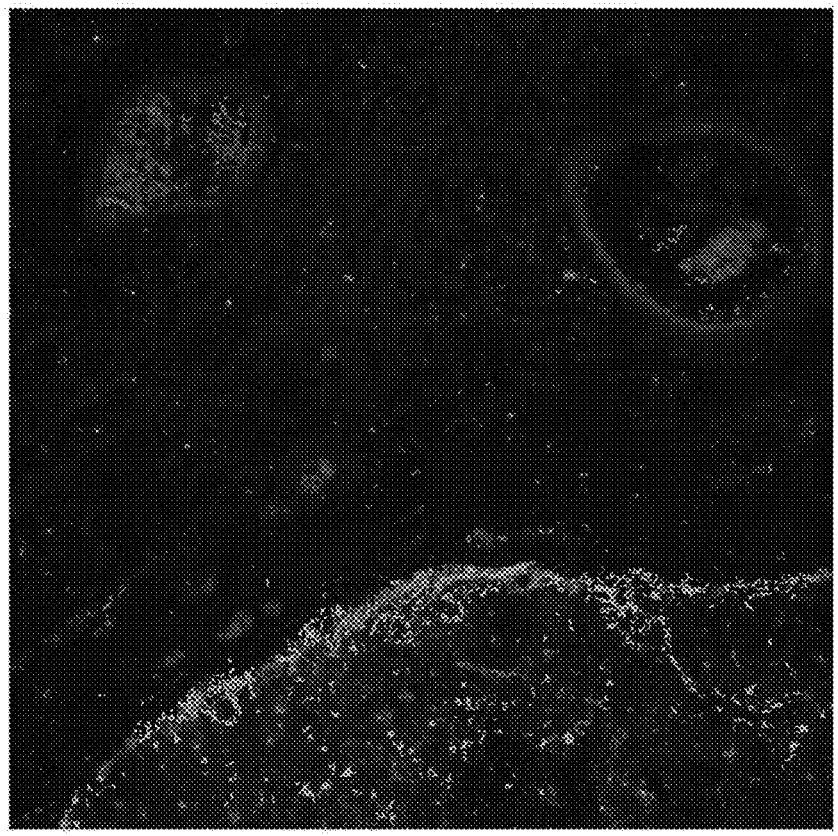
FIGS. 30A-B are a series of microscope images showing meningeal amyloid-beta deposition in models of Alzheimer's disease.
Figure 30B:
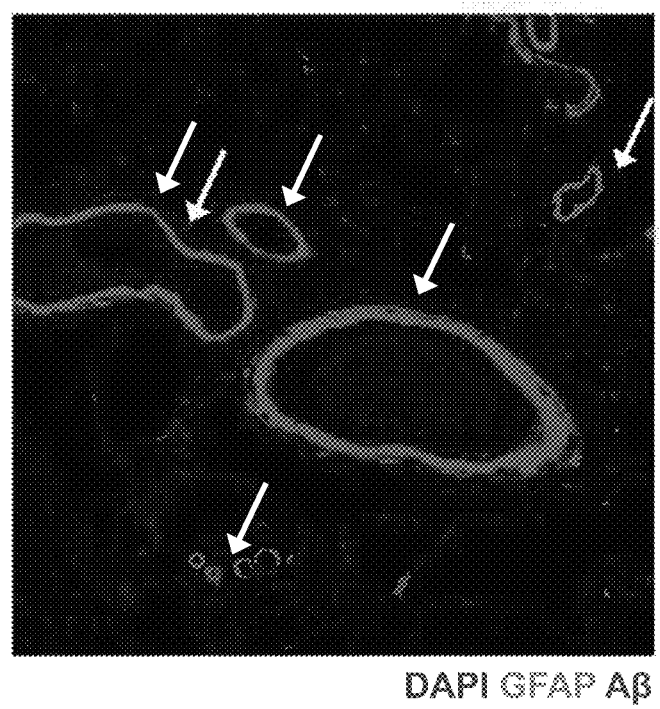

In some embodiments, the administration of the VEGFR3 agonist results in an increase in CNS fluid flow, meningeal lymphatic vessel diameter, meningeal lymphatic vessel number, meningeal lymphatic vessel drainage, or amelioration of symptoms of a neurodegenerative disease. For example, in some embodiments, the administration of the VEGFR3 agonist increases diameter of the meningeal lymphatic vessel is increased by at least about 5%, for example at least about 5%, 10%, 15%, 20%, 25%, 30%, 35%, 40%, 45% or 50%, including ranges between any two of the listed values. In some embodiments, an average diameter of a population of meningeal lymphatic vessels of the subject is increased by a value noted herein. In some embodiments, the administration of the VEGFR3 agonist increases fluid flow in the central nervous system of the subject, comprising increasing a rate of perfusion of fluid throughout an area of the subject's brain. In some embodiments, for example if the subject has AD, the administration of the VEGFR3 agonist increased the ISF flow, which in turn reduces the quantity of amyloid-beta plaques in the subject's CNS. For example, the quantity of accumulated amyloid-beta plaques can be reduced by at least 2%, for example, at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%, including ranges between any two of the listed values. It is shown herein that some brains of humans with AD have structures resembling amyloid-beta plaques in the meninges (see FIG. 30B). Accordingly, in some embodiments, at least some of the accumulated amyloid-beta plaques are in the meninges of the subject's brain. In some embodiments, increasing the fluid flow increases clearance of soluble molecules in the brain of the subject. Clearance of soluble molecules can be ascertained, for example, by monitoring the retention of a particular compound, molecule, or label over an area of the brain over a particular period of time. In some embodiments, increasing the fluid flow increases clearance of soluble molecules in the brain of the subject by at least 2%, for example, at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%, including ranges between any two of the listed values.

Methods, Compositions, and Uses for Reducing Amyloid-Beta Plaques

Some aspects include methods, compositions for use, and uses for reducing a quantity of accumulated amyloid-beta plaques, or decreasing the rate of accumulation of amyloid-beta plaques, in a subject having a neurodegenerative disease or a risk factor for such a disease, or compositions for use in such methods. The methods or uses can include determining the subject to have the neurodegenerative disease or the risk factor. The methods or uses can include administering a VEGFR3 agonist and/or FGF2 to a meningeal space of the subject, so that fluid flow (e.g., flow of ISF, CSF, or both) in the central nervous system of the subject is increased. Through increased fluid flow, the quantity of accumulated amyloid-beta plaques in the subject can be reduced, or the rate of accumulation can be reduced. In some embodiments, at least some of the accumulated amyloid-beta plaques are in the meninges of the subject's brain. In some embodiments, the quantity of accumulated amyloid-beta plaques, or the rate of accumulation, is reduced by at least 2%, for example, at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% including ranges between any two of the listed values. In some embodiments, the VEGR3 agonist and/or FGF2 is administered selectively to the meningeal space. In some embodiments, the VEGR3 agonist and/or FGF2 is administered to the CNS, but not outside the CNS. In some embodiments, the VEGR3 agonist and/or FGF2 is administered to the CNS, but not blood. In some embodiments, the VEGFR3 agonist is selected from the group consisting of at least one of the following: VEGF-c, VEGF-d, or an analog, variant, or functional fragment thereof.

In some embodiments, administering the VEGFR3 agonist and/or FGF2 increases the diameter of a meningeal lymphatic vessel of the subject's brain by at least 2%, for example at least 2%, 3%, 4%, 5%, 6%, 7%, 8%, 9%, 10%, 15%, 20%, 25%, 30%, 35%, 40%, 45%, or 50%, including ranges between any two of the listed values, thus increasing flow in ISF. As noted herein, increased fluid flow in the central nervous system of the subject comprises an increased rate of perfusion of fluid throughout an area of the subject's brain.

In some embodiments, the subject is known to have the neurodegenerative disease, for example AD, dementia. Parkinson's disease, cerebral edema, amyotrophic lateral sclerosis (ALS), Pediatric Autoimmune Neuropsychiatric Disorders Associated with Streptococcal Infections (PANDAS), meningitis, hemorrhagic stroke, autism spectrum disorder (ASD), brain tumor, or epilepsy. In some embodiments, the method further includes determining that the subject has the neurodegenerative disease. In some embodiments, for example if the method or use is prophylactic, the method included determining whether the subject has the risk factor for the neurodegenerative disease, even if the subject does not necessarily have a diagnosis for the disease itself. For example, risk factors for AD that are useful in accordance with methods, compositions, and uses of some embodiments herein include diploidy for apolipoprotein-E-epsilon-4 (apo-E-epsilon-4), a variant in apo-J, a variant in phosphatidylinositol-binding clathrin assembly protein (PICALM), a variant in complement receptor 1 (CR3), a variant in CD33 (Siglee-3), or a variant in triggering receptor expressed on myeloid cells 2 (TREM2), familial AD, advanced age, or a symptom of dementia.

Methods, Compositions, and Uses of Increasing Clearance of Molecules from the CNS Some aspects include a method, use, or composition for use in increasing clearance of molecules from the central nervous system of a subject. The method or use can comprise administering a composition comprising, consisting of, or consisting essentially of a flow modulator (e.g., VEGFR3 agonist and/or FGF2) to a meningeal space of the subject, in which fluid flow in the central nervous system of the subject is increased. Thus, the method or use can increase the clearance of molecules from the CNS of the subject. Increased clearance of molecules from the CNS of the subject can comprise an increased rate of movement of molecules from the CSF to deep cervical lymph nodes, and thus can be ascertained by monitoring the rate of movement of molecules and/or labels in the CNS to deep cervical lymph nodes. In some embodiments, the VEGR3 agonist and/or FGF2 is administered selectively to the meningeal space. In some embodiments, the composition comprising, consisting of, or consisting essentially of the flow modulator (e.g., VEGR3 agonist and/or FGF2) is administered to the CNS, but not outside the CNS. In some embodiments, the VEGR3 agonist is administered to the CNS, but not blood. In some embodiments, the VEGFR3 agonist is selected from the group consisting of one or more of the following: VEGF-c. VEGF-d, or an analog, variant, or functional fragment thereof.

Without being limited by theory, it is contemplated that, according to several embodiments herein, increasing flow by increasing the diameter of, increasing drainage by, and/or increasing the quantity of meningeal lymphatic vessels as described herein can increase clearance of molecules from the CNS of the subject, and thus reduces the concentration and/or accumulation of the molecules in the CNS and brain in accordance with some embodiments herein. Accordingly, in some embodiments, increasing clearance of molecules in the CNS reduces concentration and/or accumulation of the molecules in the CNS and brain. For example, if amyloid-beta plaques are present in the CNS of the subject, increasing clearance can reduce amyloid beta plaques, or decrease the rate of their accumulation. Without being limited by theory, it is contemplated that by clearing soluble amyloid beta from the CNS, a gradient will favor solubilization of amyloid beta plaques, so that fluids in the CNS continue to flow and the CNS continues to be cleared, amyloid beta plaques can diminish, or the rate of increase can be reduced. Thus, decreases of amyloid-beta plaques can represent a decrease in an etiology of a disease caused by amyloid-beta plaques, and, more generally can indicate an increase in fluid flow in the CNS, for example via drainage by meningeal lymphatic vessels. In some embodiments, a quantity of accumulated amyloid-beta plaques in the central nervous system, or the rate of accumulation thereof, is reduced by at least 2%, for example at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% including ranges between any two of the listed values In some embodiments, amyloid-beta plaques are cleared from meningeal portions of the central nervous system of the subject. In some embodiments, increased fluid flow in the central nervous system of the subject comprises an increased rate of perfusion of fluid throughout an area of the subject's brain.

As discussed herein, methods, uses, and compositions for increasing clearance of molecules from the CNS can be useful in treating, preventing, or ameliorating symptoms of neurodegenerative diseases, for example diseases associated with accumulation of macromolecules, cells, or debris in the CNS. Accordingly, in some embodiments, the method or use further includes determining the subject to have such a neurodegenerative disease, or a risk factor for such a neurodegenerative disease. Example neurodegenerative diseases include Alzheimer's disease (AD), dementia, Parkinson's disease, cerebral edema, amyotrophic lateral sclerosis (ALS). Pediatric Autoimmune Neuropsychiatric Disorders Associated with Streptococcal Infections (PANDAS), meningitis, hemorrhagic stroke, autism spectrum disorder (ASD), brain tumor, and epilepsy. As noted herein, in some embodiments, it a subject with a risk factor for a neurodegenerative disease can benefit from increased clearance of molecules from the CNS, even if the subject does not have a diagnosis. Accordingly, in some embodiments, the subject is determined to have a risk factor for the neurodegenerative disease, indicating that the subject is in need of, and/or may benefit from increased clearance of molecules from the CNS. For example, the subject can have a risk factor for AD as noted herein.

In some embodiments, for any of the methods, compositions, or uses for increasing flow, increasing clearance, increasing drainage, increasing meningeal lymphatic diameter, and/or reducing amyloid-beta plaques noted herein a VEGFR3 agonist as described herein can be administered. In some embodiments, the VEGFR3 agonist is selected from the group consisting of one or more of the following: VEGF-c, VEGF-d, or an analog, variant or functional fragment of either of these. In some embodiments, the VEGFR3 agonist and/or FGF2 is administered selectively to the meningeal space of the subject. In some embodiments, the VEGFR3 agonist and/or FGF2 is administered to the subject by a route selected from the group consisting of at least one of the following: nasal administration, transcranial administration, contact cerebral spinal fluid (CSF) of the subject, pumping into CSF of the subject, implantation into the skull or brain, contacting a thinned skull or skull portion of the subject with the VEGFR3 agonist and/or FGF2, or expression in the subject of a nucleic acid encoding the VEGFR3 agonist and/or FGF2, or a combination of any of the listed routes. In some embodiments, the VEGFR3 agonist and/or FGF2 is administered to the subject after determining the subject to have the risk factor for the neurodegenerative disease. In some embodiments, the VEGFR3 agonist and/or FGF2 is administered to the subject after determining the subject to have the neurodegenerative disease. The VEGFR3 agonist and/or FGF2 can be administered in an effective amount.

Methods, Compositions, and Uses of Decreasing Immune Cell Migration Through Meningeal Lymphatic Vessels Some aspects include methods, uses, or compositions for use in decreasing immune cell migration through meningeal lymphatic vessels in a subject, or compositions for use in such methods. As discussed herein, while some inflammatory neurological diseases (such as MS) can be ameliorated by decreasing the entry, exit, and/or migration of immune cells through the meningeal lymphatic vessels, for example migration of lymphocytes such as T cells. Accordingly, some aspects include a method or use of decreasing immune cell migration through meningeal lymphatic vessels in a subject (e.g., to or from the brain or deep cervical lymph nodes). The method or use can include administering a VEGFR3 antagonist to a meningeal space of the subject or ablating a meningeal lymphatic vessel of the subject, or a combination of these. The method or use can thus decrease immune cell migration through meningeal lymphatic vessels in the subject. In some embodiments, the VEGR3 antagonist is administered selectively to the meningeal space. In some embodiments, the VEGR3 antagonist is administered to the CNS, but not outside the CNS. In some embodiments, the VEGR3 antagonist is administered to the CNS, but not blood. In some embodiments, the VEGFR3 antagonist comprises or consists essentially of an antibody specific for VEGFR3 or VEGF-c or VEGF-d. In some embodiments, the VEGFR3 antagonist is administered to a subject who does not have a disease characterized by increased angiogenesis, for example a cancer or tumor.

In some embodiments, the VEGFR3 antagonist is administered to the meningeal space of the subject. In some embodiments, the VEGFR3 antagonist is administered selectively to a meningeal space of the subject. In some embodiments, the VEGFR3 agonist is administered to the subject by a route selected from the group consisting of at least one of the following: nasal administration, transcranial administration, contact with cerebral spinal fluid (CSF) of the subject, pumping into CSF of the subject, implantation into the skull or brain, contacting a thinned skull or skull portion of the subject with the VEGFR3 antagonist, or expression in the subject of a nucleic acid encoding the VEGFR3 antagonist, or a combination of any of the listed routes.

In some embodiments, the meningeal lymphatic vessels are selectively ablated by ligation, optical activation of visudyne in the lymphatic vessel, or both. The ligation can be performed surgically. In some embodiments, visudyne is used to selectively ablate meningeal vessels. The visudyne can administered to the subject (via a route of administration noted for flow modulators herein), and the administered visudyne can then be optically activated to selectively ablate meningeal lymphatic vessels. In some embodiments, the VEGFR3 antagonist comprises or consists essentially of an antibody specific for VEGFR3 or VEGF-c or VEGF-d.

As discussed herein, decreasing immune cell migration through meningeal lymphatic vessels can be useful for treating, preventing, or ameliorating symptoms of inflammatory neurological diseases such as MS. As shown in Example 27, ablation of meningeal lymphatic vessels in accordance with some embodiments herein attenuated clinical indicators of development of experimental autoimmune encephalomyelitis (EAE), an art-recognized model of MS, in rodents. Furthermore, ablation of meningeal lymphatic vessels in the EAE model inhibited the migration of T cells (See Example 25). Accordingly, in some embodiments, the method further includes determining the subject to have an inflammatory neurological disease or a risk factor for such a disease. Example diseases can include demyelinating diseases of the central nervous system, for example MS. In some embodiments, for example if the method is performed prophylactically, the method is performed on a subject who has a risk factor for MS, but does not necessarily have a diagnosis for MS. For example, the risk factor can include familial multiple sclerosis, suspicion that the subject has multiple sclerosis, infection, advanced age, or at least one symptom of inhibited neuromotor function.

In some embodiments, decreasing immune cell migration through the meningeal lymphatic vessel comprises a decrease in movement of from the parenchyma to deep cervical lymph nodes of the subject. In some embodiments, the cells include lymphocytes, for example T cells. In some embodiments, decreasing immune cell migration through the meningeal lymphatic vessel comprises a decrease in movement of lymphocytes from cerebral spinal fluid to deep cervical lymph nodes of the subject. In some embodiments, decreasing immune cell migration through the meningeal lymphatic vessel comprises decreasing a density of immune cells (e.g., lymphocytes) in the meningeal lymphatic vessel. For example, the density can be decreased by at least 5%, for example at least 5%, 10%, 15%, 20%, 25%, 30%, 35%, 40%, 45%, or 50%, including ranges between any of the listed values. In some embodiments, the lymphocytes comprise or consist essentially of T cells. In some embodiments, decreasing migration of immune cells through the meningeal lymphatic vessels decreases a quantity of activated T cells in the deep cervical lymph nodes that have a migratory phenotype. Activated T cells can be identified, for example, by a CD62L− CD44+ phenotype. Moreover, in some embodiments, the migratory phenotype can be identified as CD11a+, a CD49d+, or both. Additionally, in some embodiments, decreasing migration of immune cells through the meningeal lymphatic vessel decreases a quantity of in T cells in the central nervous system that produce inflammatory cytokines. Example inflammatory cytokines that can be reduced in accordance with some embodiments include IL-17, IFN-gamma, or both.

Methods, Compositions, and Uses for Reducing Inflammation in the Central Nervous System Some aspects include methods, uses, and compositions for use in reducing inflammation in the central nervous system, for example in inflammatory neurological diseases, or compositions for use in such methods. The method or use can reduce inflammation in the nervous system of a subject having an inflammatory disease of the central nervous system, or a risk factor for the inflammatory disease of the central nervous system. In some embodiments, the method or use includes administering a VEGFR3 antagonist to a meningeal space of the subject, ablating a meningeal lymphatic vessel of the subject, or a combination of the two. The VEGFR3 antagonist, ablation, or both, can decrease migration of immune cells through the meningeal lymphatic vessel in the subject, thus reducing inflammation in the central nervous system. In some embodiments, the method or use comprises ameliorating a neuromotor symptom in the subject. In some embodiments, the VEGFR3 antagonist is administered selectively to a meningeal space. In some embodiments, the VEGFR3 antagonist is administered to the CNS, but not administered outside the CNS. In some embodiments, the VEGFR3 antagonist is administered to the CNS, but not administered to blood. In some embodiments, the VEGFR3 antagonist comprises or consists essentially of an antibody specific for VEGFR3 or VEGF-c or VEGF-d, or a VEGFR3 decoy molecule. In some embodiments, the VEGFR3 antagonist is administered to a subject in need of reduced inflammation in the CNS, but who does not have a disease characterized by increased angiogenesis, such as a tumor or cancer.

In some embodiments, the inflammatory disease comprises or consists essentially of a demyelinating disease of the central nervous system, for example, MS. In some embodiments, the method is performed on a subject who has the inflammatory disease. Accordingly, in some embodiments, the method includes determining that the subject has the inflammatory disease. In some embodiments, for example if the method is performed prophylactically, the subject can have a risk factor for the inflammatory disease. Accordingly, in some embodiments, the method includes determining that the subject has the risk factor for the inflammatory disease. In some embodiments, the risk factor comprises or consists essentially of familial multiple sclerosis, infection, advanced age, suspicion that the subject has multiple sclerosis, or at least one symptom of inhibited neuromotor function.

In some embodiments, the method includes ablating meningeal lymphatic vessels chemically, surgically, or both. In some embodiments, the method includes selectively ablating meningeal lymphatic vessels by ligation, optical activation of visudyne in lymphatic vessels, or both.

In some embodiments, the method includes administering a VEGFR3 antagonist selectively to a meningeal space of the subject. Without being limited by theory, it is contemplated that the VEGFR3 antagonist can inhibit migration of immune cells through meningeal lymphatic vessels, for example by decreasing the size and/or quantity of the vessels. In some embodiments, the VEGFR3 antagonist comprises or consists essentially of an antibody specific for VEGFR3 or VEGF-c or VEGF-d. In some embodiments, the VEGFR3 antagonist comprises or consists essentially of a VEGFR3 decoy molecule.

In some embodiments, the VEGFR3 antagonist or visudyne is administered to the subject by a route selected from the group consisting of at least one of the following: nasal administration, transcranial administration, contact with cerebral spinal fluid (CSF) of the subject, pumping into CSF of the subject, implantation into the skull or brain, contacting a thinned skull or skull portion of the subject with the VEGFR3 antagonist, or a combination of any of the listed routes. In some embodiments, the VEGFR3 antagonist is administered by expressing a nucleic acid encoding the VEGFR3 antagonist in the subject.

In some embodiments, decreasing immune cell migration through the meningeal lymphatic vessel comprises a decrease in movement of molecules in cerebral spinal fluid in the subject to deep cervical lymph nodes of the subject. In some embodiments, decreasing immune cell migration through the meningeal lymphatic vessel comprises a decrease in movement of lymphocytes from the parenchyma to deep cervical lymph nodes of the subject. In some embodiments decreasing the immune cell migration decreases a density of lymphocytes in the meningeal lymphatic vessel. For example, the density can be decreased by at least 5%, for example at least 5%, 10%, 15%, 20%, 25%, 30%, 35%, 40%, 45%, or 50%, including ranges between any of the listed values. In some embodiments, the lymphocytes comprise or consist essentially of T cells. Moreover, reducing T-cell mediated inflammation in the central nervous system in accordance with some embodiments comprises decreasing a quantity of activated T cells in the deep cervical lymph nodes that have a migratory phenotype, as described herein. In addition to, or as an alternative to decreasing a quantity of activated T cells in the deep cervical lymph nodes that have a migratory phenotype, in some embodiments, reducing T-cell mediated inflammation in the central nervous system can decrease a quantity of in T cells in the central nervous system that produce inflammatory cytokines. Example inflammatory cytokines include IL-17, IFN-gamma, or both.

Additional Embodiments

Unless defined otherwise, all technical and scientific terms used herein have the meaning commonly understood by one of ordinary skill in the art to which this subject matter belongs.

The terms "vasodilator." "vasodilation" and the like are used herein to mean the widening of a vessel, including lymphatic vessels (e.g., meningeal lymphatic vessel(s)).

The terms "vasoconstrictor," "vasoconstriction" and the like are used herein to mean the narrowing of a vessel, including lymphatic vessels (e.g., meningeal lymphatic vessel(s)).

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g. tRNA, rRNA, or a DNA-targeting RNA: also called "non-coding" RNA or "ncRNA").

As used herein, the singular forms "a," "an," and "the" include plural reference unless the context clearly dictates otherwise. Thus, for example, reference to "a compound" is reference to one or more compounds and includes equivalents thereof known to those skilled in the art.

Additionally, the term "comprises" is intended to include embodiments where the method, apparatus, composition, etc., consists essentially of and/or consists of the listed steps, components, etc. Similarly, the term "consists essentially of" is intended to include embodiments where the method, apparatus, composition, etc., consists of the listed steps, components, etc. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the term "about" is used herein to provide literal support for the exact number that it precedes, as well as a number differs from the given number by less than 10%. In other embodiments, the term "about" indicates that the number differs from the given number by less than 9%, 8%, 7%, 6%, 5%, 4%, 3%, 2%, or 1%.

It is appreciated that certain features, which are, for clarity, described in the context of separate embodiments, may also be provided in combination in a single embodiment. Conversely, various features, which are, for brevity, described in the context of a single embodiment, may also be provided separately or in any suitable sub-combination. All combinations of the embodiments pertaining to the subject matter herein are specifically contemplated and are disclosed herein just as if each and every combination was individually and explicitly disclosed. In addition, all sub-combinations of the various embodiments and elements thereof are also specifically contemplated and are disclosed herein just as if each and every such sub-combination was individually and explicitly disclosed herein.

Some aspects provide methods of treating a condition with a neurological pathology in a subject comprising administering to the subject a therapeutically effective amount of a compound that modulates one or more of a) drainage of the meningeal lymphatic vessel(s); b) diameter of the meningeal lymphatic vessel(s); c) lymphangiogenesis of the meningeal lymphatic vessel(s); d) contractility of the meningeal lymphatic vessel(s); and/or e) permeability of the meningeal lymphatic vessel(s). The present disclosure also provides methods of treating AD in a subject by administering to the subject a compound that increases drainage of the meningeal lymphatic vessel(s), increases the diameter of the meningeal lymphatic vessel(s), causes lymphangiogenesis of the meningeal lymphatic vessel(s), modulates contractility of the meningeal lymphatic vessel(s) to increase drainage, and/or modulates the permeability of the meningeal lymphatic vessel(s) to increase drainage. The present disclosure also provides methods of treating a brain tumor in a subject by administering to the subject a compound that increases drainage of the meningeal lymphatic vessel(s), increases the diameter of the meningeal lymphatic vessel(s), causes lymphangiogenesis of the meningeal lymphatic vessel(s), modulates contractility of the meningeal lymphatic vessel(s) to increase drainage, and/or modulates the permeability of the meningeal lymphatic vessel(s) to increase drainage. The present disclosure further provides methods of treating MS in a subject by administering to the subject a compound that decreases drainage of the meningeal lymphatic vessel(s), decreases the diameter of the meningeal lymphatic vessel(s), modulates contractility of the meningeal lymphatic vessel(s) to decrease drainage, and/or modulates the permeability of the meningeal lymphatic vessel(s). The present disclosure also provides the identification and description of the meningeal lymphatic vascular system that serves as both tissue clearance and immune-cell trafficking functions of the brain.

Methods of Treating Condition with a Neurological Pathology

Some aspects include methods of treating a condition with a neurological pathology in a subject by administering to the subject a therapeutically effective amount of a compound that modulates one or more of a) drainage of the meningeal lymphatic vessel(s), b) diameter of the meningeal lymphatic vessel(s), c) lymphangiogenesis of the meningeal lymphatic vessel(s), d) contractility of the meningeal lymphatic vessel(s); and/or e) permeability of the meningeal lymphatic vessel(s).

In some embodiments, the method further comprises identifying a subject in need of said treatment. In further embodiments, the subject in need of said treatment is susceptible to or suffering from the disorder selected from the group consisting AD, dementia. Parkinson's disease, cerebral edema, amyotrophic lateral sclerosis (ALS), epilepsy, brain tumor, Pediatric Autoimmune Neuropsychiatric Disorders Associated with Streptococcal Infections (PANDAS), meningitis, hemorrhagic stroke, autism spectrum disorder (ASD), MS, and myasthenia gravis.

In some embodiments, a therapeutically effective amount of said compound is administered. In further embodiments, said compound is a vasodilator. In other embodiments, said compound is a growth faction. In further embodiments, said growth factor is selected from the group consisting of VEGF-c. VEGF-d, and FGF2. In further embodiments, said compound is noradrenaline.

In some embodiments, said compound is a vasoconstrictor. In further embodiments, said compound is selected from the group consisting of nitric oxide competitor NG-monomethyl L-arginine, cyclo-oxygenase inhibitors, and phosphatidylcholine.

In some embodiments, said therapeutically effective amount of the compound is about 0.00015 mg/kg to about 1.5 mg/kg. In further embodiments, said therapeutically effective amount of the compound is about 0.00015 mg/kg, about 0.00030 mg/kg, about 0.00045 mg/kg, about 0.00060 mg/kg, about 0.00085 mg/kg, about 0.001 mg/kg, about 0.0015 mg/kg, about 0.002 mg/kg, about 0.0025 mg/kg, about 0.003 mg/kg, about 0.0035 mg/kg, about 0.004 mg/kg, about 0.0045 mg/kg, about 0.0050 mg/kg, about 0.0055 mg/kg, about 0.006 mg/kg, about 0.0065 mg/kg, about 0.007 mg/kg, about 0.0075 mg/kg, about 0.008 mg/kg, about 0.0085 mg/kg, about 0.009 mg/kg, about 0.0095 mg/kg, about 0.01 mg/kg, about 0.015 mg/kg, about 0.02 mg/kg, about 0.025 mg/kg, about 0.03 mg/kg, about 0.035 mg/kg, about 0.040 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, or about 1.5 mg/kg.

In some embodiments, said therapeutically effective amount of the compound is less than about 0.00015 mg/kg, about 0.00030 mg/kg, about 0.00045 mg/kg, about 0.00060 mg/kg, about 0.00085 mg/kg, about 0.001 mg/kg, about 0.0015 mg/kg, about 0.002 mg/kg, about 0.0025 mg/kg, about 0.003 mg/kg, about 0.0035 mg/kg, about 0.004 mg/kg, about 0.0045 mg/kg, about 0.0050 mg/kg, about 0.0055 mg/kg, about 0.006 mg/kg, about 0.0065 mg/kg, about 0.007 mg/kg, about 0.0075 mg/kg, about 0.008 mg/kg, about 0.0085 mg/kg, about 0.009 mg/kg, about 0.0095 mg/kg, about 0.01 mg/kg, about 0.015 mg/kg, about 0.02 mg/kg, about 0.025 mg/kg, about 0.03 mg/kg, about 0.035 mg/kg, about 0.040 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, or about 1.5 mg/kg.

In some embodiments, said therapeutically effective amount of the compound is more than about 0.00015 mg/kg, about 0.00030 mg/kg, about 0.00045 mg/kg, about 0.00060 mg/kg, about 0.00085 mg/kg, about 0.001 mg/kg, about 0.0015 mg/kg, about 0.002 mg/kg, about 0.0025 mg/kg, about 0.003 mg/kg, about 0.0035 mg/kg, about 0.004 mg/kg, about 0.0045 mg/kg, about 0.0050 mg/kg, about 0.0055 mg/kg, about 0.006 mg/kg, about 0.0065 mg/kg, about 0.007 mg/kg, about 0.0075 mg/kg, about 0.008 mg/kg, about 0.0085 mg/kg, about 0.009 mg/kg, about 0.0095 mg/kg, about 0.01 mg/kg, about 0.015 mg/kg, about 0.02 mg/kg, about 0.025 mg/kg, about 0.03 mg/kg, about 0.035 mg/kg, about 0.040 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, or about 1.5 mg/kg.

In some embodiments, the compound is provided in soluble form. In some embodiments, the compound is provided absorbed in nanogels for slow and constant release. In certain embodiments, the compounds are provided on viral vectors which encode for the reagent that is a RNA or polypeptide.

In some aspects, the compound is administered into the cerebrospinal fluid (CSF) of the subject. In other aspects, an ointment comprises said compound and the ointment is administered via application of the ointment to the head of the subject.

Methods of Treating Dementia, for Example AD

Examples

Figure 5A:
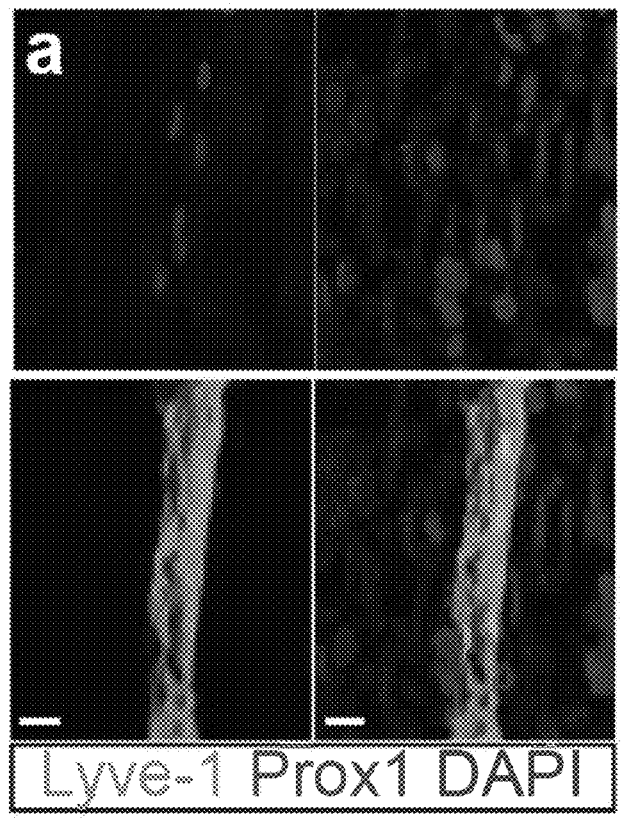
FIG. 5A is a representative image of Prox1 labelling on meningeal Lyve-1 expressing vessels (n-3 mice; scale bars, 10 μm).
Figure 5B:
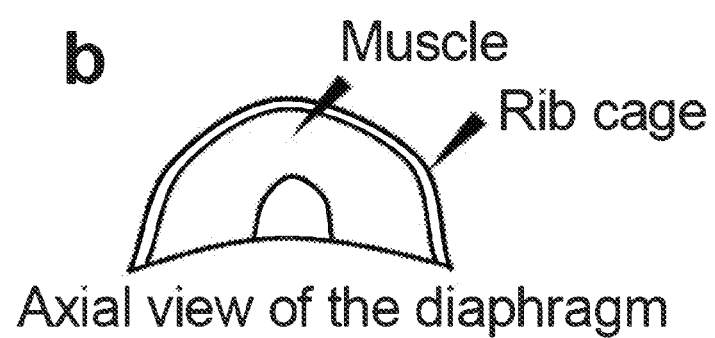
FIG. 5B is a schematic representation of the whole-mount dissection of the diaphragm.
Figure 5C:
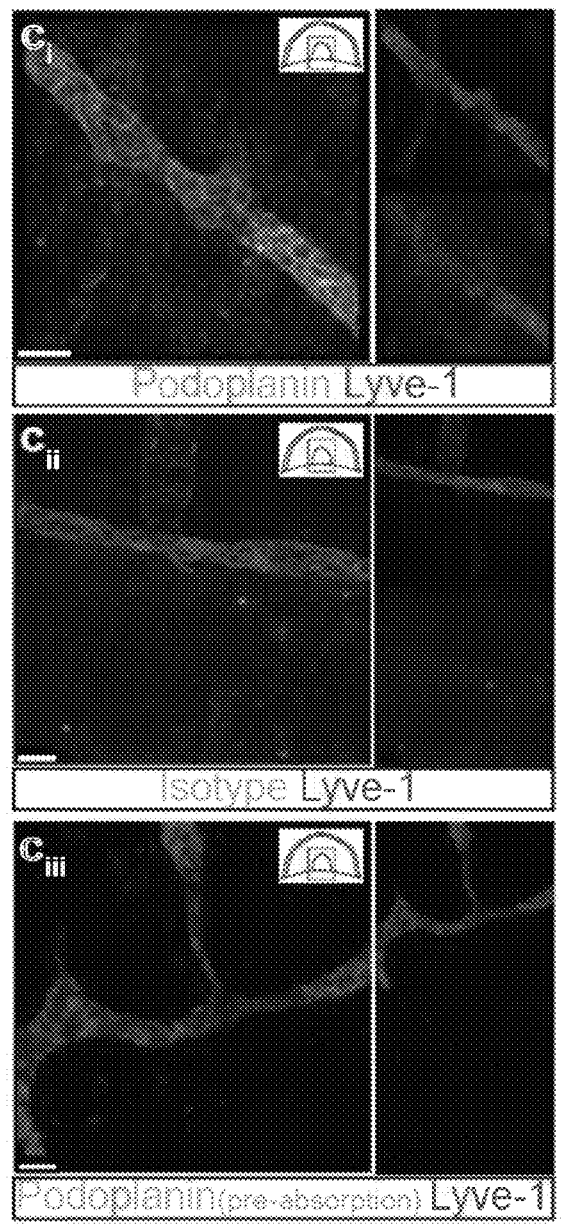
FIG. 5C shows characterization of the specificity of the podoplanin antibody. Representative images of whole-mount diaphragm labelled with anti-Lyve-1 and anti-podoplanin shows (panel ci), control isotype (panel cii) or the anti-podoplanin preincubated overnight with a saturated concentration of recombinant podoplanin protein (ciii; scale bars, 20 μm). Panel ci shows overlap of anti-Lyve1 and Podoplanin.
Figure 5D:
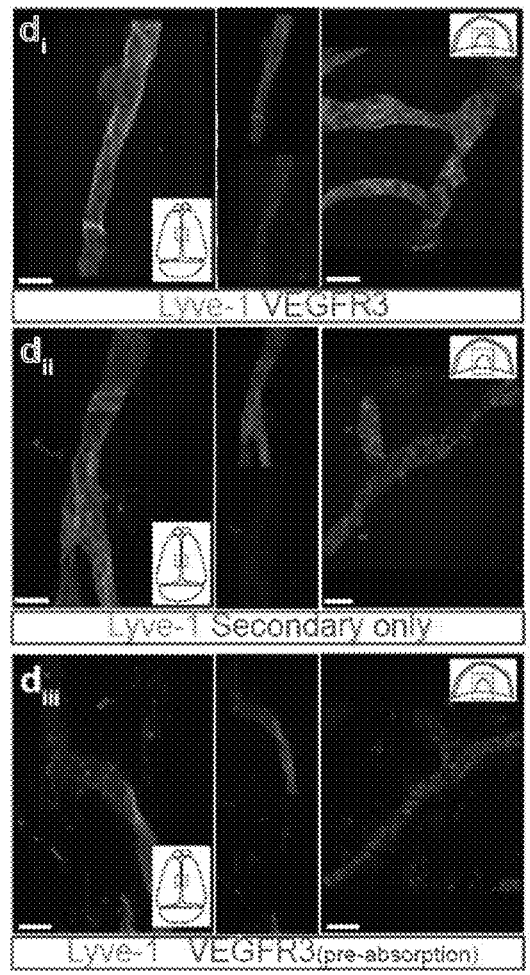
FIG. 5D shows characterization of the specificity of the VEGFR3 antibody. Representative images of whole-mount diaphragm and dura mater labelled with anti-Lyve-1 and anti-VEGFR3 (di), secondary antibody only (dii), or the anti-VEGFR3 pre-incubated overnight with a saturated concentration of recombinant VEGFR3 protein (diii; scale bars, 20 μm). Panel di show overlap of Lyve-1 and VEGFR3.
Figure 5E:
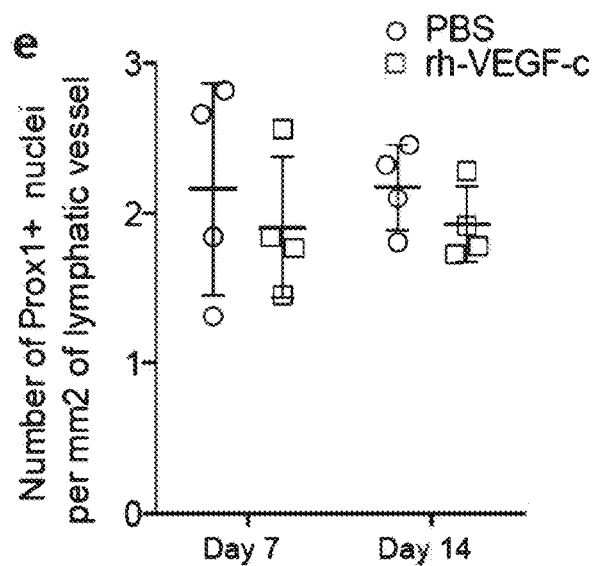
FIG. 5E shows quantification of the number of Prox1+ nuclei per mm2 of lymphatic vessel (mean±s.e.m.; n-4 animals each group).
Figure 6A:
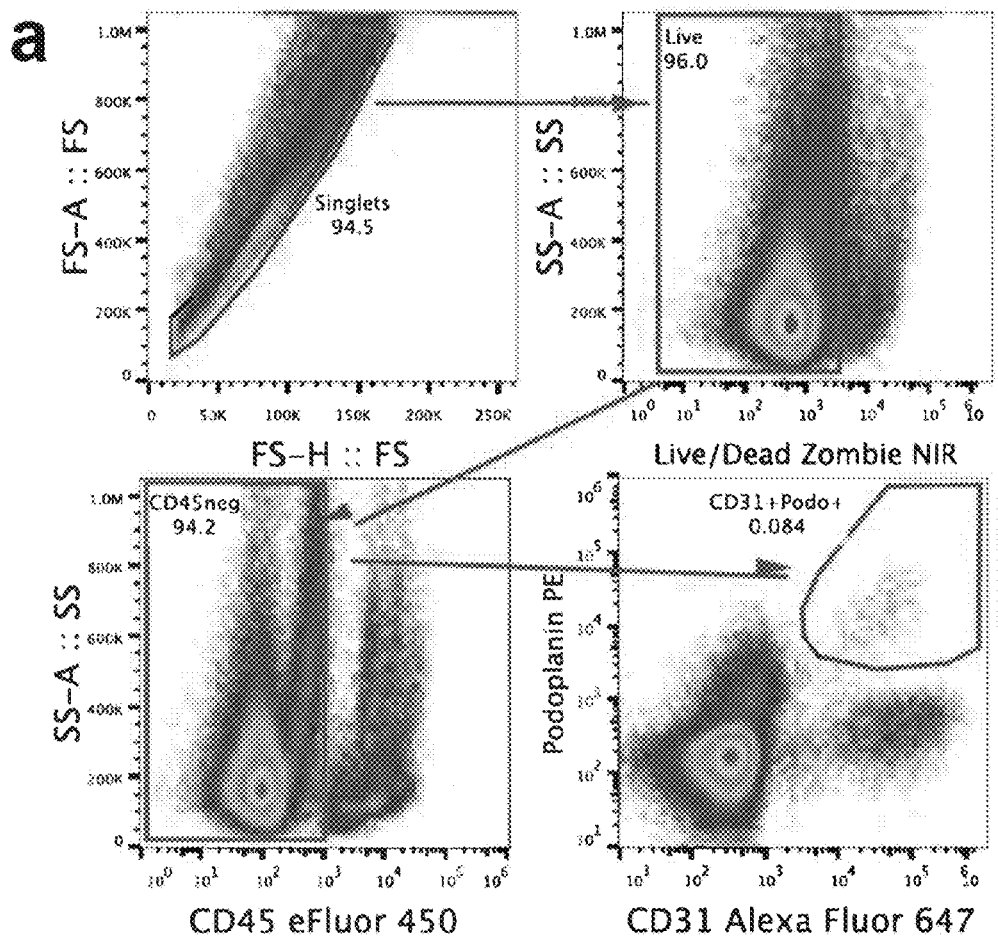
FIGS. 6A-B is a series of graphs showing identification of meningeal lymphatic endothelial cell population by flow cytometry. FACS analysis of the lymphatic endothelial cells in diaphragm, skin (ear), and dural sinuses.
Figure 6B:
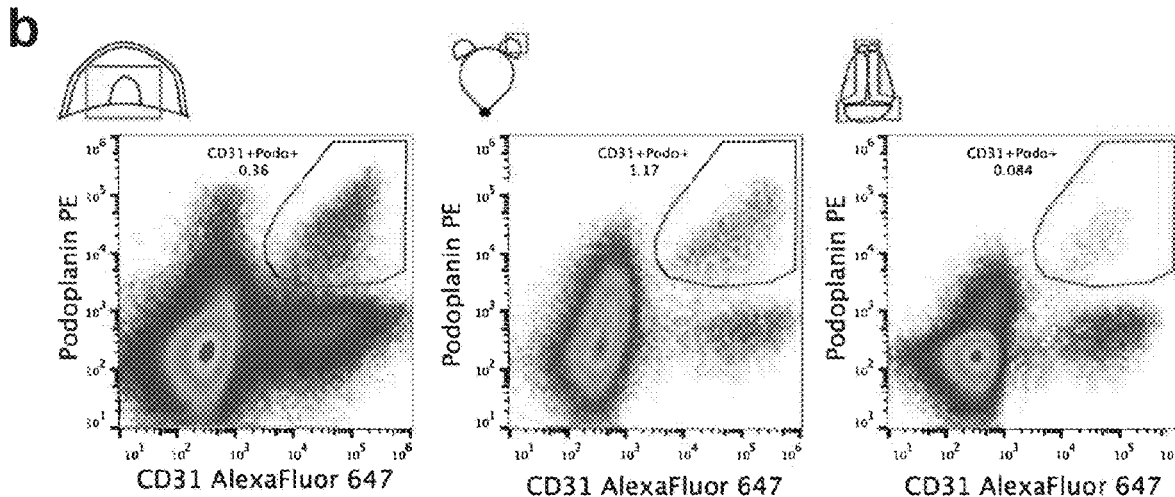

The provided data have shown that surgical ligation or pharmacological ablation (with Visudyne—FIG. 4) results in alteration of lymphatic drainage into the cervical lymph nodes (FIG. 5a-d). Moreover, we show that treatment with lymphangiogenic growth factors (VEGF-c) improves the drainage (FIG. 5e). These results emphasize the importance of the meningeal lymphatic in the removal of macromolecules from the subarachnoid spaces. Finally, we demonstrate that aged mice as well as J20 mice are characterized by impaired drainage through meningeal lymphatics (FIG. 6), suggesting that decrease efficiency of lymphatic drainage might be part of the normal aging process and participate in the lack of clearance observed in both aged and AD mice26 (Kress, B. T. et al. Impairment of paravascular clearance pathways in the aging brain. *Ann. Neurol.* 76, 845-861 (2014)).

Methods to improve the Aβ pathology and memory deficits in J20 mice by using lymphangiogenic growth factors (such as, VEGFC, VEGFD, FGF2) administered, e.g., via viral vectors, as recombinant protein (this approach has been already demonstrated by our lab to be efficient 3) either solubilized or absorbed in nanogels for slow and constant release (Baker. A. et al. Experimental assessment of pro-lymphangiogenic growth factors in the treatment of post-surgical lymphedema following lymphadenectomy. *Breast Cancer Res. BCR* 12, R70 (2010)).

Figure 2A:
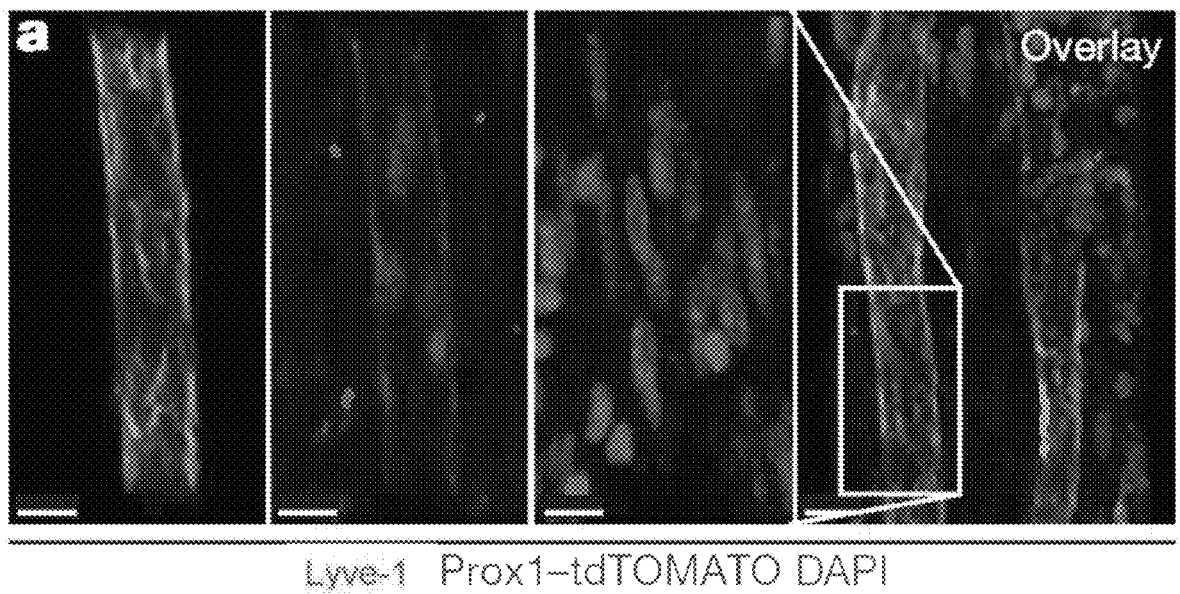
FIGS. 2A-H are a series of microscope images and graphs showing Molecular and structural characterization of meningeal lymphatic vessels.
Figure 2B:
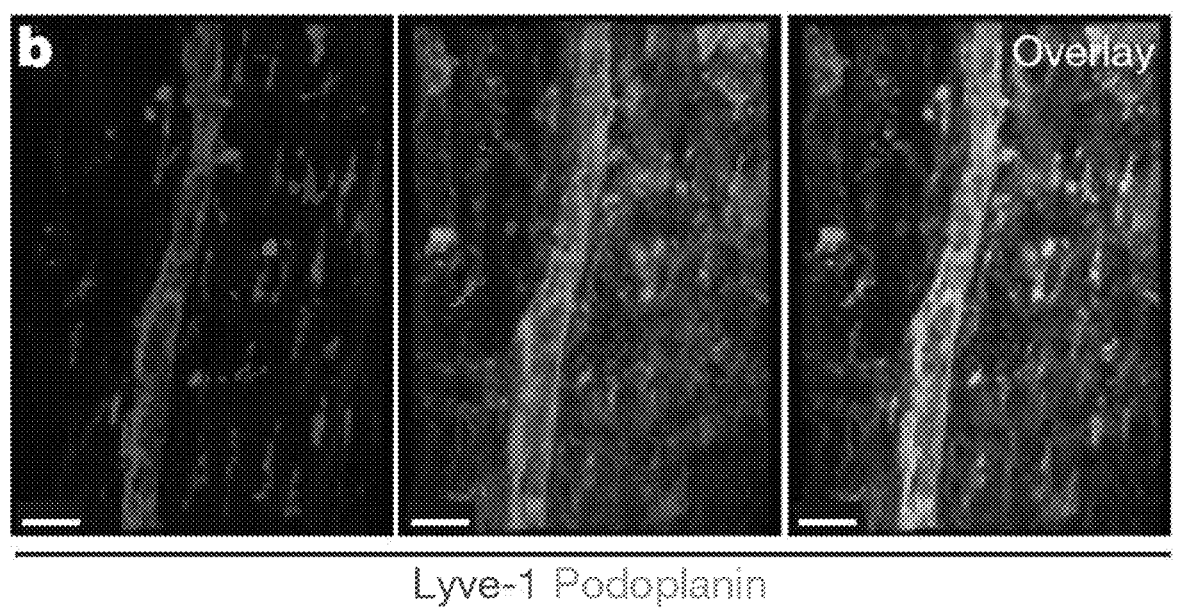
Figure 2C:
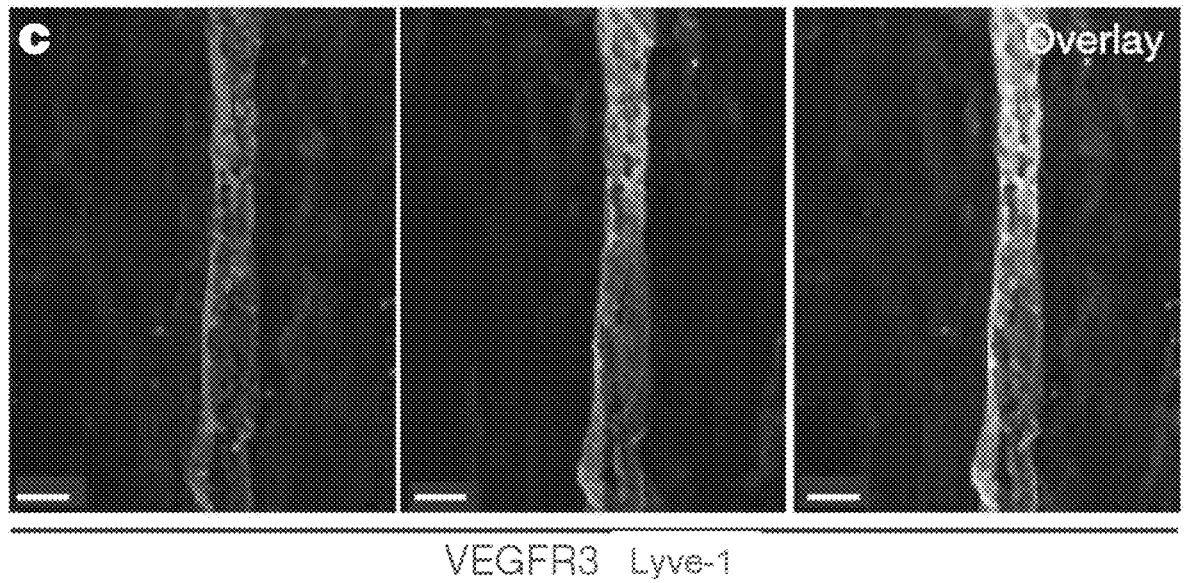
Figure 2D:
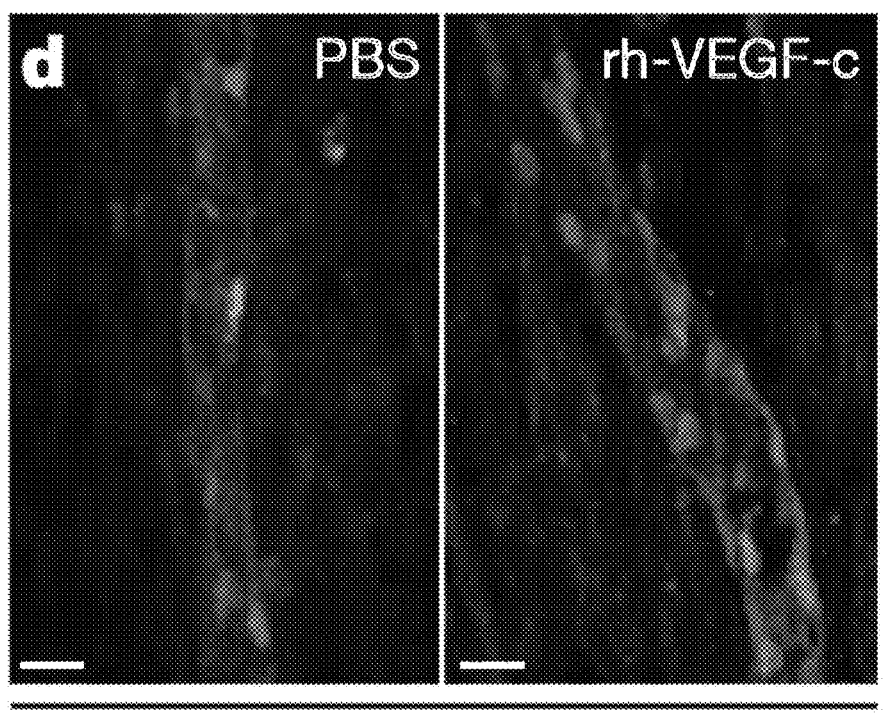
Figure 2E:
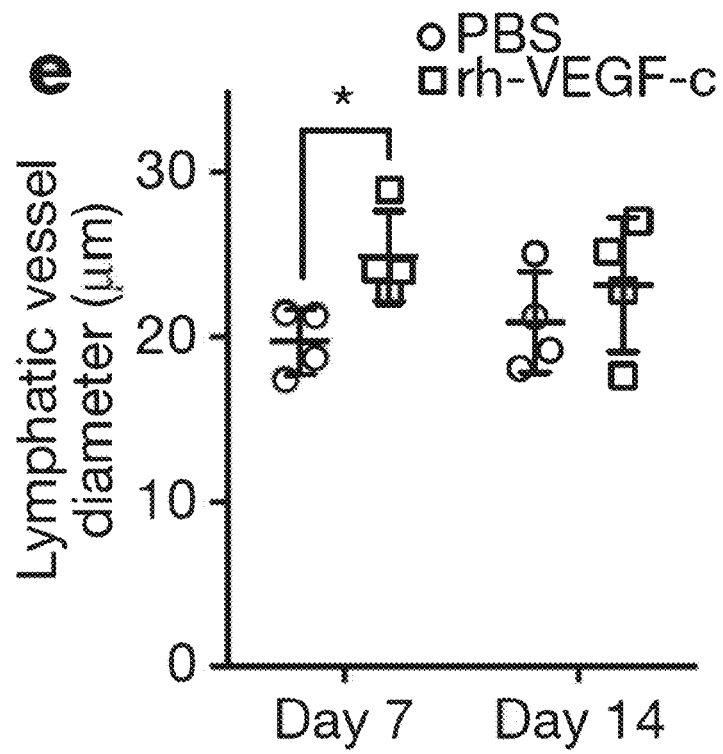
Figure 2F:
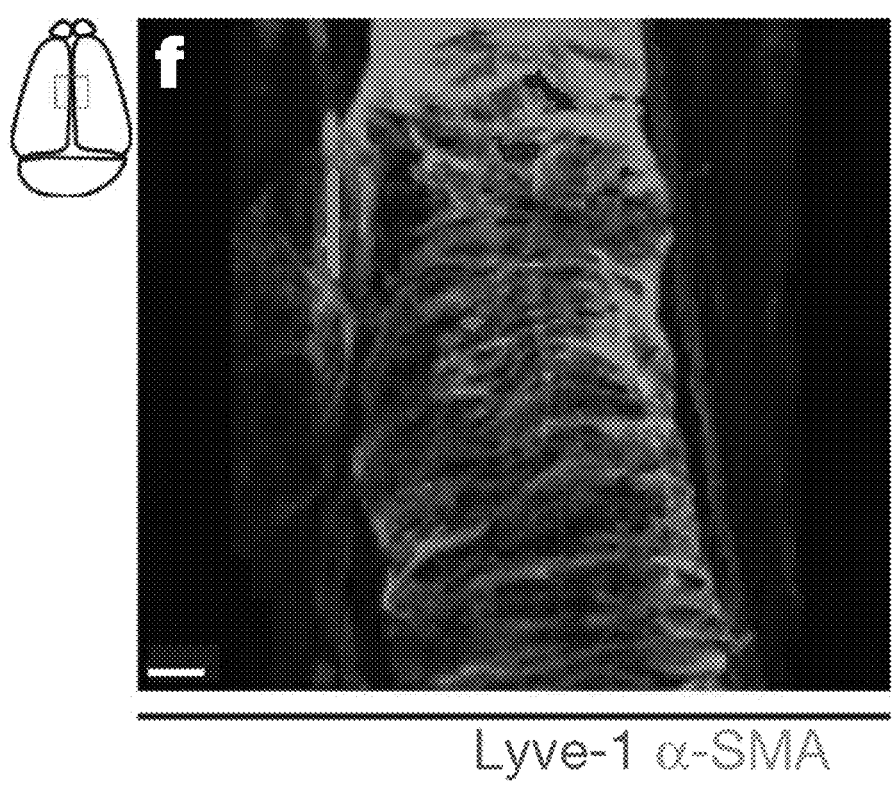
Figure 2G:
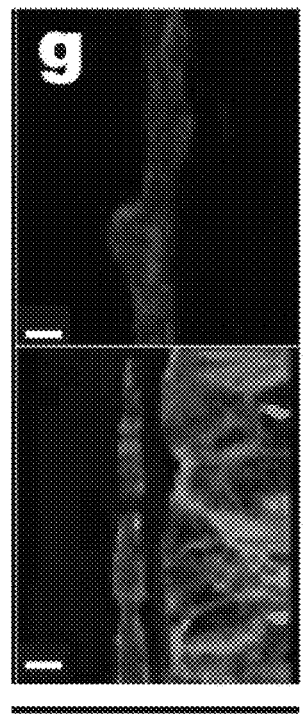
Figure 2H:
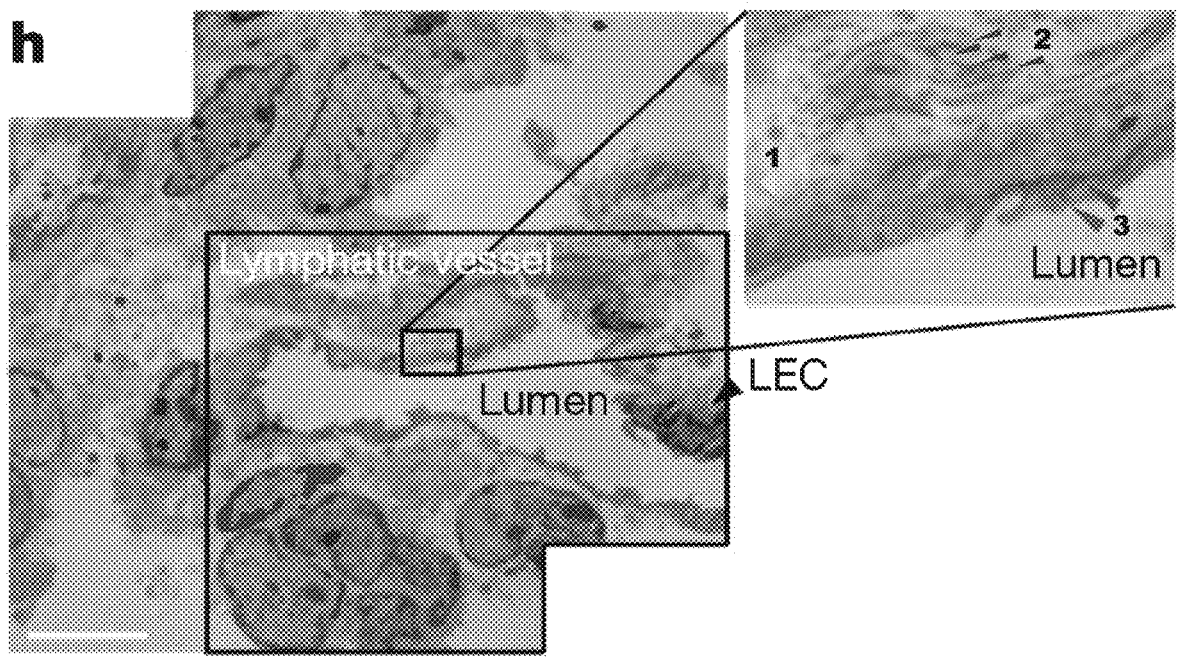

The provided data indicates that single injection of recombinant VEGF-c into the CSF is sufficient to increase diameter of meningeal lymphatic vessels and increase drainage efficacy; (FIG. 2e). Lymphatic drainage (using multiphoton microscopy), disease pathology (quantification of Aβ deposition in the meninges and the brain), and behavior (open field and Morris Water Maze) are assessed during and after treatment with the lymphangiogenic factor/s.

Methods of Treatment:

Some embodiments include methods of treating AD in a subject by administering to the subject a compound that increases drainage of the meningeal lymphatic vessel(s), increases the diameter of the meningeal lymphatic vessel(s), causes lymphangiogenesis of the meningeal lymphatic vessel(s), modulates contractility of the meningeal lymphatic vessel(s) to increase drainage, and/or modulates the permeability of the meningeal lymphatic vessel(s). The present disclosure further provides methods of treating a brain tumor in a subject by administering to the subject a compound that increases drainage of the meningeal lymphatic vessel(s), increases the diameter of the meningeal lymphatic vessel(s) causes lymphangiogenesis of the meningeal lymphatic vessel(s), modulates contractility of the meningeal lymphatic vessel(s) to increase drainage, and/or modulates the permeability of the meningeal lymphatic vessel(s).

Some aspects include methods for reducing the number and/or volume of existing amyloid plaques or other misfolded proteins comprising administering to a subject a therapeutic effective amount of a compound that increases drainage of and/or increases the diameter of the meningeal lymphatic vessels. In some cases, the subject is selected from the group consisting of subjects identified as being susceptible to Alzheimer's disease and subjects suffering from Alzheimer's disease.

In some embodiments, the method further comprises identifying a subject in need of said treatment. In further embodiments, the subject in need of said treatment is susceptible to or suffering from the disorder selected from the group consisting of AD and brain tumors.

Identification of such subjects may be made using techniques known to a person of ordinary skill in the art.

In some embodiments, a therapeutically effective amount of said compound is administered. In further embodiments, said compound is a vasodilator. In other embodiments, said compound is a growth faction. In further embodiments, said growth factor is selected from the group consisting of VEGF-c, VEGF-d, and FGF2. In further embodiments, said compound is noradrenaline.

In some embodiments, said therapeutically effective amount of the compound is about 0.00015 mg/kg to about 1.5 mg/kg. In further embodiments, said therapeutically effective amount of the compound is about 0.00015 mg/kg, about 0.00030 mg/kg, about 0.00045 mg/kg, about 0.00060 mg/kg, about 0.00085 mg/kg, about 0.001 mg/kg, about 0.0015 mg/kg, about 0.002 mg/kg, about 0.0025 mg/kg, about 0.003 mg/kg, about 0.0035 mg/kg, about 0.004 mg/kg, about 0.0045 mg/kg, about 0.0050 mg/kg, about 0.0055 mg/kg, about 0.006 mg/kg, about 0.0065 mg/kg, about 0.007 mg/kg, about 0.0075 mg/kg, about 0.008 mg/kg, about 0.0085 mg/kg, about 0.009 mg/kg, about 0.0095 mg/kg, about 0.01 mg/kg, about 0.015 mg/kg, about 0.02 mg/kg, about 0.025 mg/kg, about 0.03 mg/kg, about 0.035 mg/kg, about 0.040 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, or about 1.5 mg/kg.

In some embodiments, said therapeutically effective amount of the compound is less than about 0.00015 mg/kg, about 0.00030 mg/kg, about 0.00045 mg/kg, about 0.00060 mg/kg, about 0.00085 mg/kg, about 0.001 mg/kg, about 0.0015 mg/kg, about 0.002 mg/kg, about 0.0025 mg/kg, about 0.003 mg/kg, about 0.0035 mg/kg, about 0.004 mg/kg, about 0.0045 mg/kg, about 0.0050 mg/kg, about 0.0055 mg/kg, about 0.006 mg/kg, about 0.0065 mg/kg, about 0.007 mg/kg, about 0.0075 mg/kg, about 0.008 mg/kg, about 0.0085 mg/kg, about 0.009 mg/kg, about 0.0095 mg/kg, about 0.01 mg/kg, about 0.015 mg/kg, about 0.02 mg/kg, about 0.025 mg/kg, about 0.03 mg/kg, about 0.035 mg/kg, about 0.040 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, or about 1.5 mg/kg.

In some embodiments, said therapeutically effective amount of the compound is more than about 0.00015 mg/kg, about 0.00030 mg/kg, about 0.00045 mg/kg, about 0.00060 mg/kg, about 0.00085 mg/kg, about 0.001 mg/kg, about 0.0015 mg/kg, about 0.002 mg/kg, about 0.0025 mg/kg, about 0.003 mg/kg, about 0.0035 mg/kg, about 0.004 mg/kg, about 0.0045 mg/kg, about 0.0050 mg/kg, about 0.0055 mg/kg, about 0.006 mg/kg, about 0.0065 mg/kg, about 0.007 mg/kg, about 0.0075 mg/kg, about 0.008 mg/kg, about 0.0085 mg/kg, about 0.009 mg/kg, about 0.0095 mg/kg, about 0.01 mg/kg, about 0.015 mg/kg, about 0.02 mg/kg, about 0.025 mg/kg, about 0.03 mg/kg, about 0.035 mg/kg, about 0.040 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, or about 1.5 mg/kg.

In some embodiments, the compound is provided in soluble form. In some embodiments, the compound is provided absorbed in nanogels for slow and constant release. In certain embodiments, the compounds are provided on viral vectors which encode for the reagent that is a RNA or polypeptide.

In some aspects, the compound is administered into the cerebrospinal fluid (CSF) of the subject. In other aspects, an ointment comprises said compound and the ointment is administered via application of the ointment to the head of the subject.

Methods of Treating Multiple Sclerosis

Examples

Figure 7A:
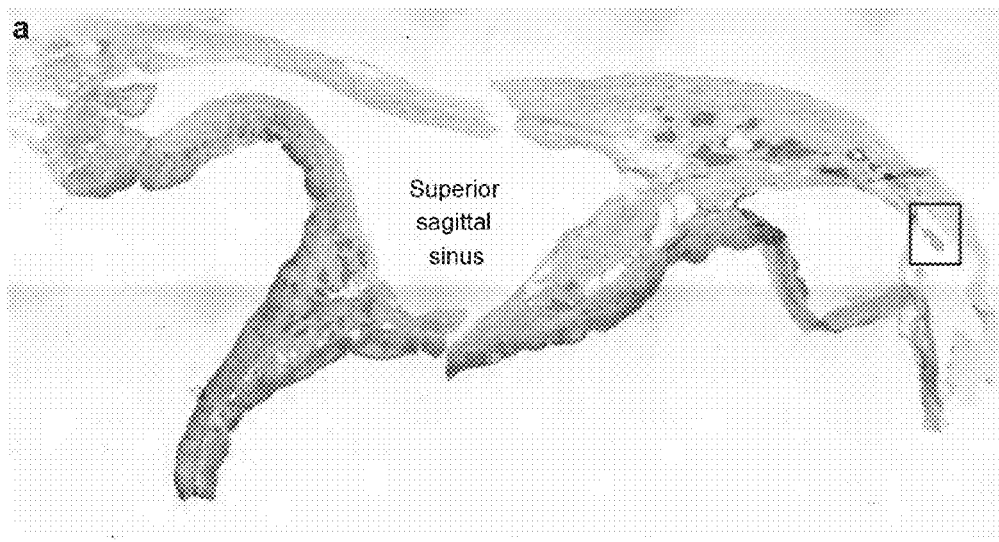
FIGS. 7A-E is a series of microscope images showing pilot identification of lymphatic vessels in human dura.
Figure 7B:
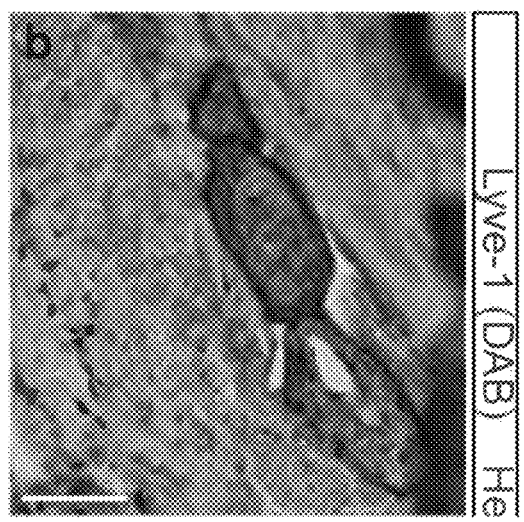
Figure 7C:
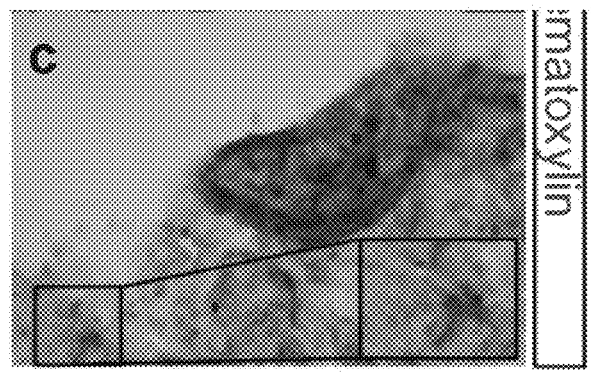
Figure 7D:
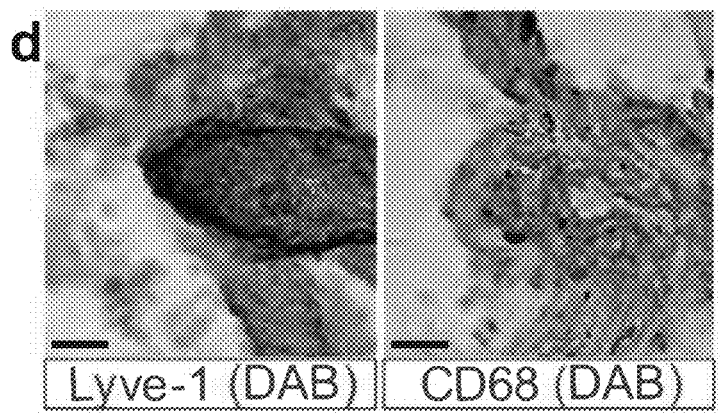
Figure 7E:
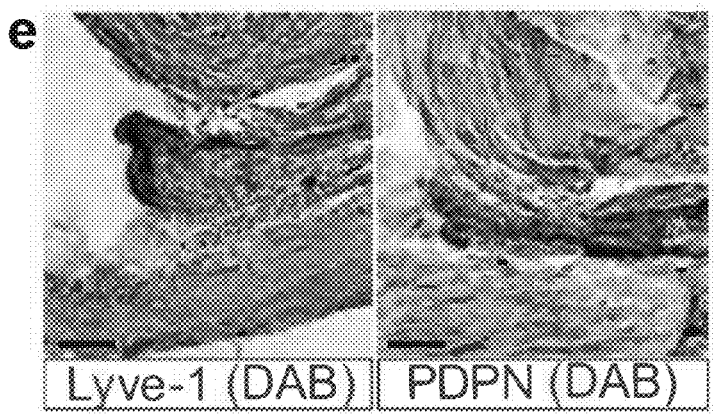
Figure 8A:
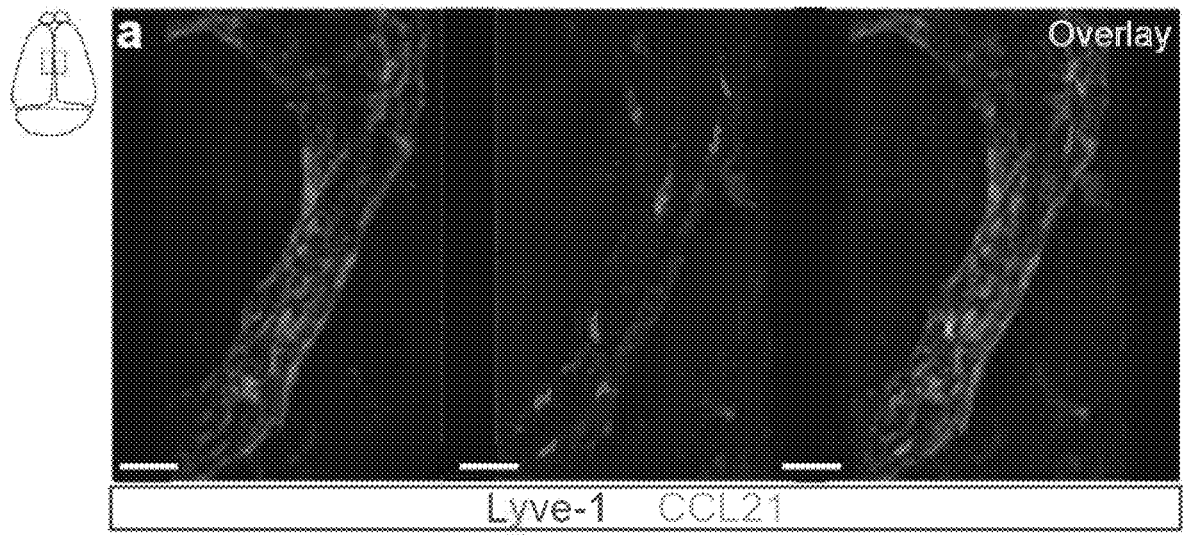
FIGS. 8A-J are a series of microscope images and diagrams showing initial lymphatic features of meningeal lymphatic vessels.
Figure 8B:
Figure 8C:
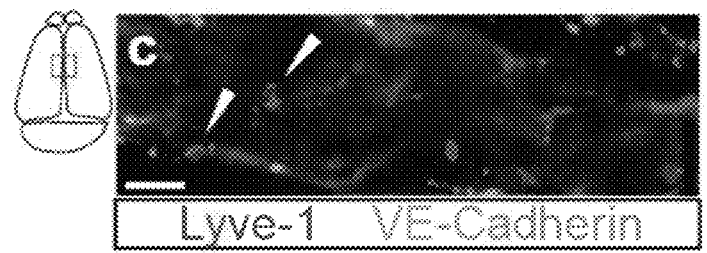
Figure 8D:
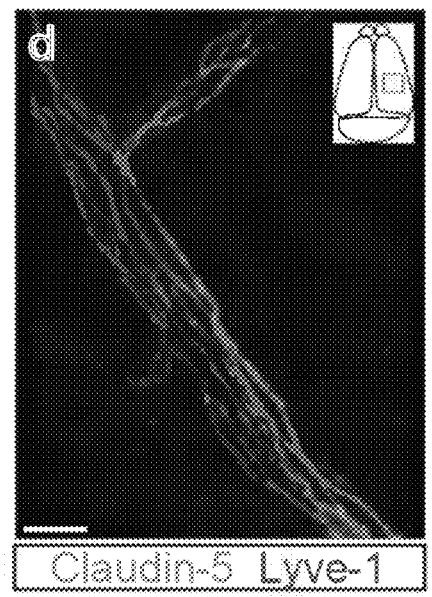
Figure 8E:
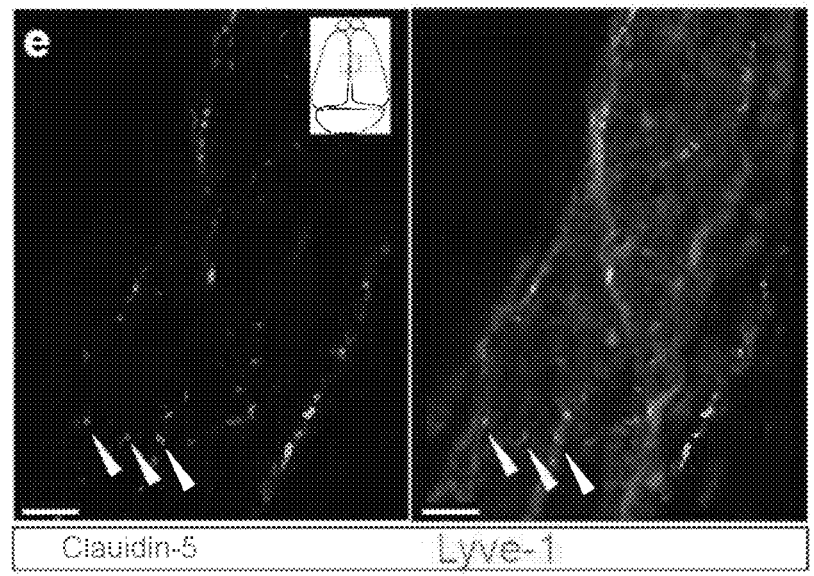
Figure 8F:
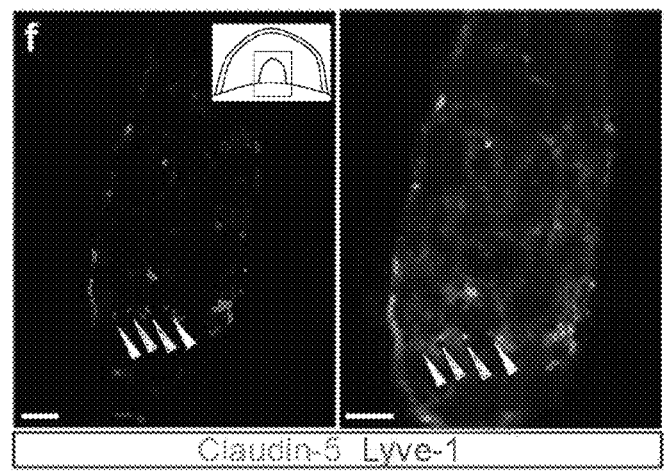
Figure 8G:
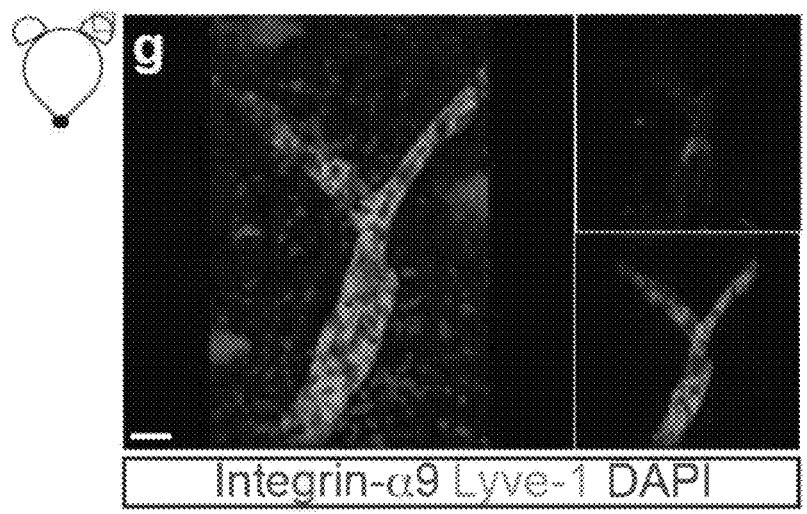
Figure 8H:
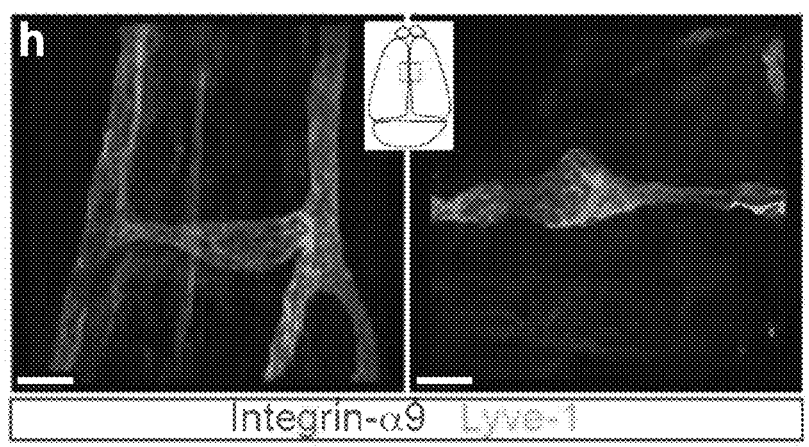
Figures 8I, 8J:
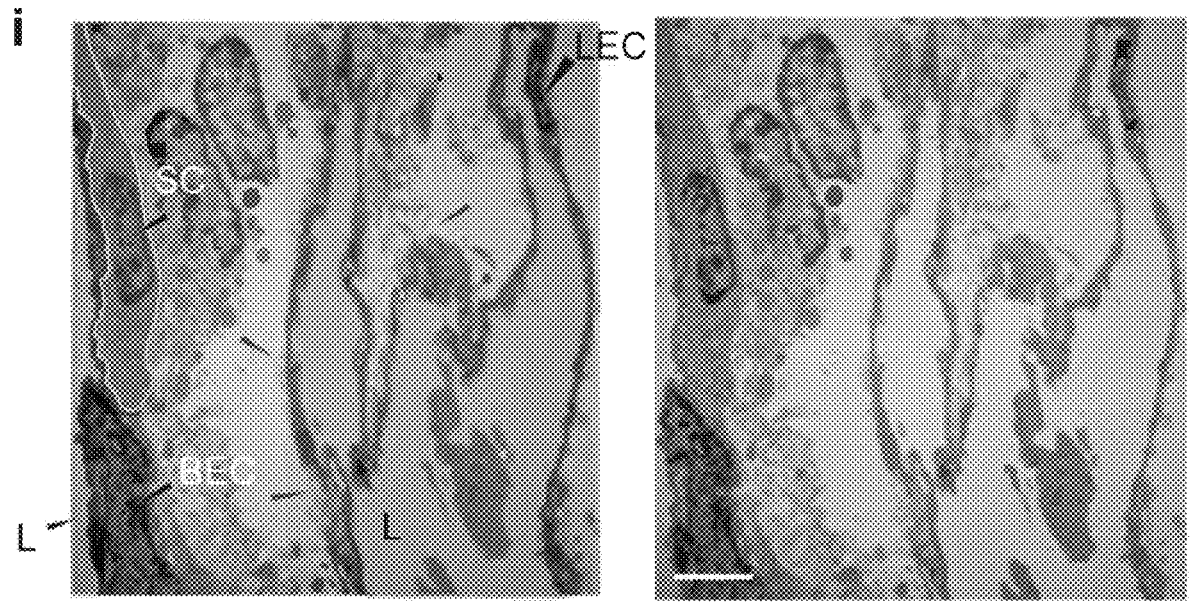

Using an EAE mouse model, data show that 7 days after immunization with CFA/Mog there is an increase in meningeal lymphatic vessel diameter (FIG. 7a) and a reduction in the number of T cells within the meningeal spaces (FIG. 7b). These results indicate that meningeal T cells have indeed been recalled to the deep cervical lymph nodes for activation. On day 13 (beginning of clinical signs) the meninges are filled with T cells again (FIG. 7b). Surgical excision of deep cervical lymph nodes prior to CFA/Mog immunization, led to ameliorated EAE, as compared to control, or sham-operated mice (FIG. 7c). Similar results were obtained when lymphatic vessels were ligated (the ligation site is indicated by arrowheads on FIG. 7dii). Upon ligation of the lymphatic vessels, mice were immediately immunized with CFA/Mog and disease course was followed. A significant, yet temporary, attenuation of the disease was evident (FIG. 7d). These results further indicate the role played by meningeal lymphatic vessels in the course of EAE. The modest and temporary effect is probably due to an ability of the lymphatic endothelial cells to grow around the ligation site and re-establish the connection. Thus, to obtain a robust effect the ligation would need to be repeated every 5-7 days.

For ablation, two published approaches are utilized (Jang, J. Y. et al. Conditional ablation of LYVE-1+ cells unveils defensive roles of lymphatic vessels in intestine and lymph nodes. *Blood* 122, 2151-2161, doi:10.1182/blood-2013-01-478941 (2013)): Proxcre-ERT2 mice were made available. Prox-1cre-ERT2::DTASTOP-lox mice will be treated i.c.v. with tamoxifen (TAM) to induce expression of intracellular diphtheria toxin (DTA) in Prox-1 expressing lymphatic endothelial cells that will kill the cells. Alternatively, wild type mice will be injected i.c.v. with a photoconvertible toxin (verteporfin (Tammela. T. et al. Photodynamic ablation of lymphatic vessels and intralymphatic cancer cells prevents metastasis. *Sci Transl Med* 3, 69ra11, doi:10.1126/scitranslmed.3001699 (2011))) that produces ROS upon photoconversion (FIG. 8). An alternative to ablation approach, is a ligation of lymphatic vessels. As demonstrated in FIG. 7d, this method is feasible and has an effect on EAE. A more efficient method for ligation/ablation will likely yield more robust effect on EAE.

Figure 9A:
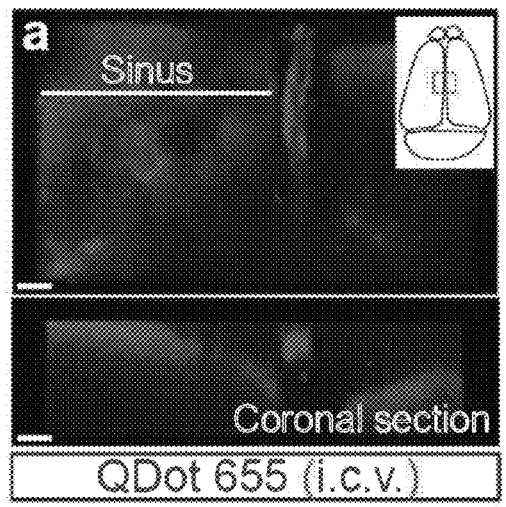
FIGS. 9A-C are a series of microscope images showing drainage of cerebrospinal fluid into the meningeal lymphatic vessels.
Figure 9B:
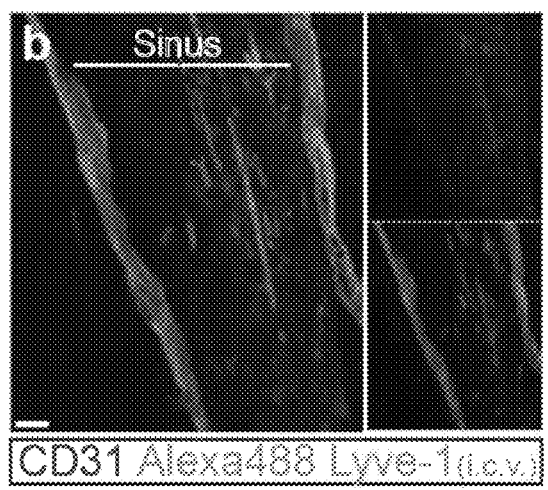
Figure 9C:
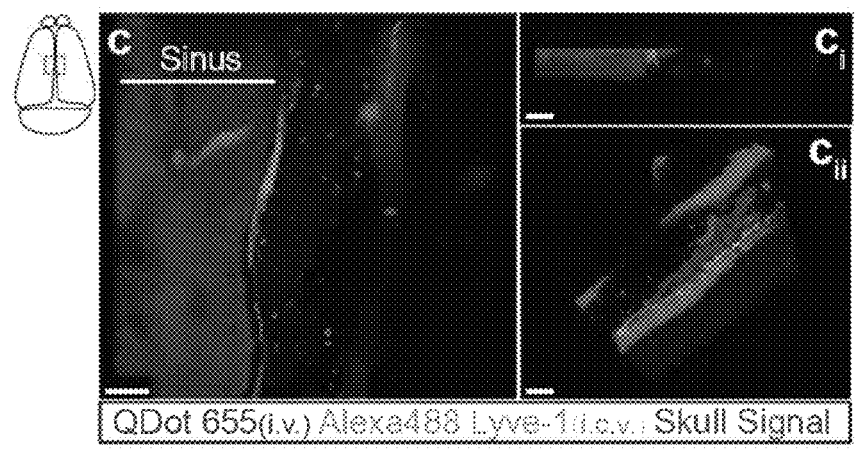
Figures 10A, 10B:
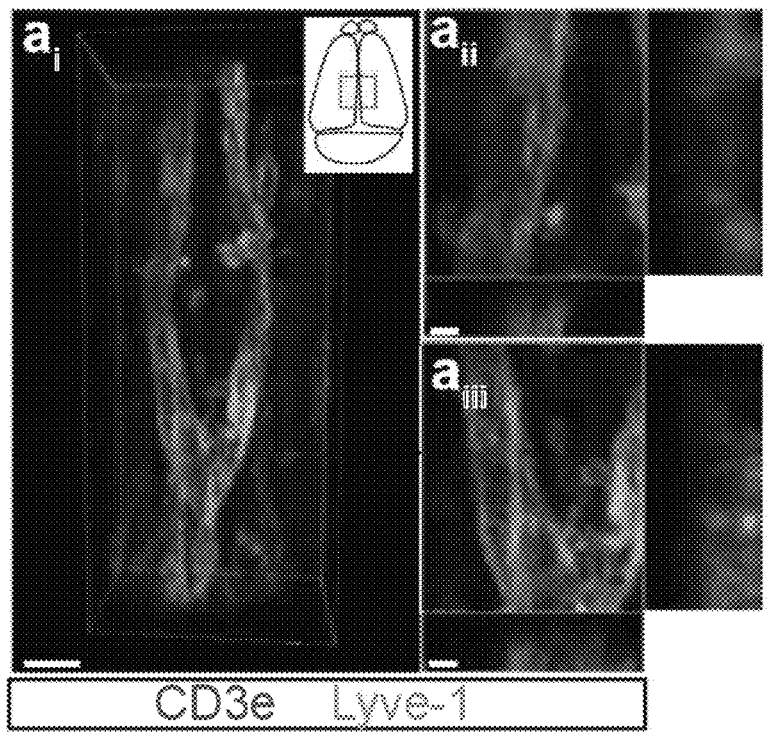
FIGS. 10A-F are a series of microscope images and graphs showing meningeal lymphatic vessels carrying immune cells.
Figure 10C:
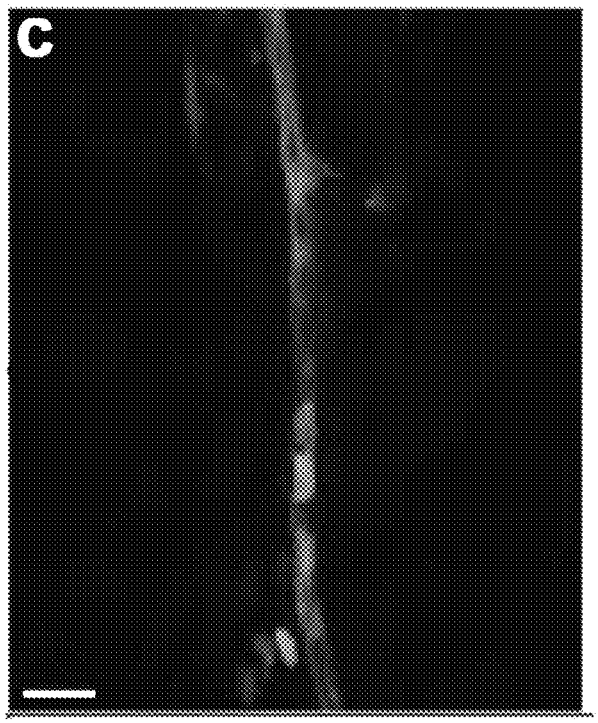
Figure 10D:
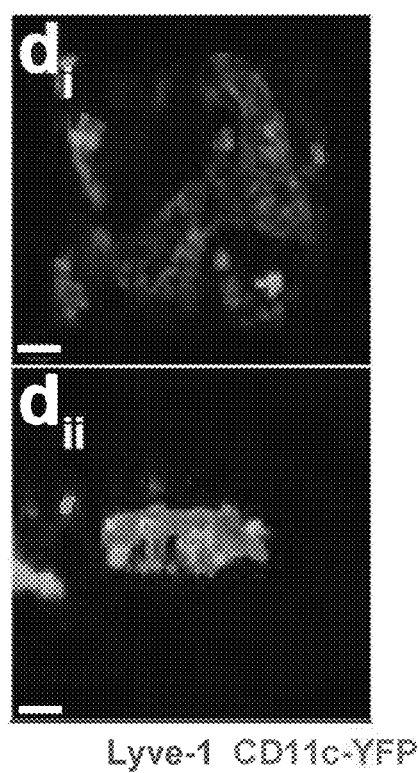
Figure 10E:
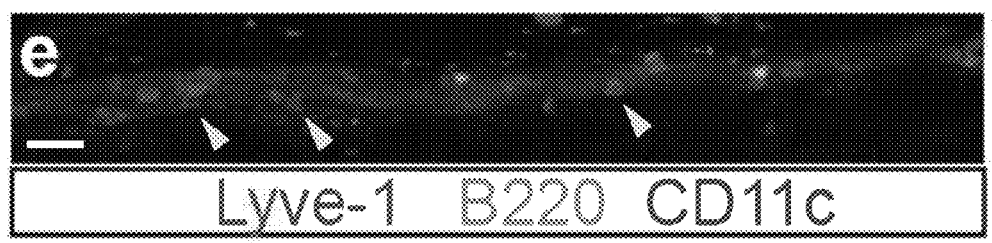
Figure 10F:
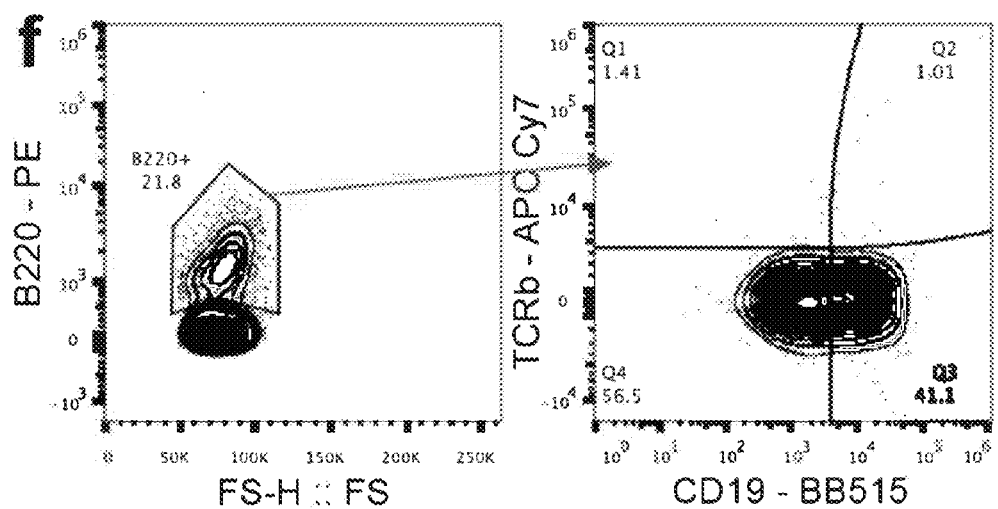
Figure 11A:
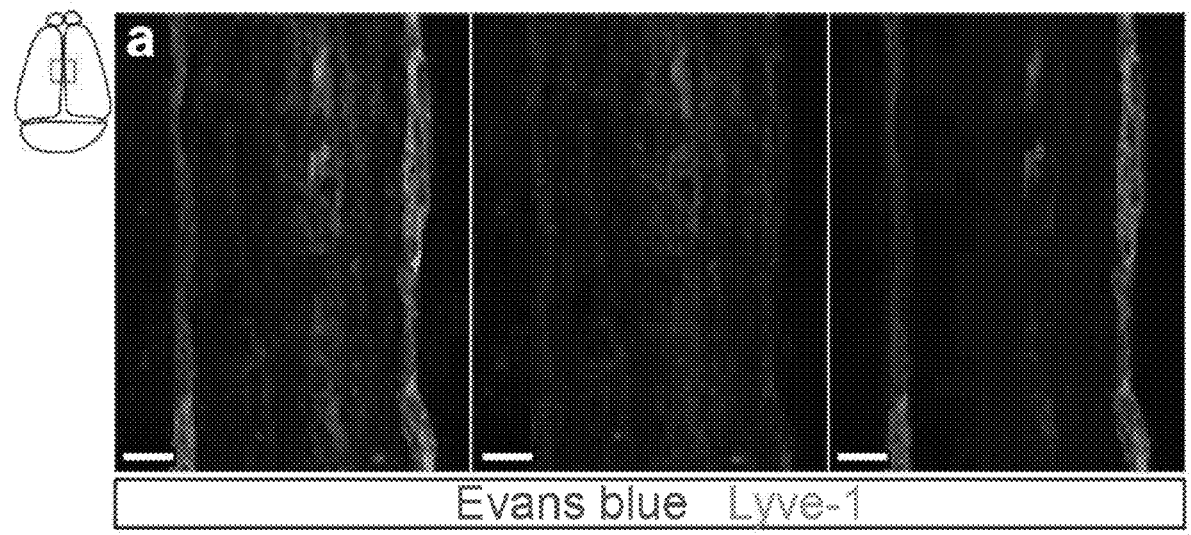
FIGS. 11A-E are a series of microscope images and graphs showing draining of Evans blue from the meningeal lymphatic vessels but not the nasal mucosa into the deep cervical lymph nodes.
Figure 11B:
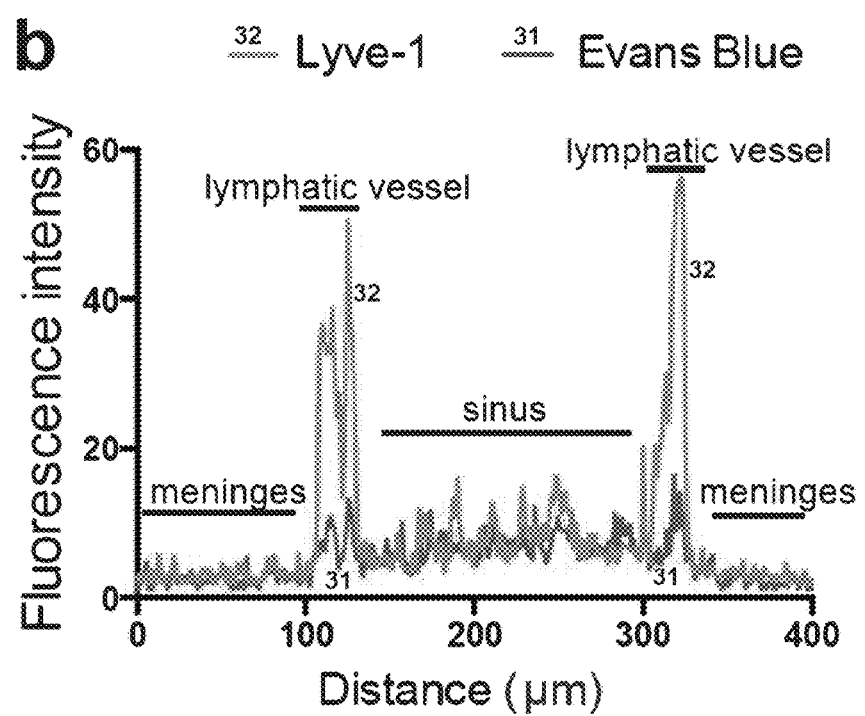
Figure 11C:
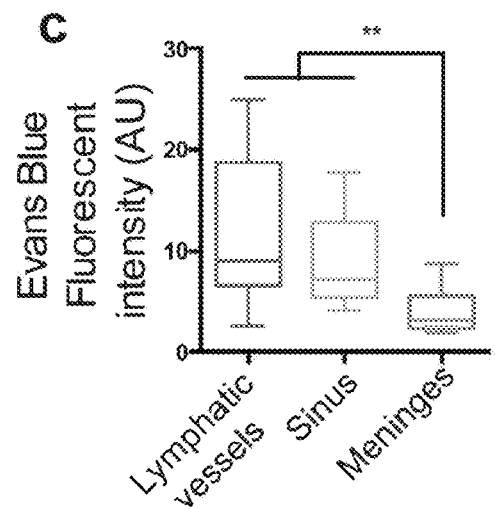
Figure 11D:
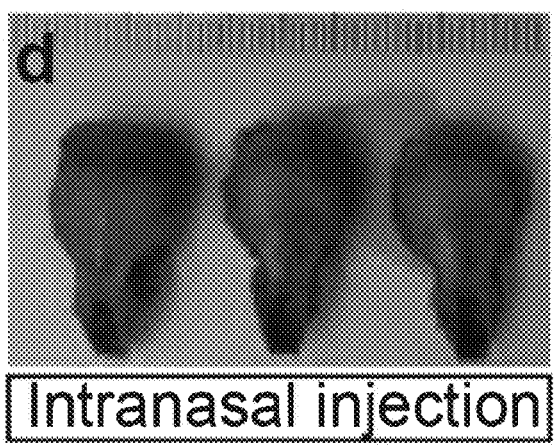
Figure 11E:
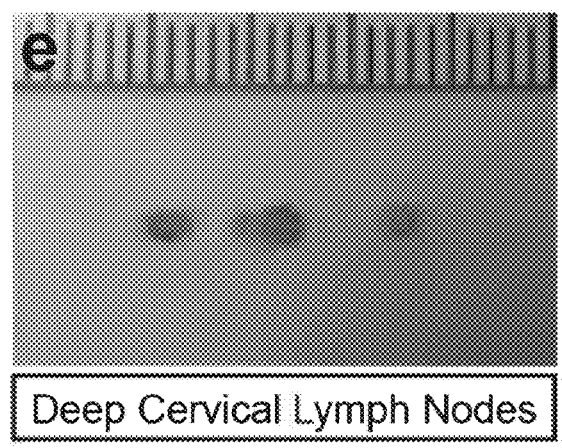
Figure 12A:
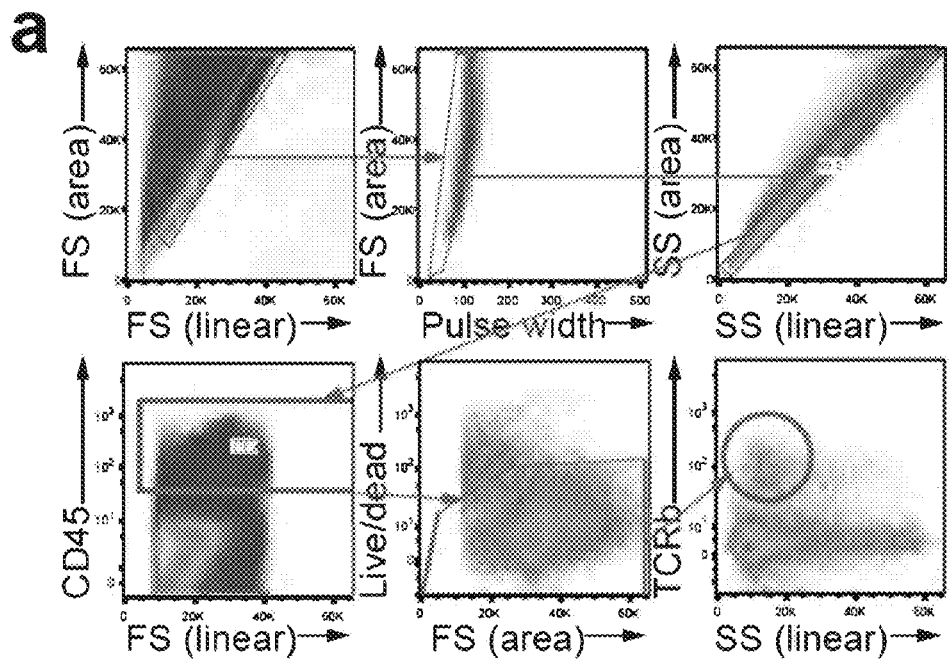
Figure 12B:
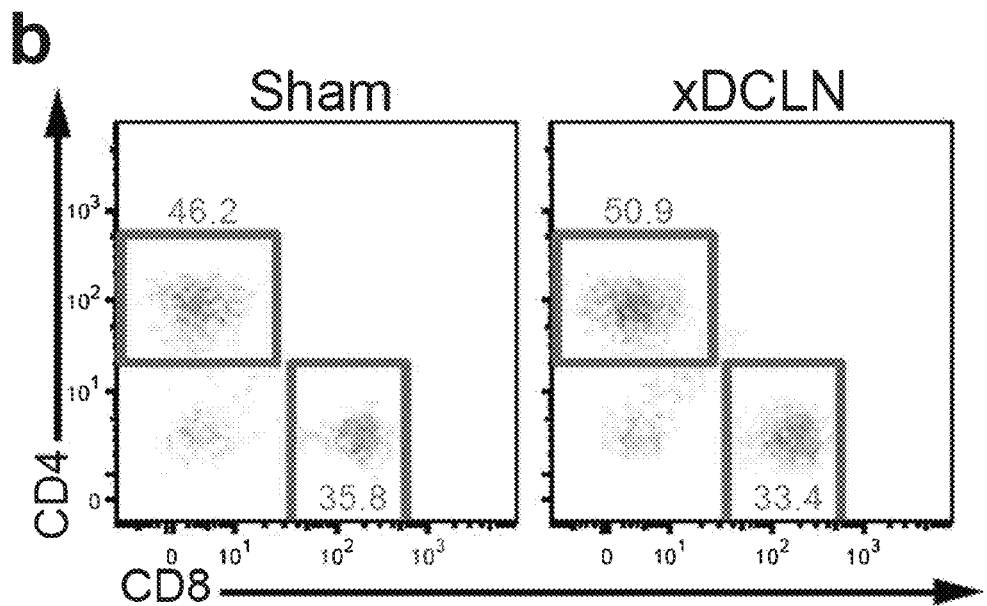
Figure 12C:
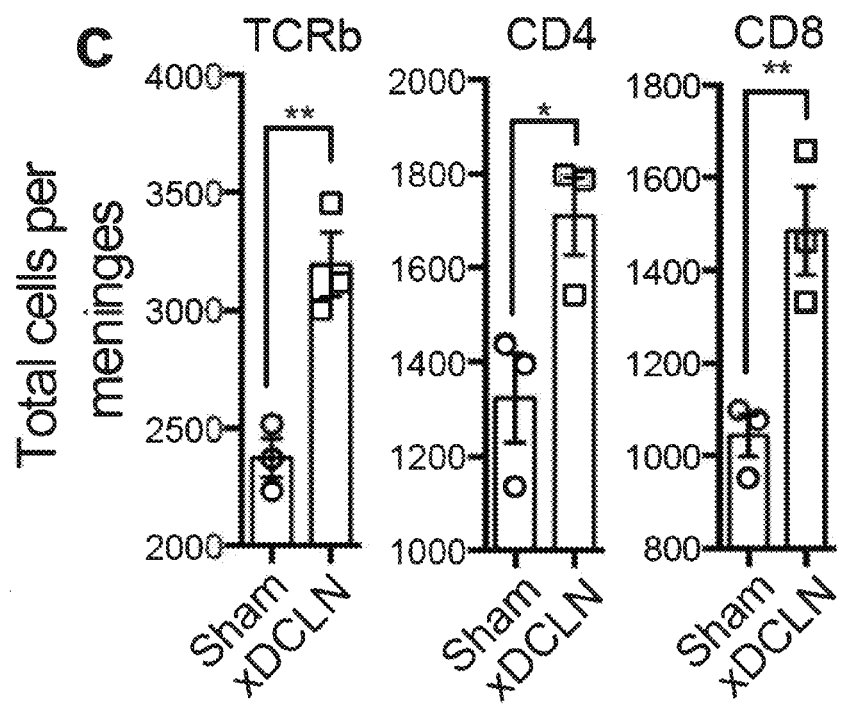
Figure 12D:
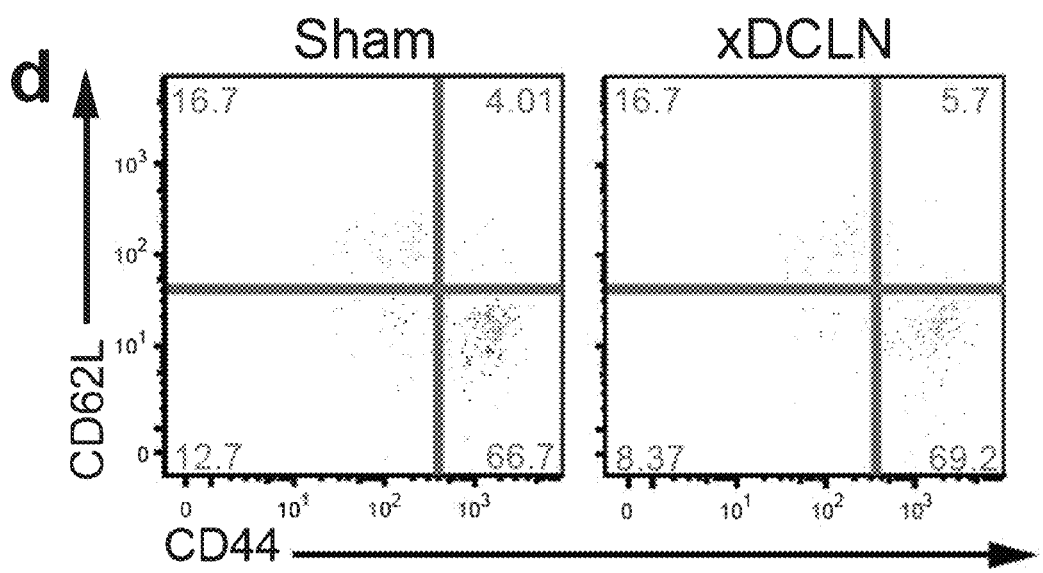
Figure 12E:
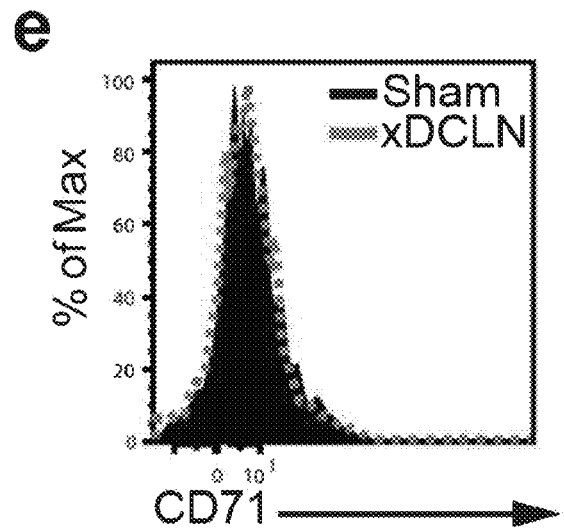
Figure 12F:
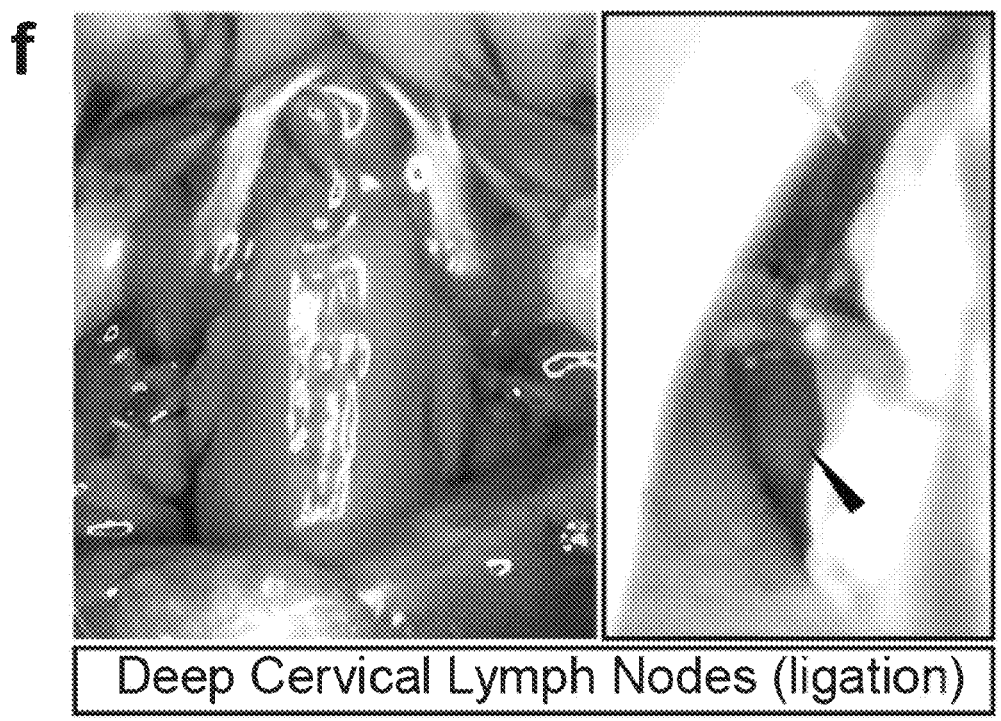
Figure 13A:
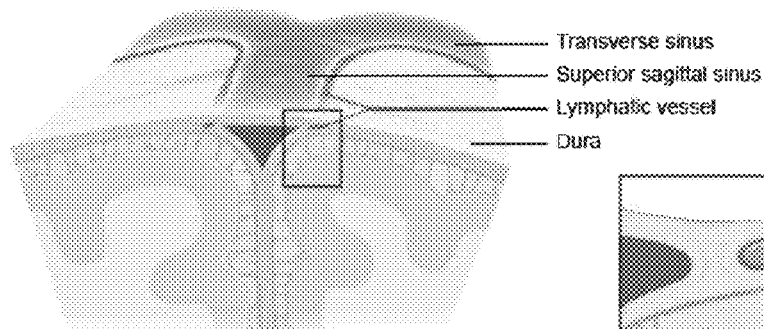
FIGS. 13A and 13B are schematic diagrams showing connection between the glymphatic system and the meningeal lymphatic system. A schematic representation of a connection between the glymphatic system, responsible for collecting of the interstitial fluids from within the central nervous system parenchyma to cerebrospinal fluid, and our newly identified meningeal lymphatic vessels.
Figure 13B:
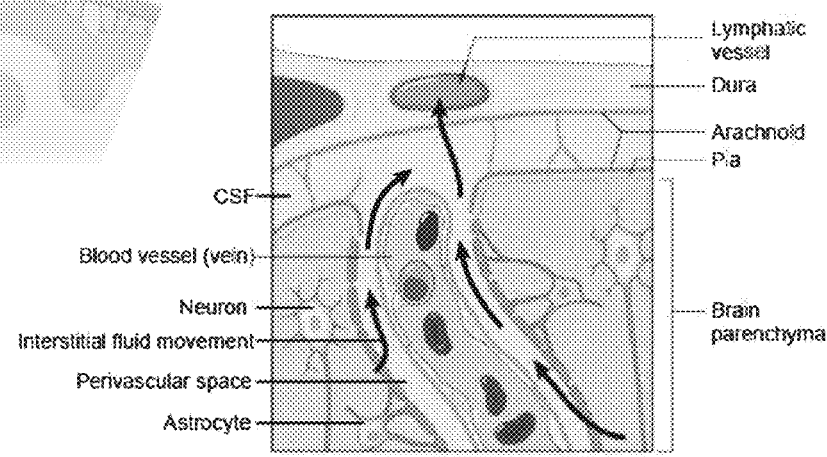
Figure 14A:
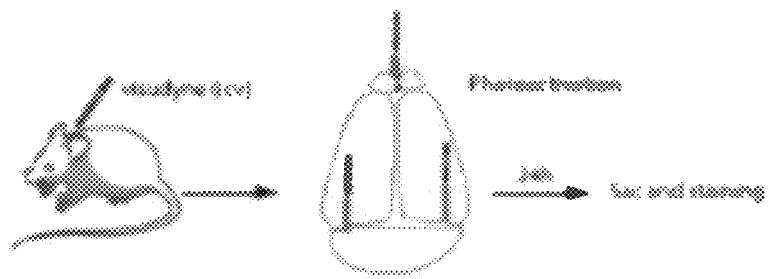
FIGS. 14A-C are a series of microscope images and graphs showing photoablation of meningeal lymphatics.
Figure 14B:
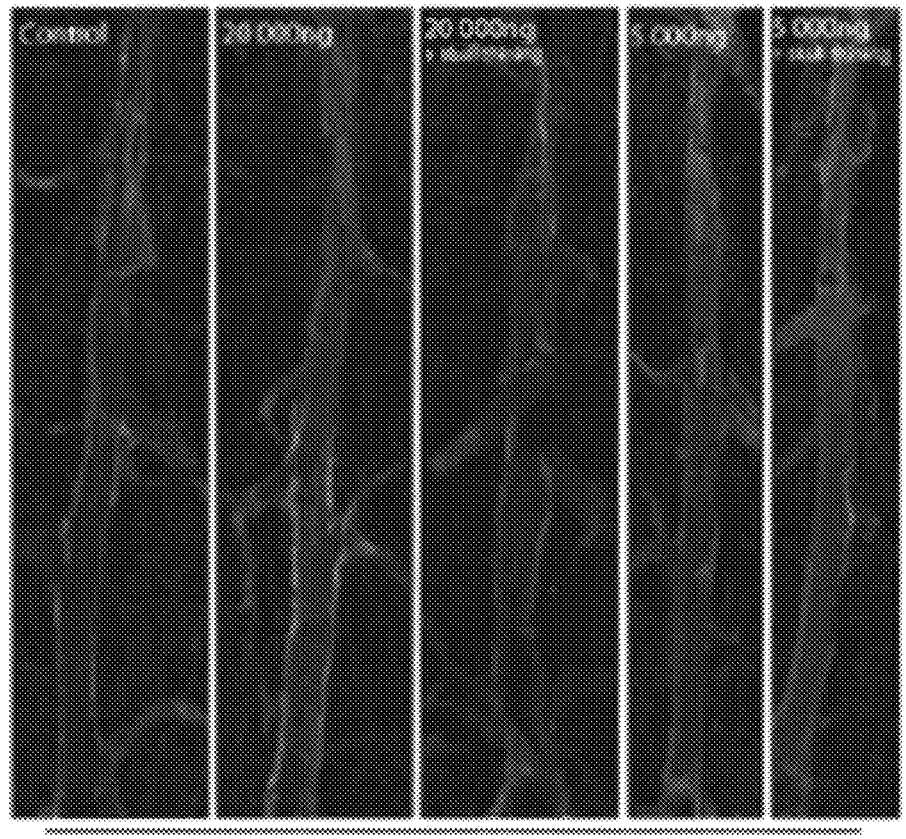
Figure 14C:
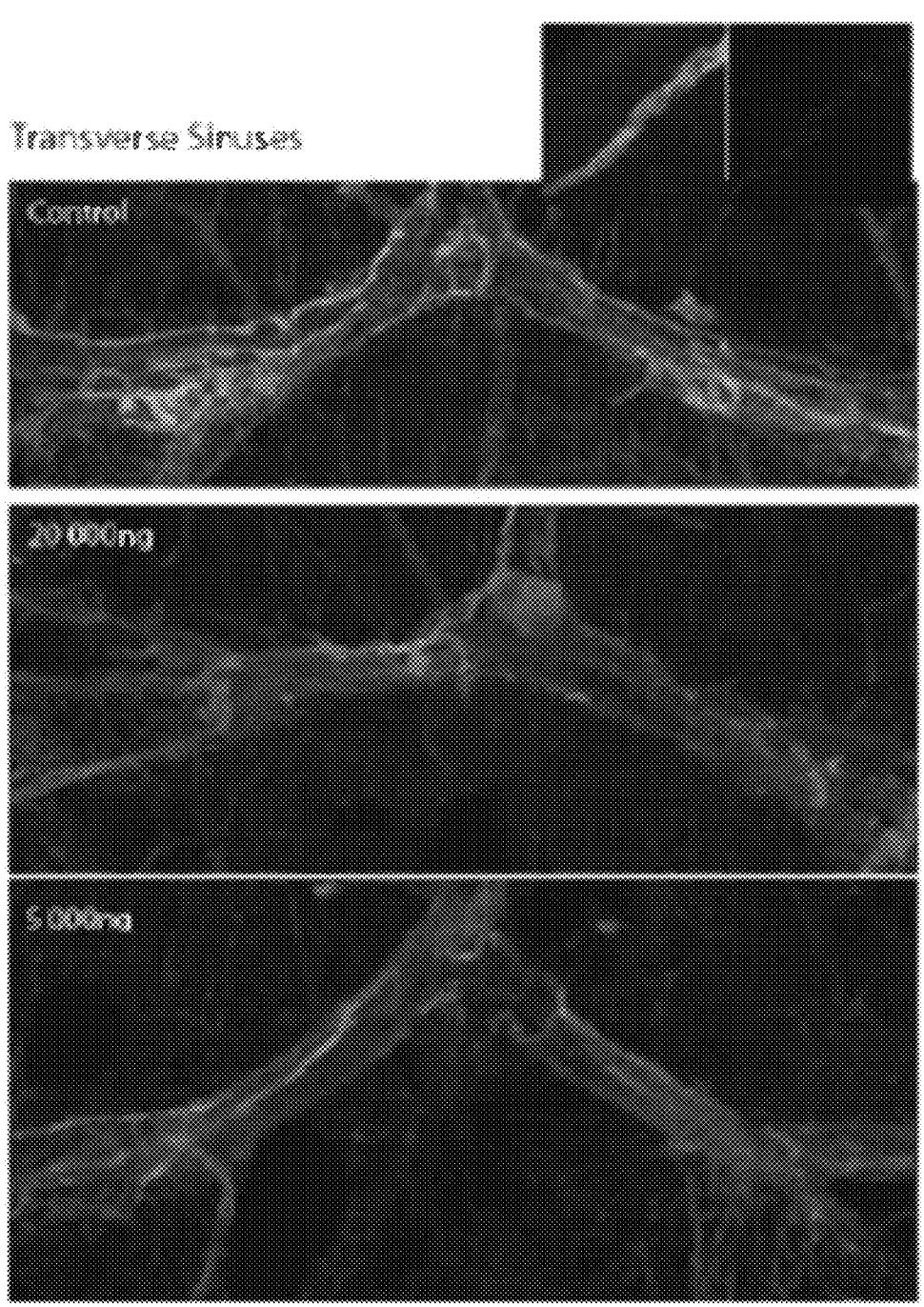
Figure 16A:
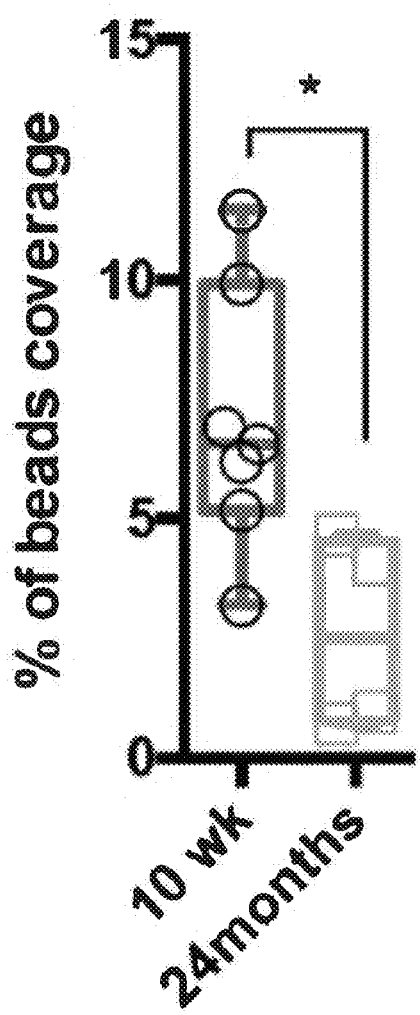
FIGS. 16A-B are a series of graphs showing impairment of lymphatic drainage in aged (24 months) and in J20 mice.
Figure 16B:
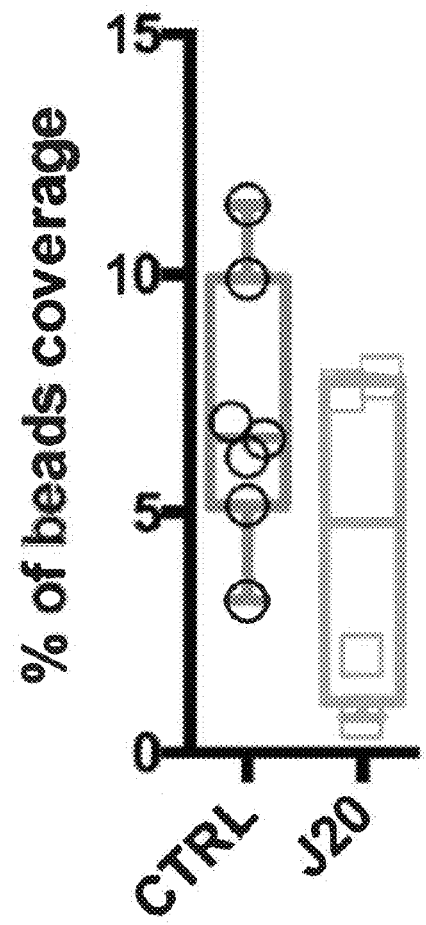
Figure 17A:
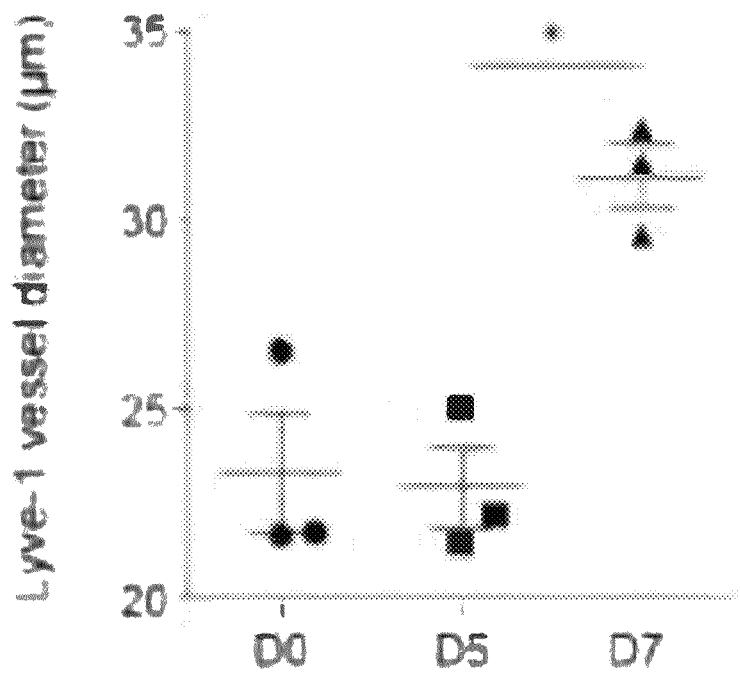
FIGS. 17A-D are a series of graphs and microscope images showing meningeal immunity and meningeal lymphatic vessels during EAE.
Figure 17B:
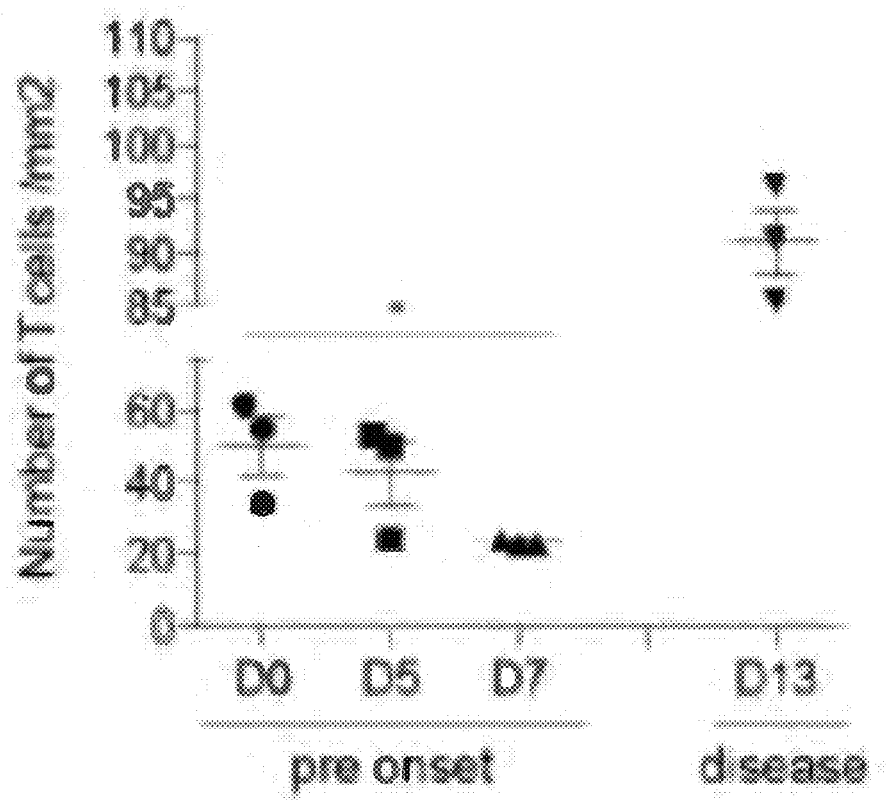
Figure 17C:
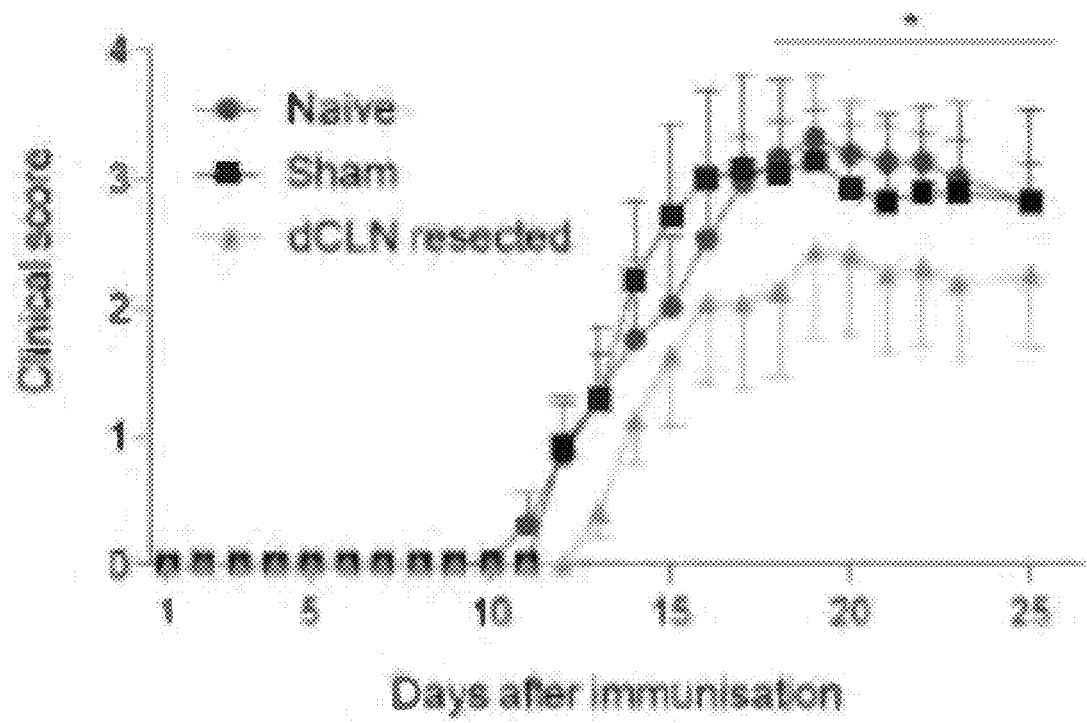
Figure 17D:
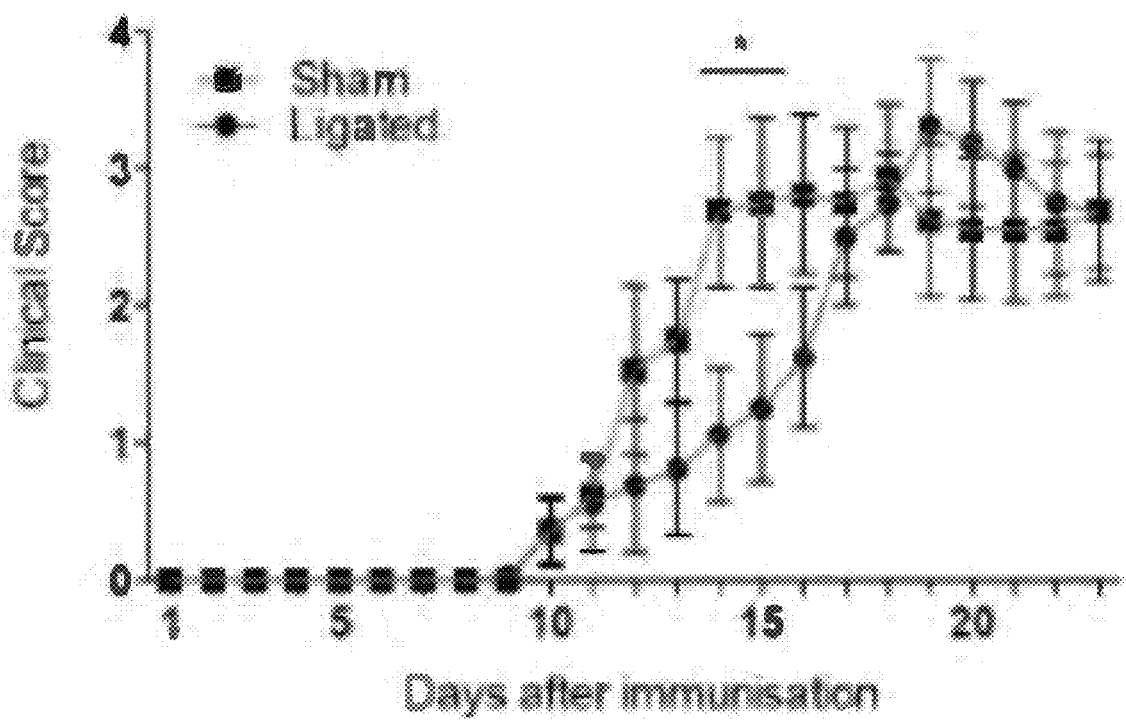
Figure 17D:
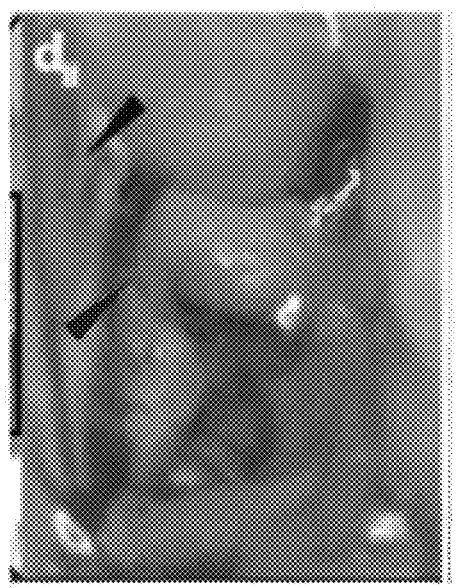
Figure 18A:
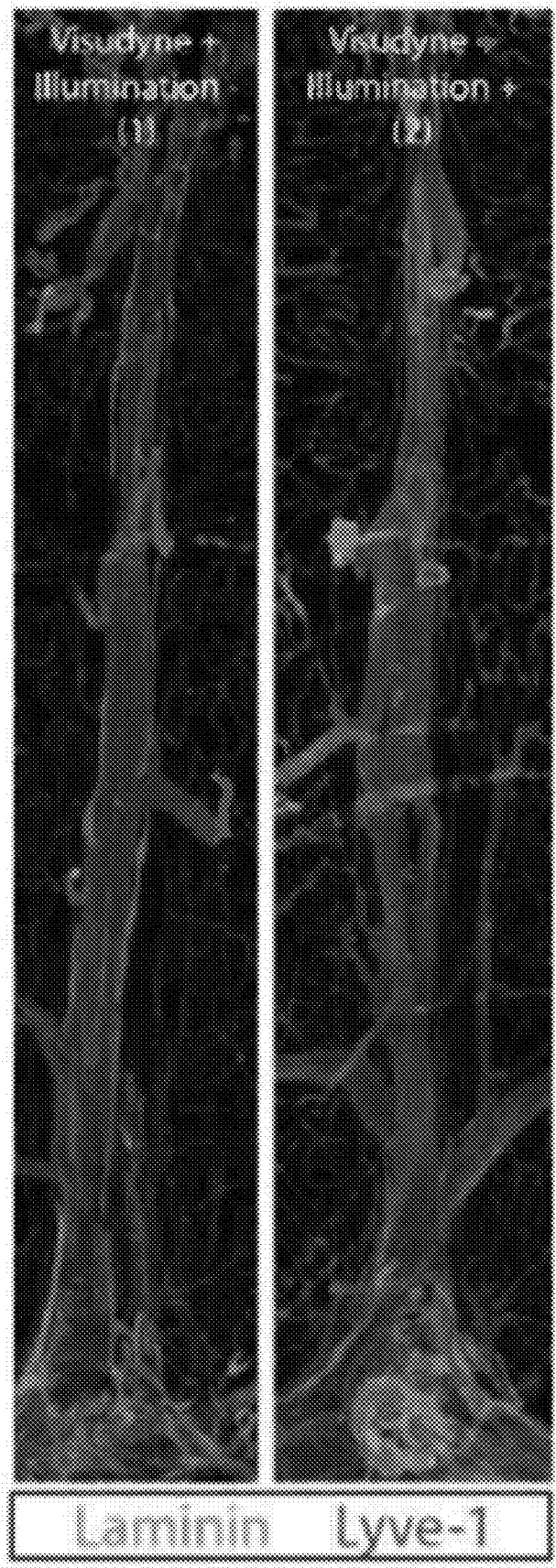
FIGS. 18A-D are a series of microscope images and graphs showing photoablation of meningeal lymphatic vessels.
Figure 18B:
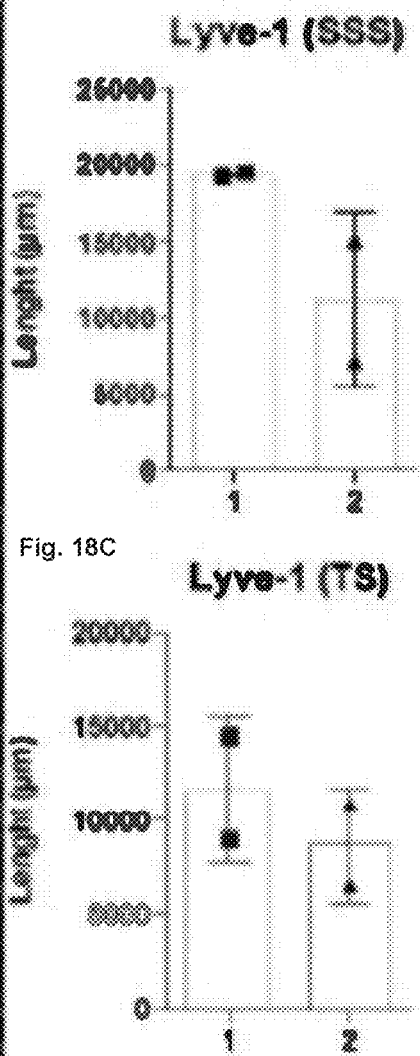
Figure 18C:
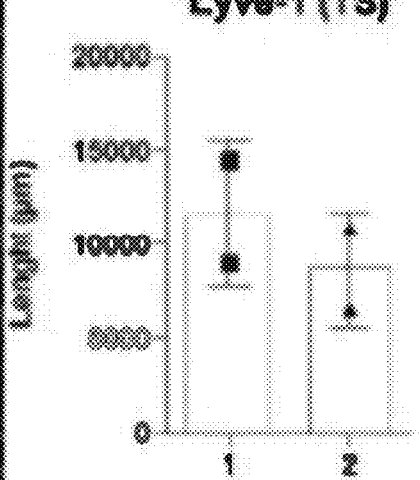
Figure 18D:
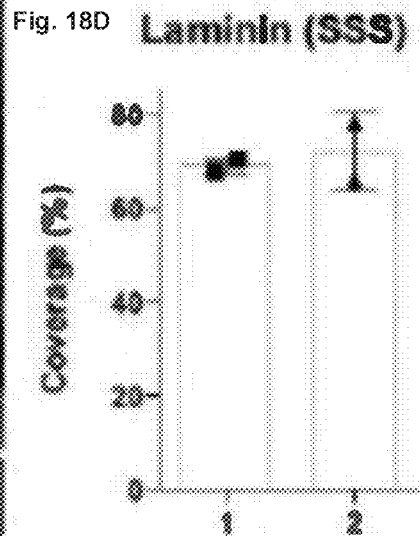
Figure 19A:
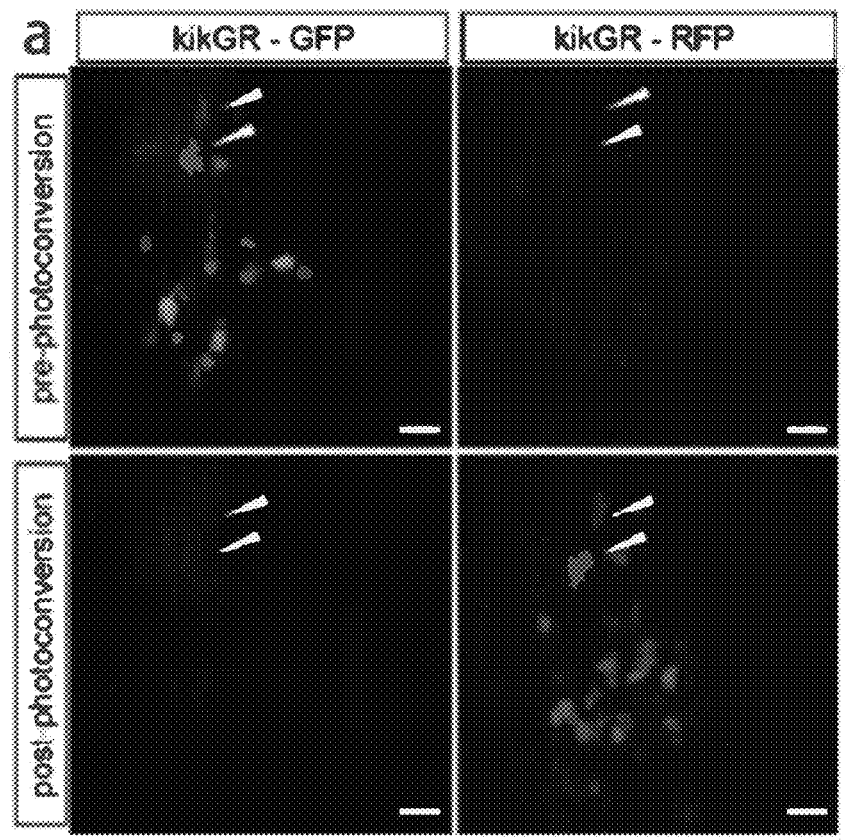
FIGS. 19A-C are a series of images showing in vivo photoconversion of meningeal T cells expressing KikGR.
Figure 19B:
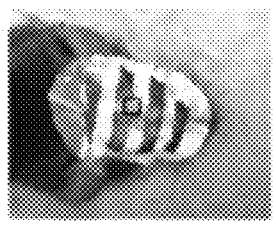
Figure 19C:
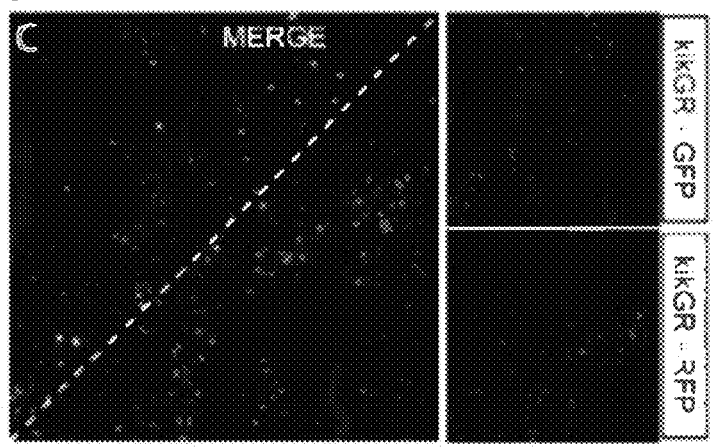
Figure 20A:
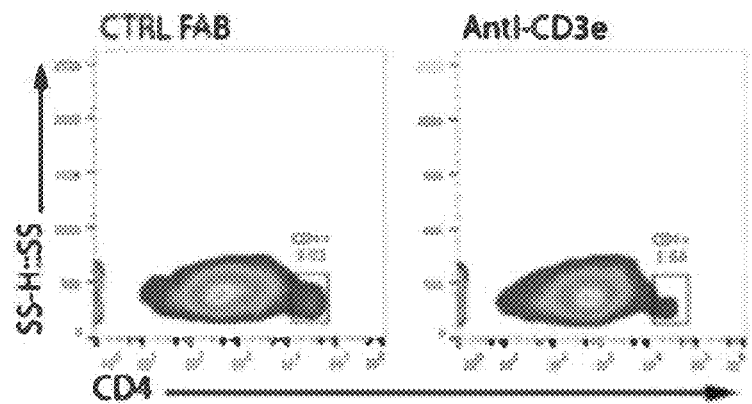
FIGS. 20A-C are a series of images showing meningeal T cell depletion. Adult mice were transcranially injected with 15 µg of anti-mCD3e f(ab')2 or control f(ab')2 every other day for 6 days. Meninges were harvested 4 days after the last injection.
Figure 20B:
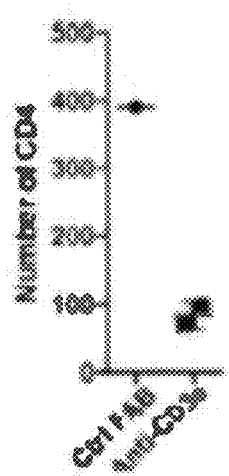
Figure 20C:
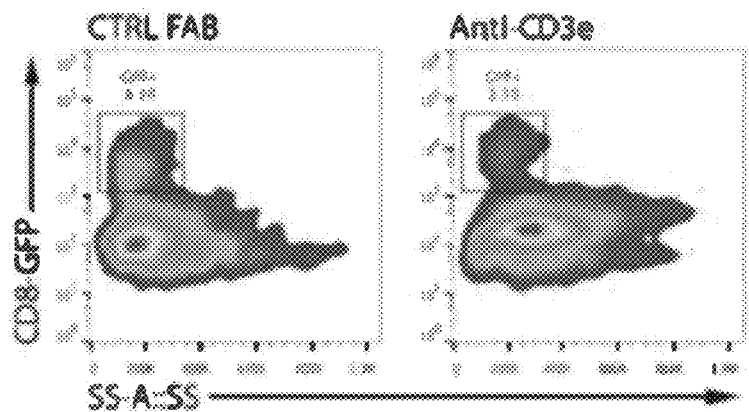
Figure 21A:
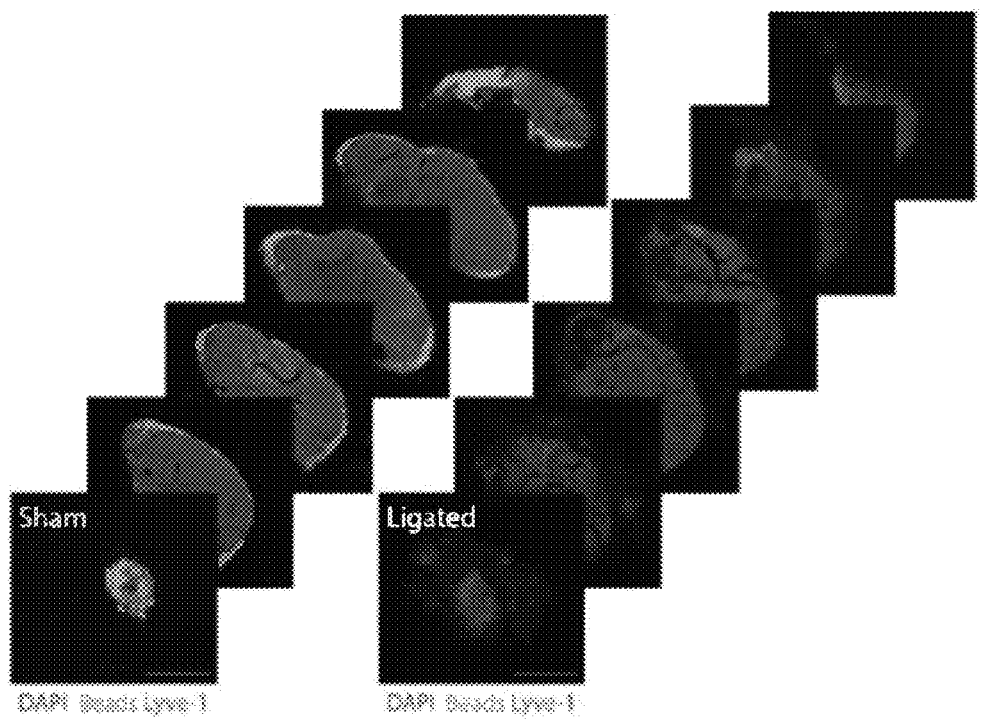
FIGS. 21A-B are a series of images and a graph showing assessment of lymphatic drainage efficiency. Adult C57B16 mice were ligated or sham operated. Fifteen hours after the ligation, 5 µl of 0.5 µm diameter fluorescent beads were injected into the right lateral ventricle at a rate of 0.5 µl/min. 30 min after the injection, the deep cervical lymph nodes were harvested, sliced (30 µm thick) and strained for DAPI and lymphatic vasculature. The whole lymph nodes were imaged and the coverage of bead was measured.
Figure 21B:
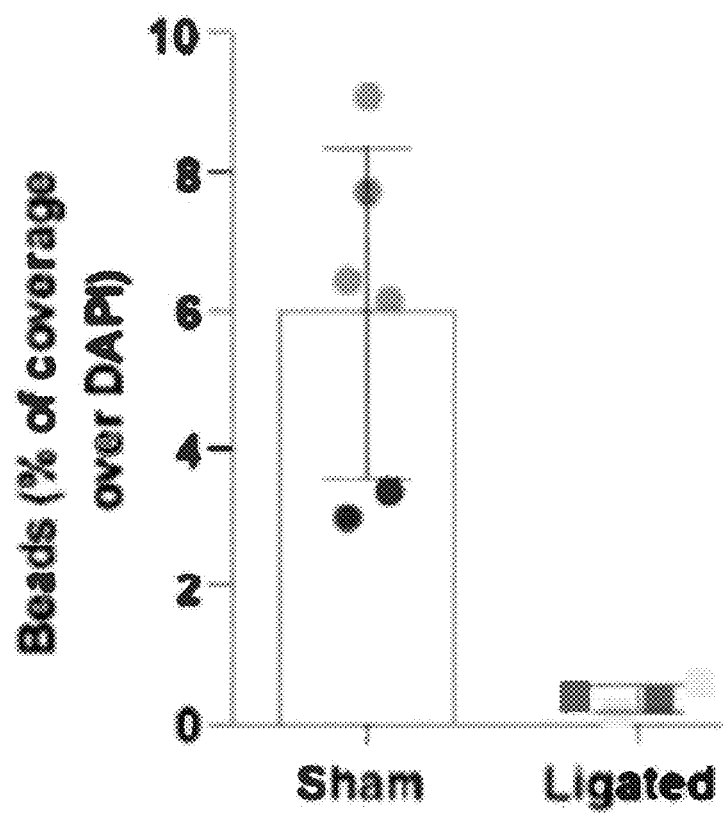
Figure 22:
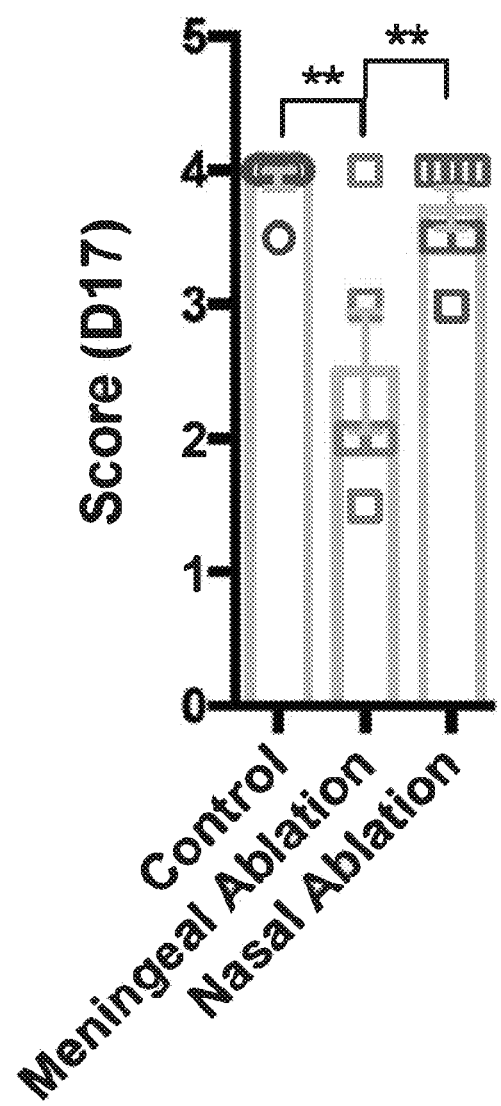
FIG. 22 is a graph showing ablation of the meningeal lymphatic decreases EAE score. Adult C57b16 mice were injected ICV (cisterna *magna*) or intranasally with Visudyne that was then photoconverted (Meningeal ablation) or not (Control). On the same day, EAE was induced by injected MOG 35-55 emulsion subcutaneously. At day 17 mice were scored prior to sacrifice (brain, meninges, and spinal cord were harvested for IHC to measure the amount of demyelination and the infiltrate). This experiment also demonstrates that the ablation of the meningeal lymphatic system decreases disease severity.

T cells from mice will be used, ubiquitously expressing a photoconvertible fluorescent protein, and transfer them into T cell deficient hosts to study the kinetics of T cell migration into the meninges (Nowotschin, S. & Hadjantonakis, A. K. Use of KikGR a photoconvertible green-to-red fluorescent protein for cell labeling and lineage analysis in ES cells and mouse embryos. *BMC developmental biology* 9, 49, doi: 10.1186/1471-213X-9-49 (2009)). T cells will be photolabeled (green-to-red fluorescence: FIG. 9) in the sinusal area through the skull, or in the deep cervical lymph nodes, using survival surgery procedure. After labeling, dynamics of T cell migration into the meninges will be studied during the resting state, and after EAE induction using two-photon microscopy, histological examination and flow cytometry. We expect T cells to recirculate between meninges and the deep cervical lymph nodes at a certain rate in healthy mice. This rate is expected to change upon EAE induction, when T cells are supposedly leaving meningeal spaces for massive proliferation in the deep cervical lymph nodes and then return and attack the brain.

PD-L is highly expressed on brain lymphatic endothelial cells (data not shown) and we suggest it mediates tolerance to brain antigens. Mice will be injected with anti-PD-L1 neutralizing antibodies i.c.v. with EAE induction.

A decrease in number of T cells around the sinuses during early onset EAE was shown, suggesting that these T cells recirculate into the deep cervical lymph nodes for re-activation. We will irradiate the meningeal area of the mice (using gamma-knife irradiation) prior to CFA/Mog immunization and 7 days after immunization (the time point when T cells are seen leaving the meningeal spaces). Immune response at the spinal cord, cerebellum, deep cervical lymph nodes, and meninges will be assessed at day 15 post immunization. Another group will be kept for 3 weeks for behavioral evaluation and then sacrificed for a histological examination of the CNS.

Figure 3C:
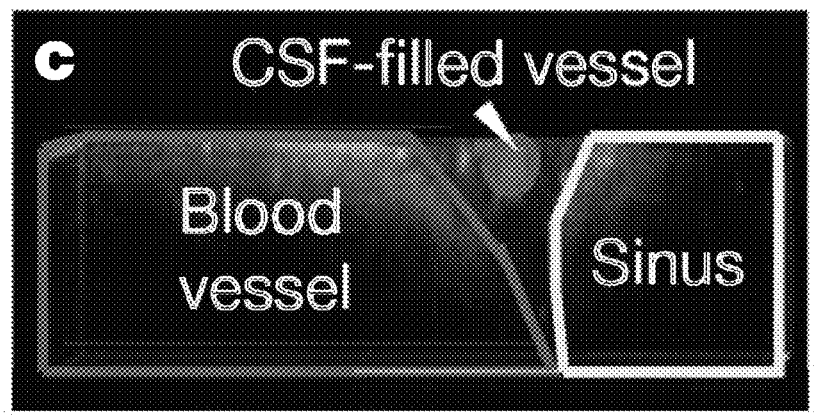
Figure 3D:
Figure 3E:
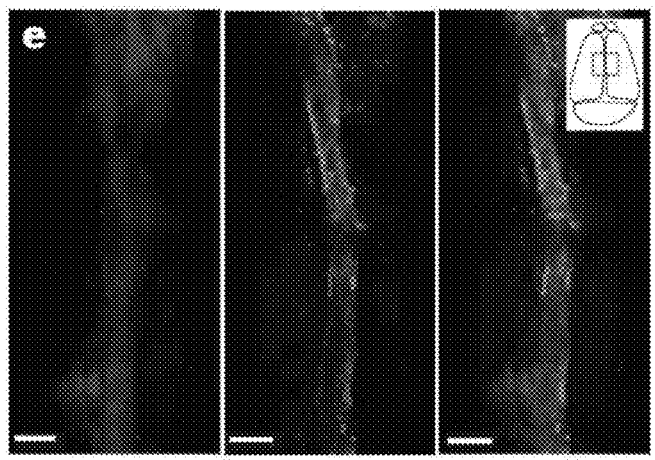
Figure 3F:
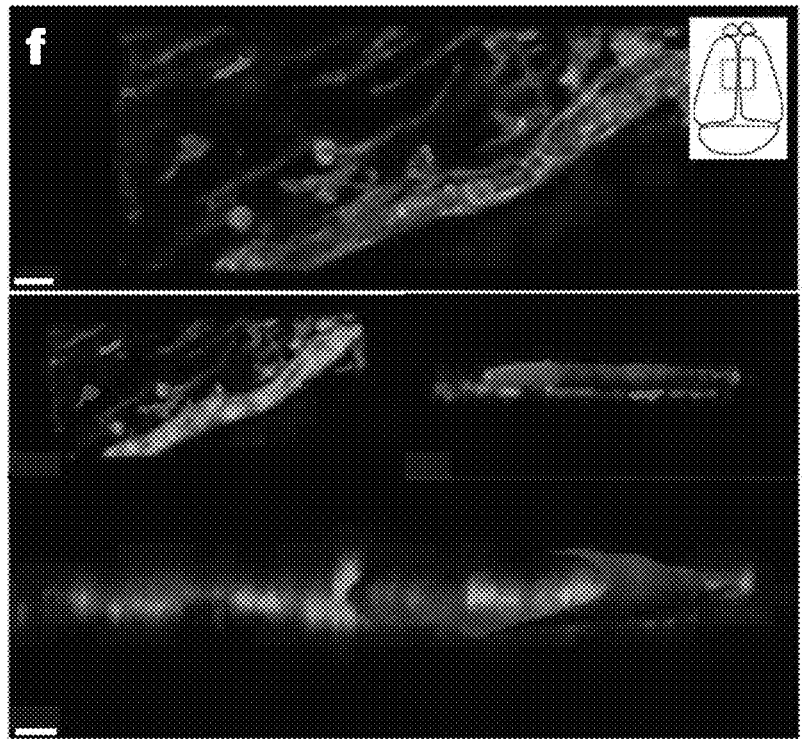
Figure 3G:
Figure 3H:
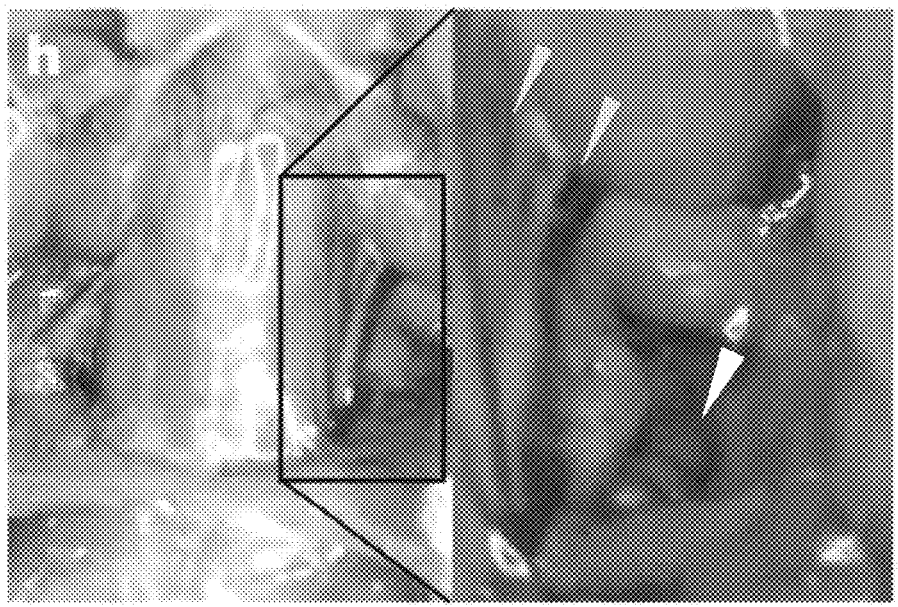
Figure 3I:
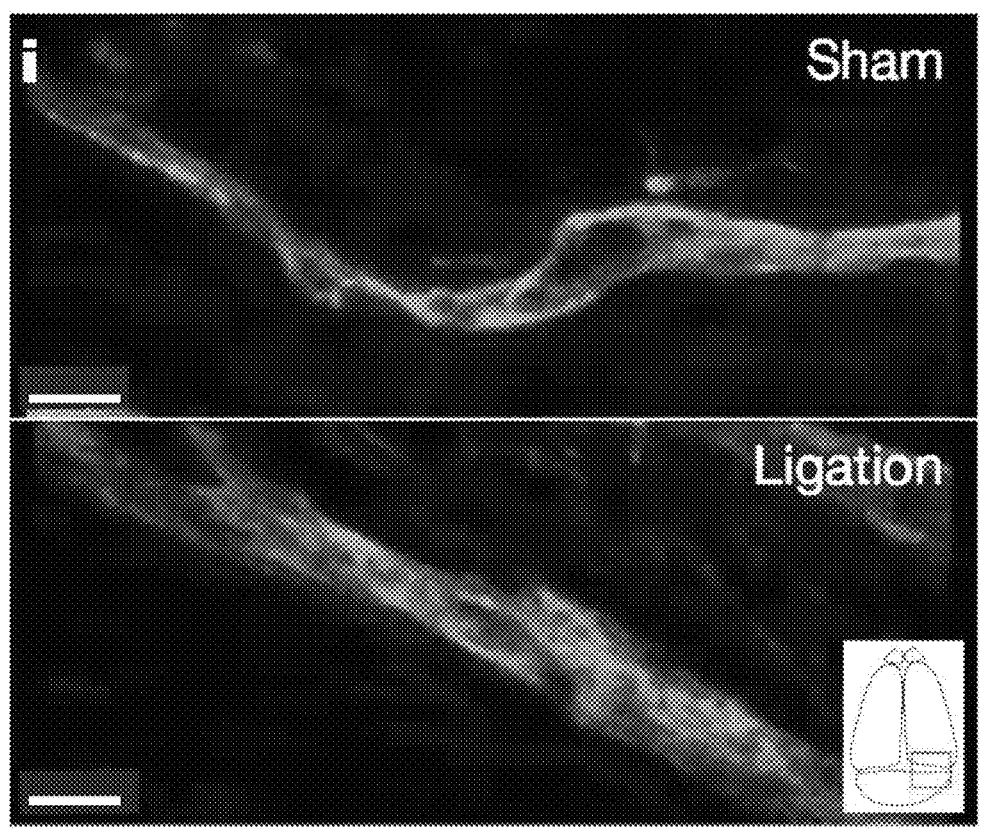
Figure 3J:
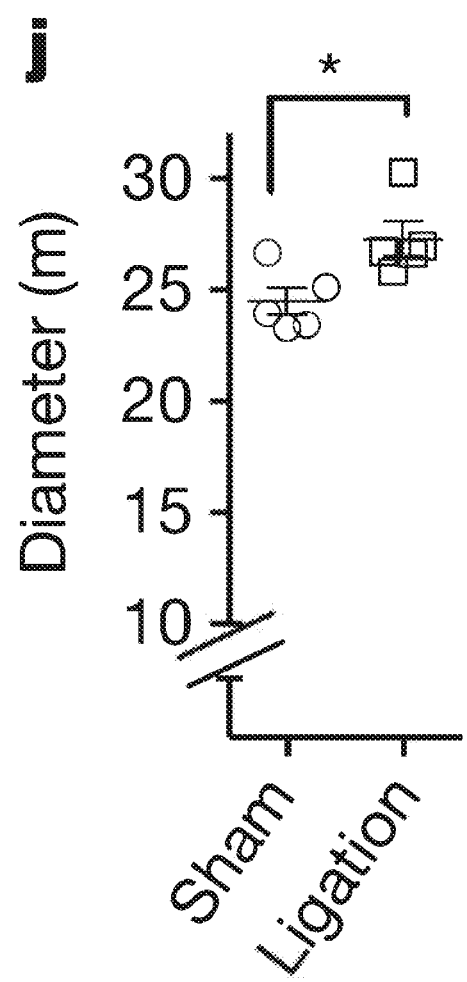
Figure 4A:
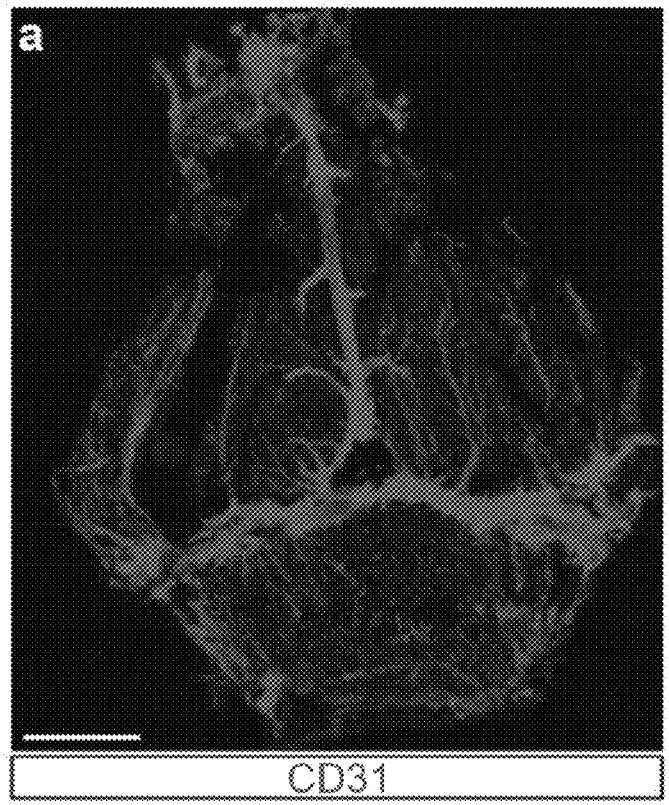
FIGS. 4A-G show meningeal immunity and lymphatic vessels in the dural sinuses.
Figure 4B:
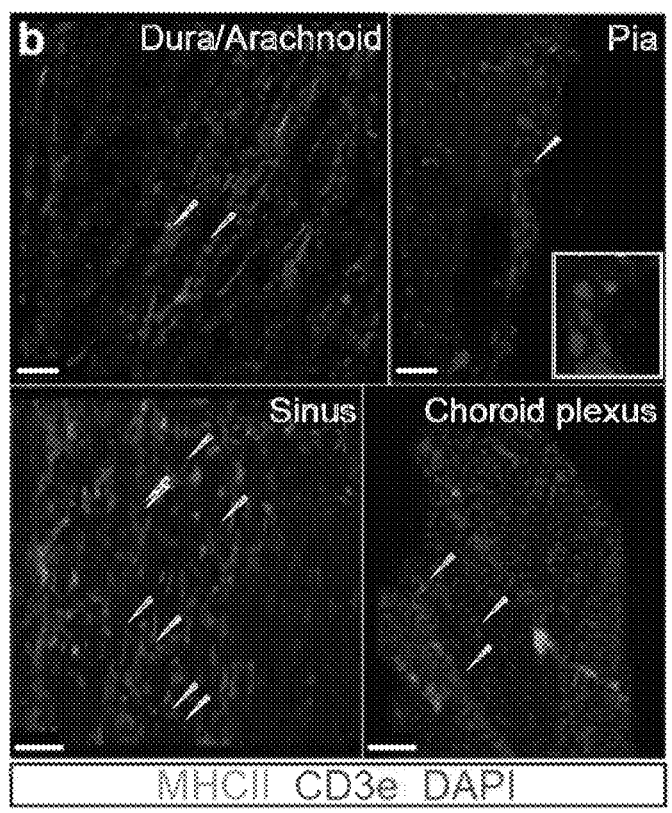
Figure 4C:
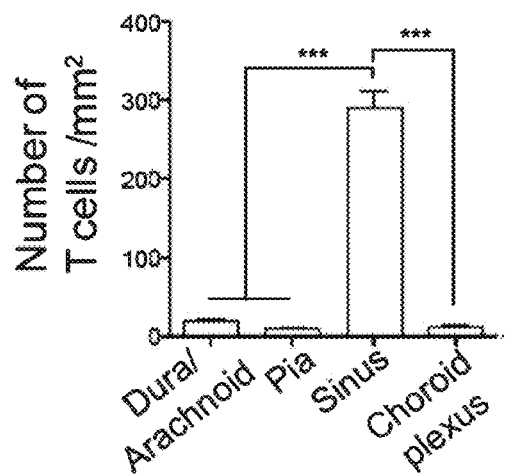
Figure 4D:
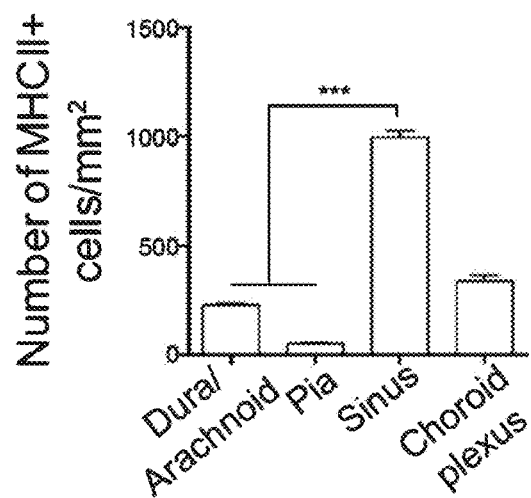
Figure 4E:
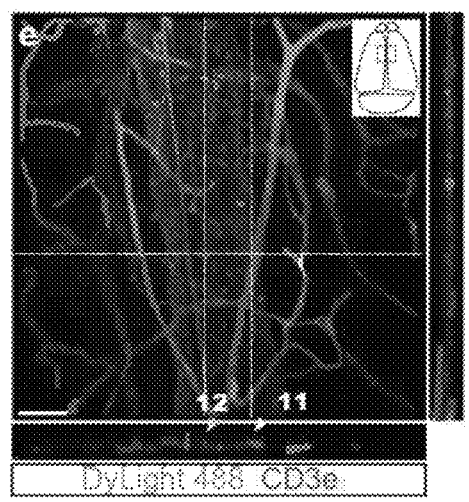
Figure 4F:
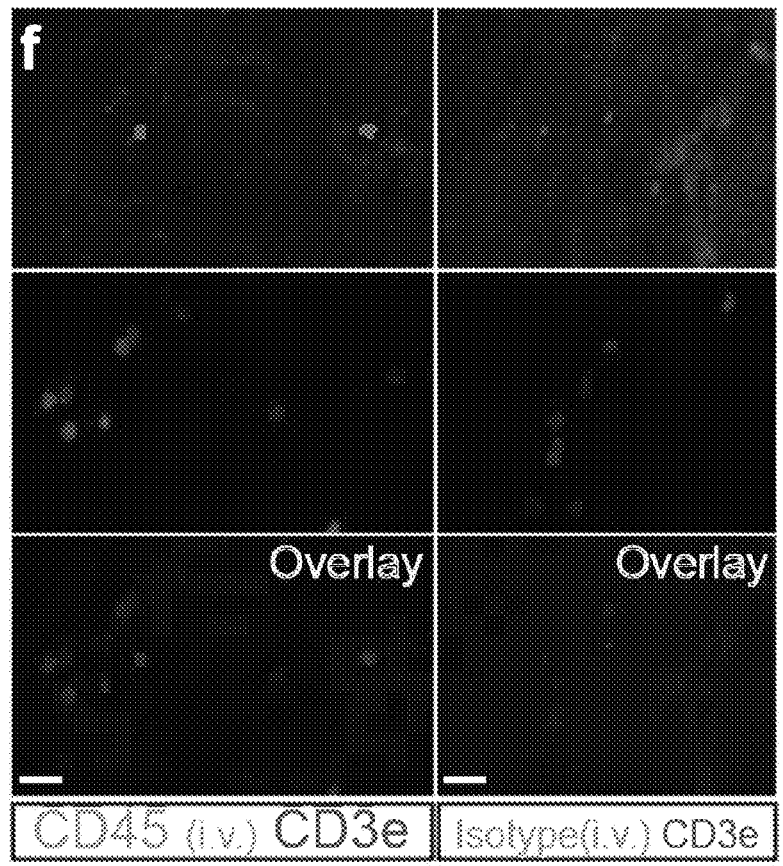
Figure 4G:
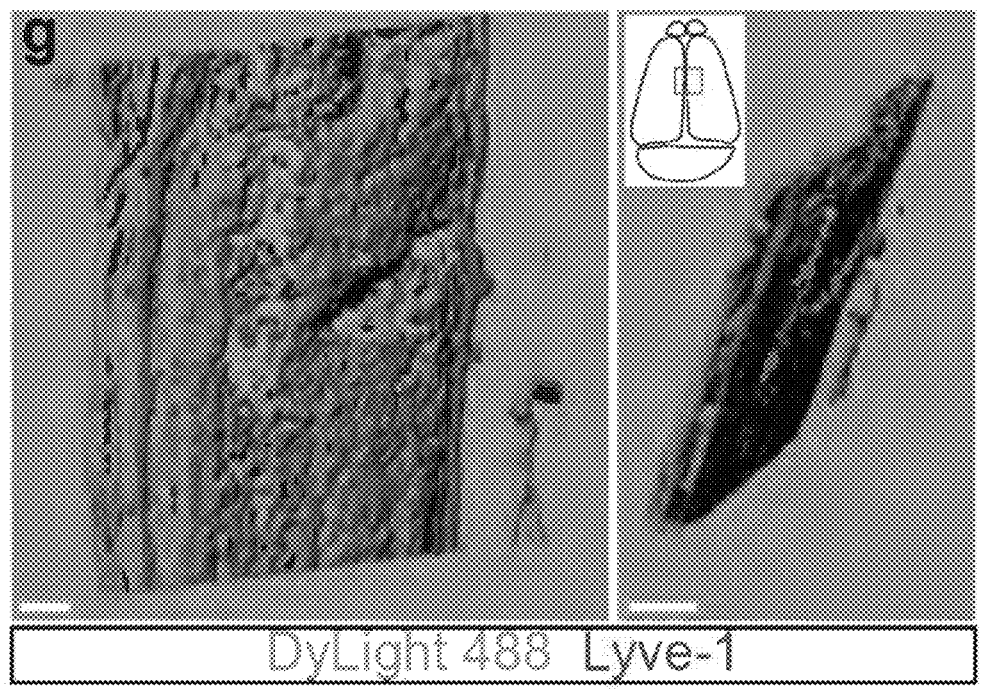

It was demonstrated that i.c.v. injection of VEGF-c results in increase in diameter of the meningeal lymphatic vessels (FIG. 3I, j above). Mice will be injected i.c.v. with VEGF-c immediately before EAE induction and EAE progression will be assessed. We expect that meningeal immune responses will be primed and boosted by expansion of the lymphatic vessels during EAE and we hypothesize this manipulation will result in a more severe EAE.

As described above, that ligation of lymphatic vessels as they access the deep cervical lymph nodes temporarily attenuates EAE (FIG. 7d above). Genetic ablation with a specific TAM-inducible cre mouse line, that drives expression in lymphatic endothelial cells (Lyve-creER) (Jang, J. Y. et al. Conditional ablation of LYVE-1+ cells unveils defensive roles of lymphatic vessels in intestine and lymph nodes. *Blood* 122, 2151-2161. doi:10.1182/blood-2013-01-478941 (2013)) is a potent method for peripheral lymphatic vessels. The transgenic mice are on B6 background, hence we will continue with Mog-induced EAE. I.c.v. TAM injection will be performed immediately prior to CFA/Mog immunization, 7 days after immunization (the time point when T cells are seen leaving the meningeal spaces), and day 10 post immunization (T cell numbers in the meningeal spaces were exploded when assessed at day 13 post immunization) to ensure prolonged ablation. Immune response at the spinal cord and cerebellum, and immune response in the meninges and the deep cervical lymph nodes will be assessed, including Teff activation and proliferation. Treg expansion, and intracellular cytokine expression (Th1 and Th17 profile of T cells) in all groups will be assessed at day 15 post immunization (early into clinical signs). Another group of mice will be kept for 3 weeks for behavioral evaluation and then sacrificed for a histological examination of the CNS.

Photoablation will be performed immediately prior to CFA/Mog immunization, 7 days after immunization (the time point when T cells are seen leaving the meningeal spaces), and day 10 post immunization (T cell numbers in the meningeal spaces were exploded when assessed at day 13 post immunization). Immune response at the spinal cord and cerebellum, and immune response in the meninges and the deep cervical lymph nodes will be assessed, including Teff activation and proliferation, Treg expansion, and intracellular cytokine expression (Th1 and Th17 profile of T cells) in all groups will be assessed at day 15 post immunization (early into clinical signs). Another group of mice will be kept for 3 weeks for behavioral evaluation and then sacrificed for a histological examination of the CNS. We expect the mice with photoablated lymphatics to exhibit reduced T cell activation, decreased number of Th1/Th17 cells, and ameliorated disease progression.

A specific depletion of meningeal T cells will be performed by transcranial application of a depleting anti-CD3e antibodies, an efficient procedure (FIG. 11).

Methods of Treatment:

Some aspects include methods of treating MS in a subject by administering to the subject a compound that decreases drainage of the meningeal lymphatic vessel(s), decreases the diameter of the meningeal lymphatic vessel(s), modulates contractility of the meningeal lymphatic vessel(s) to decrease drainage, and/or modulates the permeability of the meningeal lymphatic vessel(s).

In other embodiments, the method further comprises identifying a subject in need of said treatment. In further embodiments, the subject in need of said treatment is susceptible to or suffering from MS. Identification of such subjects may be made using techniques known to a person of ordinary skill in the art.

In some embodiments, a therapeutically effective amount of said compound is administered. In further embodiments, said compound is a vasoconstrictor. In further embodiments, said compound is selected from the group consisting of nitric oxide competitor NG-monomethyl L-arginine, cyclooxygenase inhibitors, and phosphatidylcholine.

In some embodiments, said therapeutically effective amount of the compound is about 0.00015 mg/kg to about 1.5 mg/kg. In further embodiments, said therapeutically effective amount of the compound is about 0.00015 mg/kg, about 0.00030 mg/kg, about 0.00045 mg/kg, about 0.00060 mg/kg, about 0.00085 mg/kg, about 0.001 mg/kg, about 0.0015 mg/kg, about 0.002 mg/kg, about 0.0025 mg/kg, about 0.003 mg/kg, about 0.0035 mg/kg, about 0.004 mg/kg, about 0.0045 mg/kg, about 0.0050 mg/kg, about 0.0055 mg/kg, about 0.006 mg/kg, about 0.0065 mg/kg, about 0.007 mg/kg, about 0.0075 mg/kg, about 0.008 mg/kg, about 0.0085 mg/kg, about 0.009 mg/kg, about 0.0095 mg/kg, about 0.01 mg/kg, about 0.015 mg/kg, about 0.02 mg/kg, about 0.025 mg/kg, about 0.03 mg/kg, about 0.035 mg/kg, about 0.040 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, or about 1.5 mg/kg.

In some embodiments, said therapeutically effective amount of the compound is less than about 0.00015 mg/kg, about 0.00030 mg/kg, about 0.00045 mg/kg, about 0.00060 mg/kg, about 0.00085 mg/kg, about 0.001 mg/kg, about 0.0015 mg/kg, about 0.002 mg/kg, about 0.0025 mg/kg, about 0.003 mg/kg, about 0.0035 mg/kg, about 0.004 mg/kg, about 0.0045 mg/kg, about 0.0050 mg/kg, about 0.0055 mg/kg, about 0.006 mg/kg, about 0.0065 mg/kg, about 0.007 mg/kg, about 0.0075 mg/kg, about 0.008 mg/kg, about 0.0085 mg/kg, about 0.009 mg/kg, about 0.0095 mg/kg, about 0.01 mg/kg, about 0.015 mg/kg, about 0.02 mg/kg, about 0.025 mg/kg, about 0.03 mg/kg, about 0.035 mg/kg, about 0.040 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, or about 1.5 mg/kg.

In some embodiments, said therapeutically effective amount of the compound is more than about 0.00015 mg/kg, about 0.00030 mg/kg, about 0.00045 mg/kg, about 0.00060 mg/kg, about 0.00085 mg/kg, about 0.001 mg/kg, about 0.0015 mg/kg, about 0.002 mg/kg, about 0.0025 mg/kg, about 0.003 mg/kg, about 0.0035 mg/kg, about 0.004 mg/kg, about 0.0045 mg/kg, about 0.0050 mg/kg, about 0.0055 mg/kg, about 0.006 mg/kg, about 0.0065 mg/kg, about 0.007 mg/kg, about 0.0075 mg/kg, about 0.008 mg/kg, about 0.0085 mg/kg, about 0.009 mg/kg, about 0.0095 mg/kg, about 0.01 mg/kg, about 0.015 mg/kg, about 0.02 mg/kg, about 0.025 mg/kg, about 0.03 mg/kg, about 0.035 mg/kg, about 0.040 mg/kg, about 0.045 mg/kg, about 0.05 mg/kg, about 0.055 mg/kg, about 0.06 mg/kg, about 0.065 mg/kg, about 0.07 mg/kg, about 0.075 mg/kg, about 0.08 mg/kg, about 0.085 mg/kg, about 0.09 mg/kg, about 0.095 mg/kg, about 0.1 mg/kg, about 0.15 mg/kg, about 0.2 mg/kg, about 0.25 mg/kg, about 0.3 mg/kg, about 0.35 mg/kg, about 0.4 mg/kg, about 0.45 mg/kg, about 0.5 mg/kg, about 0.55 mg/kg, about 0.6 mg/kg, about 0.65 mg/kg, about 0.7 mg/kg, about 0.75 mg/kg, about 0.8 mg/kg, about 0.85 mg/kg, about 0.9 mg/kg, about 0.95 mg/kg, about 1.0 mg/kg, about 1.1 mg/kg, about 1.2 mg/kg, about 1.3 mg/kg, about 1.4 mg/kg, or about 1.5 mg/kg.

In some embodiments, the compound is provided in soluble form. In some embodiments, the compound is provided absorbed in nanogels for slow and constant release. In certain embodiments, the compounds are provided on viral vectors which encode for the reagent that is a RNA or polypeptide.

In some aspects, the compound is administered into the cerebrospinal fluid (CSF) of the subject. In other aspects, an ointment comprises said compound and the ointment is administered via application of the ointment to the head of the subject.

Additional options are set forth below:

In some embodiments, a method of treating a condition with a neurological pathology in a subject is provided. The method can comprise administering to the subject a therapeutically effective amount of a compound that modulates one or more of a) drainage of the meningeal lymphatic vessels; b) diameter of the meningeal lymphatic vessels; c) lymphangiogenesis of the meningeal lymphatic vessels; d) contractility of the meningeal lymphatic vessels; and/or e) permeability of the meningeal lymphatic vessels. In some embodiments, the administration is into the cerebrospinal fluid (CSF) of said subject. In some embodiments, an ointment comprises said compound and wherein the administration is via application of the ointment to the head. In some embodiments, the method further comprises identifying a subject in need of said treatment. In some embodiments, the subject in need of said treatment is susceptible to or suffering from a disorder selected from the group consisting of Alzheimer's disease (AD), dementia, Parkinson's disease, cerebral edema, amyotrophic lateral sclerosis (ALS), Pediatric Autoimmune Neuropsychiatric Disorders Associated with Streptococcal Infections (PANDAS), meningitis, hemorrhagic stroke, autism spectrum disorder (ASD), brain tumor, and epilepsy, or a combination of any of the listed disorders. In some embodiments, the administration increases drainage and/or increases diameter of the meningeal lymphatic vessels. In some embodiments, the administration increases drainage and/or increased diameter of the meningeal lymphatic vessels; and wherein the subject in need of said treatment is susceptible to or suffering from a disorder selected from the group consisting of Alzheimer's disease (AD) and brain tumor, or a combination of the two. In some embodiments, the compound is a vasodilator. In some embodiments, the administration decreases drainage and/or decreases diameter of the meningeal lymphatic vessels. In some embodiments, the administration decreases drainage and/or decreases diameter of the meningeal lymphatic vessels; and wherein the subject in need of said treatment is susceptible to or suffering from multiple sclerosis (MS). In some embodiments, the compound is a vasoconstrictor.

In some embodiments, a method of treating Alzheimer's disease in a subject is provided. The method can comprise administering to the subject a therapeutically effective amount of a growth factor into the cerebrospinal fluid (CSF) of the subject, wherein the growth factor is selected from the group consisting of VEGF-c, VEGF-d, and FGF2. In some embodiments, the method further comprises identifying a subject in need of said treatment. In some embodiments, a viral vector is administered into the CSF and said viral vector encodes the growth factor. In some embodiments, the viral vector is soluble. In some embodiments, the viral vector is absorbed in a nanogel prior to administration.

In some embodiments, a method of treating MS in a subject is provided. The method can comprise ligating one or more meningeal lymphatic vessel in said subject. In some embodiments, the method further comprises identifying a subject in need of said treatment.

Below are non-limiting examples of some embodiments herein:

EXAMPLES

Figure 23A:
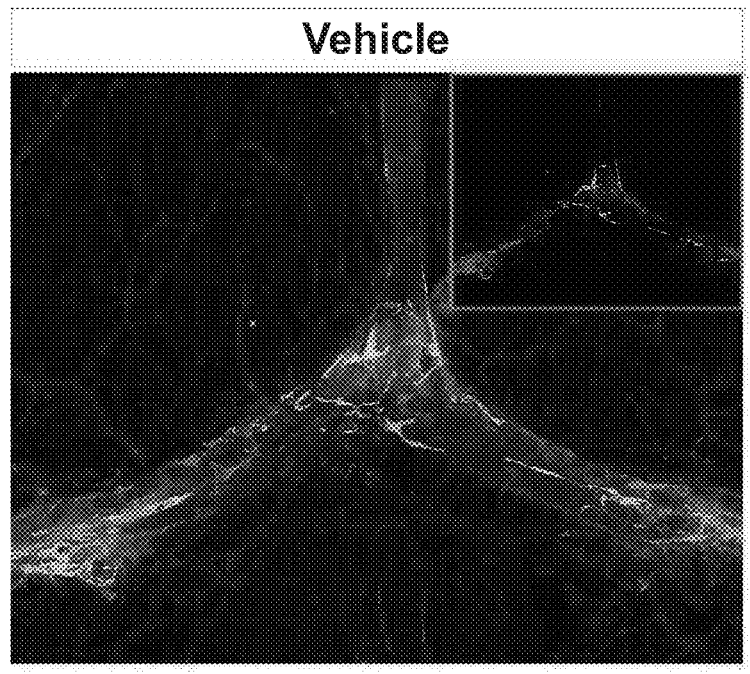
FIGS. 23A-H are a series of microscope images and graphs showing that that impairing meningeal lymphatic drainage in adult mice in accordance with some embodiments affects brain fluid homeostasis.
Figure 23B:
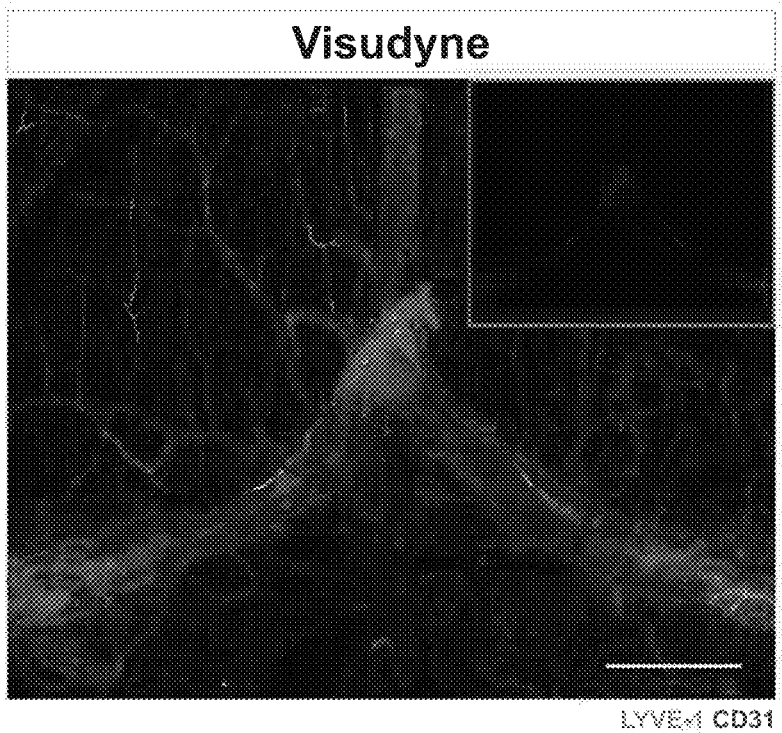
Figure 23C:
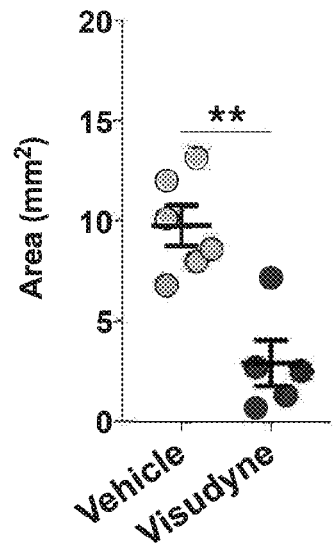
Figure 23D:
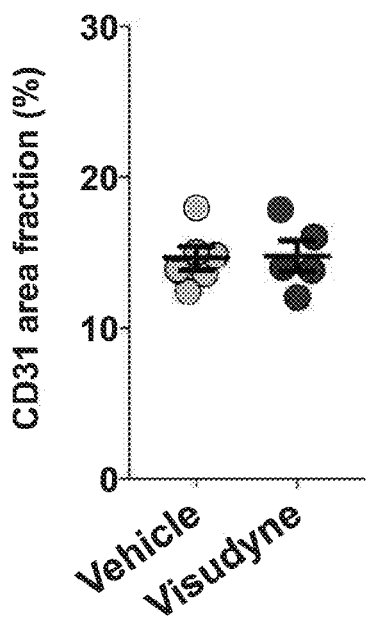
Figure 23E:
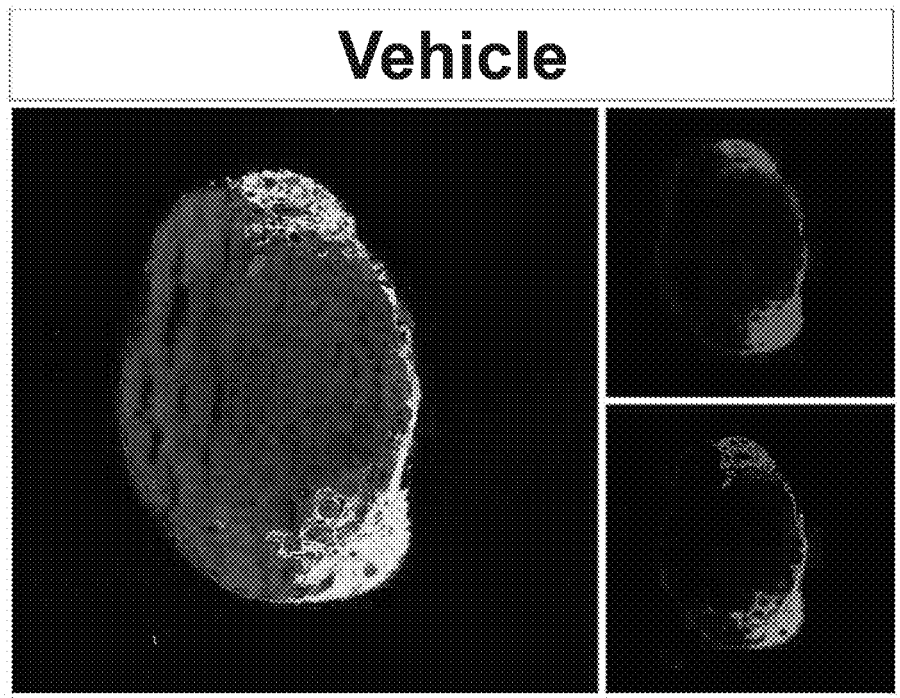
Figure 23F:
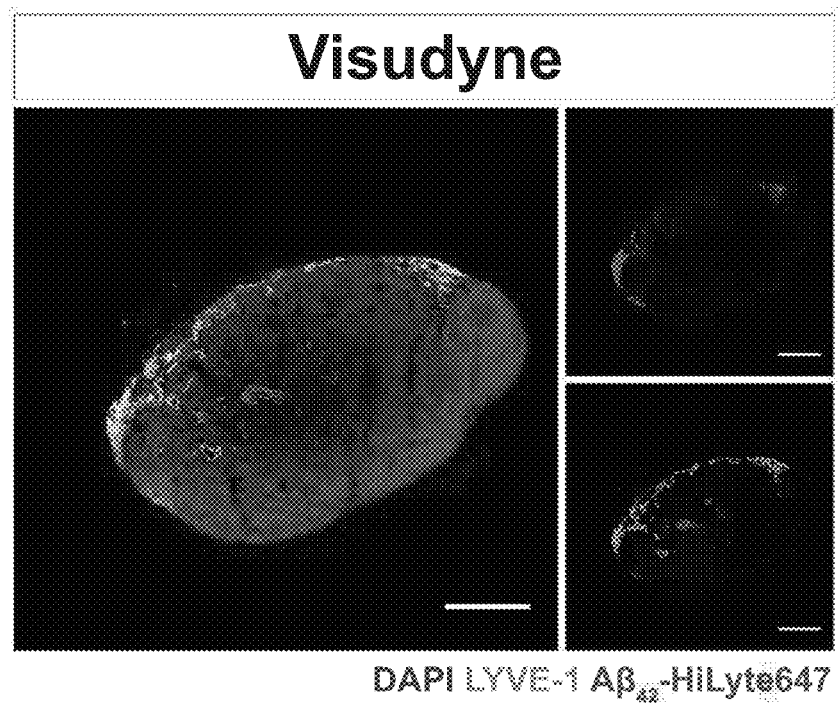
Figure 23G:
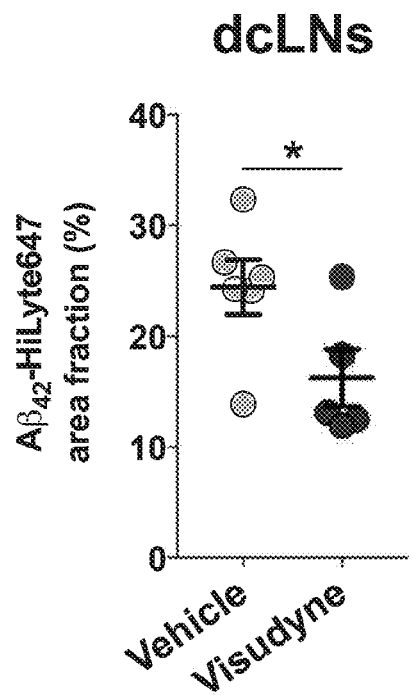
Figure 23H:
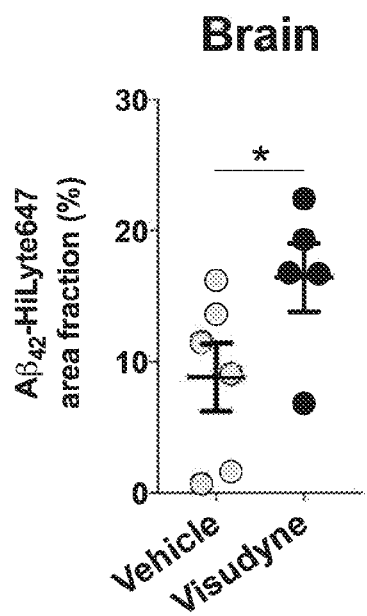

Example 1: Impairing Meningeal Lymphatic Drainage in Adult Mice Affects Brain Fluid Homeostasis Visudyne (verteporfin) or vehicle (as control) were injected into the cisterna *magna* (intra-cisterna *magna*, ICM) of anesthetized adult C57BL/6 mice (3 months of age), followed by a photoconversion step that was achieved by shining a non-thermal red light (689 nm) in 5 points above the skull. 7 days after the initial procedure, $A\beta_{42}$-HiLyte647 (1 µg) was stereotaxically injected (coordinates from bregma, AP=+1.5 mm, ML=−1.5 mm, DV=+2.5 mm) into the brain parenchyma. 1 h post injection, mice were transcardially perfused with saline and meninges, deep cervical lymph nodes (dcLNs) and brain were collected for analysis. Meningeal whole-mounts (scale bar, 1 mm) from vehicle (FIG. 23A) or visudyne (FIG. 23B) injected groups were stained for lymphatic vessel, endothelial hyaluronan receptor 1 (LYVE-1, green) and the blood vascular endothelial cell marker CD31 (red). Visudye alone is shown in the inset in the upper right corner of FIGS. 23A and 23B. A significant decrease in the area of LYVE-1$^+$ vessels was observed in the visudyne group FIG. 23C), whereas no changes between groups were detected in the coverage by CD31$^+$ vessels (FIG. 23D). Staining for 4',6-diamidino-2-phenylindole (DAPI) and LYVE-1 in dcLNs showed significantly less drainage of $A\beta_{42}$ (red) in the visudyne group (FIG. 23E for the vehicle group, FIG. 23F for the visudyne group). $A\beta_{42}$ alone is shown in the inset in the upper right corner of each of FIGS. 23E and 23F, and LYVE-1 alone is shown in the inset in the lower right corner of each of FIGS. 23E and 23F. Coronal brain sections (100 µm thick), both rostral and caudal to the injection site, were stained for glial fibrillary acidic protein (GFAP). Mice from the visudyne group showed decreased efflux of $A\beta_{42}$ from the brain, which was denoted by the increased area fraction occupied by the fluorescent peptide (FIG. 23G). Results are presented as mean±s.e.m. in FIGS. 23C, D, and G; n=6 in vehicle group and n=5 in visudyne group; *P<0.05. **P<0.01, one-tailed Mann-Whitney test; representative of 2 independent experiments).

Accordingly, these experiments show that impairing meningeal lymphatic drainage in adult mice in accordance with some embodiments affects brain fluid homeostasis.

Figure 24A:
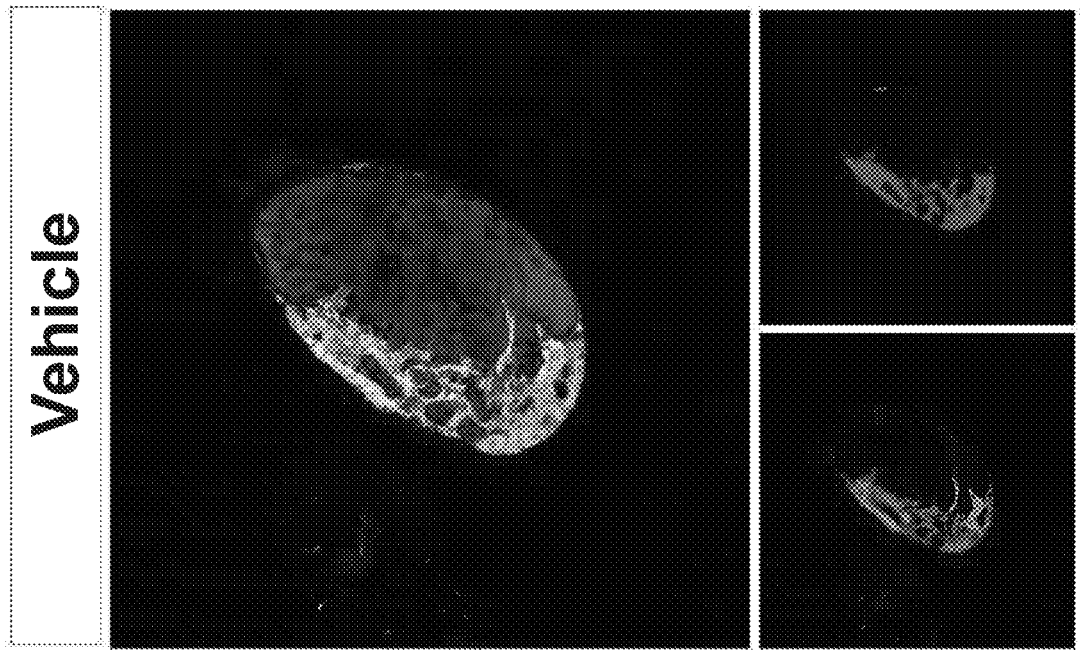
FIGS. 24A-E are a series of microscope images and graphs showing that impairing meningeal vessels significantly decreases drainage into deep cervical lymph nodes.
Figure 24B:
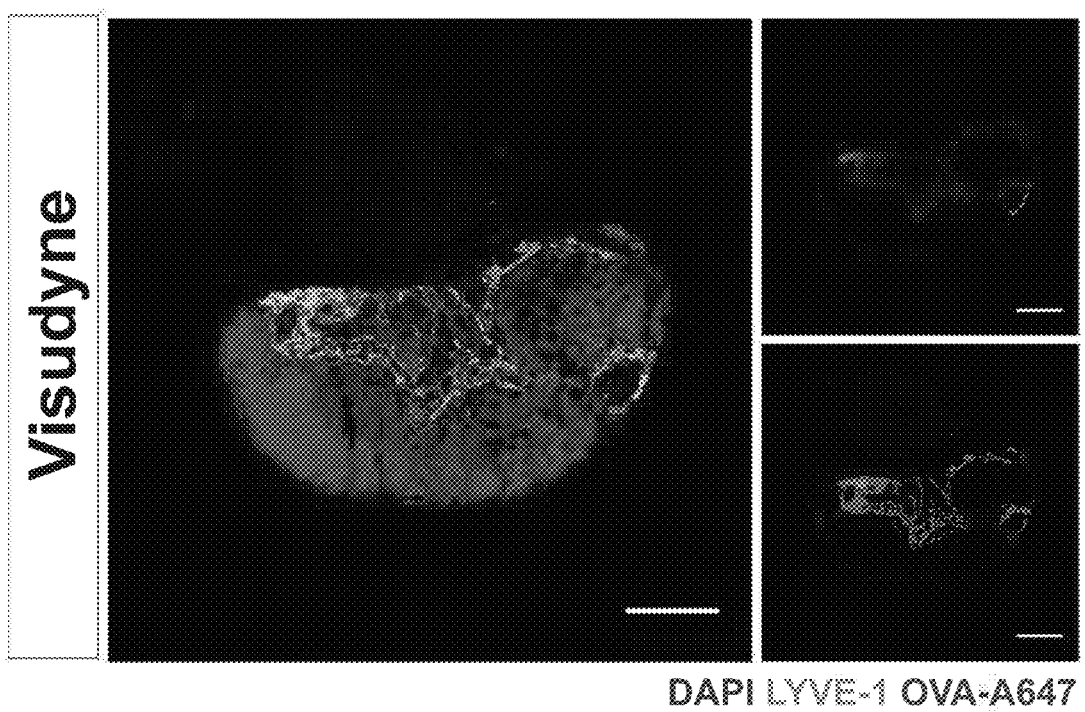
Figure 24C:
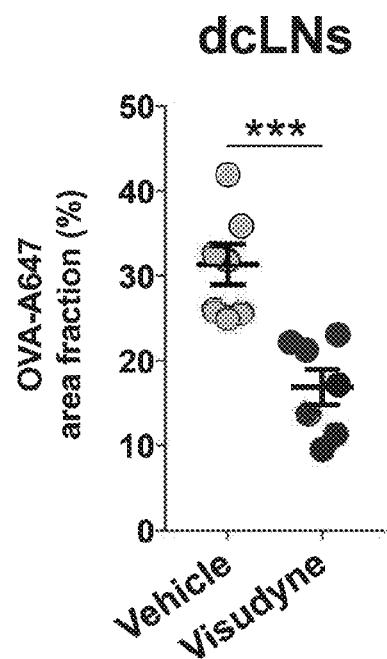
Figure 24D:
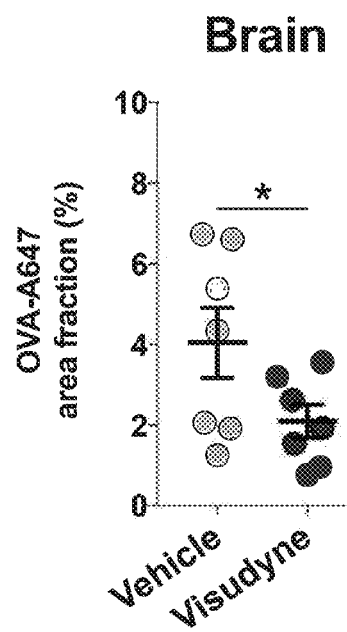
Figure 24E:
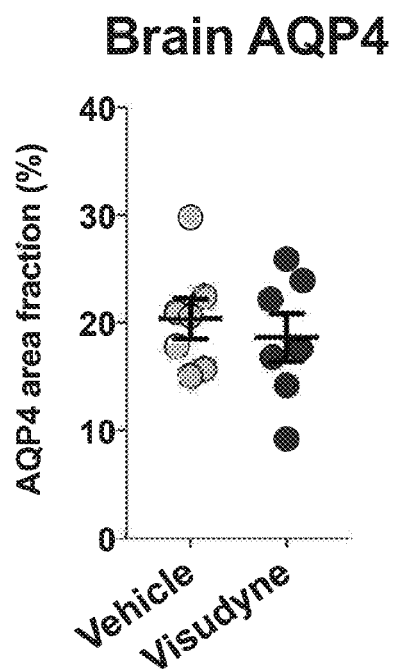

Example 2: Impairing Meningeal Vessels Significantly Decreases Drainage into Deep Cervical Lymph Nodes Adult C57BL/6 mice were injected with visudyne or vehicle (ICM) followed by a step of photoconversion. 7 days post ablation, 2.5 µg of ovalbumin-Alexa647 (OVA-A647) was injected into the CSF (ICM) and mice were transcardially perfused with saline 2 h after. j, Representative sections of dcLNs were stained with DAPI and LYVE-1, and levels of drained OVA-A647 were measured, and representative sections are shown for vehicle (FIG. 24A) and visudyne (FIG. 24B). OVA-A647 alone is shown in the inset in the upper right corner of each of FIGS. 24A and 24B, and LYVE-1 alone is shown in the inset in the lower right corner of each of FIGS. 24A and 24B. The amount of OVA-A647 drained into the dcLNs was significantly decreased in visudyne-injected mice (FIG. 24C). Brain section analysis showed a significant decrease in OVA-A647 (red) influx into the brain parenchyma of visudyne-injected mice (FIG. 24D). Adult mice that underwent visudyne-induced meningeal lymphatic ablation showed no changes in brain parenchyma coverage by aquaporin 4 (AQP4, green) expressing cells (FIG. 24E) (results are presented as mean±s.e.m.; n=7 mice per group in FIGS. 24C-E; *P<0.05, ***P<0.001, one-tailed Mann-Whitney test; pooled two independent experiments in FIGS. 24C-E; representative of three independent experiments).

Accordingly, these experiments show that impairing meningeal vessels significantly decreases drainage into deep cervical lymph nodes.

Figure 25A:
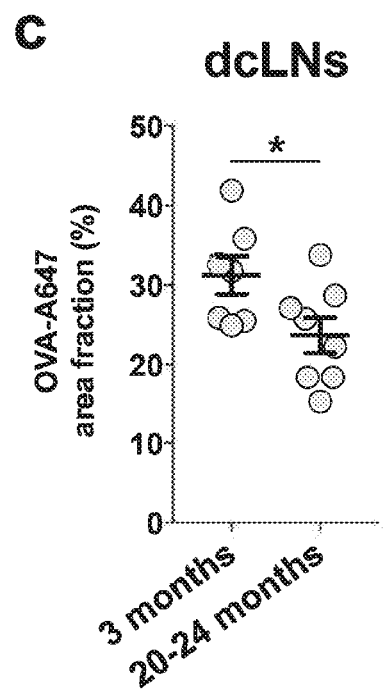
FIGS. 25A-B are a series of graphs showing that ablation of meningeal lymphatic vessels in old mice does not further aggravate influx of a CDF tracer in the brain.
Figure 25B:
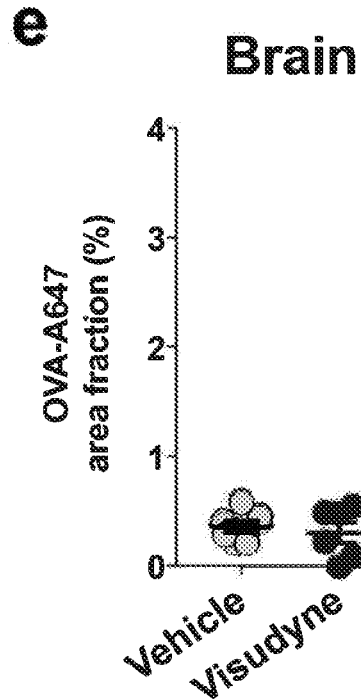

Example 3: Ablation of Meningeal Lymphatic Vessels in Old Mice does not Further Aggravate Influx of a CDF Tracer in the Brain Injections of visudyne or vehicle (ICM), followed by a photoconversion step, were performed in adult (3 months-old) or old (20-24 months-old) C57BL/6 mice. 7 days post ablation, OVA-A647 (2.5 µg) was injected into the CSF (ICM) and mice were transcardially perfused with saline 2 h after. Staining the dcLNs for LYVE-1 revealed that the amount of drained OVA-A647 was significantly decreased in old mice (FIG. 25A). Ablation of meningeal lymphatics in old mice does not further aggravate influx of a CSF tracer into the brain (FIG. 25B) (results are presented as mean±s.e.m.; n=7 in adult+vehicle and in old+visudyne groups, n=8 in old+vehicle group; *P<0.05, one-tailed Mann-Whitney test; pooled two independent experiments in FIGS. 25A and 25B; representative of three independent experiments).

Accordingly, these experiments show that ablation of meningeal lymphatic vessels in old mice does not further aggravate influx of a CDF tracer in the brain.

Figure 26:
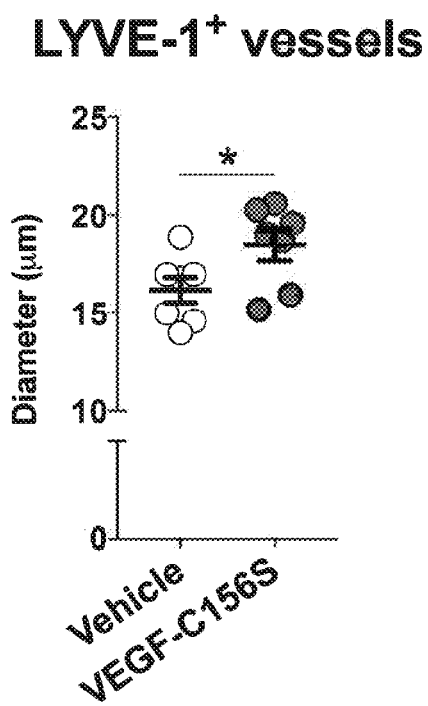
FIG. 26 is a graph showing that transcranial treatment with gel+VEGF-C156S had a significant effect on meningeal lymphatic vessel diameter.
Figure 27A:
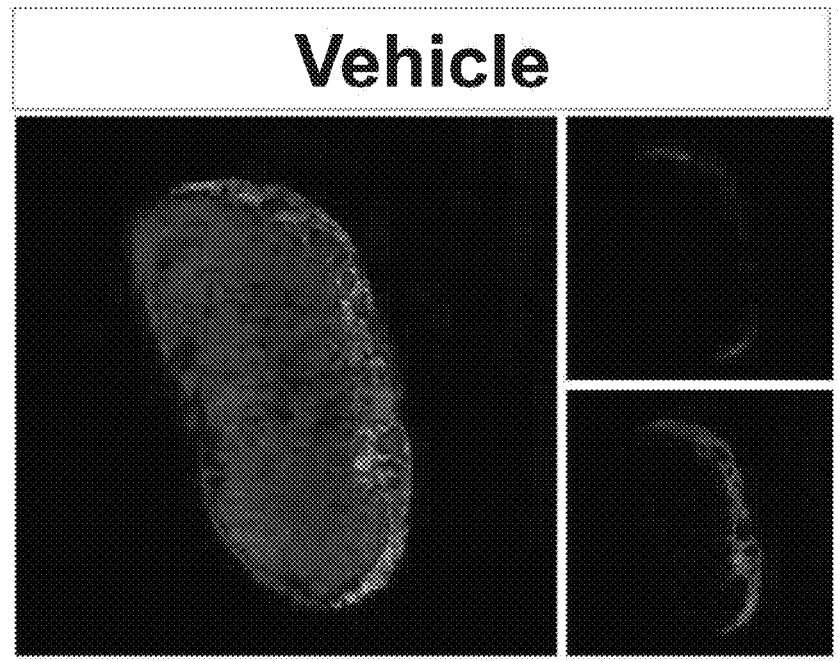
FIGS. 27A-D are a series of microscope images and graphs showing that transcranial application of VEGF-C in accordance with some embodiments leads to improved CSF influx into brain and memory in aged subjects.
Figure 27B:
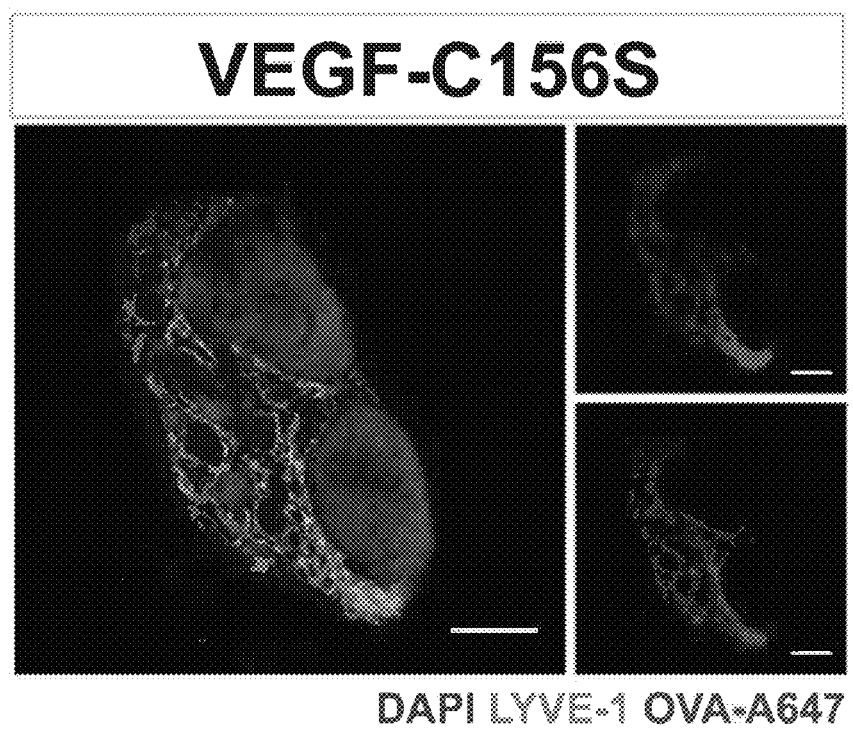
Figure 27C:
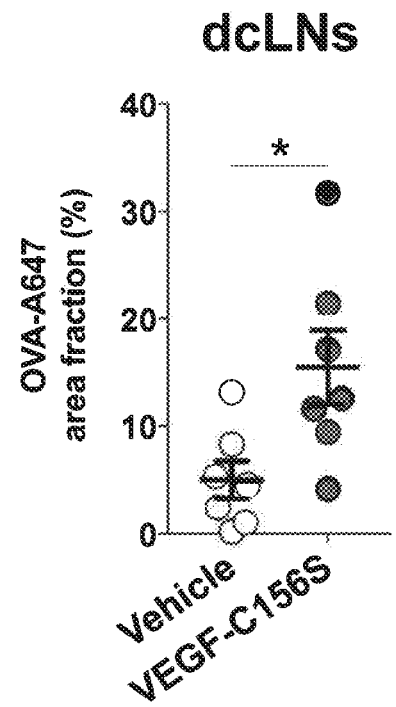
Figure 27D:
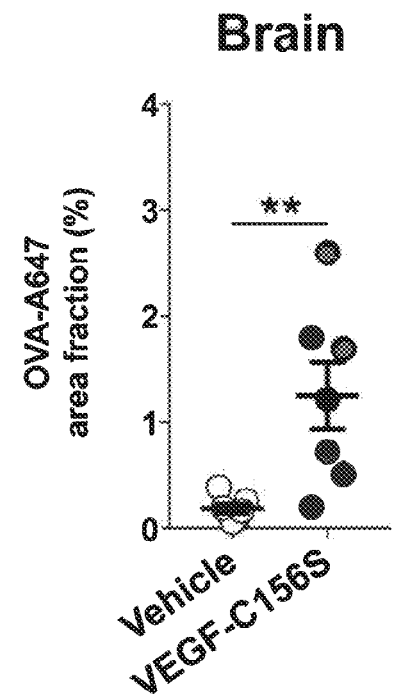
Figure 28A:
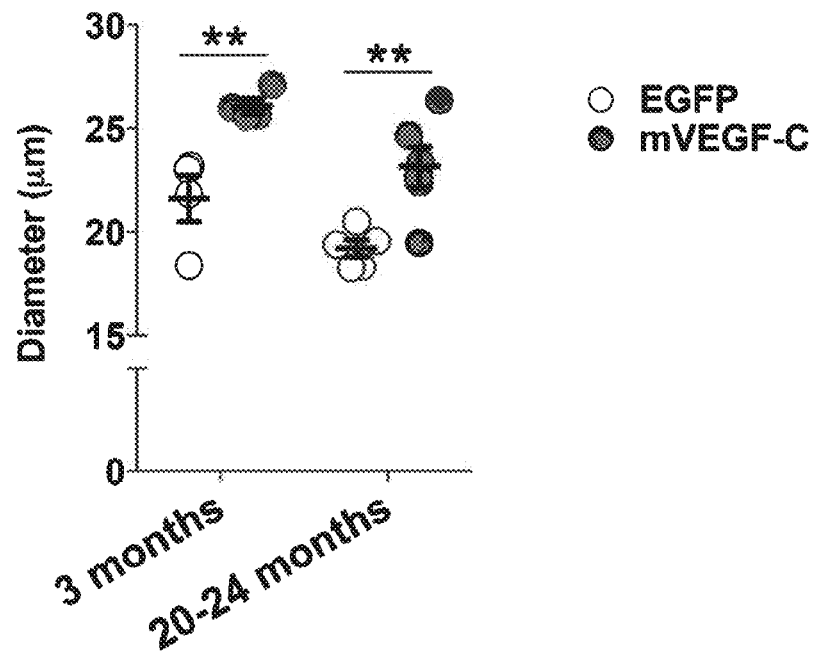
FIGS. 28A-C are a series of graphs showing that expression of an exogenous VEGF-C transgene by cells in the CNS increases flow.
Figure 28B:
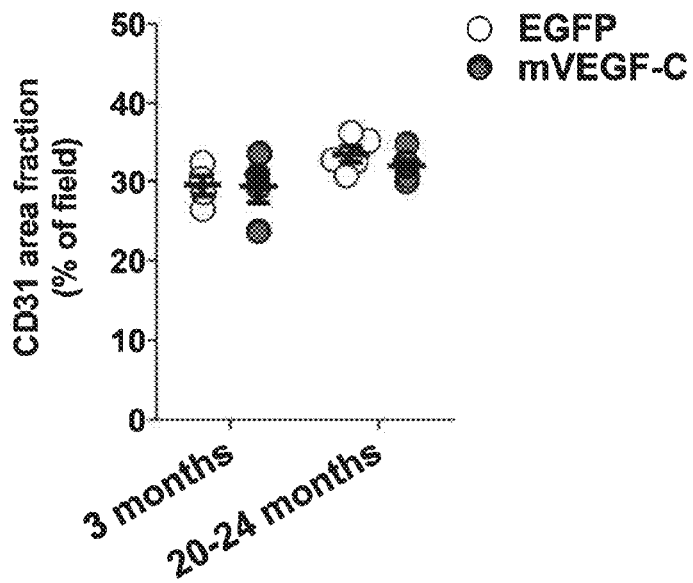
Figure 28C:
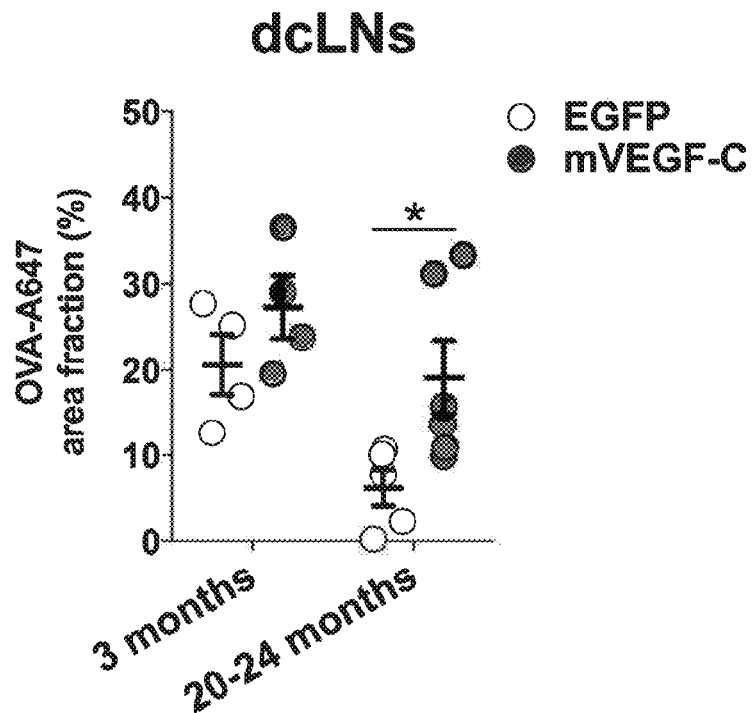

Example 4: Transcranial Application of VEGF-C in Old Mice Leads to Improved CSF Influx into the Brain 1 mL of a gel matrix alone (vehicle) or containing 200 ng of recombinant human VEGF-C156S was applied every two weeks on top of a thinned skull of old C57BL/6 mice. One month after the initial treatment, OVA-A647 was injected ICM and mice were transcardially perfused with saline 2 h post injection. Staining for LYVE-1 in meningeal lymphatic vessels from old mice revealed that treatment with gel+ VEGF-C156S had a significant effect on vessel diameter (FIG. 26). Representative images of dcLNs depicting OVA-A647 (red), and stained with DAPI (blue) and against LYVE-1 (green), show that decreased drainage of OVA-A647 into the dcLNs of old mice was increased by delivery of VEGF-C156S (FIGS. 27A-C). OVA-A647 alone is shown in the inset in the upper right corner of each of FIGS. 27A and 27B, and LYVE-1 alone is shown in the inset in the lower right corner of each of FIGS. 27A and 27B. Representative brain coronal sections from old mice (scale bar, 5 mm) showed a significant effect of VEGF-C156S on OVA-A647 (red) influx from the CSF into the parenchyma (FIG. 27D)(results are presented as mean±s.e.m.; n=7 per group in FIGS. 26, 27C, and 27D; *P<0.05, **P<0.01, one-tailed Mann-Whitney test; representative of two independent experiments).

These experiments show that transcranial application of VEGF-C in accordance with some embodiments leads to improved CSF influx into the brain in aged subjects.

Example 5: Expression of an Exogenous VEGF-C Transgene by Cells in the CNS Increases Flow Adult and old C57BL/6 mice were anesthetized and injected with $10^{12}$ genome copies (GC)/mL (ICM) of either AAV1-CMV-EGFP (or EGFP), a control virus, or AAV1-CMV-mVEGF-C (or mVEGF-C) to increase the expression of mVEGF-C by cells in the CNS. 1 month after, 2.5 µg OVA-A647 was injected ICM and mice were transcardially perfused with saline 2 h post injection. Meningeal whole mounts were stained with DAPI (blue) and for LYVE-1 and CD31. Overexpression of mVEGF-C in adult and old mice led to significant increase in the diameter of lymphatic vessels at the superior sagittal sinus (SSS) (FIG. 28A), but not in the coverage by $CD31^+$ blood vessels (FIG. 28B), dcLNs stained for DAPI and LYVE-1 showed a significant increase in OVA-A647 drainage in 20-24 months-old mice that received mVEGF-C virus, when compared to the ones receiving EGFP virus (FIG. 28C) (results are presented as mean±s.e.m.; n=4 in 3 months+EGFP and in 3 months+ mVEGF-C groups, n=5 in 20-24 months+EGFP group, n=6 in 20-24 months+mVEGF-C group in FIGS. 28A-C *P<0.05, **P<0.01, two-way ANOVA with Bonferroni post hoc test; representative of two independent experiments).

These experiments show that expression of an exogenous VEGF-C transgene by cells in the CNS in accordance with some embodiments herein increases flow in the CNS.

Figure 29A:
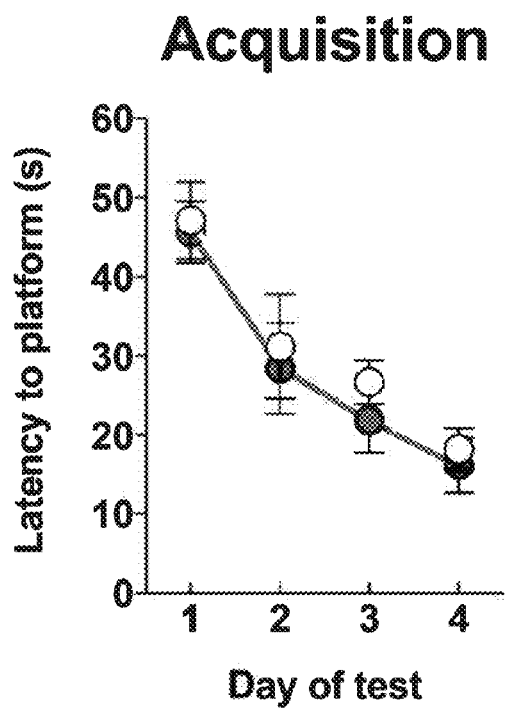
FIGS. 29A-F are a series of graphs showing that expression of an exogenous VEGF-C transgene by cells in the CNS improves cognitive performance as tested in the Morris water maze test.
Figure 29B:
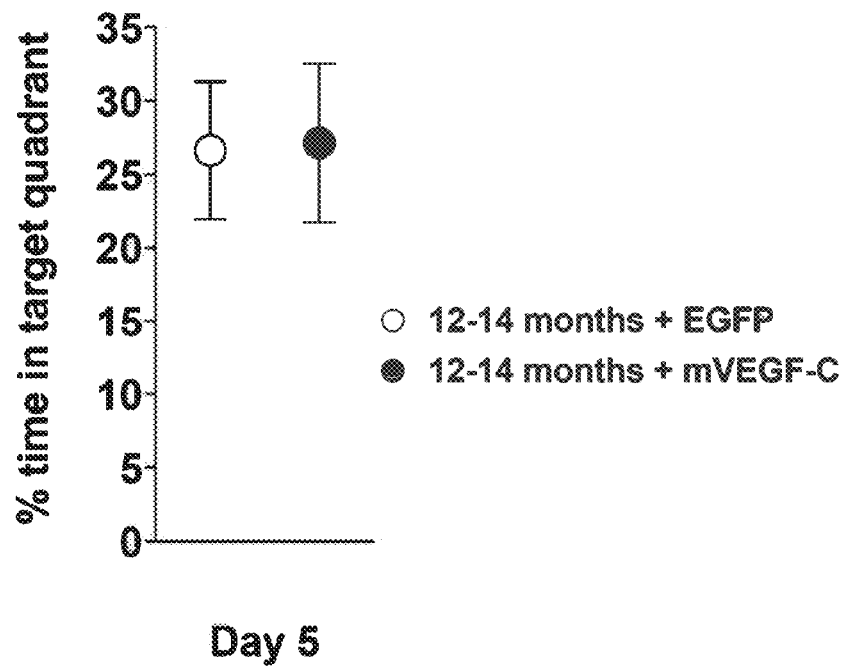
Figure 29C:
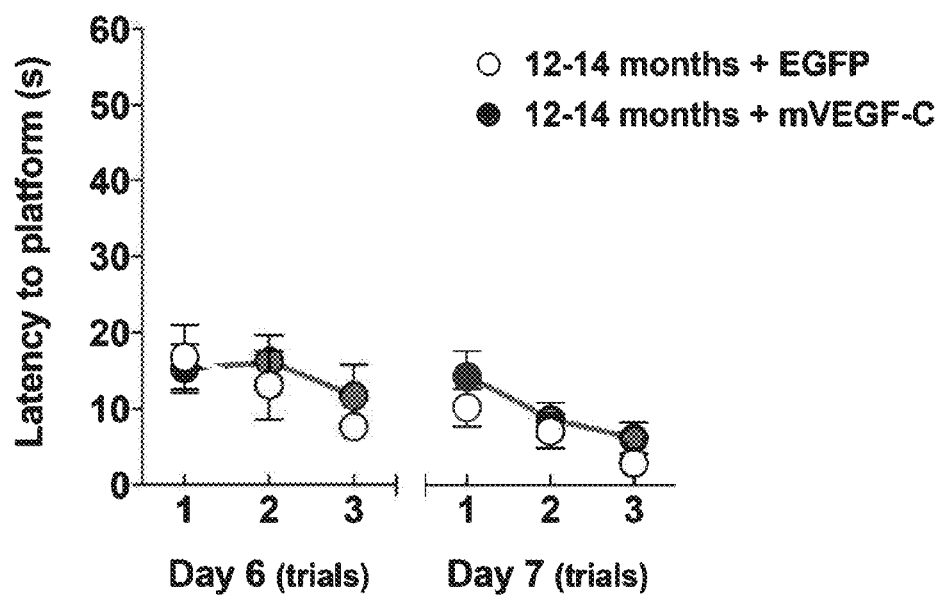
Figure 29D:
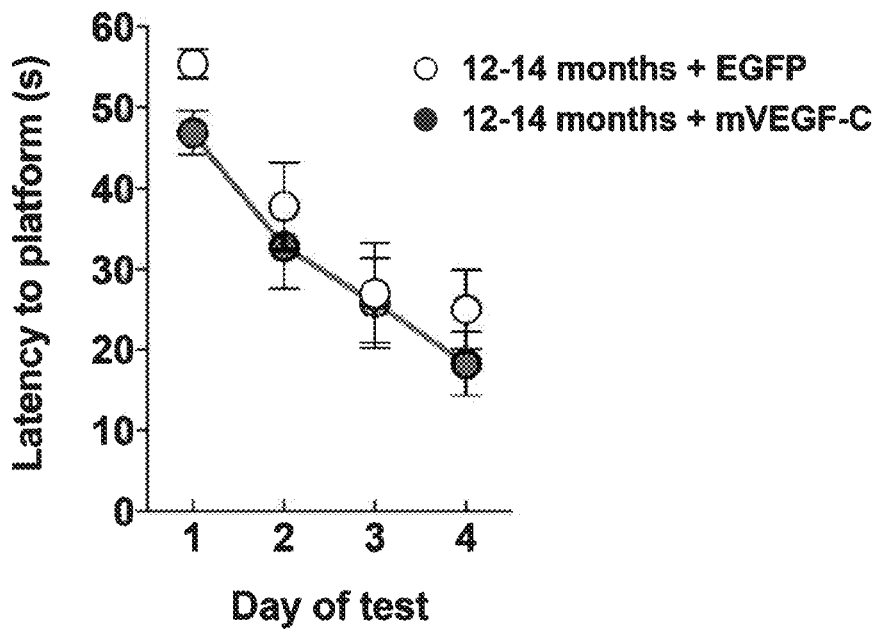
Figure 29E:
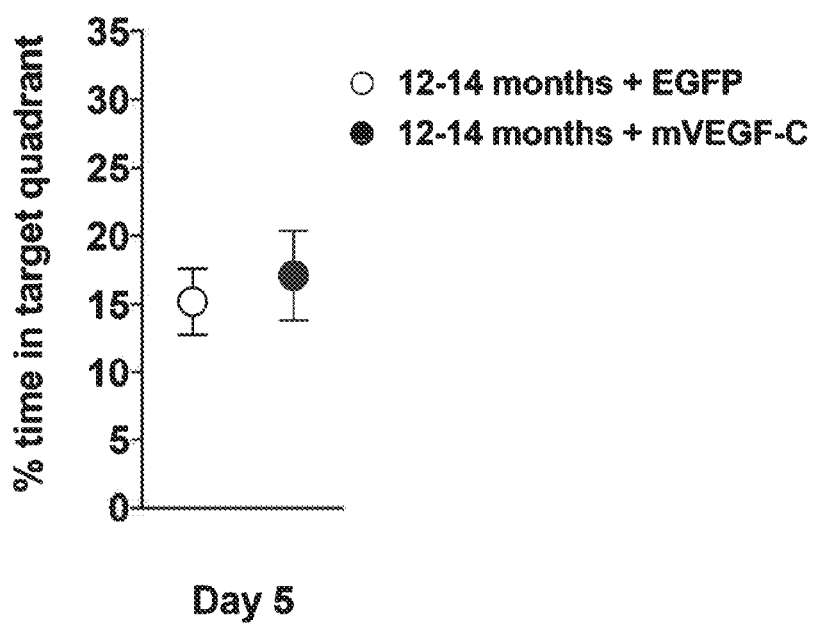
Figure 29F:
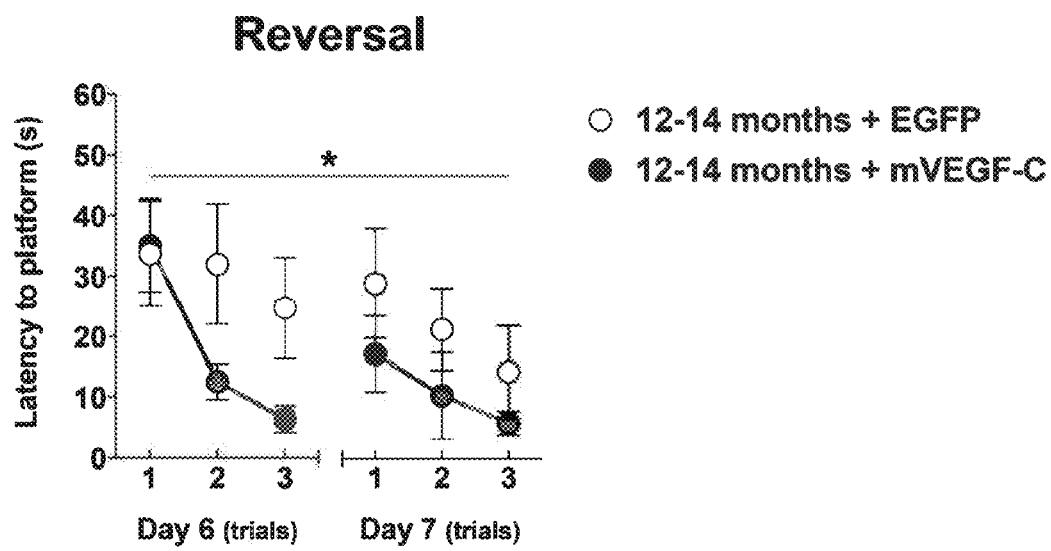

Example 6: Expression of an Exogenous VEGF-C Transgene by Cells in the CNS Increases Flow and Improves Cognitive Performance Young adult (2 months of age) and middle-aged (12-14 months) C57BL/6 mice were injected with $10^{12}$ genome copies (GC)/mL (ICM) of either AAV1-CMV-EGFP (or EGFP) or AAV1-CMV-mVEGF-C (or mVEGF-C). 1 month after, mice learning and memory capabilities were assessed in the Morris water maze (MWM) test (FIGS. 29A-C). No differences between the two groups of young adult mice were observed in the acquisition, probe trial and reversal tasks of the MWM (FIGS. 29D-F). Although no changes were observed in the acquisition and probe, injection of mVEGF-C virus in middle-aged mice led to a significantly better performance in the two days of the reversal learning task of the MWM. Results are presented as mean±s.e.m.; n=8 and 9 in 2 months+EGFP and in 2 months+mVEGF-C groups in FIGS. 29A-C, n=8 in each 12-14 months-old groups in FIGS. 29D-F; *P<0.05, two-way ANOVA—Repeated Measures, with Bonferroni post hoc test.

These experiments show that expression of an exogenous VEGF-C transgene by cells in the CNS in accordance with some embodiments herein increases flow in the CNS and performs performance in the MWM test.

Example 7: Meningeal Amyloid-Beta Deposits in AD Patients

Non-AD cortical and AD cortical brain sections, containing the respective meningeal layers attached, were stained with DAPI (cell nuclei), for the astrocyte marker GFAP and with an antibody recognizing human N-terminal amyloid beta $(A\beta)_{37\text{-}42}$ residues (clone D54D2). Amyloid deposition (arrows) was observed in the AD (FIG. 30B), but not in the non-AD (FIG. 30A), brain parenchyma, as well as in the meningeal vasculature of the cortex (scale bars, 500 µm; inset scale bars, 200 µm).

These experiments show amyloid beta deposition is observed in the meninges of AD patients, but not in controls.

Figure 31A:
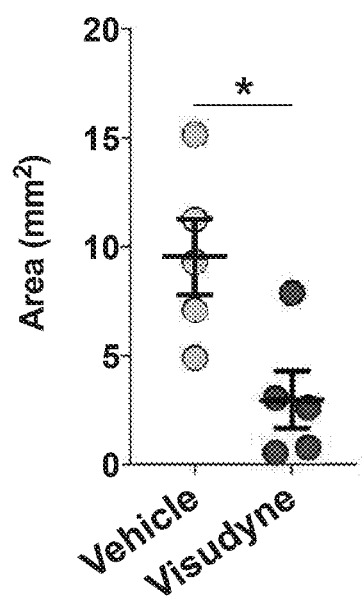
FIGS. 31A-B are a series of graphs showing quantification of the total area of LYVE-1+ lymphatic vessels (FIG. 31A) and of the area occupied by Aβ aggregates (FIG. 31B) in the meningeal whole-mounts of adult C57BL/6 mice.
Figure 31B:
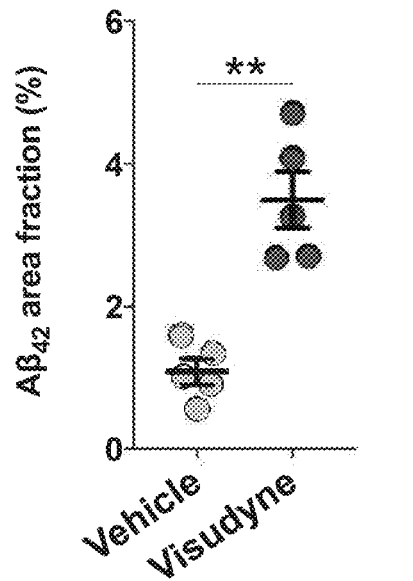

Example 8: Meningeal Lymphatic (Dys)Function Modulates Amyloid Pathology in Models of Alzheimer's Disease C57BL/6 adult mice were anesthetized and injected ICM with visudyne to induce meningeal lymphatic vessel ablation, or vehicle as a control. After the photoconversion step, mice were allowed to recover for 72 h. Then, catheters were implanted in the cisterna *magna* of all mice and 2.5 μg of Aβ$_{42}$ were injected every 24 h into the CSF for a total of 5 days. Staining with LYVE-1, Aβ, and the macrophage marker IBA1 in meningeal whole-mounts showed macrophage activation in response to formation of Aβ$_{42}$ aggregates. Quantification was performed of the total area of LYVE-1$^+$ lymphatic vessels (FIG. 31A) and of the area occupied by Aβ aggregates (FIG. 31B) in the meningeal whole-mounts, and showed a significant increase in aggregates in the group submitted to meningeal lymphatic ablation by visudyne. Results are presented as mean±s.e.m.; n=5 per group; *P<0.05, **P<0.01, one-tailed Mann-Whitney test.

These experiments show that meningeal lymphatic (dys) function modulates amyloid pathology in models of Alzheimer's disease.

Example 9: Meningeal Lymphatic Ablation Increases Amyloid-Beta (AB) Aggregates

Figure 32A:
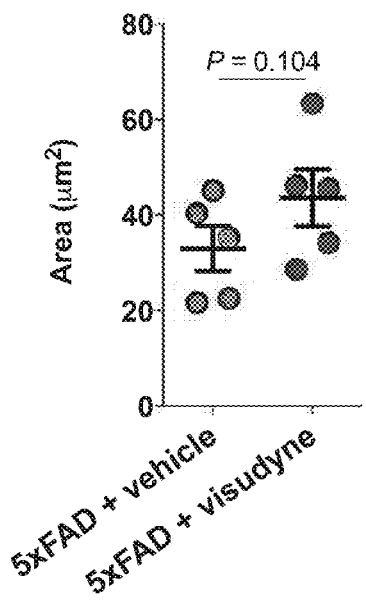
FIGS. 32A-C are a series of graphs showing meningeal lymphatic ablation increases amyloid-beta (Aβ) aggregates in 5xFAD mice.
Figure 32B:
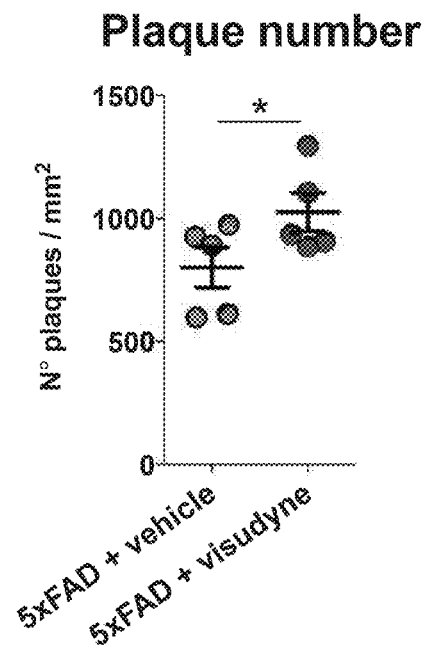
Figure 32C:
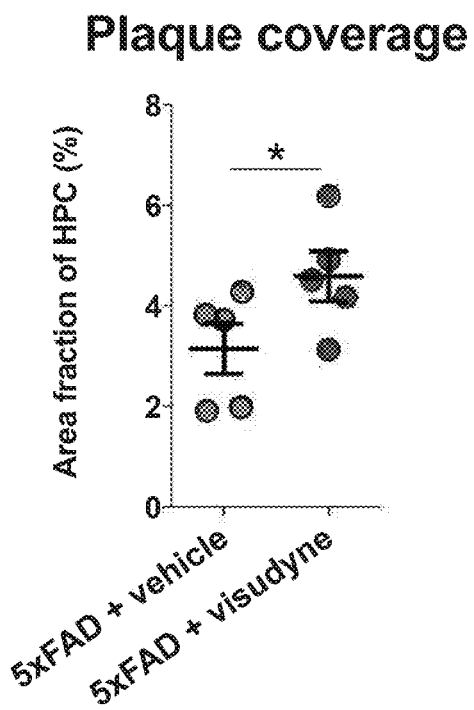

Meningeal lymphatic ablation in 1.5 months-old 5xFAD (APPSweFILon,PSEN1*M146L*L286V) transgenic mice was achieved by ICM injection of visudyne, or vehicle as a control, followed by a step of transcranial photoconversion. This procedure was repeated every 3 weeks, for a total of 1.5 months. Meninges of 5xFAD mice from the different groups were stained with DAPI and for LYVE-1 and Aβ. Aβ aggregates were detected in the meninges of 5xFAD mice that undergone lymphatic ablation by visudyne, but not in the meninges of vehicle-injected mice. Aβ aggregates formed specially around the sinuses and in the cerebellar meninges. Hippocampus was stained for DAPI and Amyloid-beta in vehicle or visudyne-injected 5xFAD mice (scale bar, 1 mm, inset, 200 μm). A statistically significant increase in amyloid plaque number (FIG. 32A) and coverage (FIG. 32B), and a trend for increased plaque size (FIG. 32C), was observed in the hippocampus of 5xFAD mice upon meningeal lymphatic ablation. Results are presented as mean±s.e.m.; n=5 per group: *P<0.05, one-tailed Mann-Whitney test.

These experiments show that meningeal lymphatic ablation increases amyloid-beta aggregates.

Figure 33A:
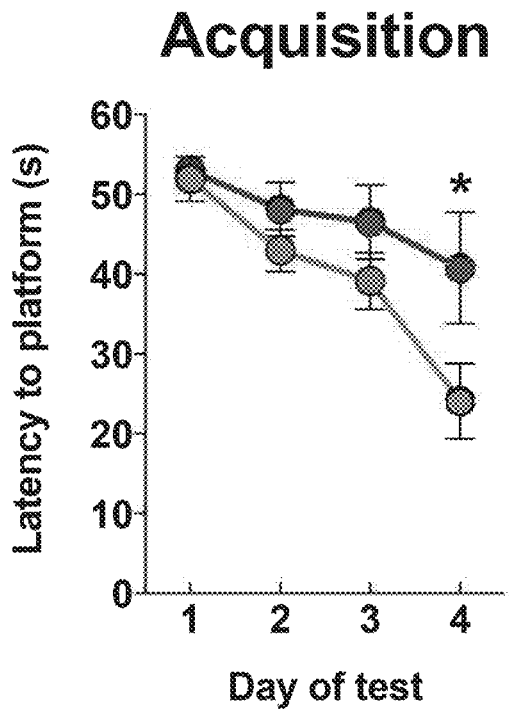
FIGS. 33A-C are a series of graphs showing that meningeal lymphatic ablation exacerbates dementia symptoms in an AD model.
Figure 33B:
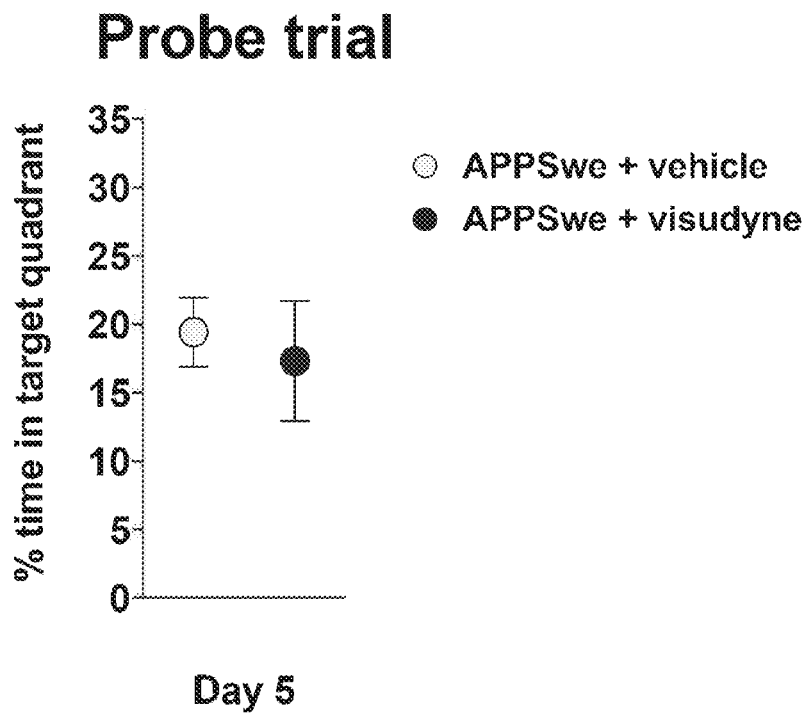
Figure 33C:
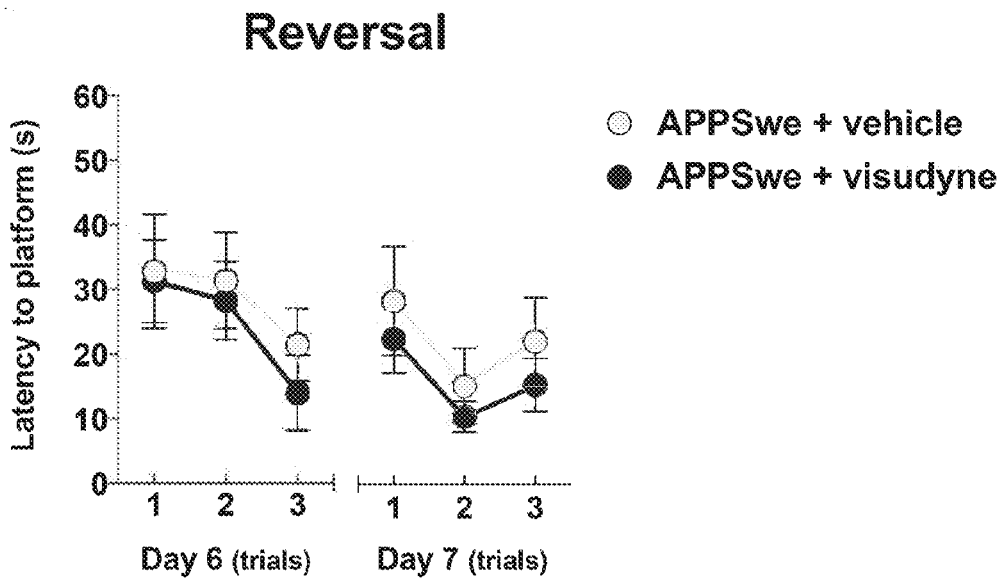

Example 10: Meningeal Lymphatic Ablation Exacerbates Dementia Symptoms in an AD Model Adult (6-7 months-old) APPSwe transgenic mice were anesthetized, injected with visudyne (ICM), or vehicle as a control, and submitted to a step of transcranial photoconversion, every 2 weeks for a total of 1 month. Changes in spatial-reference and working memory functions between the mice from different groups were then assessed in MWM, n, Significant differences were observed between visudyne and vehicle groups regarding the latency to find the platform in the 4$^{th}$ day of the acquisition phase of the MWM (FIG. 33A). No differences were found in the probe (FIG. 33B) and reversal (FIG. 33C). Results are presented as mean±s.e.m.; n=9 per group; *P<0.05, two-way ANOVA—Repeated Measures, with Bonferroni post hoc test.

These experiments show that meningeal lymphatic ablation exacerbates dementia symptoms in an AD model.

Figure 34A:
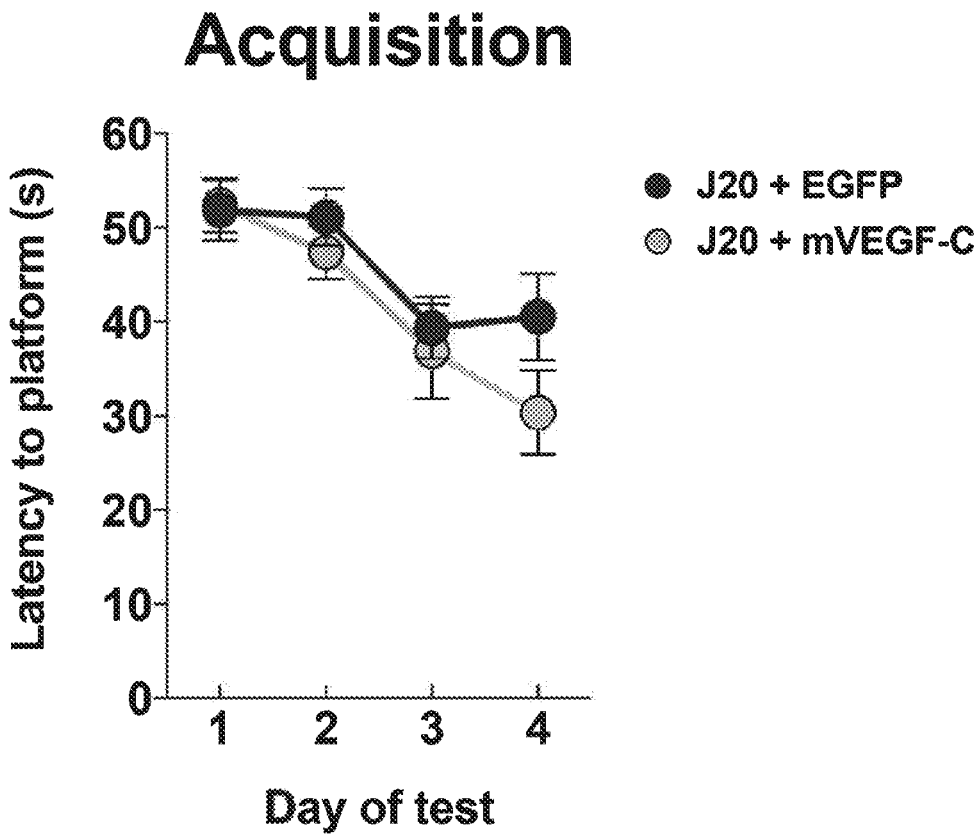
FIGS. 34A-C are a series of graphs showing that expression of VEGF-C in the CNS ameliorates dementia symptoms in an AD model.
Figure 34B:
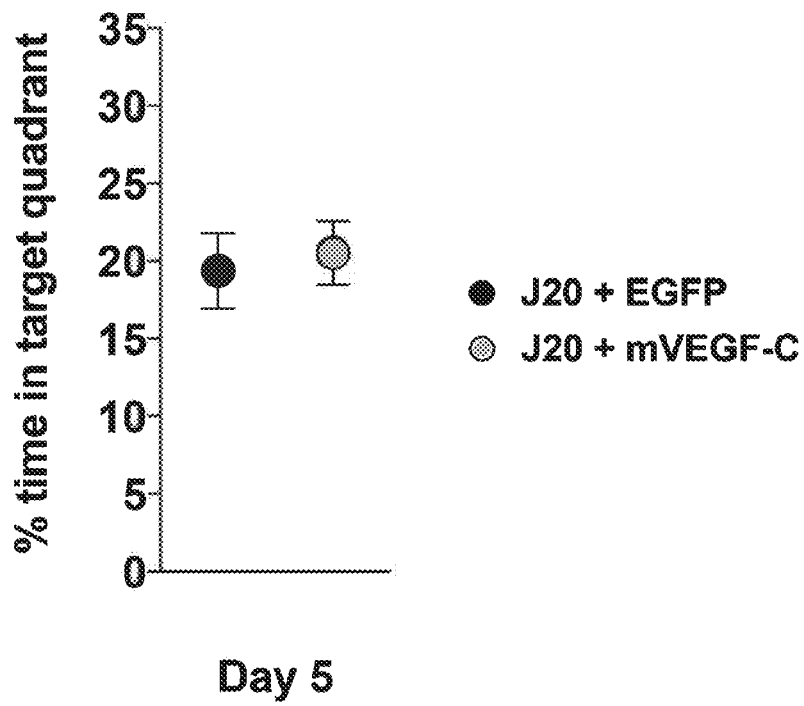
Figure 34C:
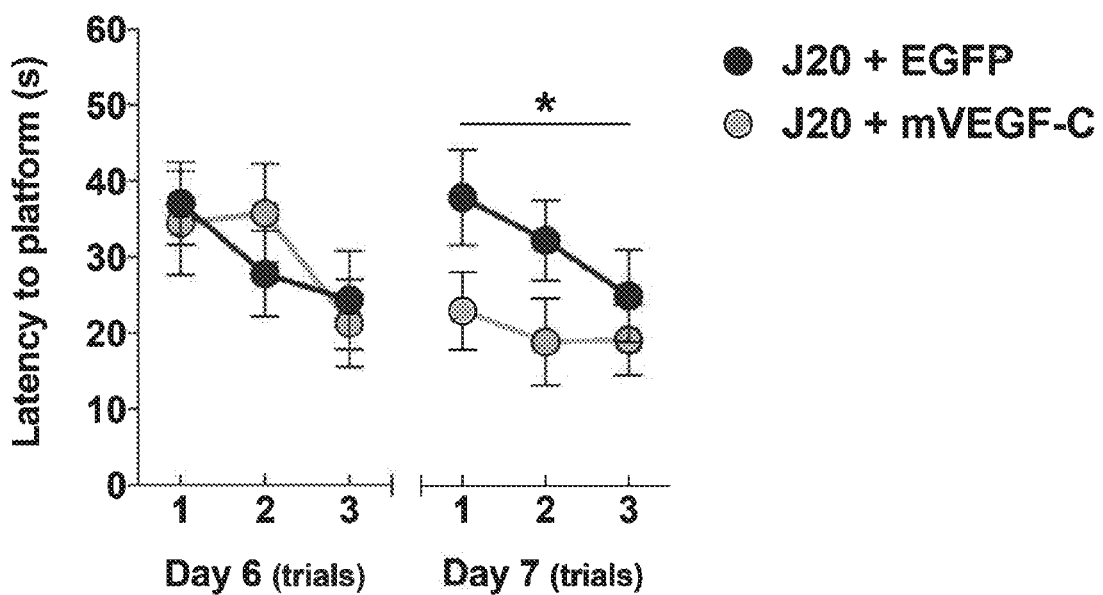

Example 11: Expression of VEGF-C in the CNS Ameliorates Dementia Symptoms in an AD Model 2 μL of AAV1-CMV-EGFP or AAV1-CMV-mVEGF-C ($10^{12}$ GC/mL), was injected into the CSF (ICM) of APPS-weInd (J20) transgenic mice at 6-7 months. One month after injection, the mice were tested in MWM (FIGS. 34A-C). By comparing the J20 mice of the different groups, it was possible to observe a statistical significant difference in the latency to find the platform in the last day of the reversal phase of the MWM (FIG. 34C)(results are presented as mean±s.e.m.; n=11 in J20+EGFP and n=12 in J20+mVEGF-C; *P<0.05 by comparing groups in the last day of the Reversal, two-way ANOVA—Repeated Measures, with Bonferroni post hoc test).

These experiments show that expression of exogenous VEGF-C in the CNS in accordance with some embodiments herein ameliorates dementia symptoms in an AD model.

Figure 35:
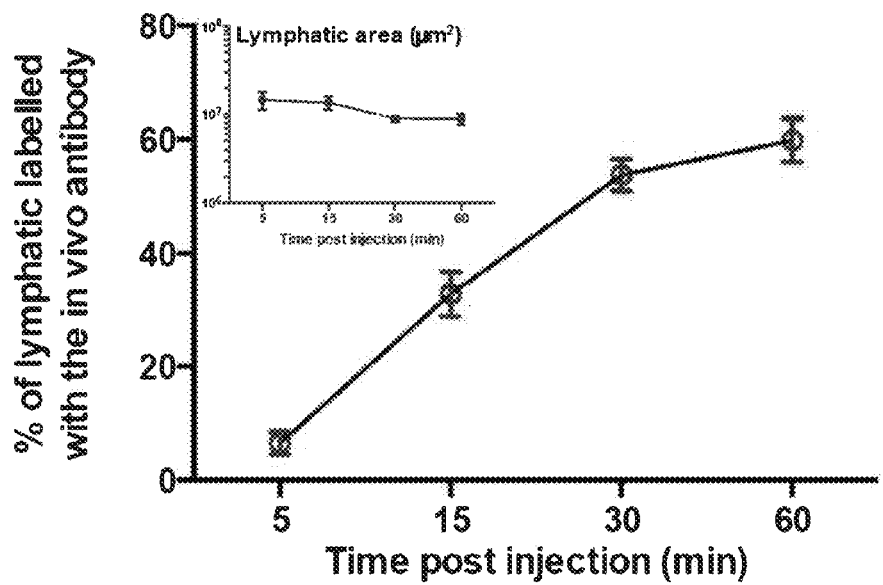
FIG. 35 is a graph showing the quantification of lymphatic vessels immunostained by i.c.m. injected antibody and total lymphatic area (inset) at different time point post injection.

Example 12: In Vivo Flow from the Cisterna *Magna* to Meningeal Lymphatic Vessels Adult C57B16 mice were injected into the cisterna *magna* (i.c.m.) with 2 μl of A488-conjugated-Lyve-1 antibody. Meninges were harvested at the different indicated time point and immunostained for lymphatic vasculature (Lyve-1). Images of the lymphatic vessels immunostained by both an i.c.m. injected anti-Lyve-1A488 and exogenously applied anti-Lyve-1A660 at different time points after i.c.m. injection. Double labeling of the meningeal lymphatic vessels by the i.c.m. injected and exogenously applicated anti-Lyve-1 antibodies was observed. Scale bar=μm. The percentage of lymphatic vessels immunostained by the i.c.m. injected antibody and total lymphatic area were quantified at different time point post injection. (FIG. 35)(mean±s.e.m, n=4 mice/group).

These experiments identify in vivo flow from the cisterna *magna* to meningeal lymphatic vessels.

Example 13: Characteristics of Meningeal Lymphatic Vessel Structures

Figure 36A:
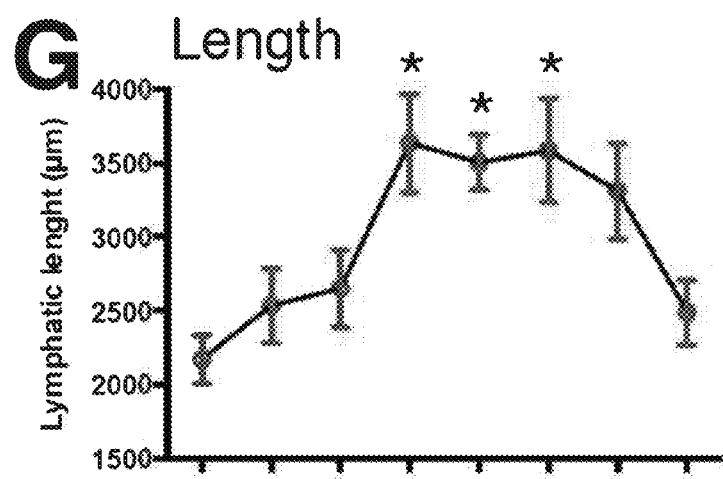
FIGS. 36A-B are a series of graphs showing characteristics of meningeal lymphatic vessel structures.
Figure 36B:
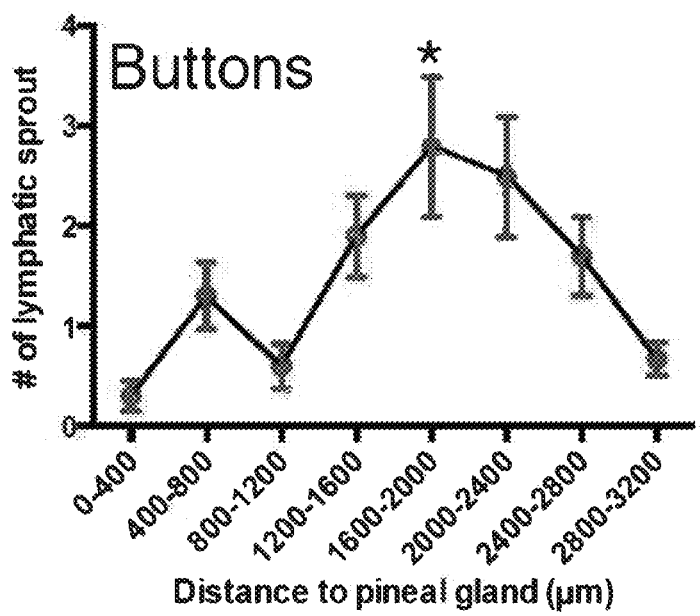
Figure 37A:
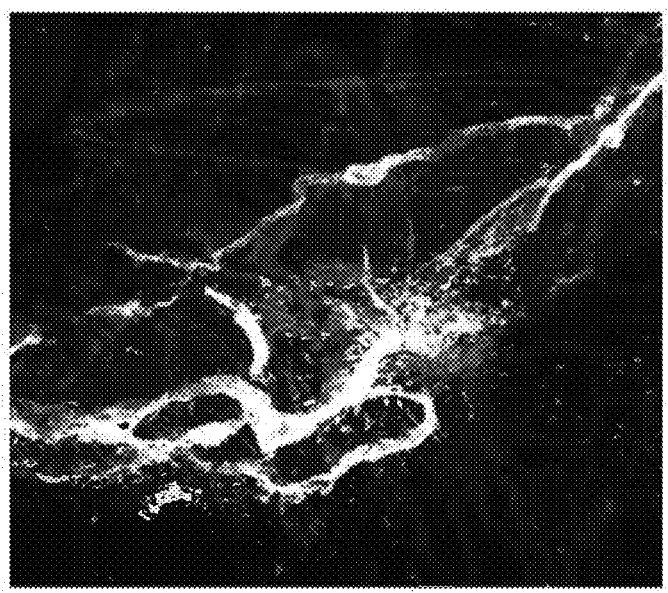
FIGS. 37A-F are a series of microscope images showing that show that T cells accumulate in meningeal lymphatics.
Figure 37B:
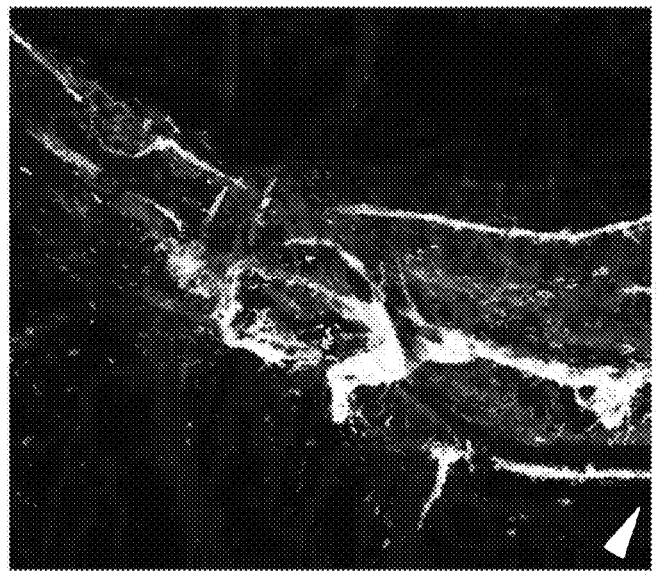
Figure 37C:
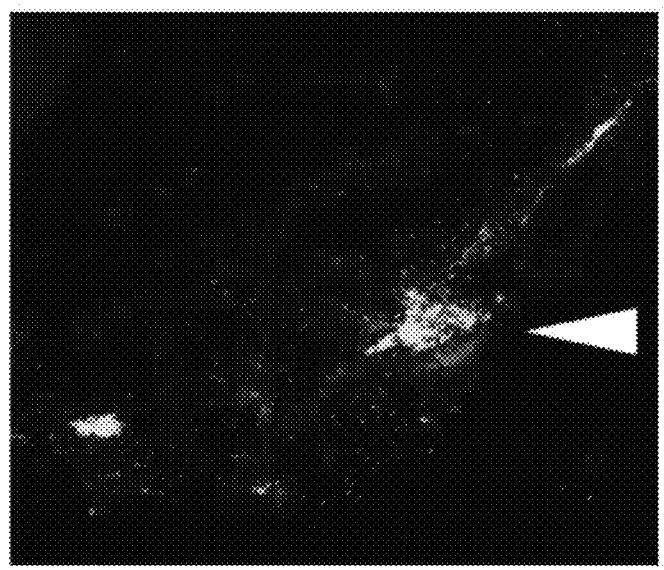
Figure 37D:
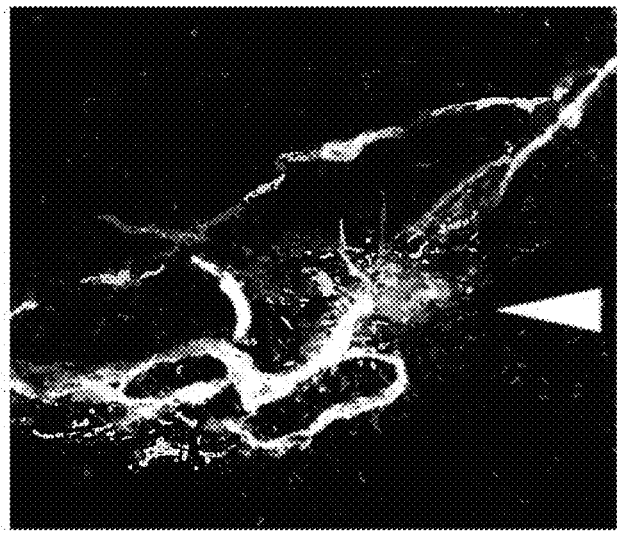
Figure 37E:
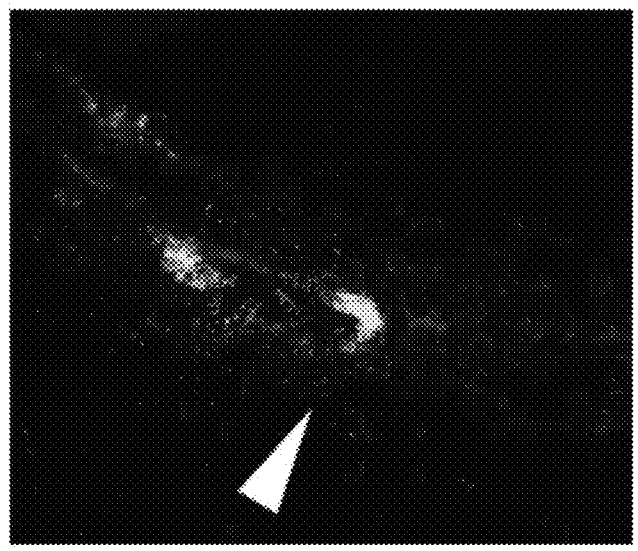
Figure 37F:
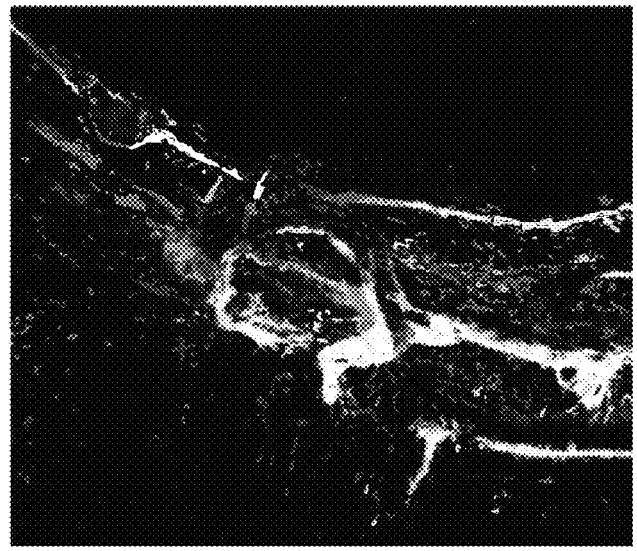

Meningeal lymphatic vessels of the transverse sinus of adult Prox1GFP mice were imaged. Button-like structures were observed along the lymphatic vessels. Scale bar=μm. Quantification of the length of lymphatics, and number of lymphatic buttons in adjacent sections of the transverse sinus starting from the middle of the pineal gland were performed (FIG. 36A-B) (mean±s.e.m, n=5 mice, n=2 transverse sinus/mouse, Length: *p=0.0252 (0-400 vs 1200-1600) *p=0.0111 (0-400 vs 1600-2000) *p=0.0456 (0-400 vs 2000-2400) (FIG. 36A); Buttons: *p=0.0402 (0-400 vs 1200-1600) repeated measures ANOVA with Tukey's multiple comparisons test)(FIG. 36B). Thus, these experiments identify characteristics of some meningeal lymphatic vessel structures.

Example 14: Accumulation of T Cells in Meningeal Lymphatics

Adult C57B16 mice were injected i.c.m. with 0.5 μl of 0.5 μm beads+2.5 μl of OVA$^{A594}$. Meninges were harvested 2 h after injection. Representative images of OVA$^{594}$ and fluorescent beads accumulation along the lymphatics (Lyve-1) of the transverse sinus are shown in FIGS. 37A-F. Exogenously injected T cells (CFSE) accumulated at the hot spots of the transverse sinuses 12 h after i.c.m. injection. These experiments show that T cells accumulate in meningeal lymphatics.

Example 15: Accumulation of Endogenous T Cells in Meningeal Lymphatics

Adult Prox1$^{GFP}$ mice were injected into the cisterna *magna* (ICM) with 5 μl of QDot$^{655}$. The transverse and the superior sagittal sinuses were imaged through a thin skull around 5 min after injection. It was observed that the lymphatics along the superior sagittal sinus are separated from the SAS while the some portion of the transverse sinus lymphatic are located within the SAS.

Adult Prox1$^{GFP}$ mice were injected intravenously (i.v.) with 5 µl of QDot$^{655}$ (diluted in 95 µl of saline). The transverse sinus was imaged through a thin skull around 5 min after injection. Images of the complex meningeal lymphatics showed the transverse sinuses at an hot spot showed a descending lymphatic button directed towards the SAS. Endogenous T cells (Lck$^{tdTOMATO}$) localized within a lymphatic button (Prox1$^{GFP}$) along the transverse sinus. These experiments show that T cells accumulate in meningeal lymphatics.

Example 16: Density of Exogenous T Cells in Meningeal Lymphatics

Figure 38:
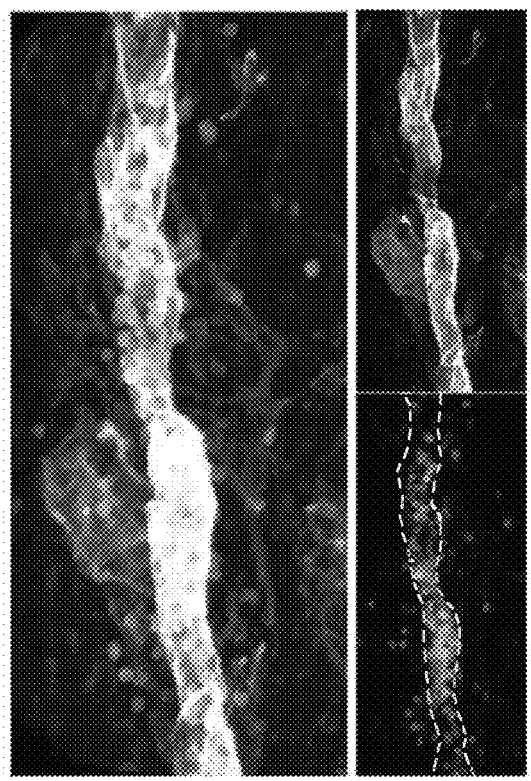
FIG. 38 is a microscope image showing that exogenously injected T cells (CFSE) located with the meningeal lymphatics (Lyve-1) of the transverse sinus (CD31).

Adult C57B16 mice were injected i.c.m. with 1 million of CFSE-labeled T cells. Meninges were collected 12 h after the cell injection. Exogenously injected T cells (CFSE) located with the meningeal lymphatics (Lyve-1) of the transverse sinus (CD31) (FIG. 38). Note that very sparse to very packed amount of exogenous T cells can be found depending on the mouse and region analyzed. These experiments show that T cells accumulate in meningeal lymphatics, and have varying densities.

Example 17: Accumulation of Exogenous Dendritic Cells in Meningeal Lymphatics

Figure 39:
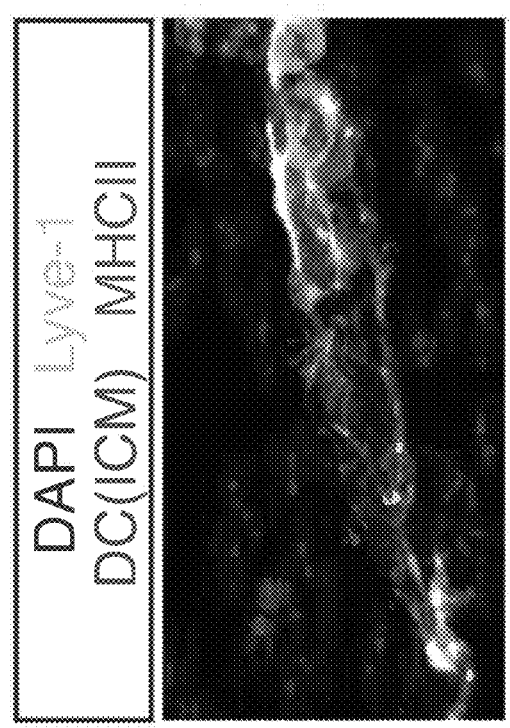
FIG. 39 is a microscope image showing that the exogenously injected DC (TAMRA—red) located within the meningeal lymphatics.

Adult C57B16 mice were injected i.c.m. with 0.5 million of TAMRA-labeled Dendritic Cells. Meninges were collected 15 h after the cell injection. The exogenously injected DC (TAMRA—red) located within the meningeal lymphatics (Lyve-1—white) of the transverse sinus (FIG. 39). These experiments show that dendritic cells accumulate in meningeal lymphatics.

Figure 40A:
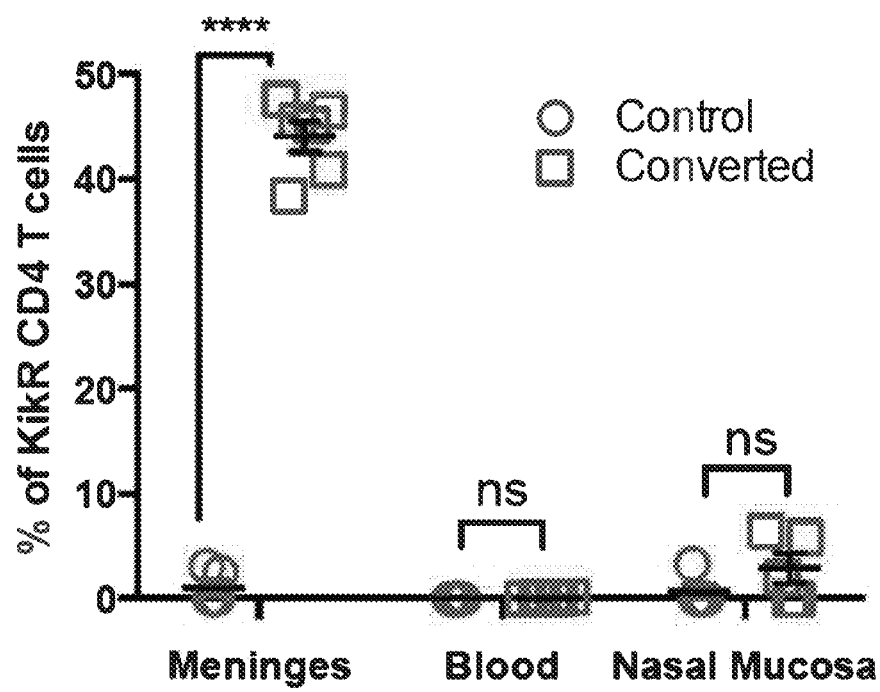
FIGS. 40A-B are a series of graphs showing quantification of the percentage of KiKR CD4 T cells in the meninges, blood and nasal mucosa (FIG. 40A) and dCLN, sCLN and ILN (FIG. 40B).
Figure 40B:
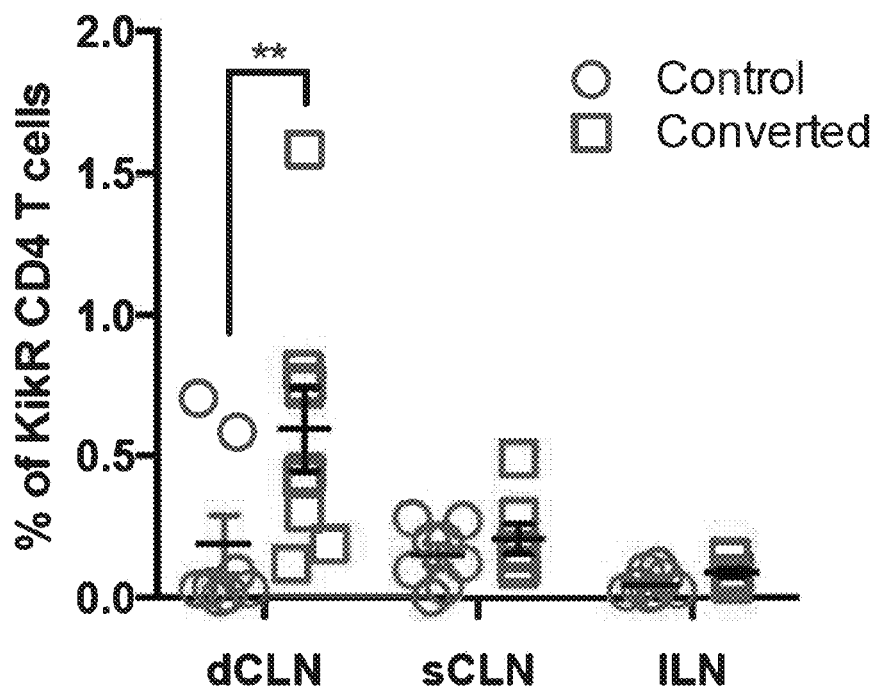

Example 18: Quantification of the Percentage of KiKR CD4 T Cells are Shown in the dCLN, sCLN and ILN C57B16 mice were reconstituted with bone marrow from KiKGR mice after lethal irradiation. Ten weeks after reconstitution, meninges were converted every twelve hours for with 2 min exposure with a violet light (through the intact skull). Ten hours after the last conversion, tissues were harvested and analyzed by FACS. Quantification of the percentage of converted CD4 T cells (KiKR+) in the meninges, blood and nasal mucosa of control and converted mice. (mean±s.e.m. n=5-6 mice/group. **p<0.0001, 2 way ANOVA with Sidak's multiple comparisons test) are shown in FIG. 40A. Quantification of the percentage of KiKR CD4 T cells are shown in the dCLN, sCLN and ILN of control and converted mice (FIG. 40B). (mean±s.e.m, n=8-9 mice/group pooled from 2 experiment, p=0.0048, 2 way ANOVA with Sidak's multiple comparisons test). These experiments show that dendritic cells cycle between the dCLN, sCLN, and ILN.

Figure 41A:
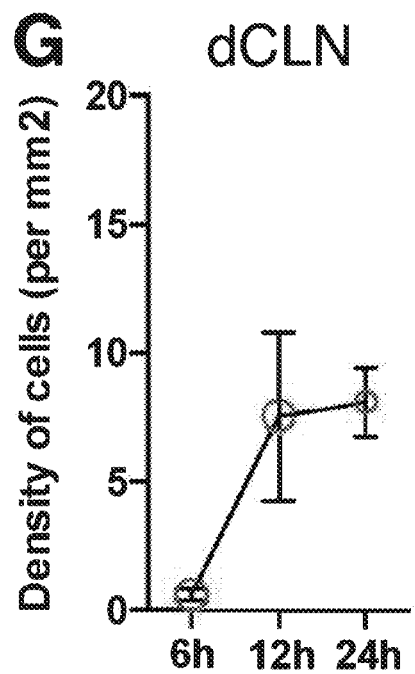
FIGS. 41A-B are a series of graphs showing activation and migration of T cells into the deep cervical lymph nodes.
Figure 41B:
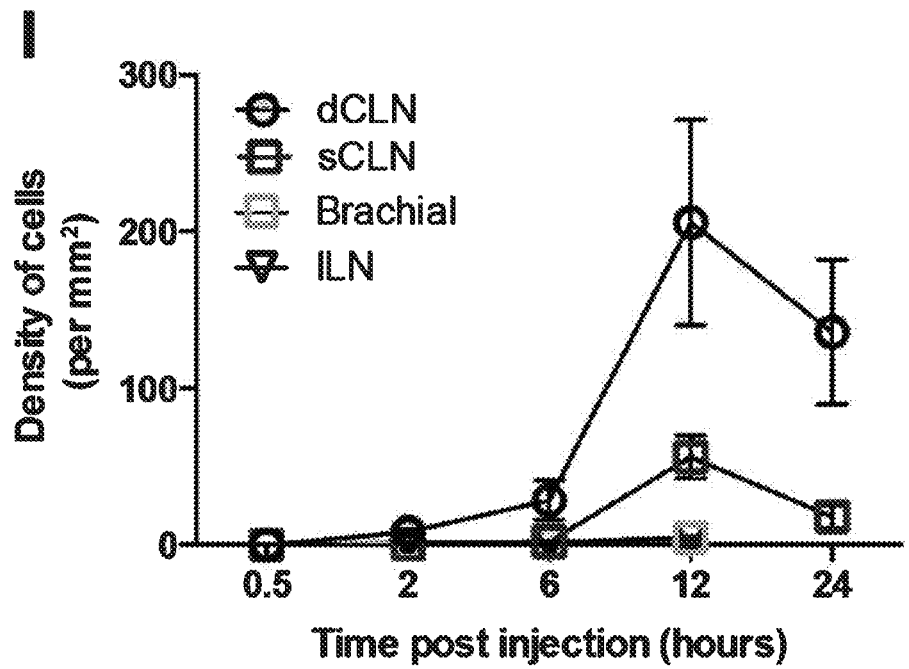
Figure 42:
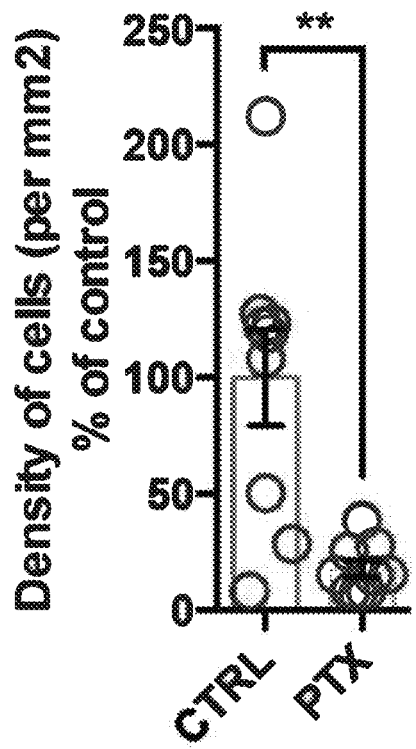
FIG. 42 is a graph showing density of T cells per mm$^2$ of dCLN.

Example 19: Activation and Migration of T Cells into the Deep Cervical Lymph Nodes Adult mice were injected i.c.m. with 1 million of exogenously labeled CD4 T cells. Lymph nodes were harvested at the indicated time point. Injected T cells were observed in the deep cervical lymph nodes (dCLN) 12 h post injection. Quantification of the density of activated T cells per mm$^2$ of dCLN at different time point post injection is shown in FIG. 41A. (mean±s.e.m, n=3-5 mice/group). Images of i.c.m. injected naïve t cells in the dCLN of mice at 6 and 12 h post injection show that at 6 h T cells mostly localized within the lymphatic capsule of the lymph nodes while they are localized in the T cells zone at 12 h post injection. The density of naïve T cells per mm$^2$ of dCLN, sCLN, brachial and ILN was quantified at different time point post injection. (mean±s.e.m, n=2-7 mice per group pooled from 2 independent experiments). Isolated CD4 T cells were incubated for 2 h with Xng of pertussis toxin prior to i.c.m. injection in C57B16 mice. Images of control and PTX-treated T cells in the dCLN of WT mice 12 h were taken after i.c.m. injection. Density of T cells per mm2 of dCLN was quantified (expressed as a percentage of the control condition) (FIG. 42). (mean±s.e.m, n=9 mice/group pooled from 2 independent experiments, **p=0.0013, Unpaired t test). These experiments show the presence of activated T cells in the dCLN.

Figure 43A:
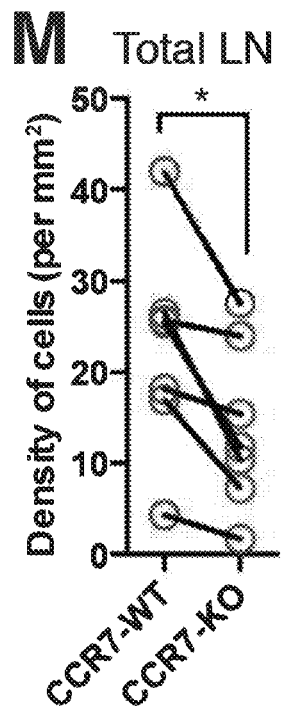
FIGS. 43A-D are a series of graphs showing that meningeal T cells circulate into the cervical lymph nodes in a CCR7-CCL21 dependent manner.
Figure 43B:
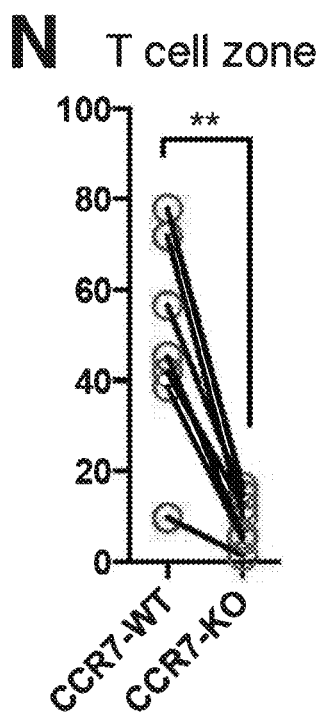
Figure 43C:
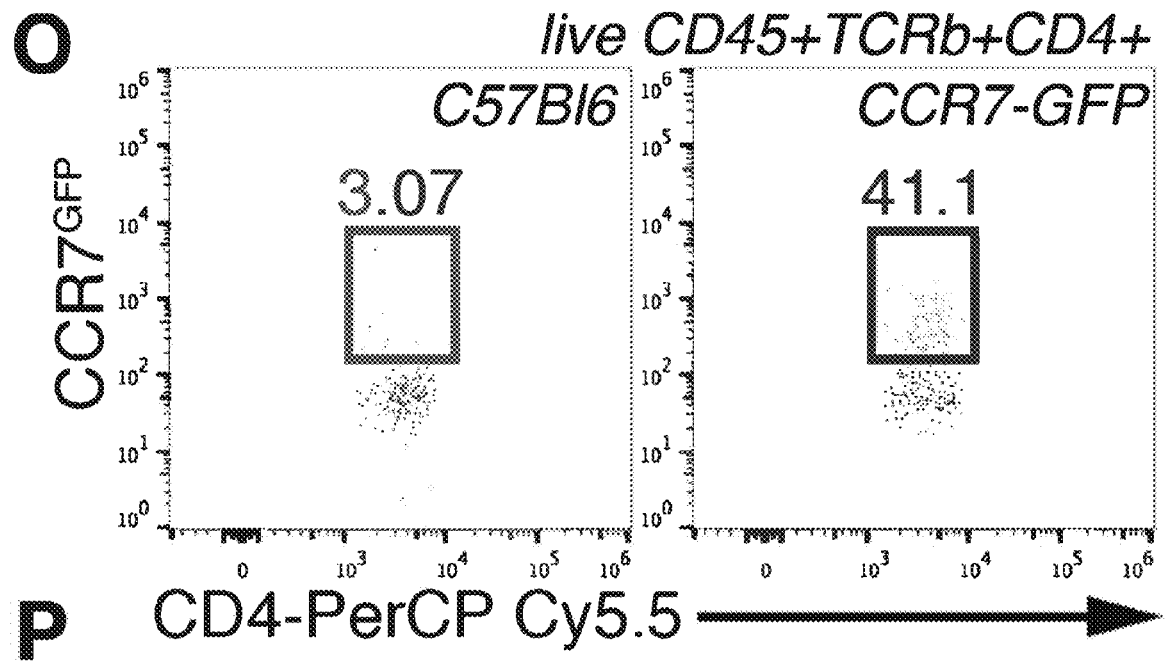
Figure 43D:
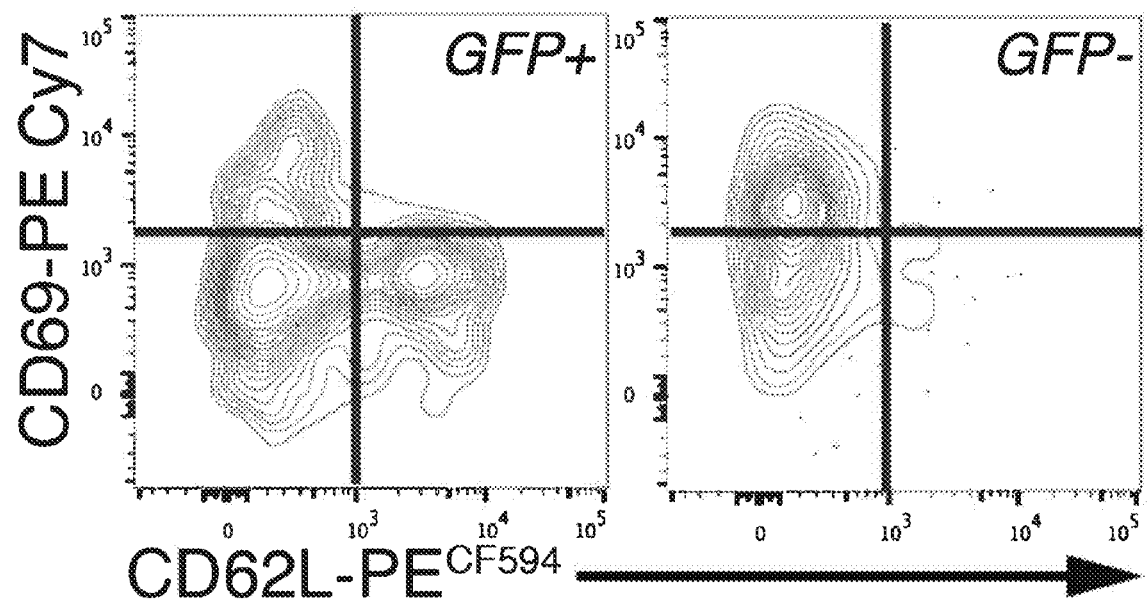

Example 20: Meningeal T Cells Circulate into the Cervical Lymph Nodes in a CCR7-CCL21 Dependent Manner Adult C57B16 mice were injected i.c.m. with a 1:1 ratio (1 million cell total) of CCR7-WT and CCR7-KO CD4 T cells. Lymph nodes were harvested 12 h post injection. Images were obtained of CCR7-WT (red) and CCR7-KO (green) CD4 T cells in the dCLN 12 h post injection. The density of CCR7-WT and CCR7-KO cells per mm$^2$ of total lymph nodes (FIG. 43A) or per T cell zone (FIG. 43B) was quantified at 12 h post injection. (mean±s.e.m, n=7 mice/group pooled from 2 independent experiment, *p=0.0102, **p=0.0014, paired t test). A representative dot plot of GFP expression by CD4 T cells in the meninges of C57B16 mice and CCR7$^{GFP}$ mice is shown in FIG. 43C (representative of 3 independent mice). A representative contour plot of phenotype CCR7$^+$ and CCR7$^-$ CD4 T cells in the meninges of CCR7$^{GFP}$ mice is shown in FIG. 43D.

Figure 44A:
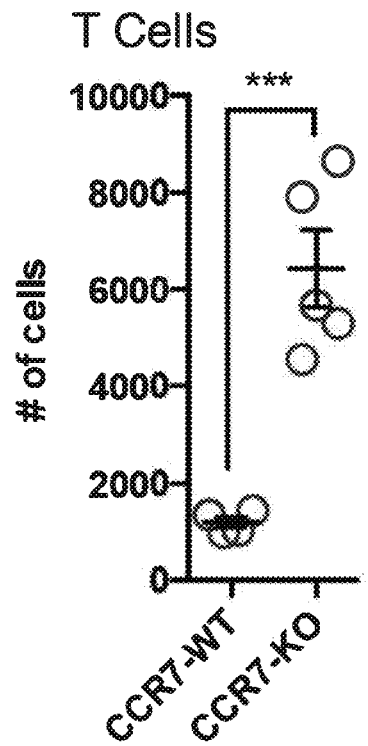
FIGS. 44A-E are a series of graphs showing that meningeal T cells circulate into the cervical lymph nodes in a CCR7-CCL21 dependent manner.
Figure 44B:
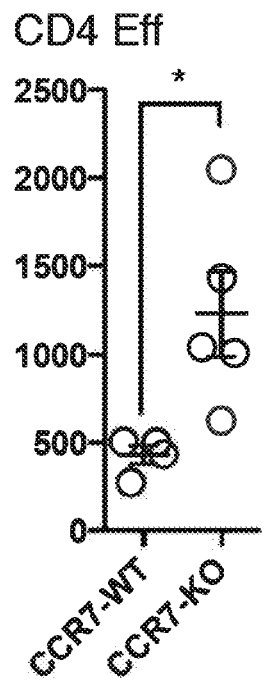
Figure 44C:
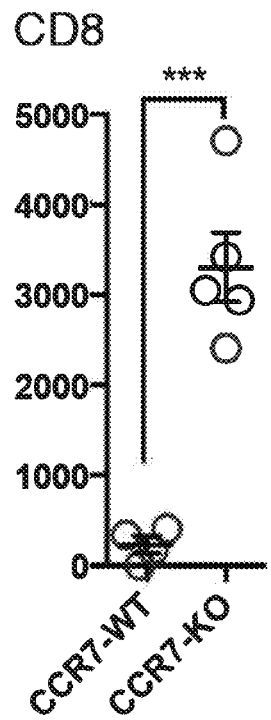
Figure 44D:
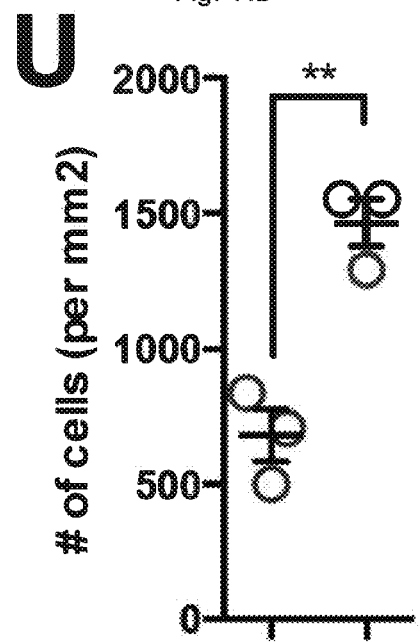
Figure 44E:
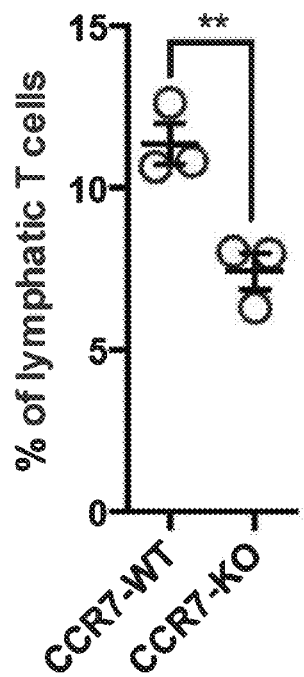

Images of CCR7 expression (CCR7GF) in and around the meningeal lymphatics (Lyve-1 and CCL21) along the transverse sinus identified T cell shaped cell expressing CCR7 located inside of the meningeal lymphatics. The number of total T cells (FIG. 44A), CD4 effector (FIG. 44B) and CD8 T cells (FIG. 44C) in the meninges of CCR7-WT and CCR7-KO mice was quantified (FIG. 44E). (mean±s.e.m, n=4-5 mice/group, *p=0.0007 (T cells), *p=0.0002 (CD8 T cells), *p=0.0231 (CD4 effector T cells), unpaired t test). Images of T cells (CD3e—red) in and around the meningeal lymphatics (Lyve-1—blue) of the superior sagittal sinus were obtained. The density of T cells on the sinuses of CCR7-WT and CCR7-KO mice was quantified (FIG. 44D) and percentage of T cells localized inside of the lymphatics (FIG. 44E). (mean±s.e.m, n=3 mice/group, p=0.0039 (density), p=0.0098 (percentage lymphatic), unpaired t test.

These experiments show that meningeal T cells circulate into the cervical lymph nodes in a CCR7-CCL21 dependent manner.

Example 21: Meningeal Dendritic Cells Circulate into the Cervical Lymph Nodes

Figure 45A:
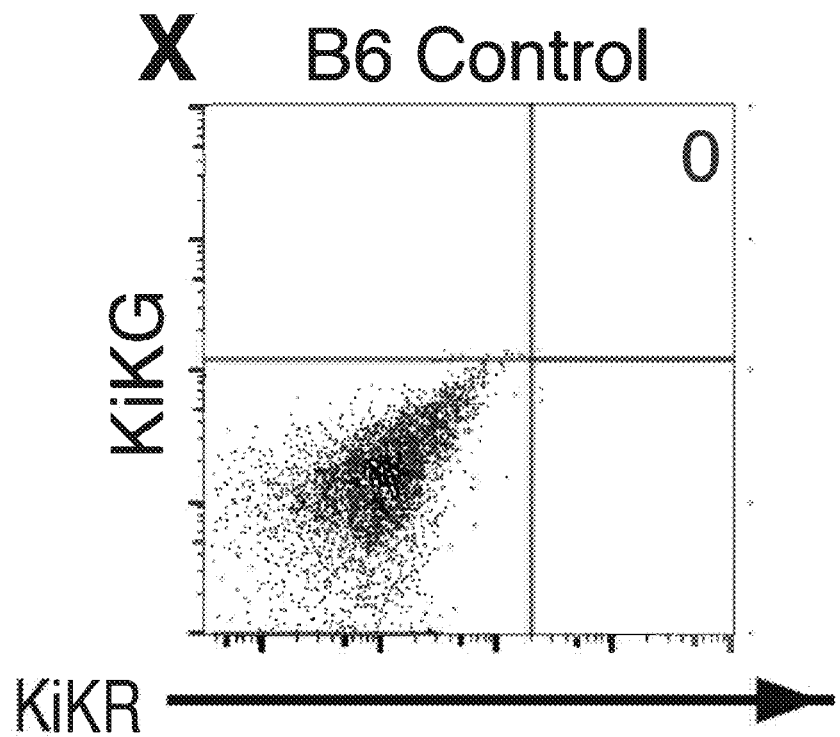
FIGS. 45A-C are a series of graphs showing that meningeal dendritic cells circulate into the cervical lymph nodes.
Figure 45B:
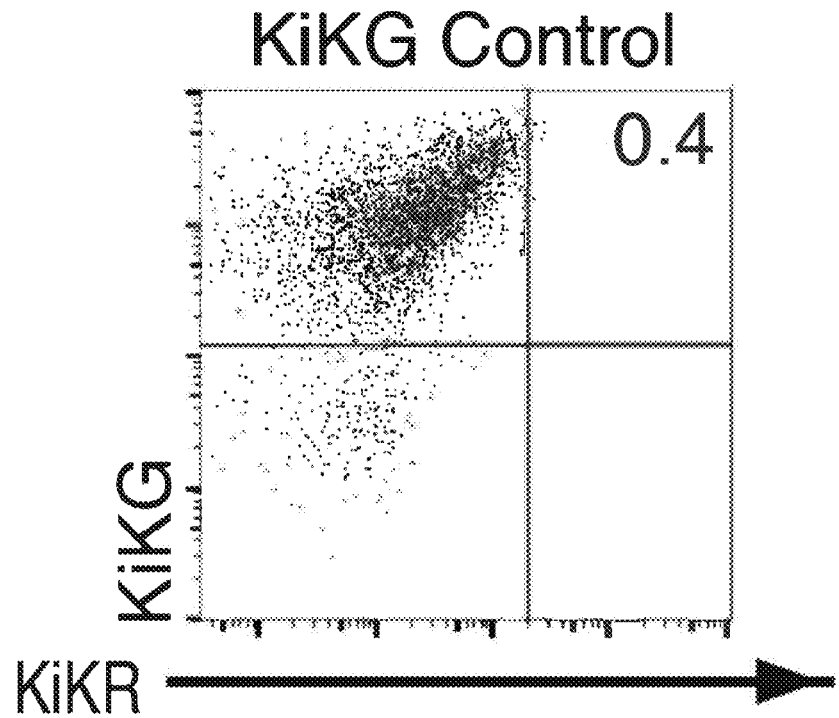
Figure 45C:
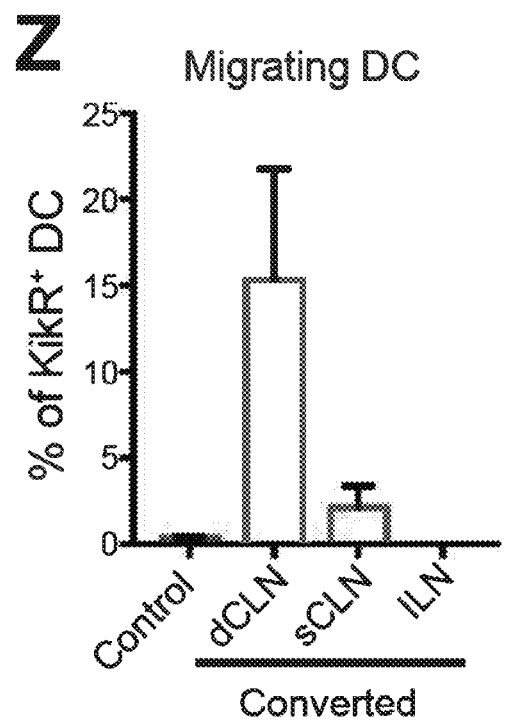

KiKGR mice meninges were converted for 2 min with violet light every 12 h for 2 days. After 2 days, mice were injected i.c.m. with Poly(I:C) with peptide. Tissue were harvested 24 h after Poly(I:C) injection. Samples were gated to identify dendritic cells. Representative dot plots are shown for B6 controls, which KiKG+ and KiKR+ dendritic cells (FIG. 45A) and for KiKGR control mice (FIG. 45B). Representative dot plots of KiKR+ dendritic cells in the dCLN, sCLN and ILN 24 h after Poly(I:C) injection in converted mice. Representative of 4 mice. Quantification of the percentage of KiKR+ dendritic cells in the dCLN, sCLN and ILN of control and converted mice 24 h after Poly(I:C) injection is shown in FIG. 45C. (mean±s.e.m, n=3-4 mice/group, representative of 2 independent experiments).

These experiments show that meningeal dendritic cells circulate into the cervical lymph nodes.

Figure 46A:
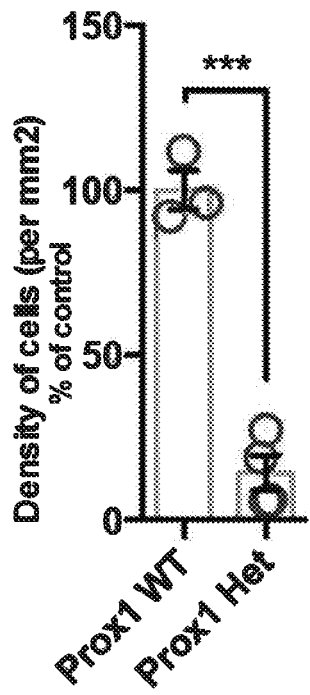
FIGS. 46A-G are a series of graphs showing that meningeal lymphatics is the main route for immune cells and macromolecules circulation into the cervical lymph nodes.
Figure 46B:
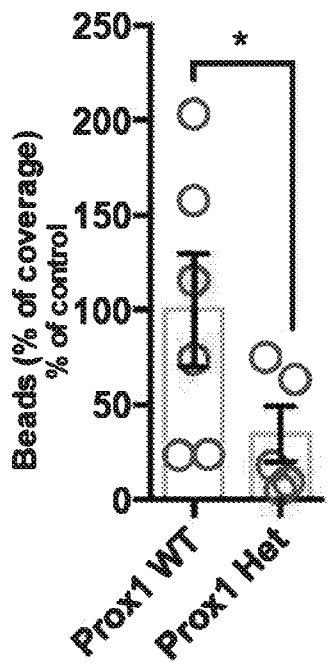
Figure 46C:
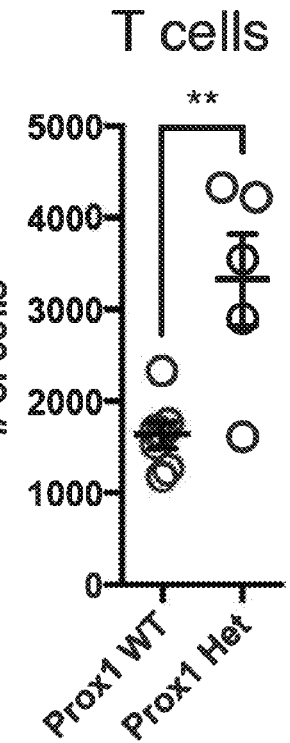
Figure 46D:
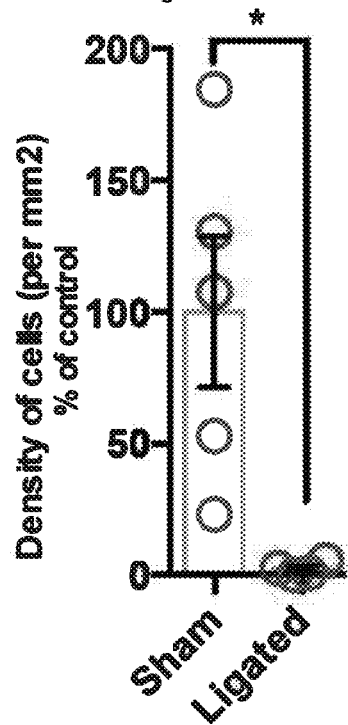
Figure 46E:
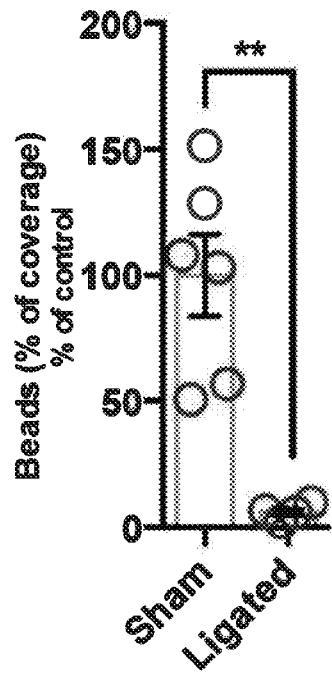
Figure 46F:
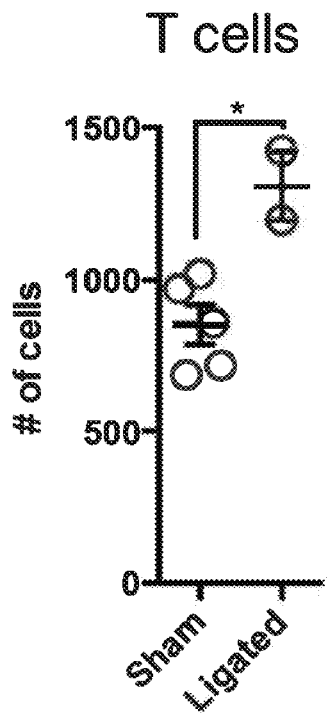
Figure 46G:
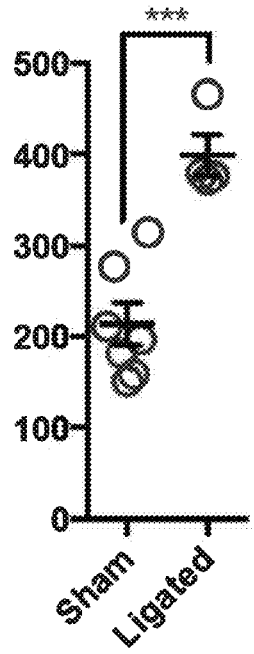

Example 22: Meningeal Lymphatics is the Main Route for Immune Cells and Macromolecules Circulation into the Cervical Lymph Nodes Images of exogenously injected T cells (CFSE) in the dCLN of Prox1 WT and Prox1 Het mice were obtained 12 h after i.c.m. injection. The density of T cells per mm$^2$ of dCLN of Prox1 WT and Prox1 Het mice were quantified (expressed as percentage of the control condition) (FIG. 46A) (mean±s.e.m, n=3-4 mice/group, ***p=0.0001 unpaired t test). Images of exogenously injected fluorescent microbeads (0.5 µm in diameter—red) in the dCLN of Prox1 WT and Prox1 Het mice were obtained 2 h after i.c.m. injection. The percentage of beads coverage in the dCLN of Prox1 WT and Prox1 Het mice was quantified (expressed as percentage of the control condition)(FIG. 46B) (mean±s.e.m, n=5-6 mice/group. *p=0.0490, one-tailed unpaired t test). The number of T cells (TCRb+) in the meninges of Prox1 WT and Prox1 Het mice were also quantified (FIG. 46C). (mean±s.e.m, n=5-7 mice/group pooled from 2 independent experiment, **p=0.0034, unpaired t test). Adult C57B16 mice had the afferent lymphatic reaching the dCLN surgically ligated of sham operated. F. Representative images of exogenously injected T cells (Deep red Cell Tracker—red) in the dCLN of sham and ligated mice (24 h post surgery) 12 h after i.c.m. injection. The density of T cells per mm$^2$ of dCLN or sham and ligated mice was quantified (FIG. 46E) (expressed as percentage of the control condition) (mean±s.e.m, n=4-5 mice/group, *p=0.0194, unpaired t test). Images of exogenously injected fluorescent microbeads (0.5 µm in diameter—green) in the dCLN of sham and ligated mice (expressed as percentage of the control condition) were obtained. The percentage of beads coverage in the dCLN or sham and ligated mice was quantified (expressed as percentage of the control condition) (FIG. 46E) (mean±s.e.m, n=4-6 mice per group, **p=0.0017, unpaired t test). T cells in the meninges of sham and ligated mice were quantified. The numbers of T cells (TCRb+; FIG. 46F) and CD4 effector T cells (TCRb+CD4+ FoxP3−; FIG. 46G) were quantified in the meninges of sham and ligated mice. (mean±s.e.m. n=2-5 mice/group (TCRb+); n=4-7 mice/group (CD4 Eff) pooled from 2 independent experiments, *p=0.0146. ***p=0.0006 unpaired t test).

These experiments show that meningeal lymphatics is the main route for immune cells and macromolecules circulation into the cervical lymph nodes

Example 23: Exogenously-Labeled T Cells Cycle in Meningeal Lymphatics

Figure 47:
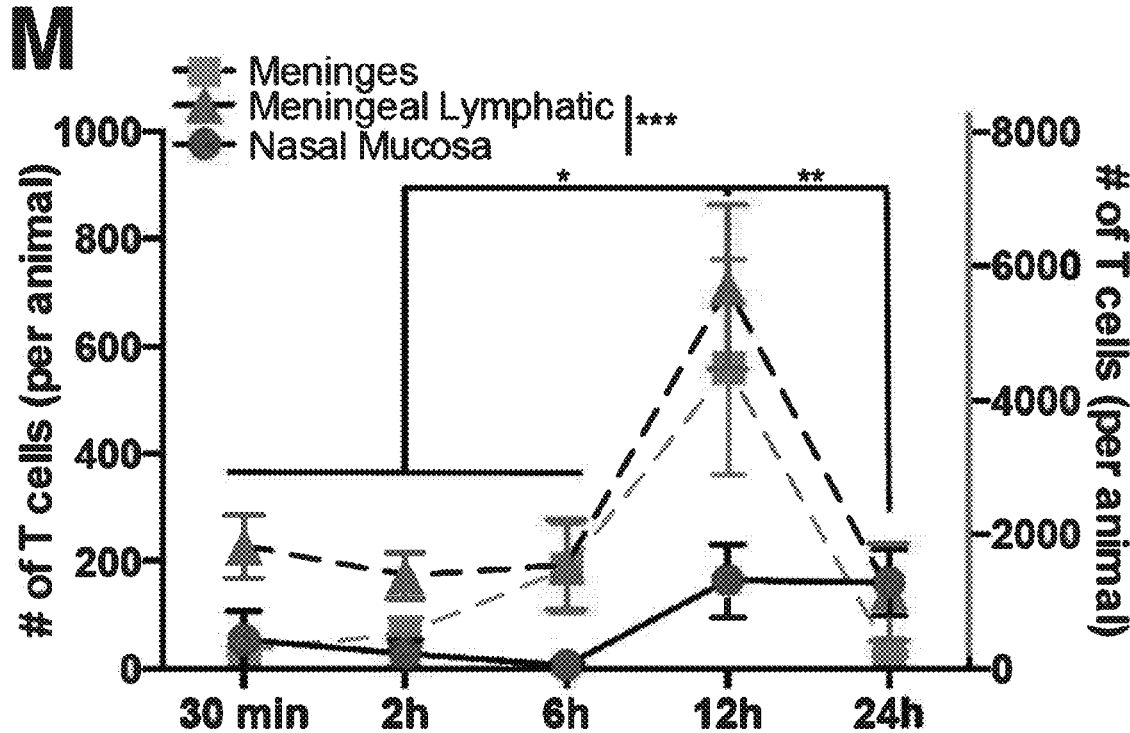
FIG. 47 is a graph showing that exogenously-labeled T cells cycle in meningeal lymphatics.

Adult mice were injected i.c.m. with 1 million of exogenously labeled T cells, Meninges and nasal cavity were harvested and analyzed at the indicated time points. Representative images of the cribriform plate region after 2 and 12 h post i.c.m. injection of CFSE-labeled T cells (green). I.c.m. injected T cells (Deep Red Cell Tracker—red) were detected in the lymphatic of the cribriform plate, but also in and around the lymphatic at the base of the nose. Intralymphatic T cells and perilymphatic T cells were observed. The number of exogenously injected T cells in the meninges was quantified, in the meningeal lymphatics and in the nasal mucosa of mice at different time post i.c.m. injection (FIG. 47). (mean±s.e.m. n=2-8 mice per group, pooled from 2 independent experiment. *p=0.0114 (Meningeal lymphatic 30 min/2 h/6 h vs 12 h), p=−0.0018 (Meningeal lymphatic 24 h vs 12 h), *p=0.0003 (Meningeal lymphatic vs Nasal mucosa), 2 way ANOVA with Sidak's multiple comparison test). These experiments show that exogenously-labeled T cells cycle in meningeal lymphatics.

Figure 48A:
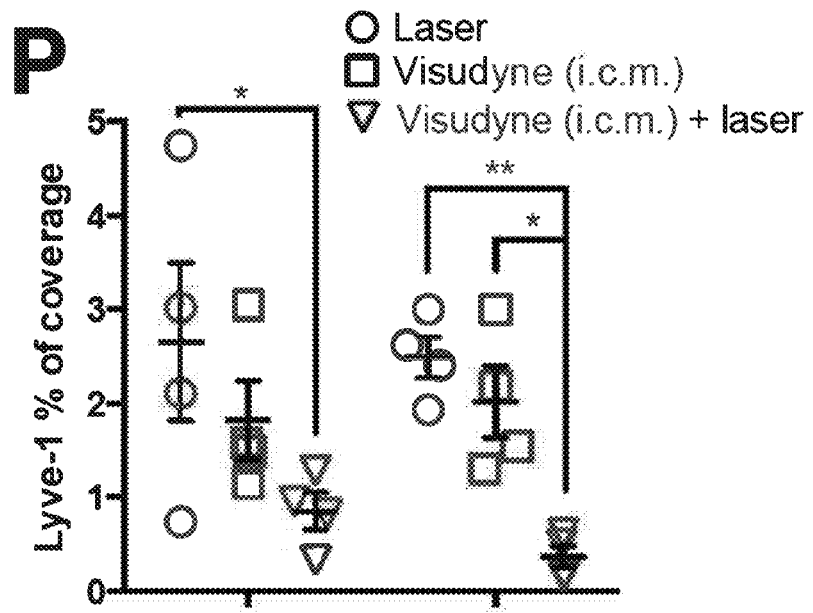
FIGS. 48A-D are a series of graphs showing that meningeal vasculature ablation in accordance with some embodiments herein affects immune cell size and coverage in the CNS.
Figure 48B:
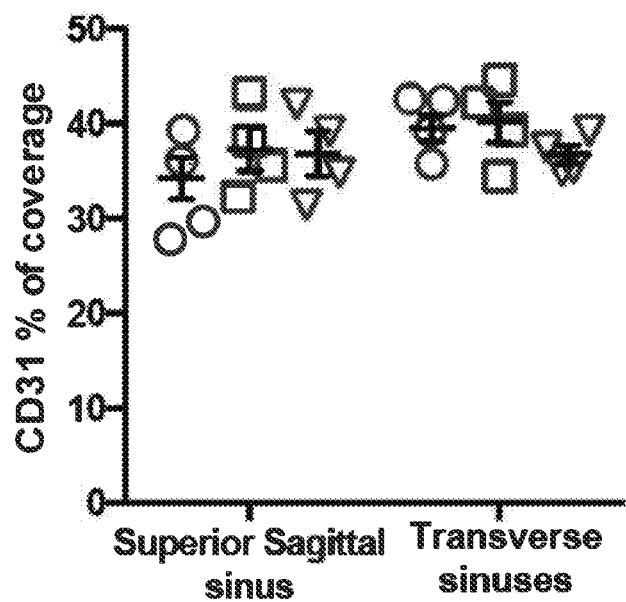
Figure 48C:
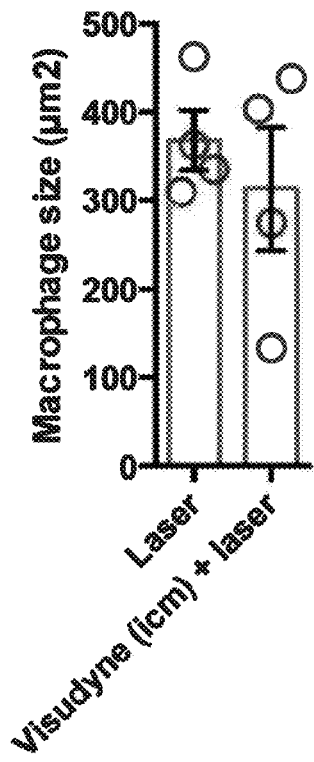
Figure 48D:
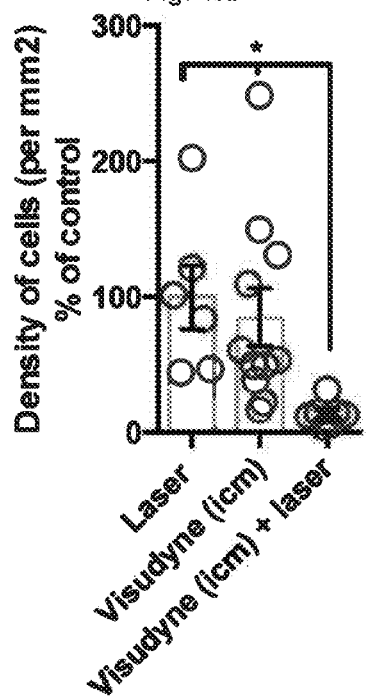

Example 24: Effects of Meningeal Vasculature Ablation of Immune Cell Size and Coverage Adult mice were injected i.c.m. with 5 µl of Visudyne (or PBS). Fifteen to 30 min post injection, Visudyne was converted using a nonthermal 689 nm laser on 5 different point above the meningeal lymphatics through the intact skull. Images of the meningeal lymphatic (Lyve-1) and blood (CD31) vasculature of laser alone, Visudyne alone and Visudyne+laser treated mice 4 days after photoconversion were obtained. Quantification was performed of the Lyve-1 (FIG. 48A) and CD31 (FIG. 48B) coverage on the superior sagittal and transverse sinuses of laser alone, Visudyne alone and Visudyne+laser treated mice 4 days after photoconversion. (mean±s.e.m, n=4 mice/group representative of 3 independent experiments, **p=0.008, *p=0.025 (TS), *p=0.045 (SSS), 2 way ANOVA with Sidak's multiple comparison test). Macrophages (Iba1, MHCII) were observed along the transverse sinus of laser, or Visudyne (i.c.m.)+laser treated mice 4 days after ablation. Scale bar=µm. Quantification of the size of the macrophages on the transverse sinus of laser and Visudyne (i.c.m.)+laser treated mice. (mean±s.e.m, n=4 mice/group) FIG. 48C. Images were obtained of exogenously injected T cells (4 days after ablation) (CFSE) in the dCLN of laser, Visudyne (i.c.m.) and Visudyne (i.c.m.)+laser treated mice 12 h after i.c.m. injection. The density of exogenously injected T cells per mm2 of dCLN in laser. Visudyne (i.c.m.) and Visudyne (i.c.m.)+laser treated mice was quantified (FIG. 48D)(expressed as percentage of the control condition). (mean±s.e.m, n=6-11 mice/group, *p=0.0298 (Laser vs Visudyne (i.c.m.)+laser), *p=0.0412 (Visudyne (i.c.m.)+vs Visudyne (i.c.m.)+laser). One-way ANOVA with Tukey's multiple comparisons test). These experiments show that meningeal vasculature ablation in accordance with some embodiments herein affects immune cell size and coverage in the CNS.

Example 25: T Cell Migration is Inhibited by the Ablation of Meningeal Lymphatic Vessels Adult mice were injected i.c.m. with Visudyne. Fifteen to thirty minutes injection, Visudyne was converted using a non-thermal 689 nm laser applied on the intact skull. In the targeted group, the laser was aimed at 5 different spots localized above the meningeal lymphatics. In the non-targeted group, the laser was aimed further away to no convert the Visudyne localized within the meningeal lymphatics.

Figure 49A:
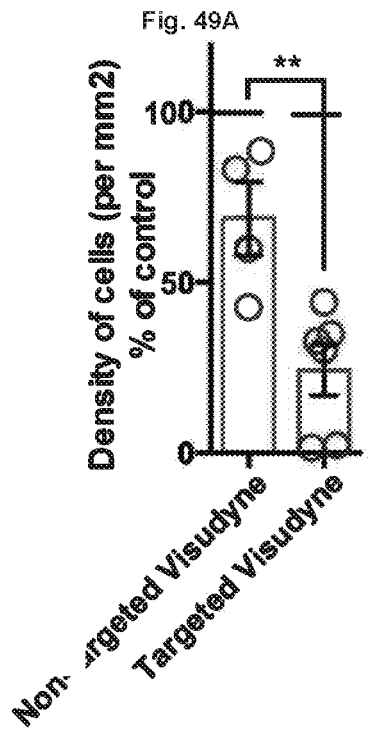
FIGS. 49A-D are a series of graphs showing that T cell migration is inhibited by the ablation of meningeal lymphatic vessels.
Figure 49B:
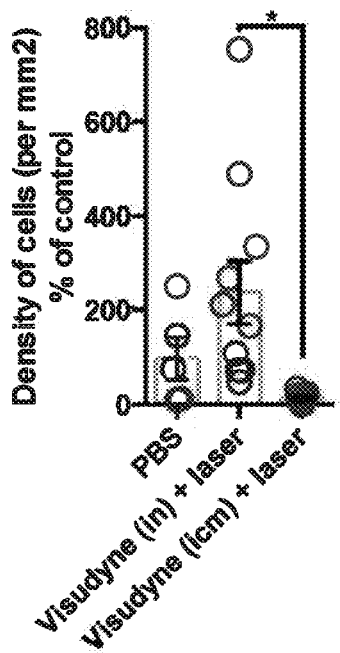
Figure 49C:
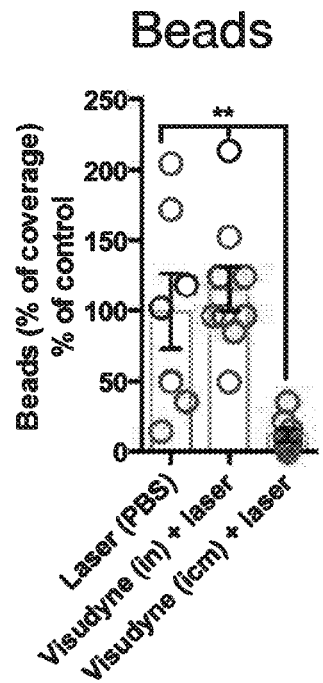
Figure 49D:
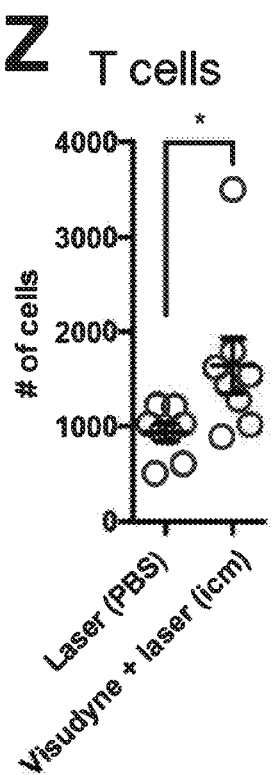

The density of exogenously injected T cells per mm2 of dCLN in targeted and non-targeted Visudyne treated mice was quantified (FIG. 49A) (expressed as percentage of the control condition)(mean±s.e.m, n=4-6 mice/group, **p=0.0072 Student t test). Images of the nasal lymphatics (Prox1GFP—green, Lyve1—red) were obtained 24 h after laser or intranasal (i.n.) injection of Visudyne. The inset illustrate the lymphatic bundle at the base of the skull that gets ablated after Visudyne treatment. Scale bar=50 µm. The density of T cells per mm2 of dCLN was quantified (FIG. 49B) or percentage of beads coverage was quantified (FIG. 49C) in the dLCN of laser, Visudyne (i.n.)+laser and Visudyne (i.c.m.)+laser treated mice (expressed as percentage of the control condition). (mean±s.e.m, n=5-9 mice/group (T cells), *p=0.0103 (T cells), n=7-9 mice/group (beads), p=0.0055 (Laser vs Visudyne (i.c.m.)+laser) *p=0.0007 (Visudyne (i.n.)+laser vs Visudyne (i.c.m.)+laser), One way ANOVA with Tukey's multiple comparisons test). T cells were quantified in the meninges of laser and Visudyne (i.c.m.)+laser treated mice at 7 days post ablation. T cells were quantified in the meninges of laser and Visudyne (i.c.m.)+laser treated mice (FIG. 49D). (mean±s.e.m, n=8 mice/group pooled from 2 independent experiment). *p=0.0360 unpaired t test).

These experiments show that T cell migration is inhibited by the ablation of meningeal lymphatic vessels in accordance with some embodiments herein.

Figure 50A:
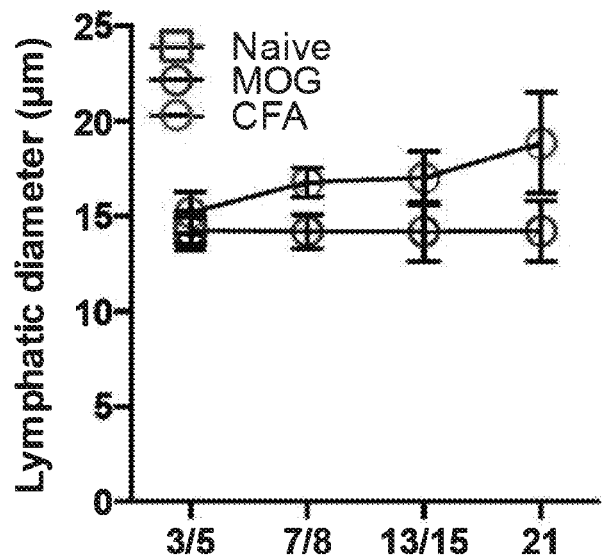
Figure 50B:
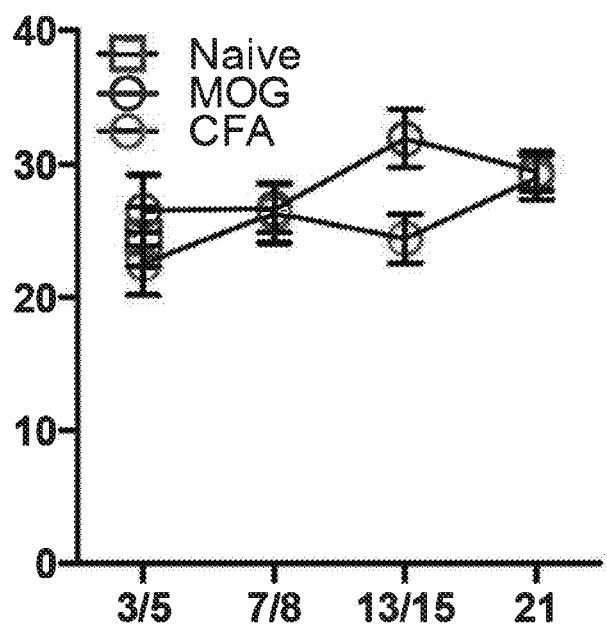
Figure 50C:
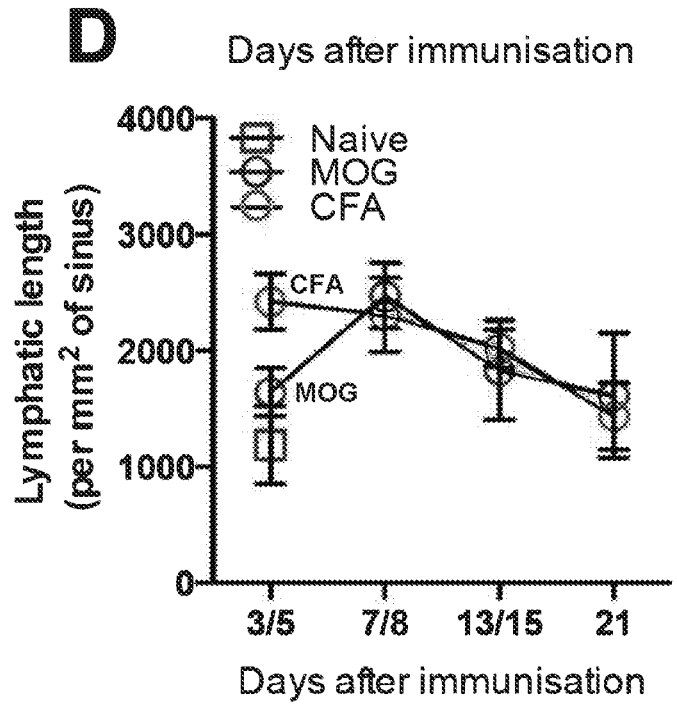
Figure 50D:
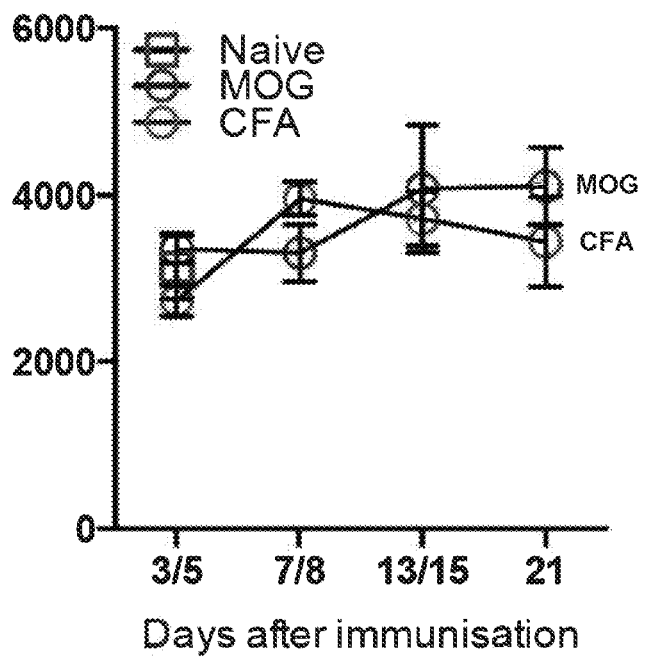
Figure 50E:
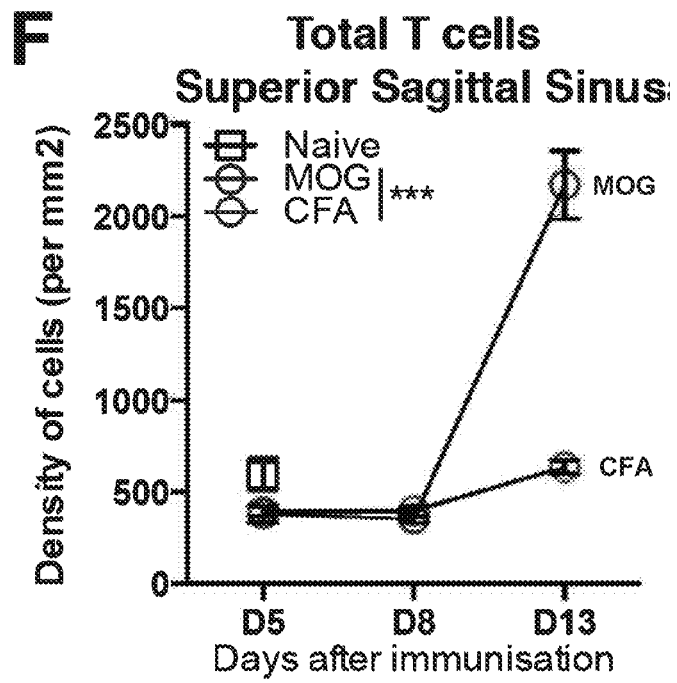
Figure 50F:
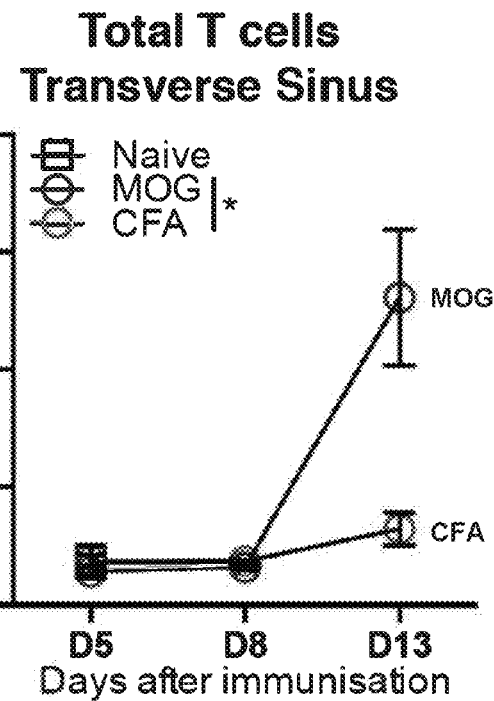

Example 26: Lack of Inflammation-Induced Lymphangiogenesis of the Meningeal Lymphatic Endothelial Cells Adult C57B16 female were injected s.c. with 200 µg of $MOG_{35-55}$+CFA along with 200 µl of Pertussis Toxin (injection of PTX is repeated at day 1). Meninges were harvested at the indicated time post immunization. Quantification of the diameter of the meningeal lymphatic of the superior sagittal (FIG. 50A) and transverse (FIG. 50B) sinuses of naïve, CFA and MOG immunized mice was performed at different time post immunization. (mean±s.e.m. n=4-8 mice/group pooled from 2 independent experiment). Quantification of the total lymphatic length on the superior sagittal (FIG. 50C) and transverse sinuses (FIG. 50D) of naïve, CFA and MOG immunized mice was performed at different time after immunization. (mean±s.e.m, n=3-5 mice/group). Images of T cells (CD3e) in and around the meningeal lymphatics (Lyve1) of the superior sagittal sinus of CFA and MOG immunized mice were obtained at D13 after immunization. The density of T cells on the superior sagittal and transverse sinuses of naïve, CFA and MOG immunized mice was quantified at different time after immunization (FIG. 50E). (mean±s.e.m, n=2-5 mice per group, ****p<0.001 (CFA vs MOG, SSS) *p=0.0113 (CFA vs MOG, TS), Two way ANOVA. The density of T cells outside and inside the meningeal lymphatic vessels of the superior sagittal sinus was quantified at different time points after immunization (non-lymphatic T cells shown in FIG. 50G; lymphatic T cells shown in FIG. 50F). (mean±s.e.m, n=2-5 mice/group, *p=0.003 (CFA vs MOG, outside the lymphatics). p=0.0092 (MOG D5 vs MOG D13), *p=0.0162 (MOG D8 vs MOG D13), 2 way ANOVA with Tukey's multiple comparisons test. Naïve and MOG immunized mice (D21) were injected i.c.m. with fluorescent microparticles (0.5 µm in diameter). Two hours after injection, lymph nodes were harvested and analyzed. Quantification of the percentage of beads coverage in the dCLN of naïve and sick MOG immunized mice (D21) (expressed as percentage of the control condition) (FIG. 50I). (mean±s.e.m, n=4-5 mice/group, *p=0.0125, unpaired t test). These experiments show a lack of inflammation-induced lymphangiogenesis of the meningeal lymphatic endothelial cells.

Figure 51B:
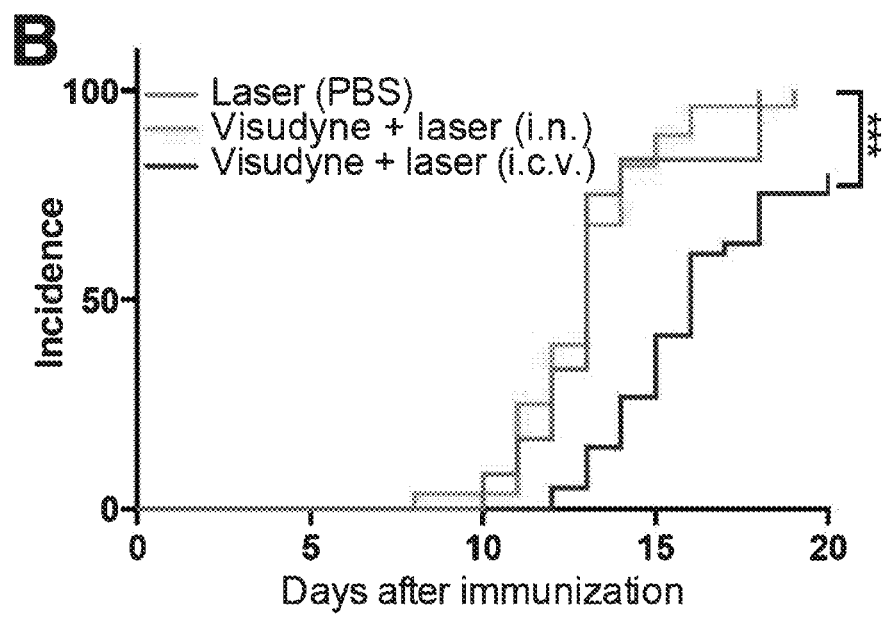
Figure 51C:
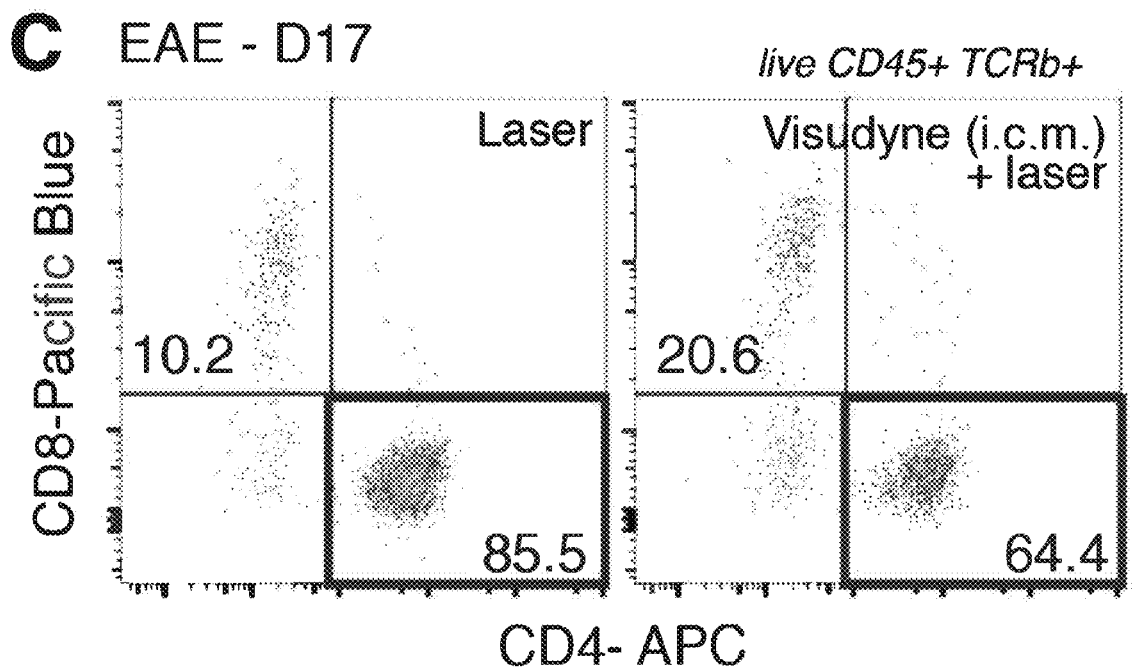
Figure 51D:
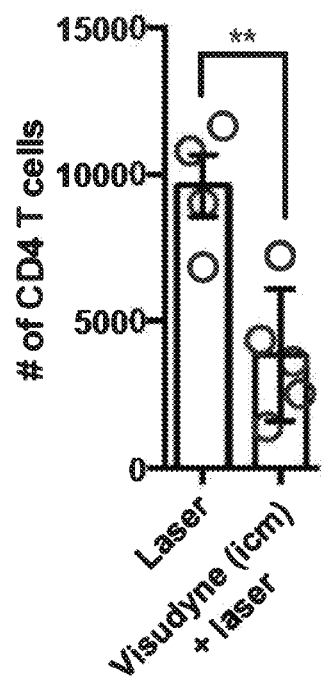

Example 27: Ablation of Lymphatic Drainage Ameliorate MOG-Specific T Cells Activation in the Deep Cervical Lymph Nodes Resulting in Ameliorated Disease Development EAE clinical symptom development in laser. Visudyne (i.n.)+laser and Visudyne (i.c.m.)+laser treated mice. (mean±s.e.m. n=12-41 mice/group pooled from 3 independent experiments, **p<0.0001, repeated measures 2 way ANOVA with Tukey's multiple comparisons test) is shown in FIG. 51A. Incidence of EAE development (day mice reach a score of 1 or above) in laser, Visudyne (i.n.)+laser and Visudyne (i.c.m.)+laser treated mice. (n=12-41 mice/group pooled from 3 independent experiments, *p<0.0001, Log-rank (Mante-Cox) test) are shown in FIG. 51B. Representative dot plots of CD4 and CD8 T cells in the spinal cord of laser and Visudyne (i.c.m.)+laser mice during late onset EAE (D17) are shown in FIG. 51C. Quantification of the number of CD4 T cells in the spinal cord of laser and Visudyne (i.c.m.)+laser treated mice at D17 post immunization. (mean±s.e.m. n=4/5 mice per group, representative of 2 independent experiments, **p=0.005, unpaired t test) is shown in FIG. 51D. These experiments show that ablating meningeal lymphatic vessels in accordance with some embodiments herein ameliorates MOG-specific T cell activation in the deep cervical lymph nodes, and further ameliorate disease development. Accordingly, it is contemplated that ablation of lymphatic vessels in accordance with some embodiments herein can ameliorate symptoms and disease development of MS, for which EAE (MOG) is a model.

In some embodiments, the method, use, or composition comprises various steps or features that are present as single steps or features (as opposed to multiple steps or features). For example, in one embodiment, the method includes a single administration of a flow modulator, or the composition comprises or consists essentially of a flow modulator for single use. The flow modulator may be present in a single dosage unit effective for increasing flow (or decreasing immune cell migration). A composition or use may comprise a single dosage unit of a flow modulator effective for increasing flow (or inhibiting migration of immune cells) as described herein. Multiple features or components are provided in alternate embodiments. In some embodiments, the method, composition, or use comprises one or more means for flow modulation. In some embodiments, the means comprises a flow modulator.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. For each method of described herein, relevant compositions for use in the method are expressly contemplated, uses of compositions in the method, and, as applicable, methods of making a medicament for use in the method are also expressly contemplated. For example, for methods of increasing flow that comprise a flow modulator, flow modulators for use in the corresponding method are also contemplated, as are uses of a flow modulator in increasing flow according to the method, as are methods of making a medicament comprising the flow modulator for use in increasing flow.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A. B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A. B, or C, etc." is used, in general such a construction is intended in the sense one having skill in the art would understand the convention (e.g., "a system having at least one of A, B, or C" would include but not be limited to systems that have A alone, B alone, C alone, A and B together. A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. For example, "about 5", shall include the number 5. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method of increasing flow of fluid in the central nervous system (CNS) of a subject, wherein the subject has a disease or disorder selected the group consisting of Pediatric Autoimmune Neuropsychiatric Disorders Associated with Streptococcal Infections (PANDAS), meningitis, and autism, the method comprising:

administering an effective amount of a Vascular Endothelial Growth Factor Receptor 3 (VEGFR3) agonist to a meningeal space of the subject, wherein the VEGFR3 agonist is VEGF-c156S, wherein said administration is effective to increase fluid flow in the central nervous system of the subject as compared to pre-administration of the VEGFR3 agonist.

2. The method of claim 1, wherein the administration of the VEGFR3 agonist increases the diameter of a meningeal lymphatic vessel of the subject as compared to pre-administration of the VEGFR3 agonist.

3. The method of claim 1, wherein increasing the fluid flow in the CNS comprises increasing flow of cerebral spinal fluid (CSF), interstitial fluid (ISF), or both.

* * * * *

SEQUENCE LISTING

```
<160> NUMBER OF SEQ ID NOS: 5

<210> SEQ ID NO 1
<211> LENGTH: 419
<212> TYPE: PRT
<213> ORGANISM: Homo sapiens

<400> SEQUENCE: 1

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
```

```
              20                  25                  30
Glu Ser Gly Leu Asp Leu Ser Asp Ala Glu Pro Asp Ala Gly Glu Ala
            35                  40                  45

Thr Ala Tyr Ala Ser Lys Asp Leu Glu Glu Gln Leu Arg Ser Val Ser
 50                  55                  60

Ser Val Asp Glu Leu Met Thr Val Leu Tyr Pro Glu Tyr Trp Lys Met
 65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
    370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 2
<211> LENGTH: 354
```

```
<212> TYPE: PRT
<213> ORGANISM: Homo sapiens

<400> SEQUENCE: 2

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

<210> SEQ ID NO 3
<211> LENGTH: 1363
<212> TYPE: PRT
<213> ORGANISM: Homo sapiens
```

-continued

```
<400> SEQUENCE: 3

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
        275                 280                 285

Thr Glu Leu Ser Ser Ile Leu Thr Ile His Asn Val Ser Gln His Asp
290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Pro Glu Phe Gln Trp
        355                 360                 365

Tyr Lys Asp Gly Lys Ala Leu Ser Gly Arg His Ser Pro His Ala Leu
370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
                405                 410                 415
```

```
Val Val Asn Val Pro Pro Gln Ile His Glu Lys Glu Ala Ser Ser Pro
            420                 425                 430

Ser Ile Tyr Ser Arg His Ser Arg Gln Ala Leu Thr Cys Thr Ala Tyr
        435                 440                 445

Gly Val Pro Leu Pro Leu Ser Ile Gln Trp His Trp Arg Pro Trp Thr
    450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
            485                 490                 495

Ala Val Asn Pro Ile Glu Ser Leu Asp Thr Trp Thr Glu Phe Val Glu
            500                 505                 510

Gly Lys Asn Lys Thr Val Ser Lys Leu Val Ile Gln Asn Ala Asn Val
        515                 520                 525

Ser Ala Met Tyr Lys Cys Val Val Ser Asn Lys Val Gly Gln Asp Glu
    530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
            565                 570                 575

Ser Cys Gln Ala Asp Ser Tyr Lys Tyr Glu His Leu Arg Trp Tyr Arg
            580                 585                 590

Leu Asn Leu Ser Thr Leu His Asp Ala His Gly Asn Pro Leu Leu Leu
        595                 600                 605

Asp Cys Lys Asn Val His Leu Phe Ala Thr Pro Leu Ala Ala Ser Leu
        610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
            645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
        675                 680                 685

Val Asn Val Ser Asp Ser Leu Glu Met Gln Cys Leu Val Ala Gly Ala
    690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
            725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
        755                 760                 765

Glu Asp Lys Gly Ser Met Glu Ile Val Ile Leu Val Gly Thr Gly Val
        770                 775                 780

Ile Ala Val Phe Phe Trp Val Leu Leu Leu Leu Ile Phe Cys Asn Met
785                 790                 795                 800

Arg Arg Pro Ala His Ala Asp Ile Lys Thr Gly Tyr Leu Ser Ile Ile
            805                 810                 815

Met Asp Pro Gly Glu Val Pro Leu Glu Glu Gln Cys Glu Tyr Leu Ser
            820                 825                 830
```

```
Tyr Asp Ala Ser Gln Trp Glu Phe Pro Arg Glu Arg Leu His Leu Gly
            835                 840                 845

Arg Val Leu Gly Tyr Gly Ala Phe Gly Lys Val Glu Ala Ser Ala
    850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
                885                 890                 895

Leu Lys Ile Leu Ile His Ile Gly Asn His Leu Asn Val Val Asn Leu
            900                 905                 910

Leu Gly Ala Cys Thr Lys Pro Gln Gly Pro Leu Met Val Ile Val Glu
            915                 920                 925

Phe Cys Lys Tyr Gly Asn Leu Ser Asn Phe Leu Arg Ala Lys Arg Asp
    930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Pro Gly Ser
                965                 970                 975

Ser Asp Arg Val Leu Phe Ala Arg Phe Ser Lys Thr Glu Gly Gly Ala
            980                 985                 990

Arg Arg Ala Ser Pro Asp Gln Glu Ala Glu Asp Leu Trp Leu Ser Pro
    995                 1000                1005

Leu Thr Met Glu Asp Leu Val Cys Tyr Ser Phe Gln Val Ala Arg Gly
        1010                1015                1020

Met Glu Phe Leu Ala Ser Arg Lys Cys Ile His Arg Asp Leu Ala Ala
1025                1030                1035                1040

Arg Asn Ile Leu Leu Ser Glu Ser Asp Val Val Lys Ile Cys Asp Phe
            1045                1050                1055

Gly Leu Ala Arg Asp Ile Tyr Lys Asp Pro Asp Tyr Val Arg Lys Gly
        1060                1065                1070

Ser Ala Arg Leu Pro Leu Lys Trp Met Ala Pro Glu Ser Ile Phe Asp
        1075                1080                1085

Lys Val Tyr Thr Thr Gln Ser Asp Val Trp Ser Phe Gly Val Leu Leu
        1090                1095                1100

Trp Glu Ile Phe Ser Leu Gly Ala Ser Pro Tyr Pro Gly Val Gln Ile
1105                1110                1115                1120

Asn Glu Glu Phe Cys Gln Arg Leu Arg Asp Gly Thr Arg Met Arg Ala
                1125                1130                1135

Pro Glu Leu Ala Thr Pro Ala Ile Arg Arg Ile Met Leu Asn Cys Trp
            1140                1145                1150

Ser Gly Asp Pro Lys Ala Arg Pro Ala Phe Ser Glu Leu Val Glu Ile
        1155                1160                1165

Leu Gly Asp Leu Leu Gln Gly Arg Gly Leu Gln Glu Glu Glu Val
    1170                1175                1180

Cys Met Ala Pro Arg Ser Ser Gln Ser Ser Glu Glu Gly Ser Phe Ser
1185                1190                1195                1200

Gln Val Ser Thr Met Ala Leu His Ile Ala Gln Ala Asp Ala Glu Asp
            1205                1210                1215

Ser Pro Pro Ser Leu Gln Arg His Ser Leu Ala Ala Arg Tyr Tyr Asn
            1220                1225                1230

Trp Val Ser Phe Pro Gly Cys Leu Ala Arg Gly Ala Glu Thr Arg Gly
            1235                1240                1245

Ser Ser Arg Met Lys Thr Phe Glu Glu Phe Pro Met Thr Pro Thr Thr
```

-continued

```
            1250                1255                1260
Tyr Lys Gly Ser Val Asp Asn Gln Thr Asp Ser Gly Met Val Leu Ala
1265                1270                1275                1280

Ser Glu Glu Phe Glu Gln Ile Glu Ser Arg His Arg Gln Glu Ser Gly
                1285                1290                1295

Phe Ser Cys Lys Gly Pro Gly Gln Asn Val Ala Val Thr Arg Ala His
                1300                1305                1310

Pro Asp Ser Gln Gly Arg Arg Arg Pro Glu Arg Gly Ala Arg Gly
            1315                1320                1325

Gly Gln Val Phe Tyr Asn Ser Glu Tyr Gly Glu Leu Ser Glu Pro Ser
        1330                1335                1340

Glu Glu Asp His Cys Ser Pro Ser Ala Arg Val Thr Phe Phe Thr Asp
1345                1350                1355                1360

Asn Ser Tyr
```

<210> SEQ ID NO 4
<211> LENGTH: 830
<212> TYPE: PRT
<213> ORGANISM: Homo sapiens

<400> SEQUENCE: 4

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
                20                  25                  30

Asn Ile Thr Glu Glu Ser His Val Ile Asp Thr Gly Asp Ser Leu Ser
            35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
                100                 105                 110

Tyr Lys Tyr Ile Lys Ala Arg Ile Glu Gly Thr Thr Ala Ala Ser Ser
            115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
                180                 185                 190

Val Ser Thr Pro Leu Leu His Asp Ala Leu Tyr Leu Gln Cys Glu Thr
            195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
```

-continued

```
                260                 265                 270
Ala Glu Arg Gly Lys Trp Val Pro Glu Arg Ser Gln Gln Thr His
            275                 280                 285

Thr Glu Leu Ser Ser Ile Leu Thr Ile His Asn Val Ser Gln His Asp
        290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
                325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Glu Phe Gln Trp
        355                 360                 365

Tyr Lys Asp Gly Lys Ala Leu Ser Gly Arg His Ser Pro His Ala Leu
        370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
            405                 410                 415

Val Val Asn Val Pro Pro Gln Ile His Glu Lys Glu Ala Ser Ser Pro
        420                 425                 430

Ser Ile Tyr Ser Arg His Ser Arg Gln Ala Leu Thr Cys Thr Ala Tyr
        435                 440                 445

Gly Val Pro Leu Pro Leu Ser Ile Gln Trp His Trp Arg Pro Trp Thr
450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
            485                 490                 495

Ala Val Asn Pro Ile Glu Ser Leu Asp Thr Trp Thr Glu Phe Val Glu
        500                 505                 510

Gly Lys Asn Lys Thr Val Ser Lys Leu Val Ile Gln Asn Ala Asn Val
        515                 520                 525

Ser Ala Met Tyr Lys Cys Val Val Ser Asn Lys Val Gly Gln Asp Glu
        530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
                565                 570                 575

Ser Cys Gln Ala Asp Ser Tyr Lys Tyr Glu His Leu Arg Trp Tyr Arg
            580                 585                 590

Leu Asn Leu Ser Thr Leu His Asp Ala His Gly Asn Pro Leu Leu Leu
        595                 600                 605

Asp Cys Lys Asn Val His Leu Phe Ala Thr Pro Leu Ala Ala Ser Leu
        610                 615                 620

Glu Glu Val Ala Pro Gly Ala Arg His Ala Thr Leu Ser Leu Ser Ile
625                 630                 635                 640

Pro Arg Val Ala Pro Glu His Glu Gly His Tyr Val Cys Glu Val Gln
                645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
        675                 680                 685
```

```
Val Asn Val Ser Asp Ser Leu Glu Met Gln Cys Leu Val Gly Ala
        690                 695                 700

His Ala Pro Ser Ile Val Trp Tyr Lys Asp Glu Arg Leu Leu Glu
705                 710                 715                 720

Lys Ser Gly Arg Glu Gly Gly Pro Gly Glu Gly Gln Val Arg Arg Pro
                725                 730                 735

Ala Arg Pro Thr Ile Pro Asn Pro Gly Gly Pro Ala Pro Pro His
            740                 745                 750

Pro Leu Gln Glu Ser Thr Trp Arg Thr Pro Thr Arg Ser Cys Lys Gly
            755                 760                 765

Pro Gly Gln Asn Val Ala Val Thr Arg Ala His Pro Asp Ser Gln Gly
        770                 775                 780

Arg Arg Arg Arg Pro Glu Arg Gly Ala Arg Gly Gly Gln Val Phe Tyr
785                 790                 795                 800

Asn Ser Glu Tyr Gly Glu Leu Ser Glu Pro Ser Glu Glu Asp His Cys
                805                 810                 815

Ser Pro Ser Ala Arg Val Thr Phe Phe Thr Asp Asn Ser Tyr
                820                 825                 830

<210> SEQ ID NO 5
<211> LENGTH: 354
<212> TYPE: PRT
<213> ORGANISM: Homo sapiens

<400> SEQUENCE: 5

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
                20                  25                  30

Ser Gln Ser Thr Leu Glu Arg Ser Glu Gln Gln Ile Arg Ala Ala Ser
            35                  40                  45

Ser Leu Glu Glu Leu Leu Arg Ile Thr His Ser Glu Asp Trp Lys Leu
        50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
                100                 105                 110

Pro Arg Glu Thr Cys Val Glu Val Ala Ser Glu Leu Gly Lys Ser Thr
            115                 120                 125

Asn Thr Phe Phe Lys Pro Pro Cys Val Asn Val Phe Arg Cys Gly Gly
        130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
```

-continued

```
            225                 230                 235                 240
Asn Pro Leu Ala Gly Thr Glu Asp His Ser His Leu Gln Glu Pro Ala
                    245                 250                 255

Leu Cys Gly Pro His Met Met Phe Asp Glu Asp Arg Cys Glu Cys Val
                260                 265                 270

Cys Lys Thr Pro Cys Pro Lys Asp Leu Ile Gln His Pro Lys Asn Cys
            275                 280                 285

Ser Cys Phe Glu Cys Lys Glu Ser Leu Glu Thr Cys Cys Gln Lys His
        290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
                340                 345                 350

Asn Pro
```